US007674828B2

(12) United States Patent
Chao et al.

(10) Patent No.: US 7,674,828 B2
(45) Date of Patent: Mar. 9, 2010

(54) UREA ANTAGONISTS OF P2Y$_1$ RECEPTOR USEFUL IN THE TREATMENT OF THROMBOTIC CONDITIONS

(75) Inventors: Hannguang J. Chao, Lawrenceville, NJ (US); Huji Tuerdi, Yardley, PA (US); Timothy F. Herpin, Princeton, NJ (US); Jacques Y. Roberge, Princeton, NJ (US); Yalei Liu, Hillsborough, NJ (US); Michael R. Lawrence, Yardley, PA (US); Robert P. Rehfuss, North Wales, PA (US); Charles G. Clark, Cherry Hill, NJ (US); Jennifer X. Qiao, Princeton, NJ (US); Timur Gungor, Pennington, NJ (US); Patrick Y. S. Lam, Chadds Ford, PA (US); Tammy C. Wang, Lawrenceville, NJ (US); Rejean Ruel, Saint-Lambert (CA); Alexandre L'Heureux, Ste Julie (CA); Carl Thibeault, Mascouche (CA); Gilles Bouthillier, Mercier (CA); Dora M. Schnur, Hamilton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 88 days.

(21) Appl. No.: 12/117,005

(22) Filed: May 8, 2008

(65) Prior Publication Data

US 2008/0280905 A1 Nov. 13, 2008

Related U.S. Application Data

(62) Division of application No. 11/126,915, filed on May 10, 2005, now Pat. No. 7,388,021.

(60) Provisional application No. 60/570,288, filed on May 12, 2004, provisional application No. 60/665,817, filed on Mar. 28, 2005.

(51) Int. Cl.
  *A61K 31/155* (2006.01)
  *C07C 275/28* (2006.01)
(52) U.S. Cl. .................................... 514/596; 564/48
(58) Field of Classification Search ............. 564/48; 514/596
  See application file for complete search history.

(56) References Cited

U.S. PATENT DOCUMENTS

| | | | |
|---|---|---|---|
| 3,230,141 A * | 1/1966 | Frick et al. .............. | 514/596 |
| 5,547,966 A | 8/1996 | Atwal et al. | |
| 5,691,364 A | 11/1997 | Buckman et al. | |
| 6,329,395 B1 | 12/2001 | Dugar et al. | |
| 6,833,378 B2 | 12/2004 | Chen | |
| 2003/0207870 A1 | 11/2003 | Dumas et al. | |
| 2003/0216396 A1 | 11/2003 | Dumas et al. | |
| 2004/0038992 A1 | 2/2004 | Bemis et al. | |
| 2005/0203146 A1 | 9/2005 | Herpin et al. | |
| 2005/0261244 A1 | 11/2005 | Tuerdi et al. | |
| 2006/0173002 A1 | 8/2006 | Sutton et al. | |
| 2006/0293522 A1 | 12/2006 | Sutton | |
| 2007/0004677 A1 | 1/2007 | Chao et al. | |

FOREIGN PATENT DOCUMENTS

| | | |
|---|---|---|
| EP | 1123918 | 8/2001 |
| JP | 62280847 | 12/1987 |
| JP | 03039740 | 2/1991 |
| JP | 1995101153 | 4/1995 |
| JP | 2001089412 | 4/2001 |
| WO | WO9617825 | 6/1996 |
| WO | WO 96/28427 | 9/1996 |
| WO | WO9818430 | 5/1998 |
| WO | WO0123358 | 4/2001 |
| WO | WO0151490 | 7/2001 |
| WO | WO0288090 | 11/2002 |
| WO | WO03007955 | 1/2003 |
| WO | WO03013517 | 2/2003 |
| WO | WO2004002481 | 1/2004 |
| WO | WO2005070920 | 8/2005 |

OTHER PUBLICATIONS

CAPLUS abstract of 1983:125577, Takeuchi et al. Yakugaku Zasshi (1982), vol. 102(11), pp. 1023-1030.*
U.S. Appl. No. 11/126,567, filed May 10, 2005, Tuerdi et al.
U.S. Appl. No. 11/038,862, filed Jan. 19, 2005, Herpin et al.
Hamada et al., "The antimicrobial activity and syntheses of carbanilide derivatives," Yakugaku Zasshi, vol. 96 (5), pp. 663-668, 1976, Abstract only, Journal written in Japanese.
Takeuchi et al., "On the antimicrobial activity and syntheses of carbanilide and salicylanilide derivatives," Yakugaku Zasshi, vol. 102(11), pp. 1023-1030, 1982.

(Continued)

*Primary Examiner*—Rei-Tsang Shiao
*Assistant Examiner*—Janet L Coppins
(74) *Attorney, Agent, or Firm*—Jing G. Sun

(57) ABSTRACT

The present invention provides novel pyridyl or phenyl ureas and analogues thereof, which are selective inhibitors of the human P2Y$_1$ receptor. The invention also provides for various pharmaceutical compositions of the same and methods for treating diseases responsive to modulation of P2Y$_1$ receptor activity.

8 Claims, No Drawings

OTHER PUBLICATIONS

Abbracchio et al., "Purinoceptors: Are there families of P2X and P2Y Purinoceptors?" Pharmac. Ther. vol. 64, pp. 445-475, 1994.

Abbracchio et al., "Characterization of the UDP-glucose receptor (re-named here the $P2Y_{14}$ receptor) adds diversity to the P2Y receptor family", TRENDS in Pharmacological Sciences, vol. 24, No. 2, Feb. 2003.

Baurand et al., "The $P2Y_1$ Receptor as a Target for the New Antithrombotic Drugs: A Review of the $P2Y_1$ Antagonist MRS-2179", Cardiovascular Drug Reviews, vol. 21, No. 1, pp. 67-76, 2003.

Boeynaems et al., "Overview of the P2Y Receptors as Therapeutic Targets", Drug Development Research, vol. 52, pp. 187-189, 2001.

Burnstock et al., "P2 Purinergic Receptors: Modulation of Cell Function and Therapeutic Potential", The Journal of Pharmacology and Experimental Therapeutics, vol. 295, No. 3, pp. 862-869, 2000.

Cobern et al., "Some New-p-Chlorophenoxycarbanilides and Their Bacteriostatic Activities", Notes, Unilever Research Laboratory, Colworth House, Sharnbrook, Bedford, England, Received Jun. 21, 1967.

Daniel et al., "Molecular Basis for ADP-induced Platelet Activation", The Journal of Bilogical Chemistry, vol. 273, No. 4, pp. 2024-2029, 1998.

Fabre et al., "Decreased platelet aggregation, increased bleeding time and resistance to thromboembolism in $P2Y_1$-deficient mice", Nature Medicine, vol. 5, No. 10, Oct. 1999.

Gramatica et al., "QSAR approach for the selection of congeneric compounds with a similar toxicological mode of action", Chemosphere, vol. 42, pp. 873-883, 2001.

Gschwend et al., "Specificity in Structure-Based Drug Design: Identification of a Novel, Selective Inhibitor of *Pneumocystis carinii* Dihydrofolate Reductase", Proteins: Structure, Function and Genetics, vol. 29, pp. 59-67, 1997.

Hechler et al., "The $P2Y_1$ receptor, necessary but not sufficient to support full ADP-induced platelet aggregation, is not the target of the drug clopidogrel", British Journal of Haematology, vol. 103, pp. 858-866, 1998.

Janssens et al., "Cloning and Tissue Distribution of the Human $P2Y_1$ Receptor", Biochemical and Biophysical Research Communications, vol. 221, pp. 588-593, 1996.

Jin et al., "Coactivation of two different G protein-coupled receptors is essential for ADP-induced platelet aggregation", Proc. Natl. Acad. Sci., vol. 95, pp. 8070-8074, 1998.

Leon et al., "Key Role of the $P2Y_1$ Receptor in Tissue Factor-Induced Thrombin-Dependent Acute Thromboembolism Studies in $P2Y_1$-Knockout Mice and Mice Treated with a $P2Y_1$ Antagonist", Circulation, pp. 718-723, 2000.

Norenberg, et al., "Characterization and possible function of adenosine 5'-triphosphate receptors in activated rat microglia", Br. J. Pharmacol., vol. 111, pp. 942-950, 1994.

Phillips et al, "Design, Synthesis, and Activity of 2,6-Diphenoxypyridine-Derived Factor Xa Inhibitors", J. Med. Cham., vol. 42, pp. 1749-1756, 1999.

Salter et al., "ATP Causes Release of Intracellular $Ca^{2+}$ via the Phospholipase $C\beta/IP_3$ Pathway in Astrocytes from the Dorsal Spinal Cord", The Journal of Neuroscience, vol. 15(4), pp. 2961-2971, 1995.

Savi et al., "Role of P2Y1 purinoceptor in ADP-induced platelet activation", FEBS Letters, vol. 422, pp. 291-295, 1998.

Wisterowicz, K. et al., "Badania Nad Pochodnymi Pyrazuyny", Acta Poloniae Pharmaceutica, vol. 46, No. 2, 1989, pp. 101-113.

* cited by examiner

UREA ANTAGONISTS OF P2Y₁ RECEPTOR USEFUL IN THE TREATMENT OF THROMBOTIC CONDITIONS

CROSS-REFERENCE TO RELATED APPLICATIONS

This is a divisional application of U.S. application Ser. No. 11/126,915, filed May 11, 2005, which claims the priority benefit of U.S. Provisional Application No. 60/570,288, filed May 12, 2004 and the priority benefit of U.S. Provisional Application No. 60/665,817, filed Mar. 28, 2005, all of which are expressly incorporated fully herein by reference.

FIELD OF THE INVENTION

The present invention provides novel pyridyl or phenyl ureas and analogues thereof, which are selective inhibitors of the human $P2Y_1$ receptor. The invention also provides for various pharmaceutical compositions of the same and methods for treating diseases responsive to modulation of $P2Y_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b and A3), which bind to and are activated by the nucleoside adenosine, and the P2 receptors, which comprise a second, more diverse class of receptors which are activated by a wide variety of nucleotides including ATP, ADP, UTP and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; $P2Y_1$, $P2Y_2$, $P2Y_4$, $P2Y_6$, $P2Y_{11}$, $P2Y_{12}$, and $P2Y_{13}$ (Boeynaems, J. M. et al. *Drug Development Research* 2000, 52, 187-9). In addition, an eighth receptor, $P2Y_{14}$, has been considered by some to be a member of this class although it does not respond to ribosylated nucleotides and is activated by UDP-glucose (Abbracchio, M. P. et al. *Trends Pharmacol. Sci.* 2003, 24, 52-5).

Several studies have suggested that modulators of specific members of the P2Y family of receptors could have therapeutic potential for the treatment of a variety of disorders (for review, see Burnstock, G. and Williams, M. *J. Pharm. Exp Ther.* 2000, 295, 862-9), including diabetes, cancer, CF, and treatment of ischemia-reperfusion injury (Abbracchio M. P., Burnstock G. *Pharmacol. Ther.* 1994, 64, 445-475). P2Y1 receptors, almost ubiquitous among human organs (Jassens R; Communi D.; Pirotton S. et al. *Biochem. Biophys. Res. Comm.* 1996, 221, 588-593) have been identified on microglia (Norenberg W. et al.; *Br. J. Pharmacol.* 1994, 111, 942-950) and on astrocytes (Salter M. W. and Hicks J. L. *J. Neurosc.* 1995, 15, 2961-2971). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, $P2Y_1$ and $P2Y_{12}$, are of particular interest as they have now both been shown to act as important receptors for ADP in platelets (Jin, J. et al. *Proc. Natl. Acad. Sci.* 1998, 95, 8070). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both $P2Y_1$ and $P2Y_{12}$ to produce two separate intracellular signals which synergize together to produce complete platelet activation. The first signal arises from ADP driven activation of the $P2Y_1$ receptor and can most easily be tracked by measuring the transitory increase in intracellular free $Ca^{+2}$. This signal appears to mediate the initial shape change reaction and to initiate the process of platelet activation. The second signal appears to be derived from ADP activation of the $P2Y_{12}$ receptor and serves to consolidate the process and produce an irreversible platelet aggregate. Using three structurally related but distinct inhibitors of $P2Y_1$ (A3P5P, A3P5PS and A2P5P), Daniel, J. L. et al. (*J. Biol. Chem.* 1998, 273, 2024-9), Savi, P. et al. (*FEBS Letters* 1998, 422, 291-5), and Hechler, B. et al. (*Br. J. Haematol.* 1998, 103, 858-66) were the first to publish the observation that the inhibition of $P2Y_1$ activity alone could block ADP-driven aggregation independently of the $P2Y_{12}$ receptor. Although inhibition of platelet reactivity is often thought of as firm evidence of an anti-thrombotic activity, these antagonists lacked the necessary pharmacological properties for in vivo study. The first direct demonstration that inhibition of $P2Y_1$ activity could lead to an anti-thrombotic effect in vivo was reported by Leon, C. et al. *Circulation* 2001, 103, 718-23, in a model of thromboplastin induced thromboembolism using both a $P2Y_1$ knock-out mouse and the $P2Y_1$ antagonist MRS-2179 (Baurand, A. and Gachet, C. *Cardiovascular Drug Reviews* 2003, 21, 67-76). These results were subsequently extended to include the inhibition of both venous and arterial thrombosis in the rat (Lenain, N. et al. *J. Thromb. Haemost.* 2003, 1, 1144-9) and confirmed by a second laboratory using an independently derived $P2Y_1$ knock-out mouse (Fabre, J-E. et al. *Nature Medicine* 1999, 5, 1199-1202). Taken together, these data suggest that the discovery of novel $P2Y_1$ antagonists with improved pharmaceutical characteristics could have significant utility in the treatment of a variety of thromboembolic disorders.

SUMMARY OF THE INVENTION

Accordingly, the present invention provides novel pyridyl ureas, which are useful as selective inhibitors of the $P2Y_1$ receptor including stereoisomers, pharmaceutically acceptable salts, solvates, or prodrugs thereof.

The present invention also provides processes and intermediates for making the compounds of the present invention or a stereoisomer or a pharmaceutically acceptable salt, solvate, or prodrug form thereof.

The present invention also provides pharmaceutical compositions comprising a pharmaceutically acceptable carrier and a therapeutically effective amount of at least one of the compounds of the present invention or a pharmaceutically acceptable salt, solvate, or prodrug form thereof.

The present invention also provides a method for modulation of platelet reactivity comprising administering to a host in need of such treatment a therapeutically effective amount of at least one of the compounds of the present invention or a pharmaceutically acceptable salt, solvate, or prodrug form thereof.

The present invention also provides a method for treating thromboembolic disorders comprising administering to a host in need of such treatment a therapeutically effective amount of at least one of the compounds of the present invention or a pharmaceutically acceptable salt, solvate, or prodrug form thereof.

The present invention also provides novel pyridyl ureas for use in therapy for other disease states which are responsive to modulation of P2Y$_1$ activity.

The present invention also provides the use of novel pyridyl ureas for the manufacture of a medicament for the treatment of a thromboembolic or other disorders.

These and other embodiments, which will become apparent during the following detailed description, have been achieved by the inventors' discovery that the presently claimed novel compounds of the present invention, or pharmaceutically acceptable salt or prodrug forms thereof, are effective P2Y$_1$ inhibitors.

DETAILED DESCRIPTION OF PREFERRED EMBODIMENTS

In a first embodiment, the present invention provides, inter alia, a compound of Formula (I):

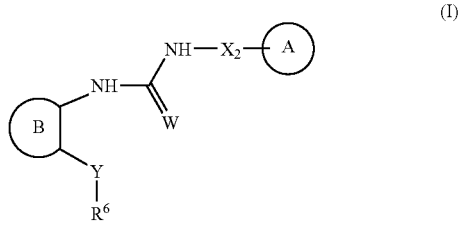

or a stereoisomer or pharmaceutically acceptable salt, solvate, or prodrug thereof, wherein:

ring A is $C_{6-10}$ aryl substituted with 0-5 $R^1$, or a 5- to 10-membered heterocycle comprising: carbon atoms and 1-4 heteroatoms selected from N, $NR^{11}$, O, and $S(O)_p$, wherein said heterocycle is substituted with 0-5 $R^1$;

ring B is a 5- to 6-membered heteroaryl comprising: carbon atoms and 1-4 ring heteroatoms selected from N, $NR^{11}$, N→O, $S(O)_p$, and O, wherein said heteroaryl is substituted with 0-4 $R^7$; provided that ring B is other than thiazolyl;

W is O or S;

$X_2$ is $-(CR^{16}R^{17})_s-$, or $-(CR^{16}R^{17})_tC(O)(CR^{16}R^{17})_r-$;

Y is O, S, NH, $-OCR^{18}R^{19}-$, $-CH=CH-$, or $-CONH-$;

$R^1$ is, independently at each occurrence, =O, F, Cl, Br, I, $CF_3$, $-CF_2CF_3$, $OCF_3$, $-OCF_2CF_2H$, $-OCF_2CF_3$, $SiMe_3$, $-(CR^fR^f)_r-OR^c$, $SR^c$, CN, $NO_2$, $-(CR^fR^f)_r-NR^{12}R^{13}$, $-(CR^fR^f)_r-C(O)R^c$, $-(CR^fR^f)_r-CO_2R^c$, $-(CR^fR^f)_r-C(O)NR^{12}R^{13}$, $-C(O)NR^{14}(CR^fR^f)_nN^{12}R^{13}$, $-(CR^fR^f)_r-OC(O)NR^{12}R^{13}$, $-(CR^fR^f)_r-NR^{14}C(O)NR^{12}R^{13}$, $-(CR^fR^f)_r-NR^{14}C(O)R^d$, $-(CR^fR^f)_r-NR^{14}C(O)OR^h$, $-NR^{14}(CR^fR^f)_nC(O)R^d$, $-NR^{14}CO(CR^fR^f)_nOR^c$, $-(CH_2)_r-CR^{13}(=NOR^c)$, $-S(O)_pNR^{12}R^{13}$, $-(CR^fR^f)_r-NR^{14}S(O)_pNR^{12}R^{13}$, $-NR^{14}SO_2CF_3$, $-NR^{14}S(O)_pR^d$, $-S(O)_2CF_3$, $-S(O)R^d$, $-S(O)_2R^d$, $-OP(O)(OEt)_2$, $-O(CH_2)_2OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-13}$ carbocycle substituted with 0-5 $R^b$, or $-(CR^fR^f)_r-5-$ to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 7-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

$R^6$ is $-(CR^fR^f)_n$-phenyl substituted with 0-3 $R^{6a}$ or $-(CR^fR^f)_n$-pyridyl substituted with 0-3 $R^{6a}$;

$R^{6a}$ is, independently at each occurrence, F, Cl, Br, I, $-(CR^fR^f)_r-OR^c$, $SR^c$, CN, $NO_2$, $CF_3$, $OCF_3$, $-CF_2CF_3$, $-OCF_2CF_2H$, $-OCF_2CF_3$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $Si(Me)_3$, $Si(C_{1-4}$ alkyl$)_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-10}$ carbocycle substituted with 0-2 $R^e$, or $-(CR^fR^f)_r-5-$ to 10-membered heterocycle comprising: carbon atoms and 1-4 heteroatoms selected from N, $NR^{11}$, O, and $S(O)_p$, wherein said heterocycle is substituted with 0-2 $R^e$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is, independently at each occurrence, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-10}$ carbocycle substituted with 0-3 $R^b$, or $-(CR^fR^f)_r-5-$ to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s on two adjacent carbon atoms form a 5- to 7-membered carbocyclic or heterocyclic ring comprising: carbon atoms and 0-3 ring heteroatoms selected from O, N, $NR^{7b}$, and $S(O)_p$, wherein said carbocyclic or heterocyclic ring is substituted with 0-2 $R^{7c}$;

$R^{7b}$ is H, $C_{1-4}$ alkyl, $-C(O)(C_{1-4}$ alkyl), $-C(O)$phenyl, $-C(O)$benzyl, or benzyl;

$R^{7c}$ is, independently at each occurrence, H, F, Cl, Br, I, $OCF_3$, $CF_3$, $OR^c$, $SR^c$, CN, $NO_2$, $-NR^{12}R^{13}$, $-C(O)R^c$, $-C(O)OR^c$, $-C(O)NR^{12}R^{13}$, $-NR^{14}C(O)R^d$, $-S(O)_pNR^{12}R^{13}$, $-S(O)R^d$, $-S(O)_2R^d$, $C_{1-4}$ alkyl, phenyl substituted with 0-3 $R^b$, or benzyl substituted with 0-3 $R^b$;

$R^{11}$ is, independently at each occurrence, H, $C_{1-4}$ alkoxy, $C_{1-8}$ alkyl substituted with 0-2 $R^a$, $C_{2-4}$ alkenyl substituted with 0-1 $R^a$, $C_{2-4}$ alkynyl substituted with 0-1 $R^a$, $-C(O)(C_{1-6}$ alkyl), $-C(O)(CH_2)_n(C_{3-6}$ cycloalkyl), $-C(O)(CH_2)_n(C_{6-10}$ aryl), $-C(O)(CH_2)_n$(5- to 10-membered heteroaryl), $-C(O)O(C_{1-8}$ alkyl), $-C(O)O(CH_2)_n(C_{3-6}$ cycloalkyl), $-C(O)O(CH_2)_n(C_{6-10}$ aryl), $-C(O)O(CH_2)_n$(5- to 10-membered heteroaryl), $-C(O)O(CH_2)_{2-4}(C_{1-4}$ alkyl), $-C(O)NH(C_{1-8}$ alkyl), $-C(O)NH(CH_2)_n(C_{3-6}$ cycloalkyl), $-C(O)NH(CH_2)_n(C_{6-10}$ aryl), $-C(O)NH(CH_2)_n$(5- to 10-membered heteroaryl), $-S(O)_2(C_{1-8}$ alkyl), $-S(O)_2(CH_2)_n(C_{3-6}$ cycloalkyl), $-S(O)_2(CH_2)_n(C_{6-10}$ aryl), $-S(O)_2(CH_2)_n$(5- to 10-membered heteroaryl), $-(CR^fR^f)_r-C_{3-10}$ carbocycle, or —(CR$^f$R$^f$)$_r$-5- to 10-membered heterocycle; wherein said alkyl, cycloalkyl, phenyl, aryl, and carbocycle are substituted with 0-2 R$^b$, and said heteroaryl and heterocycle are substituted with 0-2 R$^b$ and comprise: carbon atoms and 1-4 heteroatoms selected from N, NR$^f$, O, and S(O)$_p$;

R$^{12}$ is, independently at each occurrence, H, C$_{1-6}$ alkyl, —C(O)(C$_{1-6}$ alkyl), —C(O)(CH$_2$)$_n$(C$_{6-10}$ aryl), —C(O)(CH$_2$)$_n$(5- to 10-membered heteroaryl), —C(O)O(C$_{1-4}$ alkyl), —C(O)OCH$_2$(C$_{6-10}$ aryl), —(CH$_2$)$_n$C(O)OCH$_2$(5- to 10-membered heteroaryl), —(CH$_2$)$_n$OC(O)(C$_{1-4}$ alkyl), —(CH$_2$)$_n$OC(O)(C$_{6-10}$ aryl), —(CH$_2$)$_n$OC(O)(5- to 10-membered heteroaryl), —(CH$_2$)$_n$C(O)O(C$_{1-4}$ alkyl), —(CH$_2$)$_n$C(O)O(C$_{6-10}$ aryl), —(CH$_2$)$_n$C(O)O(5- to 10-membered heteroaryl), —(CH$_2$)$_n$C(O)NH(C$_{1-6}$ alkyl), —(CH$_2$)$_n$C(O)NH(C$_{6-10}$ aryl), —(CH$_2$)$_n$C(O)NH(5- to 10-membered heteroaryl), —(CH$_2$)$_n$OC(O)NH(C$_{1-6}$ alkyl), —(CH$_2$)$_n$OC(O)NH(C$_{6-10}$ aryl), —(CH$_2$)$_n$OC(O)NH(5- to 10-membered heteroaryl), —S(O)$_2$(C$_{1-6}$ alkyl), —S(O)$_2$(CH$_2$)$_n$(C$_{6-10}$ aryl), —S(O)$_2$(CH$_2$)$_n$(5- to 10-membered heteroaryl), —(CR$^f$R$^f$)$_n$—(C$_{6-10}$ aryl), or —(CR$^f$R$^f$)$_n$-5- to 10-membered heteroaryl; wherein said alkyl, and aryl are substituted with 0-2 R$^g$; and said heteroaryl is substituted with 0-2 R$^g$ and comprises: carbon atoms and 1-4 heteroatoms selected from N, NR$^{11}$, O, and S(O)$_p$;

R$^{13}$ is, independently at each occurrence, H, C$_{1-6}$ alkyl, or —(CH$_2$)$_n$-phenyl;

alternatively, R$^{12}$ and R$^{13}$, when attached to the same nitrogen, combine to form a 5- to 10-membered heterocyclic ring comprising: carbon atoms and 1-2 additional heteroatoms selected from N, NR$^{11}$, O, and S(O)$_p$;

R$^{14}$ is, independently at each occurrence, H, C$_{1-6}$ alkyl substituted with 0-2 R$^{14a}$, C$_{2-6}$ alkenyl substituted with 0-2 R$^{14a}$, C$_{2-6}$ alkynyl substituted with 0-2 R$^{14a}$, —(CH$_2$)$_r$—C$_{3-10}$ carbocycle substituted with 0-3 R$^g$, or —(CH$_2$)$_r$-5- to 10-membered heterocycle comprising: carbon atoms and 1-4 heteroatoms selected from N, NR$^{11}$, O, and S(O)$_p$, wherein said heterocycle is substituted with 0-3 R$^g$;

R$^{14a}$ is, independently at each occurrence, H, C$_{1-4}$ alkyl, OR$^f$, Cl, F, Br, I, =O, CF$_3$, CN, NO$_2$, —C(O)R$^f$, —C(O)OR$^f$, —C(O)NR$^{12}$R$^{13}$, or —S(O)$_p$R$^f$;

R$^{16}$ is, independently at each occurrence, H, F, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, or —(CH$_2$)$_r$-phenyl substituted with 0-2 R$^b$;

R$^{17}$ is, independently at each occurrence, H, C$_{1-6}$ alkyl, or —(CH$_2$)$_n$-phenyl;

alternatively, R$^{16}$ and R$^{17}$ on the same carbon atom combine to form a 3- to 7-membered carbocyclic or heterocyclic ring comprising: carbon atoms and 0-2 heteroatoms selected from N, NR$^{11}$, O, and S(O)$_p$, 0-1 carbonyl, and 0-3 double bonds, wherein said carbocyclic or heterocyclic ring is substituted with 0-2 R$^b$;

alternatively, two R$^{16}$ groups on adjacent atoms combine to form a 3- to 7-membered carbocyclic or heterocyclic ring comprising: carbon atoms and 0-2 heteroatoms selected from N, NR$^{11}$, O, and S(O)$_p$, 0-1 carbonyl, and 0-3 double bonds, wherein said carbocyclic or heterocyclic ring is substituted with 0-2 R$^b$;

R$^{18}$ is, independently at each occurrence, H, F, or C$_{1-6}$ alkyl;

R$^{19}$ is, independently at each occurrence, H, OH, —C(O)OR$^f$, or C$_{1-6}$ alkyl;

R$^a$ is, independently at each occurrence, F, OCF$_3$, CF$_3$, OR$^c$, SR$^c$, CN, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^b$ is, independently at each occurrence, H, =O, F, Cl, Br, I, —(CH$_2$)$_r$—OR$^c$, SR$^c$, CN, NO$_2$, CF$_3$, OCF$_3$, —(CH$_2$)$_r$—NR$^{12}$R$^{13}$, —C(O)R$^c$, —(CH$_2$)$_r$—C(O)OR$^c$, —(CH$_2$)$_r$—C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^c$ is, independently at each occurrence, H, —OP(O)(OEt)$_2$, C$_{1-8}$ alkyl substituted with 0-2 R$^e$, C$_{2-8}$ alkenyl substituted with 0-2 R$^e$, C$_{2-8}$ alkynyl substituted with 0-2 R$^e$, —(CR$^f$R$^f$)$_r$—C$_{3-8}$ cycloalkyl substituted with 0-2 R$^e$, —(CR$^f$R$^f$)$_r$—C$_{6-10}$ aryl substituted with 0-2 R$^e$, or —(CR$^f$R$^f$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^d$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^e$ is, independently at each occurrence, H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—OR$^h$, —(CF$_2$)$_r$CF$_3$, Si(Me)$_3$, Si(Me)$_2$(t-Bu), Si(C$_{1-4}$ alkyl)$_3$, C$_{1-8}$ alkyl substituted with 0-2 R$^g$, C$_{2-8}$ alkenyl substituted with 0-2 R$^g$, C$_{2-8}$ alkynyl substituted with 0-2 R$^g$, —(CH$_2$)$_r$—C$_{3-8}$ cycloalkyl substituted with 0-2 R$^g$, —(CH$_2$)$_r$—C$_{6-10}$ aryl substituted with 0-2 R$^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^g$;

R$^f$ is, independently at each occurrence, H, C$_{1-6}$ alkyl, or —(CH$_2$)$_n$-phenyl;

R$^g$ is, independently at each occurrence, H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, or C$_{2-6}$ alkynyl;

R$^h$ is, independently at each occurrence, C$_{1-6}$ alkyl substituted with 0-2 R$^g$, —(CH$_2$)$_n$-phenyl substituted with 0-2 R$^g$, or —(CH$_2$)$_n$-5- to 10-membered heterocycle comprising: carbon atoms and 1-4 heteroatoms selected from N, NR$^f$, O, and S(O)$_p$, wherein said heterocycle is substituted with 0-2 R$^g$;

R$^i$ is, independently at each occurrence, H, C$_{1-6}$ alkyl substituted with 0-2 R$^g$, —(CH$_2$)$_n$-phenyl substituted with 0-2 R$^g$, or —(CH$_2$)$_n$-5- to 10-membered heterocycle comprising: carbon atoms and 1-4 heteroatoms selected from N, NR$^f$, O, and S(O)$_p$, wherein said heterocycle is substituted with 0-2 R$^g$;

n, at each occurrence, is selected from 0, 1, 2, 3, and 4;
p, at each occurrence, is selected from 0, 1, and 2;
r, at each occurrence, is selected from 0, 1, 2, 3, and 4;
s, at each occurrence, is selected from 0, 1, 2, and 3; and t, at each occurrence, is selected from 1, 2, 3, and 4;
provided that:
(i) when ring B is

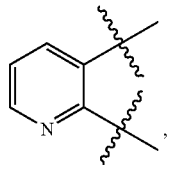

a) Y is O, ring A is 3-CF$_3$-phenyl, then R$^6$ is other than 4-OMe-phenyl;
b) Y is O, ring A is thienyl, phenyl, dimethyl substituted phenyl or fluorophenyl, then R$^6$ is other than methyl substituted dihydroindenyl;
c) Y is O, ring A is unsubstituted thiazolyl, then R$^6$ is other than phenyl or substituted phenyl;
d) Y is S, ring A is phenyl, then R$^6$ is other than 4-Me-phenyl;
(ii) when ring B is

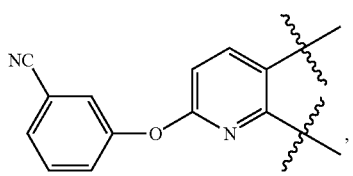

Y is O, then ring A is other than 3-CN-phenyl; or
(iii) when ring B is

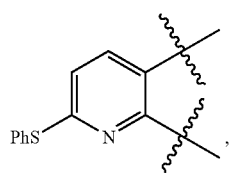

Y is S, then ring A is other than phenyl or substituted phenyl.

In a second embodiment, the present invention provides a compound of Formula (I), within the scope of the first embodiment wherein:
X$_2$ is a bond, —CH$_2$—, —CH$_2$CH$_2$—, —CHMe—, —CH$_2$CHMe—, —CH$_2$CO—,

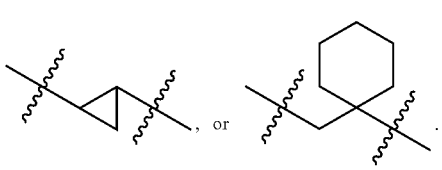

In a third embodiment, the present invention provides a compound of Formula (I), within the scope of the first embodiment wherein:
Y is O, S, NH, —OCH$_2$—, —OCHMe—, —OCH(CO$_2$Me)—, —CH=CH—, or —CONH—.

In a fourth embodiment, the present invention provides a compound of Formula (I), within the scope of the first embodiment wherein:
W is O; and
Y is O, S, or NH.

In a fifth embodiment, the present invention provides a compound of Formula (I), within the scope of the first embodiment wherein:
ring A is substituted with 0-5 R$^1$ and selected from: phenyl, pyridinyl, pyrimidinyl, furanyl, isoxazolyl, thiazolyl, thiadiazolyl, benzothiazolyl, indolyl, and benzimidazolyl.

In a sixth embodiment, the present invention provides a compound of Formula (I), within the scope of the first embodiment wherein:
ring A is substituted with 0-5 R$^1$ and selected from:

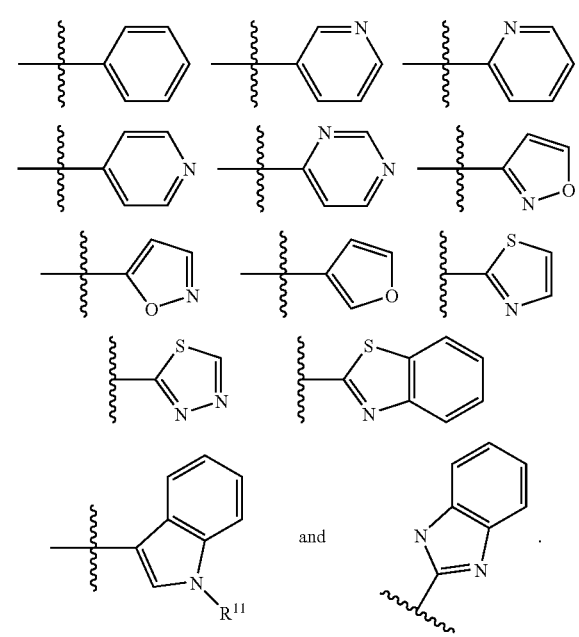

In a seventh embodiment, the present invention provides a compound of Formula (I), within the scope of the first embodiment wherein:
ring B is substituted with 0-3 R$^7$ and selected from:

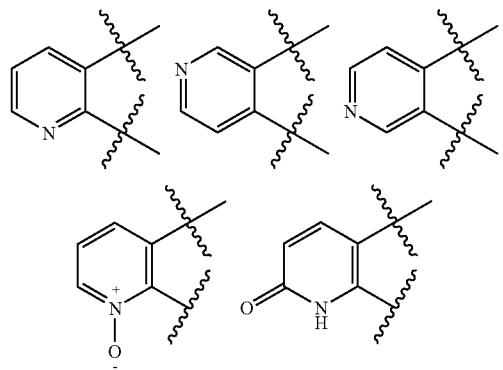

-continued

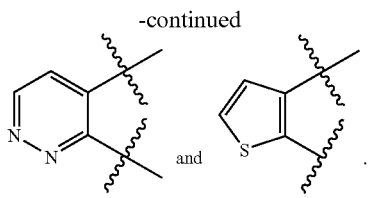
and

In an eighth embodiment, the present invention provides a compound of Formula (I), within the scope of the first embodiment wherein:

$R^1$ is, independently at each occurrence, F, Cl, Br, I, $CF_3$, —$CF_2CF_3$, $OCF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—$C(O)NR^{12}R^{13}$, —$OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 7-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$.

In a ninth embodiment, the present invention provides a compound of Formula (I), within the scope of the first embodiment wherein:

$R^6$ is —$(CH_2)_n$-phenyl substituted with 0-3 $R^{6a}$ or —$(CH_2)_n$-pyridyl substituted with 0-3 $R^{6a}$; and $R^{6a}$ is, independently at each occurrence, F, Cl, Br, I, —$(CR^iR^i)_r$—$OR^c$, $SR^c$, CN, $CF_3$, $OCF_3$, —$CF_2CF_3$, —$OCF_2CF_2H$, —$OCF_2CF_3$, —$NR^{12}R^{13}$, —$C(O)R^c$, $Si(Me)_3$, $Si(C_{1-4}$ alkyl$)_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-2 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$;

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$.

In a tenth embodiment, the present invention provides a compound of Formula (I), within the scope of the first embodiment wherein:

$R^{11}$ is, independently at each occurrence, H, $C_{1-4}$ alkoxy, $C_{1-8}$ alkyl substituted with 0-2 $R^a$, —$C(O)(C_{1-6}$ alkyl), —$C(O)(CH_2)_n(C_{3-6}$ cycloalkyl), —$C(O)(CH_2)_n$phenyl, —$C(O)O(C_{1-8}$ alkyl), —$C(O)O(CH_2)_n(C_{3-6}$ cycloalkyl), —$C(O)O(CH_2)_n$phenyl, —$C(O)O(CH_2)_{2-4}(C_{1-4}$ alkyl), —$C(O)NH(C_{1-6}$ alkyl), —$S(O)_2(C_{1-6}$ alkyl), —$S(O)_2(CH_2)_n$phenyl, —$(CR^fR^f)_r$—$C_{3-10}$ carbocycle, or —$(CR^fR^f)_r$-5- to 10-membered heterocycle; wherein said alkyl, cycloalkyl, phenyl, and carbocycle are substituted with 0-2 $R^b$, and said heterocycle is substituted with 0-2 $R^b$ and comprises: carbon atoms and 1-4 heteroatoms selected from N, $NR^f$, O, and $S(O)_p$.

In an eleventh embodiment, the present invention provides a compound of Formula (I), within the scope of the first embodiment wherein:

ring A is substituted with 0-5 $R^1$ and selected from:

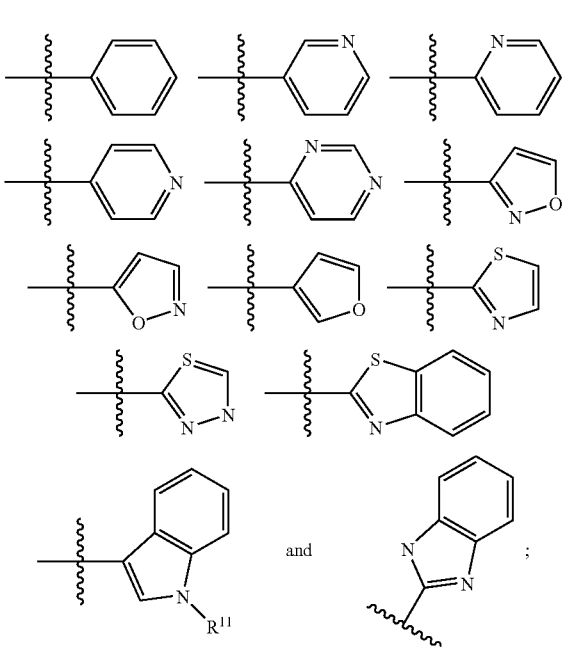

ring B is substituted with 0-3 $R^7$ and selected from:

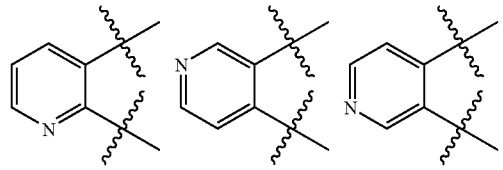

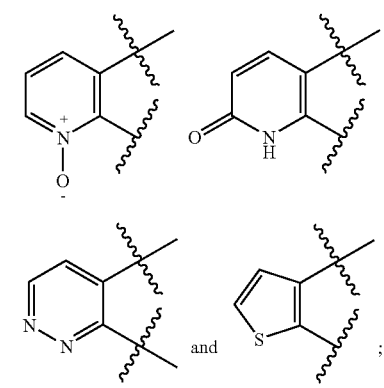
and

W is O;

$X_2$ is a bond, —$CH_2$—, —$CH_2CH_2$—, —CHMe—, —$CH_2$CHMe—, —$CH_2$CO—,

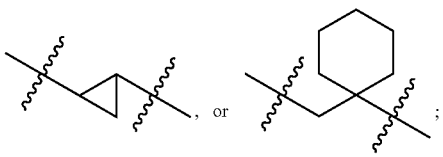, or 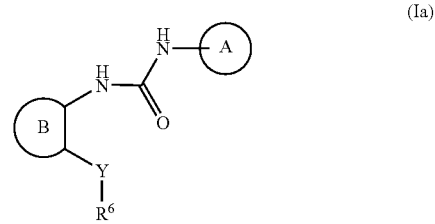;

Y is O, S, NH, —OCH$_2$—, —OCHMe—, —OCH (CO$_2$Me)—, —CH=CH—, or —CONH—;

R$^1$ is, independently at each occurrence, F, Cl, Br, I, CF$_3$, —CF$_2$CF$_3$, OCF$_3$, —OCF$_2$CF$_2$H, —OCF$_2$CF$_3$, SiMe$_3$, —(CR$^f$R$^f$)$_r$—OR$^c$, SR$^c$, CN, NO$_2$, —(CR$^f$R$^f$)$_r$—NR$^{12}$R$^{13}$, —(CR$^f$R$^f$)$_r$—C(O)R$^c$, —(CR$^f$R$^f$)$_r$—CO$_2$R$^c$, —(CR$^f$R$^f$)$_r$—C(O)NR$^{12}$R$^{13}$, —OP(O)(OEt)$_2$, 4,4,5,5-tetramethyl-1,3,2-dioxaborolanyl, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-13}$ carbocycle substituted with 0-5 R$^b$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-5 R$^b$;

alternatively, two R$^1$s on two adjacent carbon atoms are combined with the carbon atoms to which they attached, form a 5- to 7-membered carbocycle or heterocycle comprising: carbon atoms and 0-3 additional heteroatoms selected from N, NR$^{11}$, O, and S(O)$_p$, and 0-2 carbonyl groups, wherein said carbocycle or heterocycle is substituted with 0-4 R$^b$;

R$^6$ is —(CH$_2$)$_n$-phenyl substituted with 0-3 R$^{6a}$ or —(CH$_2$)$_n$ -pyridyl substituted with 0-3 R$^{6a}$;

R$^{6a}$ is, independently at each occurrence, F, Cl, Br, I, —(CR$^i$R$^i$)$_r$—OR$^c$, SR$^c$, CN, CF$_3$, OCF$_3$, —NR$^{12}$R$^{13}$, —C(O)R$^c$, Si(Me)$_3$, Si(C$_{1-4}$ alkyl)$_3$, C$_{1-4}$ haloalkyl, C$_{1-4}$ haloalkyloxy-, C$_{1-4}$ alkyloxy-, C$_{1-4}$ alkylthio-, C$_1$-C$_4$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-2 R$^e$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-2 R$^e$;

alternatively, when two R$^{6a}$ groups are attached to adjacent atoms, together with the atoms to which they are attached they form a 5- to 7-membered carbocyclic or heterocyclic ring comprising: carbon atoms and 0-2 heteroatoms selected from N, NR$^{11}$, O, and S(O)$_p$, 0-1 carbonyl and 0-3 ring double bonds, wherein said carbocyclic or heterocyclic ring is substituted with 0-2 R$^b$; and R$^{11}$ is, independently at each occurrence, H, C$_{1-4}$ alkoxy, C$_{1-8}$ alkyl substituted with 0-2 R$^a$, —C(O)(C$_{1-6}$ alkyl), —C(O)(CH$_2$)$_n$(C$_{3-6}$ cycloalkyl), —C(O)(CH$_2$)$_n$phenyl, —C(O)O(C$_{1-8}$ alkyl), —C(O)O(CH$_2$)$_n$(C$_{3-6}$ cycloalkyl), —C(O)O(CH$_2$)$_n$phenyl, —C(O)O(CH$_2$)$_{2-4}$(C$_{1-4}$ alkyl), —C(O)NH(C$_{1-6}$ alkyl), —S(O)$_2$(C$_{1-6}$ alkyl), —S(O)$_2$(CH$_2$)$_n$ phenyl, —(CR$^f$R$^f$)$_r$—C$_{3-10}$ carbocycle, or —(CR$^f$R$^f$)$_r$-5- to 10-membered heterocycle; wherein said alkyl, cycloalkyl, phenyl, and carbocycle are substituted with 0-2 R$^b$, and said heterocycle is substituted with 0-2 R$^b$ and comprises: carbon atoms and 1-4 heteroatoms selected from N, NR$^f$, O, and S(O)$_p$.

In a twelfth embodiment, the present invention provides, a compound of Formula (Ia):

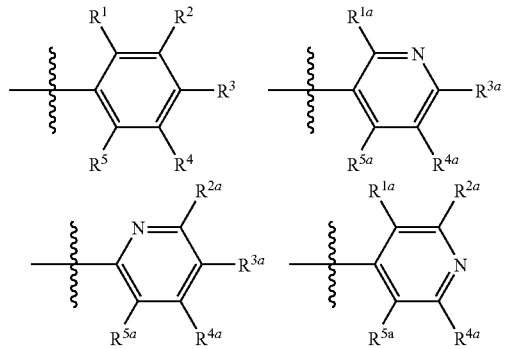

(Ia)

or a stereoisomer or pharmaceutically acceptable salt, solvate, or prodrug thereof, wherein:

ring A is

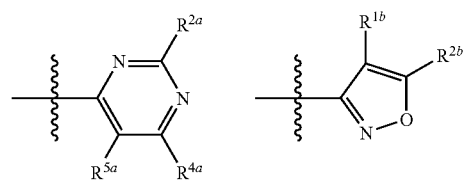

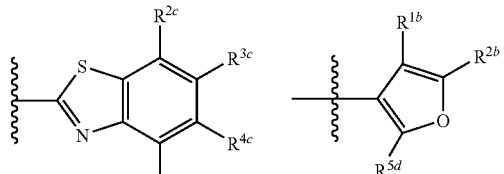

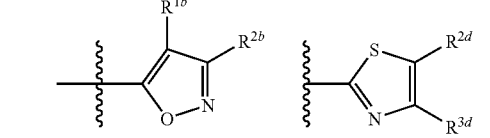

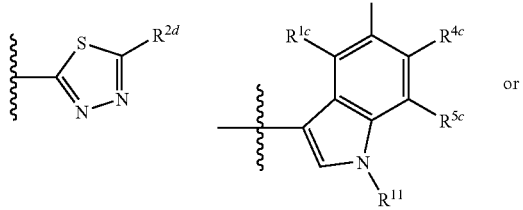

or

-continued

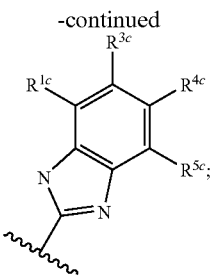

ring B is

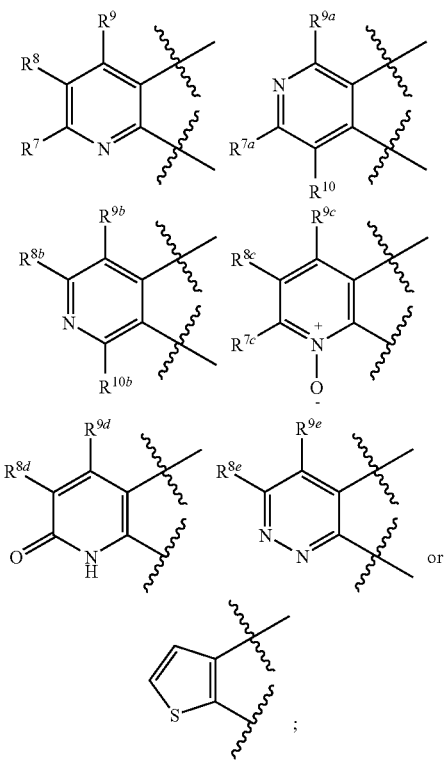

;

R¹, R¹ᵃ, R¹ᵇ, and R¹ᶜ are, independently at each occurrence, H, F, Cl, Me, NH₂, or OH;

R², R²ᵃ, R²ᵇ, R²ᶜ, R²ᵈ and R³ᵈ are, independently at each occurrence, H, F, Cl, Br, Me, t-Bu, OMe, OBu, pentoxy, isopentoxy, neohexoxy, —O(CH₂)₂OMe, —O(CH₂)₂O(i-Pr), —O(CH₂)₈CO₂Me, —O(CH₂)₂C(Me)₂OMe, —O(CH₂)₂NMe₂, —OCH₂C(Me)₂CH₂NMe₂, —O(CH₂)₂OCOMe, —OCH(Et)CH₂OMe, —OCH(Me)CH₂O(t-Bu), NO₂, CF₃, OCF₃, 2-CH₂N(Me)₂-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe₂-benzoxy, 2-CF₃-benzoxy, 3-OCF₃-benzoxy, 4-OCF₃-benzoxy, 4-CO₂Me-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl)ethoxy, or —OCH(Et)(pyridine-4-yl);

R³, R³ᵃ, R³ᶜ, R⁴, R⁴ᵃ, R⁴ᶜ, R⁵, R⁵ᵃ, R⁵ᶜ, and R⁵ᵈ, are, independently at each occurrence, H, F, Cl, Br, —OCH(Me)CH₂O-t-Bu, CF₃, OCHF₂, OCF₃, —O(CH₂)₂OMe, —O(CH₂)₃NMe₂, —O(CH₂)₄NMe₂, —OCH(Et)CH₂OMe, CN, NH₂, NMe₂, —CH₂NMe₂, NEt₂, —NHPh, —N(Me)Ph, —NH(4-OMe-Ph), —NH(2-CF₃-Ph), —CH(Me)NHCH(Me)Ph, —CH(Me)N(Me)(3-CF₃-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF₃-Bn), —CH(Me)O(4-CF₃-Bn), —CH(Me)O(1-Bn-pyrrolidin-3-ylmethyl), —CH(Me)OCH₂C(Me)₂CH₂NMe₂, —CH(Me)OBn, —CH(Me)O(4-i-Pr-Bn), —CH(Me)O(4-OPh-Bn), —CH(Me)O(3,5-diCl-Bn), —CH(Me)OCH₂(1-Bn-piperidin-4-yl), —CH₂NHBn, —CH₂NH(4-CF₃-Bn), —CH₂N(Me)Bn, —CH(Me)NHCH₂-pyridin-2-yl, —CH(Me)NHCH₂-pyridin-4-yl, —CH(Me)NHCH₂(6-Cl-pyridin-3-yl), —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3,4-diCl-Bn), —CH(Me)N(Me)CH₂CH₂Ph, —CH(Me)N(Me)CH₂-pyridin-2-yl, —CH(Me)N(Me)CH₂-pyridin-3-yl, —CH(Me)N(Me)CH₂-pyridin-4-yl, —CH(Me)N(Me)CH₂-furan-2-yl, —CH(Me)N(Me)CH₂-thien-2-yl, —CH(Me)N(Me)CH₂-(5-Me-thien-2-yl), —CH(Me)N(Me)CH₂-(5-Cl-thien-2-yl), —CH(Me)N(Et)Bn, —CH(Me)N(Et)(4-Me-Bn), —CH(Me)N(Et)(2-Cl-Bn), —CH(Me)N(Bn)CH₂CN, —CH(Me)N(Bn)CH₂CH₂OH, —CH(Me)N(Bn)CH₂CO₂Me, —CH(Me)N(Bn)CH₂CONMe₂, —CH(Me)N(Bn)CH₂CON(Me)(Bn), —CH(Me)-isoindolin-2-yl, —CH(Me)-(1,2,3,4-tetrahydroisoquinolin-2-yl), —CH(Me)(4-Bn-piperazin-1-yl), —C(CF₃)₂OH, —COMe, CO₂Et, —CH₂CO₂Me, —C(Me)₂CO₂Me, —O(CH₂)₅CO₂Et, —O(CH₂)₈CO₂Me, —O(CH₂)₂C(Me)₂OMe, —O(CH₂)₂OCOMe, —OCH₂C(Me)₂CH₂NMe₂, Ph, 2-CH₂OH-Ph, 2-CH₂N(Me)-2-Ph, 3-CH₂N(Me)-2-Ph, 4-CH₂N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 2-OMe-benzoxy, 3-CN-benzoxy, 4-CN-benzoxy, 3-NMe₂-benzoxy, 4-CO₂Me-benzoxy, 3-CF₃-benzoxy, 3-OCF₃-benzoxy, 4-OCF₃-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO₂Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO₂Et-5-Me-1H-pyrazol-1-yl, 4-CO₂Et-5-Me-1H-pyrazol-1-yl, 5-CO₂Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO₂(t-Bu)-piperidin-4-yl)methoxy, (1-CO₂Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-2-yl)ethoxy, (pyridin-4-yl)ethoxy, (4-Bn-morpholin-2-yl)methoxy, 4,4,5,5-tetramethyl-1,3,2-dioxaborolanyl, —OP(O)(OEt)₂, C₁₋₆ alkyl, C₁₋₆ alkoxy, or $C_{3-6}$ cycloalkyl optionally substituted with the group selected from: —$CO_2Me$, —$CH_2OH$, and —$CH_2OMe$;

alternatively, $R^1+R^2$, $R^2+R^3$, $R^3+R^4$, $R^4+R^5$, $R^{1a}+R^{2a}$, $R^{2a}+R^{3a}$, $R^{3a}+R^{4a}$, $R^{4a}+R^{5a}$, $R^{1b}+R^{2b}$, $R^{1c}+R^{3c}$, $R^{2c}+R^{3c}$, $R^{2d}+R^{3d}$, $R^{3c}+R^{4c}$, or $R^{4c}+R^{5c}$, combine with the carbon atoms to which they attached, form 5- to 10-membered carbocyclic or heterocyclic ring comprising: carbon atoms and 0-3 heteroatoms selected from N, $NR^{11}$, O, and $S(O)_p$, 0-1 carbonyl group, and additional 0-3 double bonds, wherein said carbocyclic or heterocyclic ring is substituted with 0-2 $R^b$;

$R^6$ is —$(CH_2)_n$-phenyl substituted with 0-3 $R^{6a}$ or —$(CH_2)_n$-pyridyl substituted with 0-3 $R^{6a}$;

$R^{6a}$ is, independently at each occurrence, H, F, Cl, Br, I, CN, —$C(Me)_2CN$, $C_{1-8}$ alkyl, $C_{2-8}$ alkenyl, OH, SMe, S(i-Pr), —$C(Me)_2OMe$, —$C(Me)_2OEt$, —$C(Me)_2OPr$, —$CHMeO(CH_2)_2OMe$, —$C(Me)_2OBu$, —$C(Me)_2O(CH_2)_2OMe$, —$C(Me)(OMe)CH_2OMe$, —$C(Me)_2O(CH_2)_2N(i-Bu)_2$, —$C(Me)_2O(CH_2)_2S(i-Bu)$, —$C(Me)_2O(CH_2)_2S(O)(i-Bu)$, —$C(Me)_2O(CH_2)_2S(furan-2-ylmethyl)$, —$C(Me)_2O(CH_2)_2S(pyridin-2-yl)$, —$C(Me)_2O(CH_2)_2S(O)_2(pyridin-2-yl)$, —$C(Me)_2CH_2OSi(Me)_2(t-Bu)$, —$C(Me)_2O(CH_2)_2Si(Me)_2(t-Bu)$, —$C(Et)_2OH$, —$C(Pr)_2OH$, —$C(CH_2CH=CH_2)_2OH$, —$C(CH_2CH=CH_2)_2OMe$, —$C(Et)_2OEt$, —$C(Et)_2OPr$, COMe, COPh, $CO_2Me$, $CO_2Et$, —NH(i-Bu), —CH=CHCO_2(t-Bu), —$OCH_2CO_2(t-Bu)$, $CF_3$, $OCF_3$, $C_{1-4}$ alkyloxy, $C_{3-7}$ cycloalkyl, $C_{3-7}$ cycloalkenyl, Ph, Bn, naphthyl, 1-pyrrolidinyl, 5-isoxazolyl, N-morpholinyl, 4-Bn-piperazinyl, 1-piperidinyl, 1-Bn-piperidin-4-yl, 1-i-Bu-piperidin-4-yl, 1-neopentyl-piperidin-4-yl, 1-COPh-piperidin-4-yl, —$SiMe_3$,

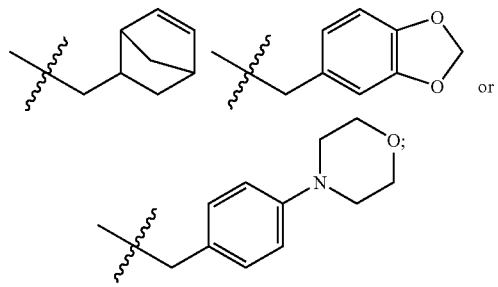

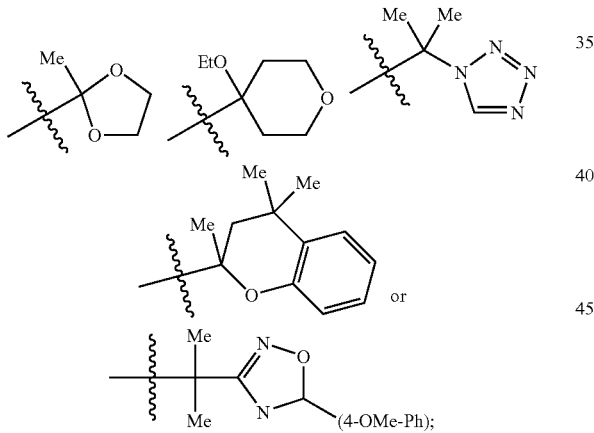

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$, $R^{7a}$, and $R^{7c}$ are, independently at each occurrence, H, Me, Cl, Br, CN, OH, OMe, SMe, NHMe, $NMe_2$, $CO_2Me$, imidazol-1-yl, or —$CH_2NH(CO)H$;

$R^8$, $R^{8b}$, $R^{8c}$, $R^{8d}$, and $R^{8e}$ are, independently at each occurrence, H, Me, Cl, Br, CN, or $CF_3$;

$R^9$, $R^{9a}$, $R^{9b}$, $R^{9c}$, $R^{9d}$, and $R^{9e}$ are, independently at each occurrence, H or Me;

$R^{10}$ and $R^{10a}$ are, independently at each occurrence, H or Me;

$R^{11}$ is, independently at each occurrence, H, $C_{1-6}$ alkyl, OMe, —$C(O)(C_{1-6}$ alkyl), —C(O)phenyl, —C(O)benzyl, —$C(O)O(C_{1-6}$ alkyl), —C(O)Obenzyl, —$S(O)_2(C_{1-6}$ alkyl), —$S(O)_2$phenyl, —$S(O)_2$benzyl, cyclohexylmethyl, phenyl, benzyl, phenethyl, phenylpropyl, —$CH_2CH(Me)Ph$, 1H-pyrrol-2-ylmethyl, 1-Me-pyrrol-2-ylmethyl, thieny-2-ylmethyl, furan-2-ylmethyl, furan-3-ylmethyl, 2-F-Bn, 2-OH-Bn, 2-CN-Bn, 3-CN-Bn, 4-CN-Bn, 4-OMe-Bn, 4-$CO_2Me$-Bn,

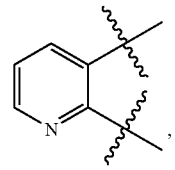

Y is O, S, or NH;
$R^b$ is, independently at each occurrence, H, F, Cl, Br, $C_{1-4}$ alkyl, OH, $CO_2H$, $NH_2$, $CF_3$, $OCF_3$, $C_{1-4}$ alkyloxy, $C_{3-7}$ cycloalkyl, phenyl, or benzyl;

n, at each occurrence, is selected from 0, 1, and 2;
p, at each occurrence, is selected from 0, 1, and 2;
provided that: when ring B is a) Y is O, ring A is 3-$CF_3$-phenyl, then $R^6$ is other than 4-OMe-phenyl;
b) Y is O, ring A is unsubstituted thiazolyl, then $R^6$ is other than phenyl or substituted phenyl;
c) Y is S, ring A is phenyl, then $R^6$ is other than 4-Me-phenyl.

In a thirteenth embodiment, the present invention provides a compound of Formula (Ia), within the scope of the twelfth embodiment wherein:

$R^1$, $R^{1a}$, $R^{1b}$, and $R^{1c}$ are, independently at each occurrence, H, F, Cl, or OH;

$R^2$, $R^{2a}$, $R^{2b}$, $R^{2c}$, $R^{2d}$ and $R^{3d}$ are, independently at each occurrence, H, F, Cl, Br, Me, t-Bu, OMe, OBu, pentoxy, isopentoxy, neohexoxy, —$O(CH_2)_2OMe$, —$O(CH_2)_2O(i-Pr)$, —$O(CH_2)_8CO_2Me$, —$O(CH_2)_2C(Me)_2OMe$, —$O(CH_2)_2NMe_2$, —$OCH_2C(Me)_2CH_2NMe_2$, —$O(CH_2)_2OCOMe$, —$OCH(Et)CH_2OMe$, —$OCH(Me)CH_2O(t-Bu)$, $NO_2$, $CF_3$, $OCF_3$, 2-$CH_2N(Me)_2$-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-$NMe_2$-benzoxy, 2-$CF_3$-benzoxy, 3-$OCF_3$-benzoxy, 4-$OCF_3$-benzoxy, 4-$CO_2Me$-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl) methoxy, (1H-pyrrol-1-yl)ethoxy, (2-Bu-1H-imidazol-4-yl)

methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl)ethoxy, or —OCH(Et)(pyridine-4-yl);

$R^3$, $R^{3a}$, $R^{3c}$, and $R^{4c}$ are, independently at each occurrence, H, F, Cl, Br, —OCH(Me)CH$_2$O-t-Bu, CF$_3$, OCHF$_2$, OCF$_3$, —O(CH$_2$)$_2$OMe, —O(CH$_2$)$_3$NMe$_2$, —O(CH$_2$)$_4$NMe$_2$, —OCH(Et)CH$_2$OMe, CN, NH$_2$, NMe$_2$, —CH$_2$NMe$_2$, NEt$_2$, —NHPh, —N(Me)Ph, —NH(4-OMe-Ph), —NH(2-CF$_3$-Ph), —CH(Me)NHCH(Me)Ph, —CH(Me)N(Me)(3-CF$_3$-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH(Me)O(1-Bn-pyrrolidin-3-ylmethyl), —C(Me)$_2$OH, —C(Me)$_2$CH$_2$OH, —C(CF$_3$)$_2$OH, —COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)-2-Ph, 3-CH$_2$N(Me)-2-Ph, 4-CH$_2$N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 4-OMe-benzoxy, 3-CN-benzoxy, 4-CN-benzoxy, 3-NMe$_2$-benzoxy, 4-CO$_2$Me-benzoxy, 3-CF$_3$-benzoxy, 3-OCF$_3$-benzoxy, 4-OCF$_3$-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO$_2$(t-Bu)-piperidin-4-yl)methoxy, (1-CO$_2$Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 4,4,5,5-tetramethyl-1,3,2-dioxaborolanyl, —OP(O)(OEt)$_2$, C$_{1-6}$ alkyl, C$_{1-6}$ alkoxy, or C$_{3-6}$ cycloalkyl optionally substituted with the group selected from: —CO$_2$Me, —CH$_2$OH, and —CH$_2$OMe; and $R^4$, $R^{4a}$, $R^5$, $R^{5a}$, $R^{5c}$, and $R^{5d}$, are, independently at each occurrence, H, F, Cl, Me, or OMe;

alternatively, $R^1+R^2$, $R^2+R^3$, $R^3+R^4$, $R^4+R^5$, $R^{1a}+R^{2a}$, $R^{2a}+R^{3a}$, $R^{3a}+R^{4a}$, $R^{4a}+R^{5a}$, $R^{1b}+R^{2b}$, $R^{1c}+R^{3c}$, $R^{2c}+R^{3c}$, $R^{2d}+R^{3d}$, $R^{3c}+R^{4c}$, or $R^{4c}+R^{5c}$, combine with the carbon atoms to which they attached, form 5- to 10-membered carbocyclic or heterocyclic ring comprising: carbon atoms and 0-3 heteroatoms selected from N, NR$^{11}$, O, and S(O)$_p$, 0-1 carbonyl group, and additional 0-3 double bonds, wherein said carbocyclic or heterocyclic ring is substituted with 0-2 R$^b$.

In a fourteenth embodiment, the present invention provides a compound of Formula (Ia), within the scope of the twelfth embodiment wherein:

ring A is

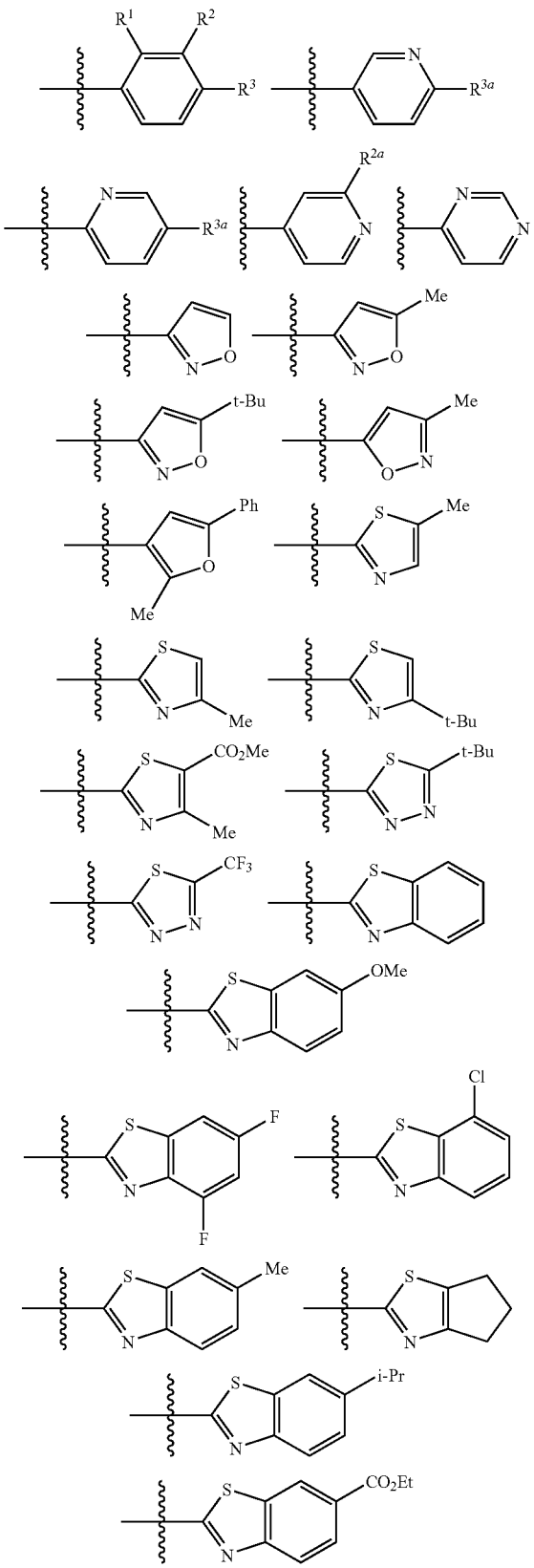

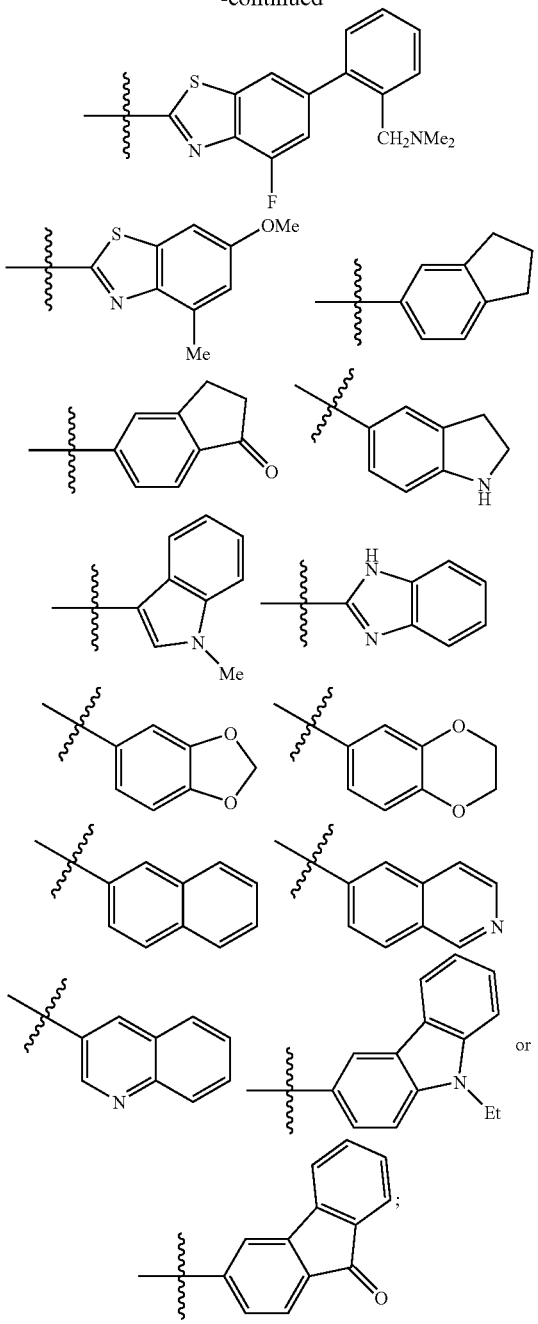

R¹ is H, or F;

R² is H, F, Cl, Br, Me, t-Bu, OMe, OBu, pentoxy, isopentoxy, neohexoxy, —O(CH₂)₂OMe, —O(CH₂)₂O(i-Pr), —O(CH₂)₈CO₂Me, —O(CH₂)₂C(Me)₂OMe, —O(CH₂)₂NMe₂, —OCH₂C(Me)₂CH₂NMe₂, —O(CH₂)₂OCOMe, —OCH(Et)CH₂OMe, —OCH(Me)CH₂O(t-Bu), NO₂, CF₃, OCF₃, 2-CH₂N(Me)₂-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe₂-benzoxy, 2-CF₃-benzoxy, 3-OCF₃-benzoxy, 4-OCF₃-benzoxy, 4-CO₂Me-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl) methoxy, (furan-3-yl)methoxy, (tetrahydrofuran-2-yl) methoxy, (tetrahydrofuran-3-yl)methoxy, (thien-3-yl) methoxy, (1H-pyrrol-1-yl)ethoxy, (2-Bu-1H-imidazol-4-yl) methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl) ethoxy, or —OCH(Et)(pyridine-4-yl);

R²ᵃ is F, Cl, Br, Me, or t-Bu;

R³ is H, F, Cl, Br, Me, Et, Pr, Bu, t-Bu, OMe, OEt, OPr, O-i-Pr, OBu, O-t-Bu, pentoxy, isopentoxy, neohexoxy, —OCH(Me)CH₂O-t-Bu, CF₃, OCHF₂, OCF₃, —O(CH₂)₂OMe, —O(CH₂)₃NMe₂, —O(CH₂)₄NMe₂, —OCH(Et)CH₂OMe, CN, NH₂, NMe₂, —CH₂NMe₂, NEt₂, —NHPh, —N(Me)Ph, —NH(4-OMe-Ph), —NH(2-CF₃-Ph), —CH(Me)NHCH(Me)Ph, —CH(Me)N(Me)(3-CF₃-Bn), —CH(Me)N(Me)(furan-2-ylmethyl), —CH(Me)N(Me)(thien-2-ylmethyl), —CH(Me)OH, —CH(Me)O(i-Pr), —CH(Me)O (i-Bu), —CH(Me)O(3-CF₃-Bn), —CH(Me)O(4-CF₃-Bn), —CH(Me)O(1-Bn-pyrrolidin-3-ylmethyl), —C(Me)₂OH, —C(Me)₂CH₂OH, —C(CF₃)₂OH, —COMe, CO₂Et, —CH₂CO₂Me, —C(Me)₂CO₂Me, —O(CH₂)₅CO₂Et, —O(CH₂)₈CO₂Me, —O(CH₂)₂C(Me)₂OMe, —O(CH₂)₂OCOMe, —OCH₂C(Me)₂CH₂NMe₂, Ph, 2-CH₂OH-Ph, 2-CH₂N(Me)-2-Ph, 3-CH₂N(Me)-2-Ph, 4-CH₂N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 4-OMe-benzoxy, 3-CN-benzoxy, 4-CN-benzoxy, 3-NMe₂-benzoxy, 4-CO₂Me-benzoxy, 3-CF₃-benzoxy, 3-OCF₃-benzoxy, 4-OCF₃-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO₂Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO₂Et-5-Me-1H-pyrazol-1-yl, 4-CO₂Et-5-Me-1H-pyrazol-1-yl, 5-CO₂Et-3-Me-1H-pyrazol-1-yl, (2-Bu-1H-imidazol-4-yl) methoxy, 1H-1,2,4-triazol-1-yl, (1-Ph-1H-1,2,3-triazol-4-yl) methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO₂(t-Bu)-piperidin-4-yl)methoxy, (1-CO₂Bn-piperidin-4-yl)methoxy, (1-Bn-piperidin-4-yl)methoxy, (1-phenethyl-piperidin-4-yl)methoxy, (1-(4-phenylbutyl)-piperidin-4-yl) methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 1-CH₂OH-cyclopropyl, 1-CO₂Me-cyclopropyl, 1-CH₂OMe-cyclopropyl, 1-CO₂Me-cyclobutyl, 1-CO₂Me-cyclopentyl, cyclohexyl, 1-CO₂Me-cyclohexyl, 4,4,5,5-tetramethyl-1,3,2-dioxaborolanyl, or —OP(O)(OEt)₂;

R³ᵃ is Me, Cl, CF₃, —NHPh, —NH(2-CF₃-Ph), —NH(2-t-Bu-Ph), 2-t-Bu-phenoxy, or 2-CF₃-phenoxy;

R⁶ is 2-Me-Ph, 3-Me-Ph, 2-Et-Ph, 3-Et-Ph, 2-Pr-Ph, 2-i-Pr-Ph, 3-i-Pr-Ph, 2-i-Bu-Ph, 2-t-Bu-Ph, 3-t-Bu-Ph, 2-vinyl-Ph, 2-isopropenyl-Ph, 3-isopropenyl-Ph, 3-Br-Ph, 2-I-Ph, 2-SMe-Ph, 2-S(i-Pr)-Ph, 2-C(Me)₂CN-Ph, 2-CF₃-Ph, 3-CF₃-Ph, 2-OCF₃-Ph, 3-OCF₃-Ph, 3-Ph-Ph, 2-Bn-Ph, 2-SiMe₃-Ph, 3-SiMe₃-Ph, 2-C(Me)₂OMe-Ph, 2-C(Me)₂OEt-Ph, 2-C(Me)₂ OPr-Ph, 2-CH(Me)O(CH₂)₂OMe-Ph, 2-C(Me)₂O (CH₂)₂ OMe-Ph, 2-C(Et)₂OH-Ph, 2-C(Et)₂OMe-Ph, 2-C (Et)₂ OEt-Ph, 2-C(Et)₂OPr-Ph, 3-COPh-Ph, 2-CO₂Et-Ph, 3-CO₂Et-Ph, 2-NH(i-Bu)-Ph, 2-cyclopropyl-Ph, 2-cyclopentyl-Ph, 2,3-dimethoxy-Ph, 2,3-diCl-Ph, 2,6-diMe-Ph, 2-Me-5-F-Ph, 2-i-Pr-5-Me-Ph, 2-t-Bu-4-Me-Ph, 2-t-Bu-5-Me-Ph, 2-t-Bu-6-CN-Ph, 2-F-3-CF₃-Ph, 2-F-5-CF₃-Ph, 2-Cl-5-CF₃-Ph, 2-COMe-3-F-Ph, 2-CO₂Me-3-F-Ph, 2-CF₃-Bn, 1-naphthyl,
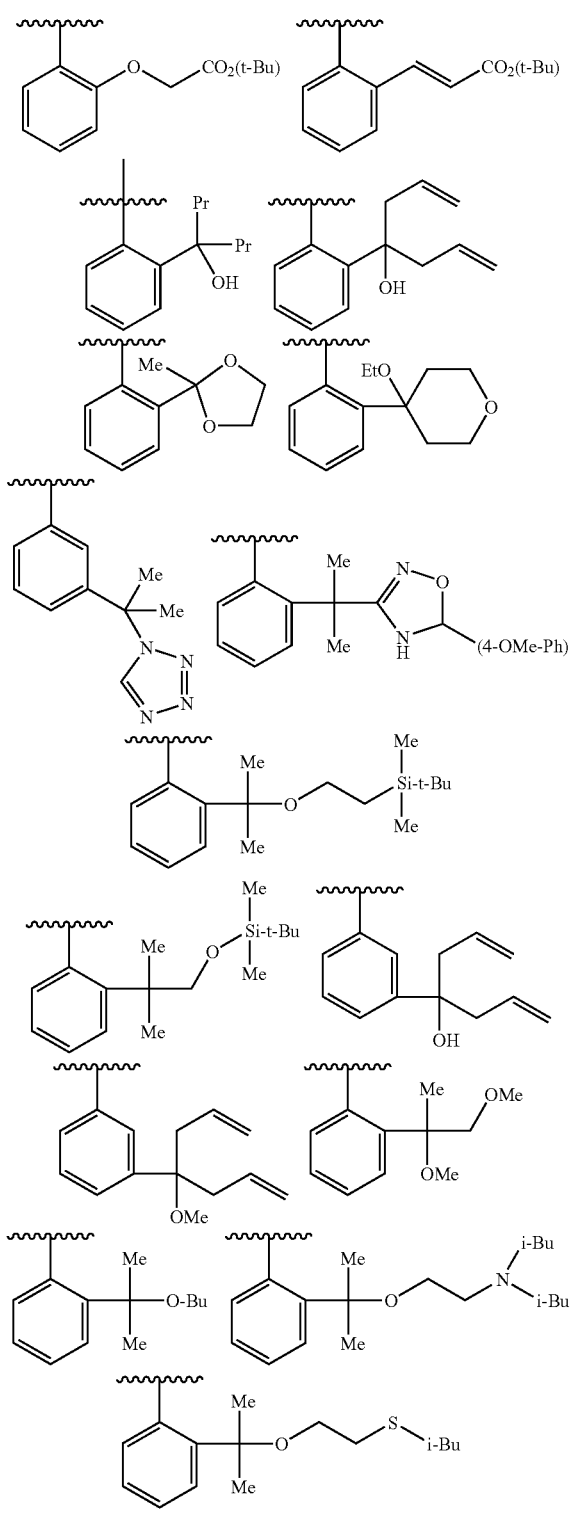
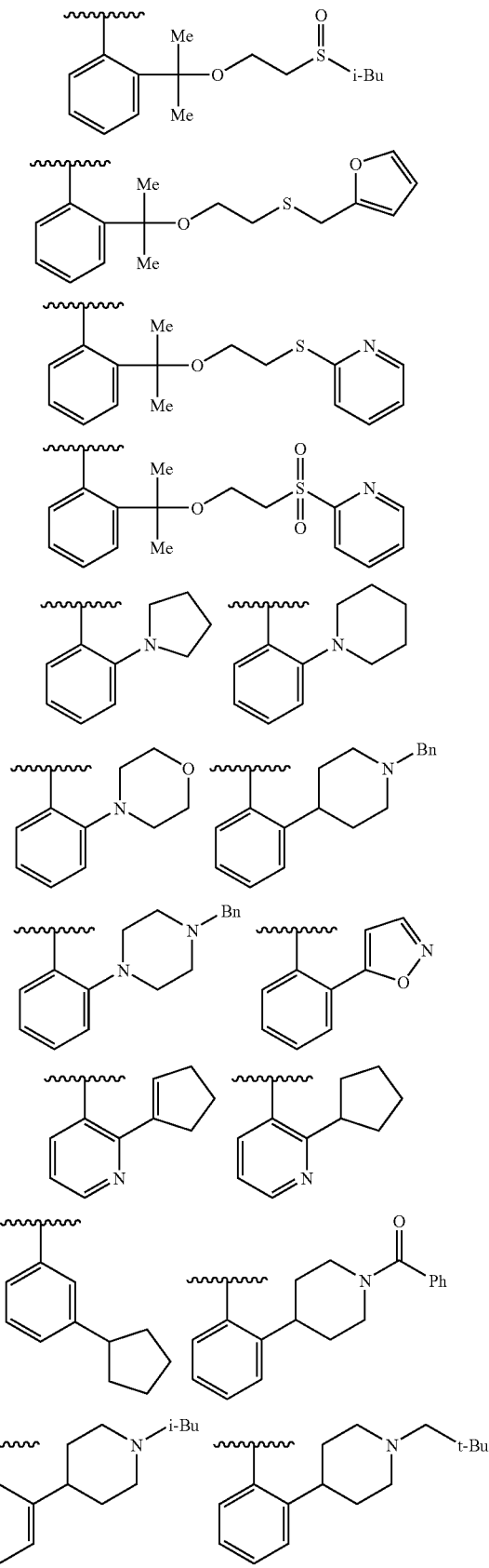

-continued
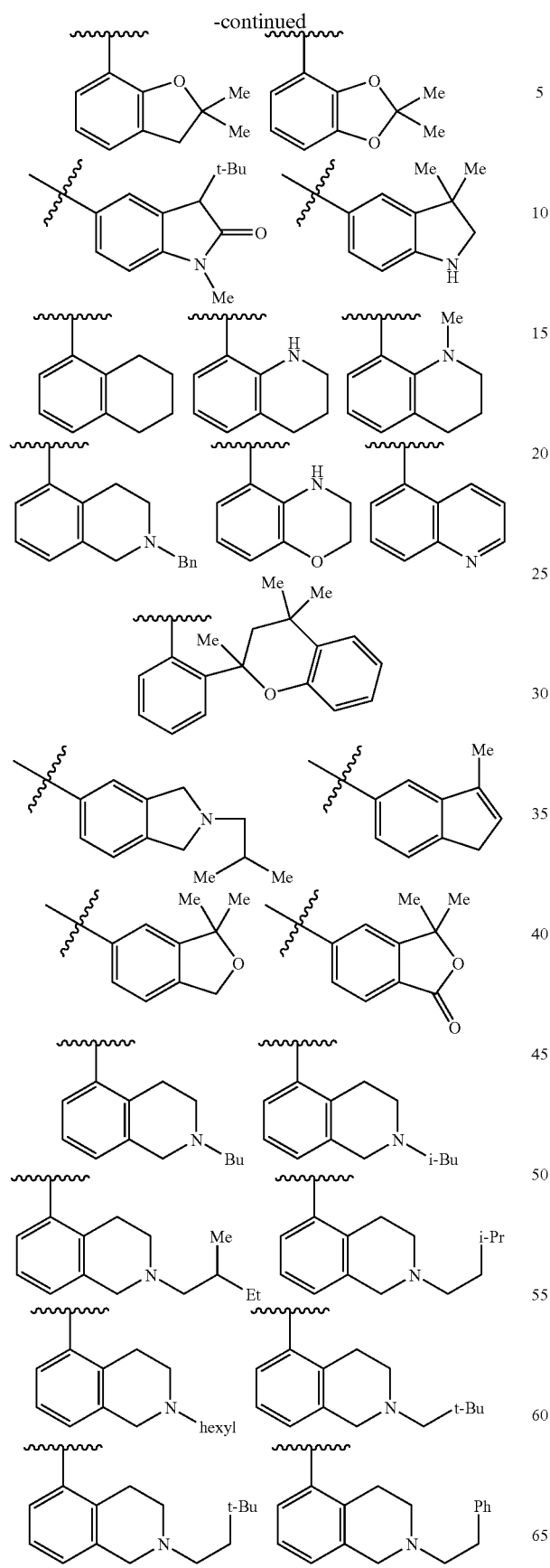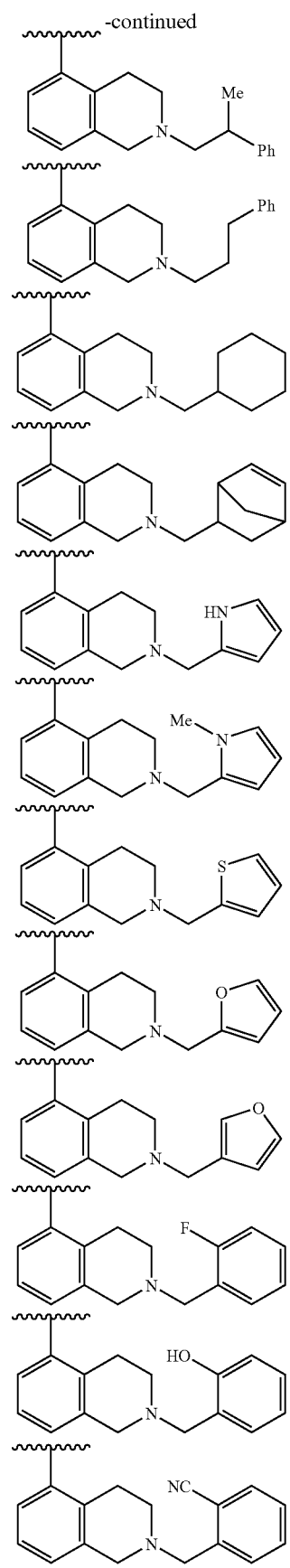

-continued

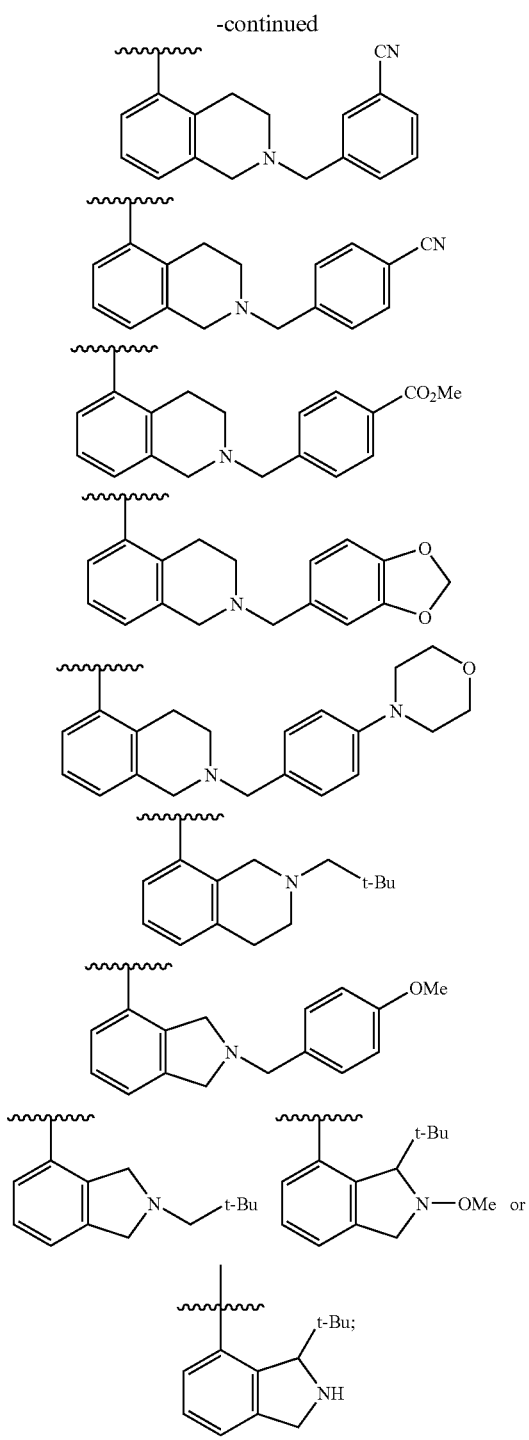

ring B is

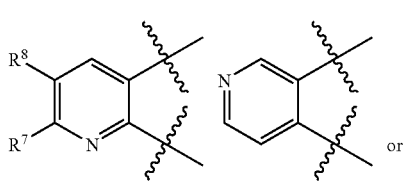

-continued

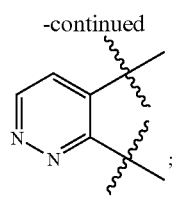

$R^7$ is H, Me, Cl, Br, CN, OH, OMe, SMe, NHMe, NMe$_2$, CO$_2$Me, imidazol-1-yl, or —CH$_2$NH(CO)H;

$R^8$ is H, Me, Cl, Br, CN, or CF$_3$; and

Y is O, S, or NH.

In a fifteenth embodiment, the present invention includes a compound of Formula (Ia), within the scope of the twelfth embodiment wherein:

ring A is

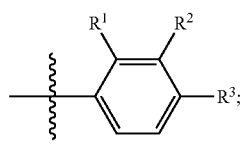

ring B is

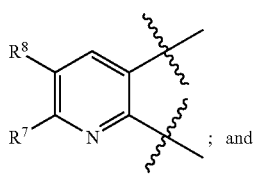

Y is O.

In another embodiment, the present invention includes a compound of Formula (Ia) wherein ring A is

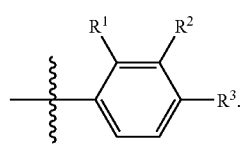

In another embodiment, the present invention includes a compound of Formula (Ia) wherein ring B is

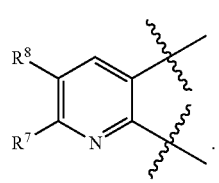

In another embodiment, the present invention includes a compound of Formula (Ia) wherein Y is O.

In a sixteenth embodiment, the present invention provides a compound of Formula (IIb):

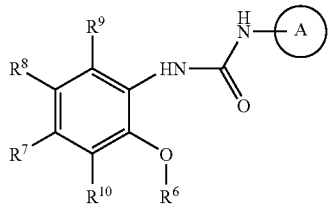

(IIb)

or a stereoisomer or pharmaceutically acceptable salts, solvates, or prodrugs thereof, wherein:
ring A is

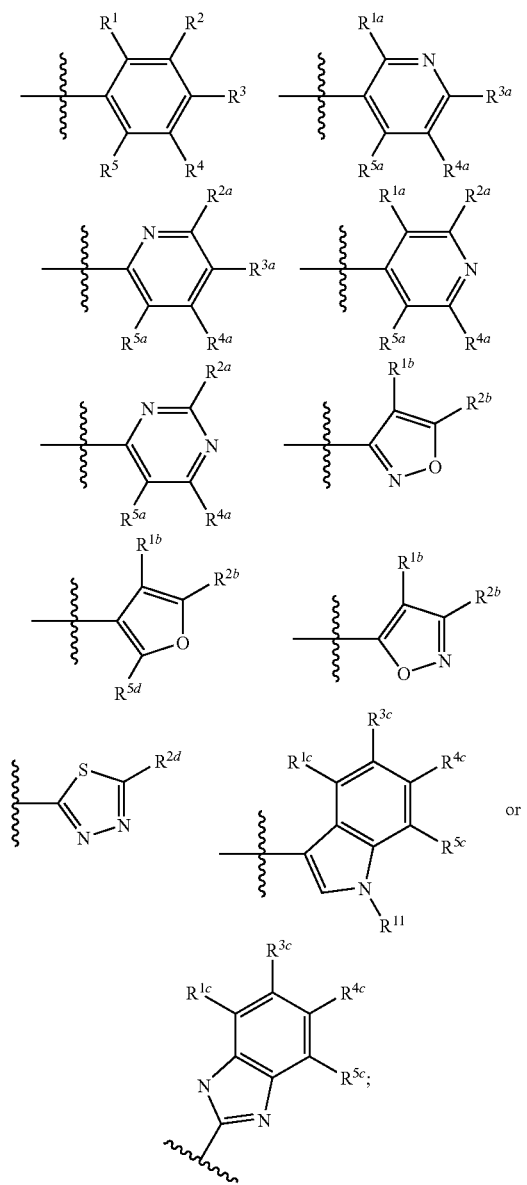

$R^1$, $R^{1a}$, $R^{1b}$, and $R^{1c}$ are, independently at each occurrence, H, F, Cl, or OH;

$R^2$, $R^{2a}$, $R^{2b}$, $R^{2c}$, $R^{2d}$ and $R^{3d}$ are, independently at each occurrence, H, F, Cl, Br, Me, t-Bu, OMe, OBu, pentoxy, isopentoxy, neohexoxy, —O(CH$_2$)$_2$OMe, —O(CH$_2$)$_2$O(i-Pr), —O(CH$_2$)$_8$CO$_2$Me, —O(CH$_2$)$_2$C(Me)$_2$OMe, —O(CH$_2$)$_2$NMe$_2$, —OCH$_2$C(Me)$_2$CH$_2$NMe$_2$, —O(CH$_2$)$_2$OCOMe, —OCH(Et)CH$_2$OMe, —OCH(Me)CH$_2$O(t-Bu), NO$_2$, CF$_3$, OCF$_3$, 2-CH$_2$N(Me)$_2$-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe$_2$-benzoxy, 2-CF$_3$-benzoxy, 3-OCF$_3$-benzoxy, 4-OCF$_3$-benzoxy, 4-CO$_2$Me-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl)ethoxy, or —OCH(Et)(pyridine-4-yl);

$R^3$, $R^{3a}$, $R^{3c}$, and $R^{4c}$ are, independently at each occurrence, H, F, Cl, Br, —OCH(Me)CH$_2$O-t-Bu, CF$_3$, OCHF$_2$, OCF$_3$, —O(CH$_2$)$_2$OMe, —O(CH$_2$)$_3$NMe$_2$, —O(CH$_2$)$_4$NMe$_2$, —OCH(Et)CH$_2$OMe, CN, NH$_2$, NMe$_2$, —CH$_2$NMe$_2$, NEt$_2$, —NHPh, —N(Me)Ph, —NH(4-OMe-Ph), —NH(2-CF$_3$-Ph), —CH(Me)NHCH(Me)Ph, —CH(Me)N(Me)(3-CF$_3$-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH(Me)O(1-Bn-pyrrolidin-3-ylmethyl), —C(CF$_3$)$_2$OH, —COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)-2-Ph, 3-CH$_2$N(Me)-2-Ph, 4-CH$_2$N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 4-OMe-benzoxy, 3-CN-benzoxy, 4-CN-benzoxy, 3-NMe$_2$-benzoxy, 4-CO$_2$Me-benzoxy, 3-CF$_3$-benzoxy, 3-OCF$_3$-benzoxy, 4-OCF$_3$-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO$_2$(t-Bu)-piperidin-4-yl)methoxy, (1-CO$_2$Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 4,4,5,5-tetramethyl-1,3,2-dioxaborolanyl, —OP(O)(OEt)$_2$, C$_{1-6}$ alkyl, C$_{1-6}$ alkoxy, or C$_{3-6}$ cycloalkyl optionally substituted with the group selected from: —CO$_2$Me, —CH$_2$OH, and —CH$_2$OMe; and $R^4$, $R^{4a}$, $R^5$, $R^{5a}$, $R^{5c}$, and $R^{5d}$, are, independently at each occurrence, H, F, Cl, Me, or OMe;

alternatively, $R^1+R^2$, $R^2+R^3$, $R^3+R^4$, $R^4+R^5$, $R^{1a}+R^{2a}$, $R^{2a}+R^{3a}$, $R^{3a}+R^{4a}$, $R^{4a}+R^{5a}$, $R^{1b}+R^{2b}$, $R^{1c}+R^{3c}$, $R^{2c}+R^{3c}$, $R^{2d}+R^{3d}$, $R^{3c}+R^{4c}$, or $R^{4c}+R^{5c}$, combine with the carbon atoms to which they attached, form 5- to 10-membered carbocyclic or heterocyclic ring comprising: carbon atoms and 0-3 heteroatoms selected from N, $NR^{11}$, O, and $S(O)_p$, 0-1 carbonyl group, and additional 0-3 double bonds, wherein said carbocyclic or heterocyclic ring is substituted with 0-2 $R^b$;

$R^6$ is —$(CH_2)_n$-phenyl substituted with 0-3 $R^{6a}$ or —$(CH_2)_n$-pyridyl substituted with 0-3 $R^{6a}$;

$R^{6a}$ is, independently at each occurrence, H, F, Cl, Br, I, CN, —$C(Me)_2CN$, $C_{1-8}$ alkyl, $C_{2-8}$ alkenyl, OH, SMe, S(i-Pr), —$C(Me)_2OMe$, —$C(Me)_2OEt$, —$C(Me)_2OPr$, —$CHMeO(CH_2)_2OMe$, —$C(Me)_2OBu$, —$C(Me)_2O(CH_2)_2OMe$, —$C(Me)(OMe)CH_2OMe$, —$C(Me)_2O(CH_2)_2N(i-Bu)_2$, —$C(Me)_2O(CH_2)_2S(i-Bu)$, —$C(Me)_2O(CH_2)_2S(O)(i-Bu)$, —$C(Me)_2O(CH_2)_2S(furan-2-ylmethyl)$, —$C(Me)_2O(CH_2)_2S(pyridin-2-yl)$, —$C(Me)_2O(CH_2)_2S(O)_2(pyridin-2-yl)$, —$C(Me)_2CH_2OSi(Me)_2(t-Bu)$, —$C(Me)_2O(CH_2)_2Si(Me)_2(t-Bu)$, —$C(Et)_2OH$, —$C(Pr)_2OH$, —$C(CH_2CH=CH_2)_2OH$, —$C(CH_2CH=CH_2)_2OMe$, —$C(Et)_2OMe$, —$C(Et)_2OEt$, —$C(Et)_2OPr$, COMe, COPh, $CO_2Me$, $CO_2Et$, —$NH(i-Bu)$, —$CH=CHCO_2(t-Bu)$, —$OCH_2CO_2(t-Bu)$, $CF_3$, $OCF_3$, $C_{1-4}$ alkyloxy, $C_{3-7}$ cycloalkyl, $C_{3-7}$ cycloalkenyl, Ph, Bn, naphthyl, 1-pyrrolidinyl, 5-isoxazolyl, N-morpholinyl, 4-Bn-piperazinyl, 1-piperidinyl, 1-Bn-piperidin-4-yl, 1-i-Bu-piperidin-4-yl, 1-neopentyl-piperidin-4-yl, 1-COPh-piperidin-4-yl, —$SiMe_3$,

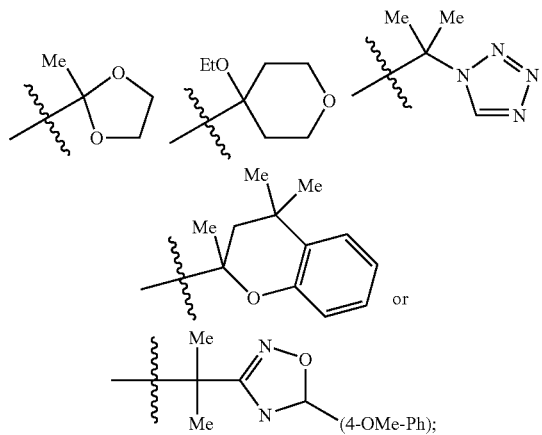

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is H, Me, Cl, Br, CN, OH, OMe, SMe, NHMe, $NMe_2$, $CO_2Me$, imidazol-1-yl, or —$CH_2NH(CO)H$;

$R^8$ is H, Me, Cl, Br, or CN;

$R^9$ is H or Me;

$R^{10}$ is H or Me;

$R^{11}$ is, independently at each occurrence, H, $C_{1-6}$ alkyl, OMe, —$C(O)(C_{1-6}$ alkyl), —$C(O)$phenyl, —$C(O)$benzyl, —$C(O)O(C_{1-6}$ alkyl), —$C(O)O$benzyl, —$S(O)_2(C_{1-6}$ alkyl), —$S(O)_2$phenyl, —$S(O)_2$benzyl, cyclohexylmethyl, phenyl, benzyl, phenethyl, phenylpropyl, —$CH_2CH(Me)Ph$, 1H-pyrrol-2-ylmethyl, 1-Me-pyrrol-2-ylmethyl, thieny-2-ylmethyl, furan-2-ylmethyl, furan-3-ylmethyl, 2-F-Bn, 2-OH-Bn, 2-CN-Bn, 3-CN-Bn, 4-CN-Bn, 4-OMe-Bn, 4-$CO_2$Me-Bn,

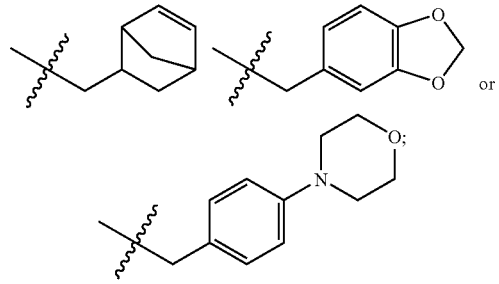

$R^b$ is, independently at each occurrence, H, F, Cl, Br, $C_{1-4}$ alkyl, OH, $CO_2H$, $NH_2$, $CF_3$, $OCF_3$, $C_{1-4}$ alkyloxy, $C_{3-7}$ cycloalkyl, phenyl, or benzyl;

n, at each occurrence, is selected from 0, 1, and 2;

p, at each occurrence, is selected from 0, 1, and 2;

provided that:

(i) when $R^7$, $R^8$, $R^9$ and $R^{10}$ are H, $R^6$ is Ph, then ring A is other than Ph, 4-F-Ph, 4-Cl-Ph, 4-Me-Ph, 4-OMe-Ph, 4-OBn-Ph, 2,4-diCl-Ph, or 3,4-diOMe-Ph;

(ii) when $R^7$, $R^8$, $R^9$ and $R^{10}$ are H, $R^6$ is 4-Cl-Ph, then ring A is other than Ph or 4-Cl-Ph;

(iii) when $R^7$, $R^9$ and $R^{10}$ are H, $R^8$ is Cl, $R^6$ is Ph, then ring A is other than 4-$CO_2$Et-Ph;

(iv) when $R^7$, $R^9$ and $R^{10}$ are H, $R^8$ is F or Cl, $R^6$ is 4-F-Ph, then ring A is other than 4-Cl-Ph;

(v) when $R^7$, $R^9$ and $R^{10}$ are H, $R^8$ is F, Cl or Br, $R^6$ is 4-F-Ph, 4-Cl-Ph or 4-Br-Ph, then ring A is other than 3-Cl-Ph, 2,4-diCl-Ph, or 3,4-diCl-Ph; or (vi) when $R^7$ and $R^8$ are Cl, $R^9$ and $R^{10}$ are H, $R^6$ is 4-Cl-Ph, then ring A is other than 3,4-diCl-Ph.

In a seventeenth embodiment, the present invention provides a compound of Formula (IIb), within the scope of the sixteenth wherein:

ring A is

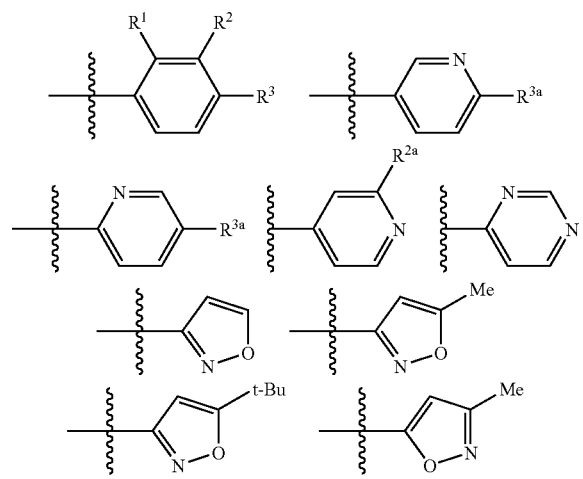

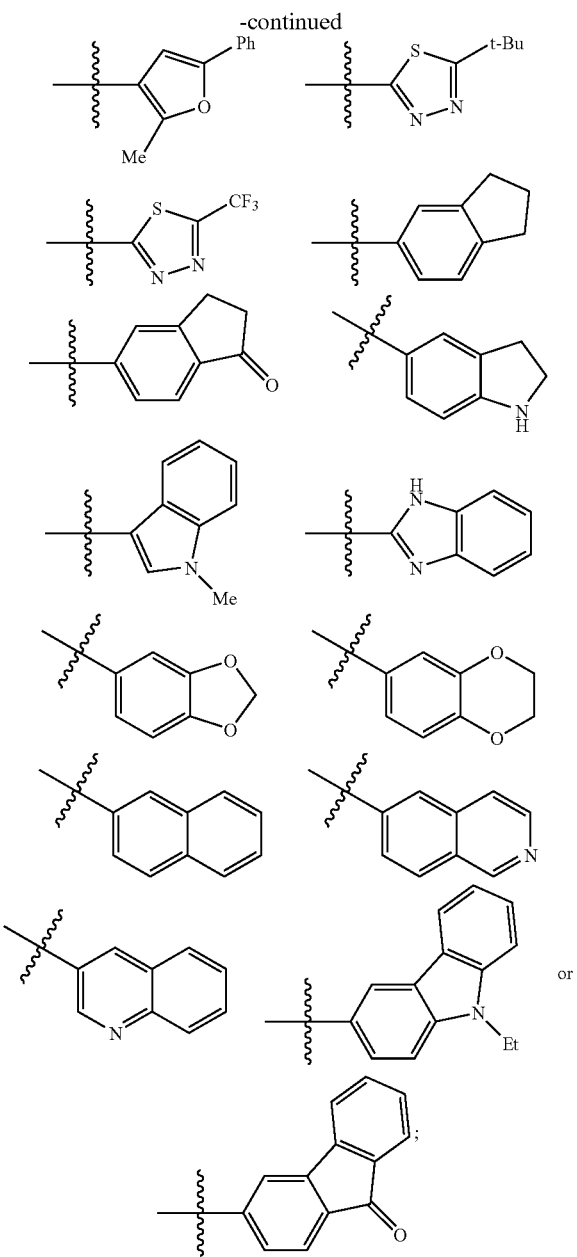

R[1] is H or F;

R[2] is H, F, Cl, Br, Me, t-Bu, OMe, OBu, pentoxy, isopentoxy, neohexoxy, —O(CH$_2$)$_2$OMe, —O(CH$_2$)$_2$O(i-Pr), —O(CH$_2$)$_8$CO$_2$Me, —O(CH$_2$)$_2$C(Me)$_2$OMe, —O(CH$_2$)$_2$NMe$_2$, —OCH$_2$C(Me)$_2$CH$_2$NMe$_2$, —O(CH$_2$)$_2$OCOMe, —OCH(Et)CH$_2$OMe, —OCH(Me)CH$_2$O(t-Bu), NO$_2$, CF$_3$, OCF$_3$, 2-CH$_2$N(Me)$_2$-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe$_2$-benzoxy, 2-CF$_3$-benzoxy, 3-OCF$_3$-benzoxy, 4-OCF$_3$-benzoxy, 4-CO$_2$Me-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl)methoxy, (1H-pyrrol-1-yl)ethoxy, (2-Bu-1H-imidazol-4-yl) methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl) ethoxy, or —OCH(Et)(pyridine-4-yl);

R$^{2a}$ is F, Cl, Br, Me, or t-Bu;

R[3] is H, F, Cl, Br, Me, Et, Pr, Bu, t-Bu, OMe, OEt, OPr, O-i-Pr, OBu, O-t-Bu, pentoxy, isopentoxy, neohexoxy, —OCH(Me)CH$_2$O-t-Bu, CF$_3$, OCHF$_2$, OCF$_3$, —O(CH$_2$)$_2$OMe, —O(CH$_2$)$_3$NMe$_2$, —O(CH$_2$)$_4$NMe$_2$, —OCH(Et)CH$_2$OMe, CN, NH$_2$, NMe$_2$, —CH$_2$NMe$_2$, NEt$_2$, —NHPh, —N(Me)Ph, —NH(4-OMe-Ph), —NH(2-CF$_3$-Ph), —CH(Me)NHCH(Me)Ph, —CH(Me)N(Me)(3-CF$_3$-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH(Me)O(1-Bn-pyrrolidin-3-ylmethyl), —C(Me)$_2$OH, —C(Me)$_2$CH$_2$OH, —C(CF$_3$)$_2$OH, —COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)-2-Ph, 3-CH$_2$N(Me)-2-Ph, 4-CH$_2$N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 4-OMe-benzoxy, 3-CN-benzoxy, 4-CN-benzoxy, 3-NMe$_2$-benzoxy, 4-CO$_2$Me-benzoxy, 3-CF$_3$-benzoxy, 3-OCF$_3$-benzoxy, 4-OCF$_3$-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl) methoxy, 1H-1,2,4-triazol-1-yl, (1-Ph-1H-1,2,3-triazol-4-yl) methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO$_2$(t-Bu)-piperidin-4-yl)methoxy, (1-CO$_2$Bn-piperidin-4-yl)methoxy, (1-Bn-piperidin-4-yl)methoxy, (1-phenethyl-piperidin-4-yl)methoxy, (1-(4-phenylbutyl)-piperidin-4-yl) methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 1-CH$_2$OH-cyclopropyl, 1-CO$_2$Me-cyclopropyl, 1-CH$_2$OMe-cyclopropyl, 1-CO$_2$Me-cyclobutyl, 1-CO$_2$Me-cyclopentyl, cyclohexyl, 1-CO$_2$Me-cyclohexyl, 4,4,5,5-tetramethyl-1,3,2-dioxaborolanyl, or —OP(O)(OEt)$_2$;

R$^{3a}$ is Me, Cl, CF$_3$, —NHPh, —NH(2-CF$_3$-Ph), —NH(2-t-Bu-Ph), 2-t-Bu-phenoxy, or 2-CF$_3$-phenoxy;

R[6] is 2-Me-Ph, 3-Me-Ph, 2-Et-Ph, 3-Et-Ph, 2-Pr-Ph, 2-i-Pr-Ph, 3-i-Pr-Ph, 2-i-Bu-Ph, 2-t-Bu-Ph, 3-t-Bu-Ph, 2-vinyl-Ph, 2-isopropenyl-Ph, 3-isopropenyl-Ph, 3-Br-Ph, 2-I-Ph, 2-SMe-Ph, 2-S(i-Pr)-Ph, 2-C(Me)$_2$CN-Ph, 2-CF$_3$-Ph, 3-CF$_3$-Ph, 2-OCF$_3$-Ph, 3-OCF$_3$-Ph, 3-Ph-Ph, 2-Bn-Ph, 2-SiMe$_3$-Ph, 3-SiMe$_3$-Ph, 2-C(Me)$_2$OMe-Ph, 2-C(Me)$_2$OEt-Ph, 2-C(Me)$_2$OPr-Ph, 2-CH(Me)O(CH$_2$)$_2$OMe-Ph, 2-C(Me)$_2$O(CH$_2$)$_2$OMe-Ph, 2-C(Et)$_2$OH-Ph, 2-C(Et)$_2$OMe-Ph, 2-C(Et)$_2$OEt-Ph, 2-C(Et)$_2$OPr-Ph, 3-COPh-Ph, 2-CO$_2$Et-Ph, 3-CO$_2$Et-Ph, 2-NH(i-Bu)-Ph, 2-cyclopropyl-Ph, 2-cyclopentyl-Ph, 2,3-dimethoxy-Ph, 2,3-diCl-Ph, 2,6-diMe-Ph, 2-Me- 5-F-Ph, 2-i-Pr-5-Me-Ph, 2-t-Bu-4-Me-Ph, 2-t-Bu-5-Me-Ph, 2-t-Bu-6-CN-Ph, 2-F-3-CF$_3$-Ph, 2-F-5-CF$_3$-Ph, 2-Cl-5-CF$_3$-Ph, 2-COMe-3-F-Ph, 2-CO$_2$Me-3-F-Ph, 2-CF$_3$-Bn, 1-naphthyl,
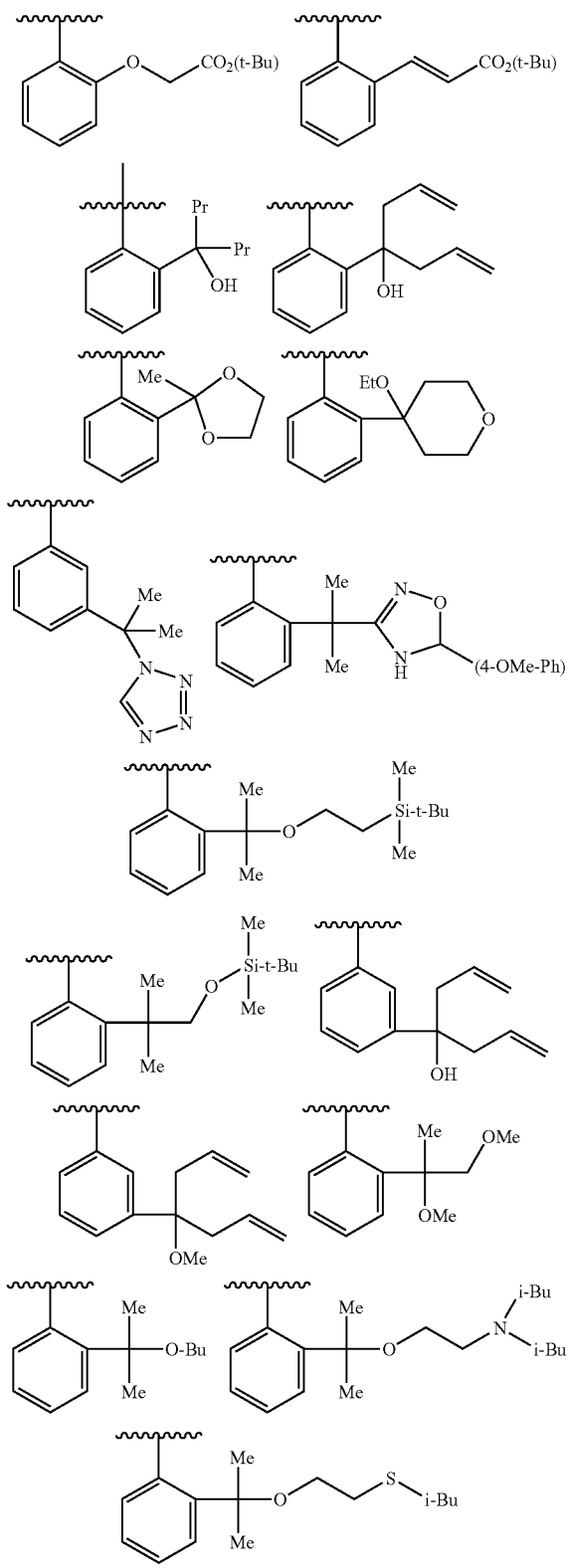
-continued
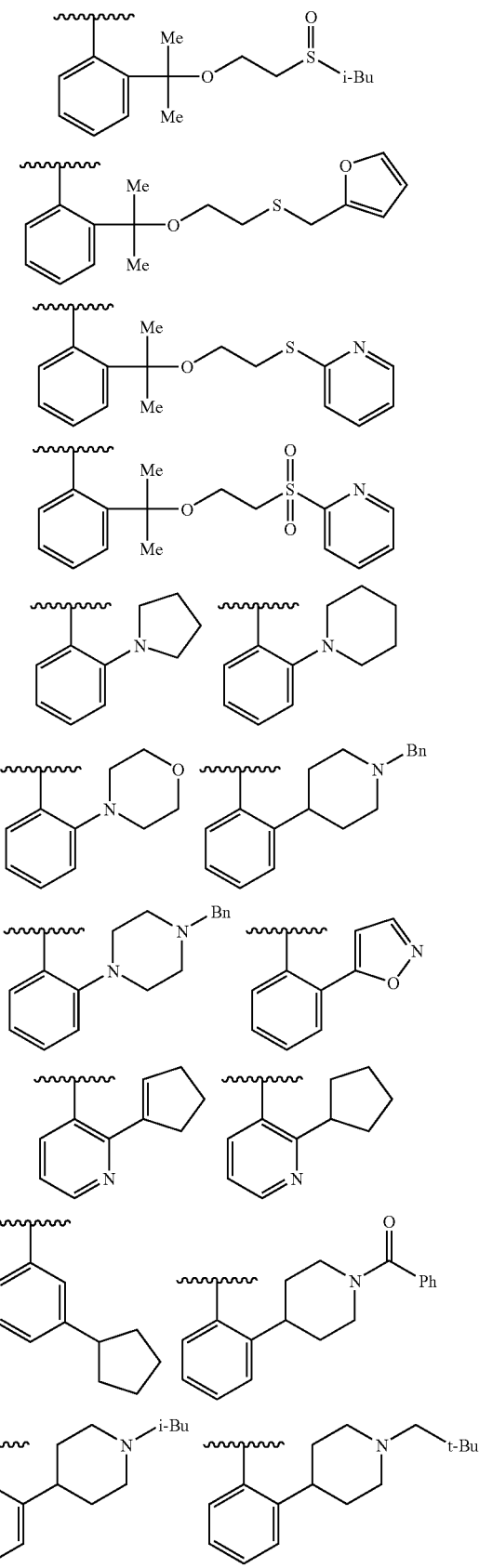

-continued
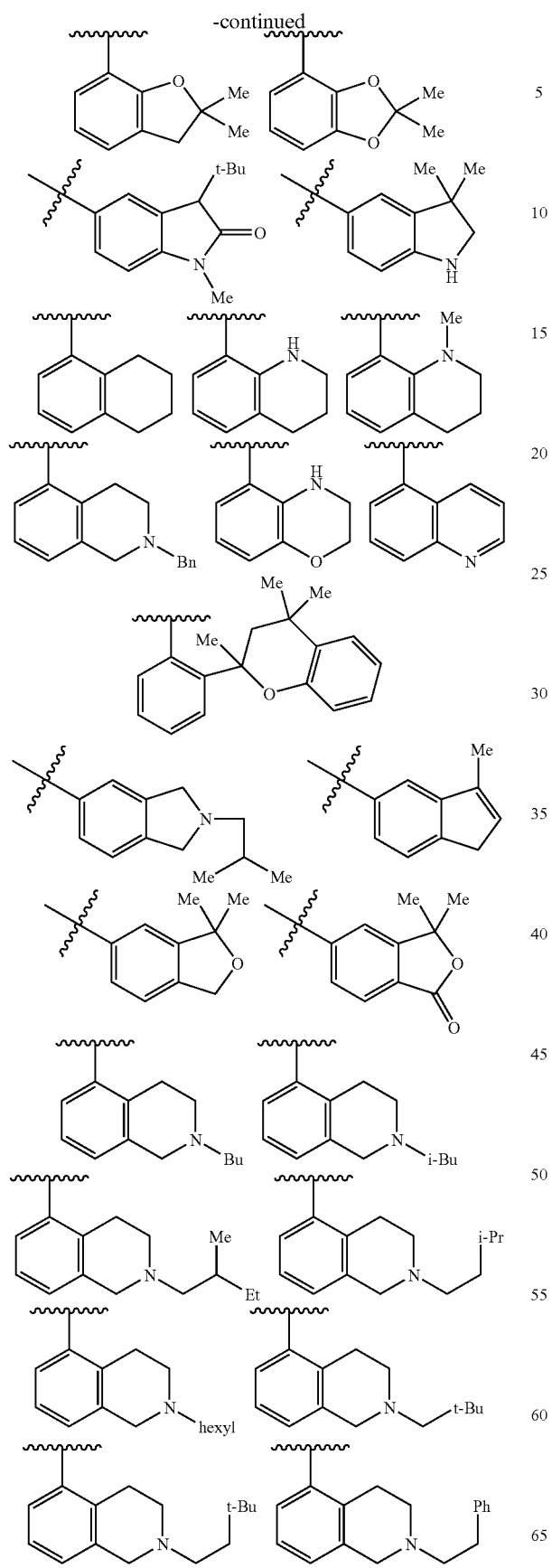
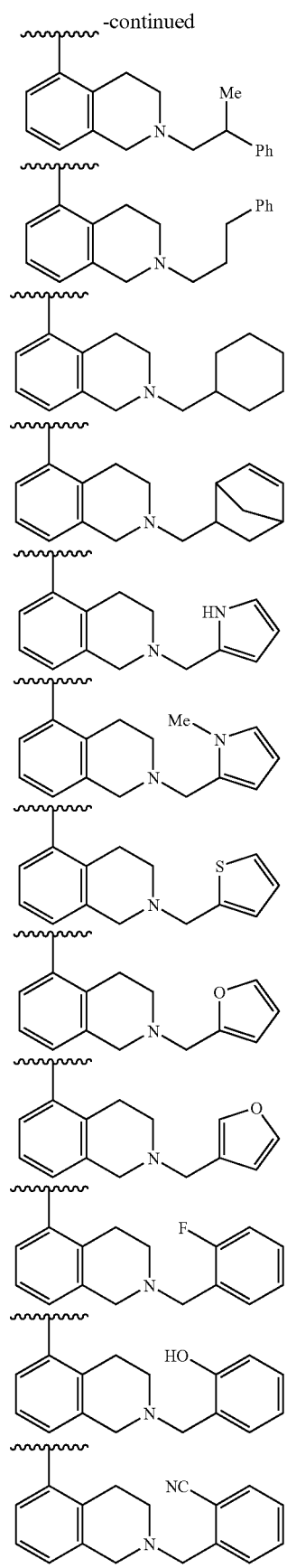

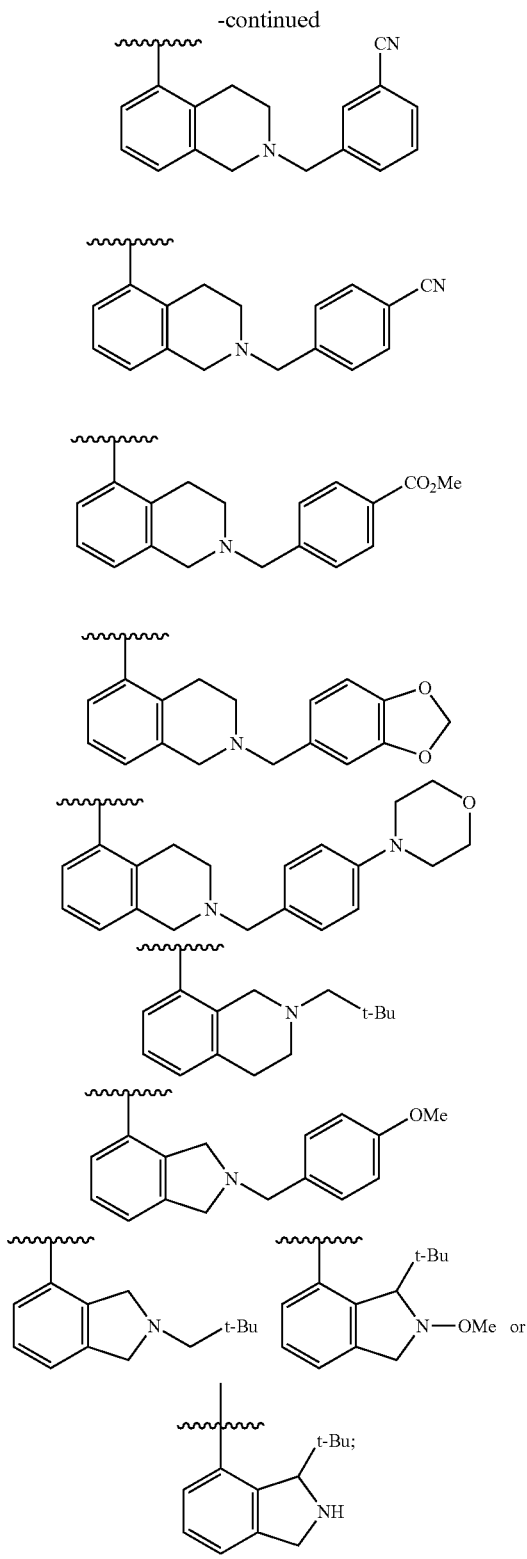

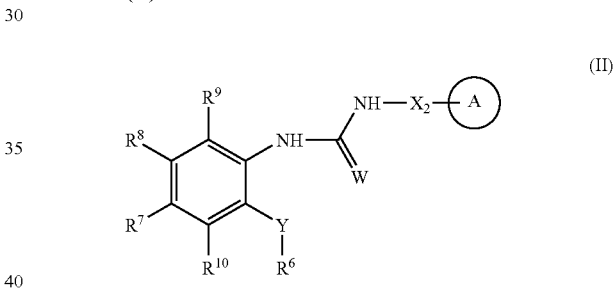

$R^7$ is H, Me, Cl, Br, CN, OH, OMe, SMe, NHMe, NMe$_2$, CO$_2$Me, imidazol-1-yl, or —CH$_2$NH(CO)H; and $R^8$ is H, Me, Cl, Br, or CN.

In an eighteenth embodiment, the present invention includes compounds of Formula (IIc):

or a stereoisomer or pharmaceutically acceptable salts, solvates, or prodrugs thereof, wherein:

$R^1$ is H or F;
$R^2$ is H or F;
$R^3$ is H, Me, t-Bu, F, OCF$_3$, or O-t-Bu;
$R^6$ is 2-t-Bu-Ph, 3-CF$_3$-Ph, 3-I-Ph, 3-CH$_2$OMe-Ph, 2-Me-5-F-Ph, Bn, 4-t-Bu-Bn, 4-Br-Bn, 4-OCF$_3$-Bn, —CH(Me)Ph, or —CH(CO$_2$Me)Ph;
$R^7$ is H or CN;
$R^8$ is H, CN, CO$_2$Me;
$R^9$ is H; and
$R^{10}$ is H, Me, NH$_2$, or —CH$_2$OMe.

In a nineteenth embodiment, the present invention provides, inter alia, a method for treating a thromboembolic disorder, comprising: administering to a patient in need thereof a therapeutically effective amount of a compound of Formula (II):

or a stereoisomer or pharmaceutically acceptable salt, solvate, or prodrug thereof, wherein:

ring A is C$_{6-10}$ aryl substituted with 0-5 R$^1$, or a 5- to 10-membered heterocycle comprising: carbon atoms and 1-4 heteroatoms selected from N, NR$^{11}$, O, and S(O)$_p$, wherein said heterocycle is substituted with 0-5 R$^1$;

W is O or S;

X$_2$ is —(CR$^{16}$R$^{17}$)$_s$—, or —(CR$^{16}$R$^{17}$)$_t$C(O)(CR$^{16}$R$^{17}$)$_r$—;

Y is O, S, NH, —OCR$^{18}$R$^{19}$—, —CH=CH—, or —CONH—;

$R^1$ is, independently at each occurrence, =O, F, Cl, Br, I, CF$_3$,
—CF$_2$CF$_3$, OCF$_3$, —OCF$_2$CF$_2$H, —OCF$_2$CF$_3$, SiMe$_3$,
—(CR$^f$R$^f$)$_r$—OR$^c$, SR$^c$, CN, NO$_2$,
—(CR$^f$R$^f$)$_r$—NR$^{12}$R$^{13}$, —(CR$^f$R$^f$)$_r$—C(O)R$^c$, —(CR$^f$R$^f$)$_r$—CO$_2$R$^c$, —(CR$^f$R$^f$)$_r$—C(O)NR$^{12}$R$^{13}$,
—C(O)NR$^{14}$(CR$^f$R$^f$)$_t$N$^{12}$R$^{13}$, —(CR$^f$R$^f$)$_r$—OC(O)NR$^{12}$R$^{13}$,
—(CR$^f$R$^f$)$_r$—NR$^{14}$C(O)NR$^{12}$R$^{13}$, —(CR$^f$R$^f$)$_r$—NR$^{14}$C(O)R$^d$,
—(CR$^f$R$^f$)$_r$—NR$^{14}$C(O)OR$^h$, —NR$^{14}$(CR$^f$R$^f$)$_n$C(O)R$^d$,
—NR$^{14}$CO(CR$^f$R$^f$)$_n$OR$^c$,
—(CH$_2$)$_r$—CR$^{13}$(=NOR$^c$), —S(O)$_p$NR$^{12}$R$^{13}$, —(CR$^f$R$^f$)$_r$—NR$^{14}$S(O)$_p$NR$^{12}$R$^{13}$, —NR$^{14}$SO$_2$CF$_3$, —NR$^{14}$S(O)$_p$R$^d$, —S(O)$_2$CF$_3$, —S(O)R$^d$, —S(O)$_2$R$^d$, —OP(O)(OEt)$_2$,
—O(CH$_2$)$_2$OP(O)(OEt)$_2$, 4,4,5,5-tetramethyl-1,3,2-dioxaborolanyl, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-13}$ carbocycle substituted with 0-5 R$^b$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-5 R$^b$;

alternatively, two R$^1$s on two adjacent carbon atoms are combined with the carbon atoms to which they attached, form a 5- to 7-membered carbocycle or heterocycle comprising: carbon atoms and 0-3 additional heteroatoms selected from N, NR$^{11}$, O, and S(O)$_p$, and 0-2 carbonyl groups, wherein said carbocycle or heterocycle is substituted with 0-4 R$^b$;

R$^6$ is —(CR$^f$R$^f$)$_n$-phenyl substituted with 0-3 R$^{6a}$ or —(CR$^f$R$^f$)$_n$-pyridyl substituted with 0-3 R$^{6a}$;

R$^{6a}$ is, independently at each occurrence, F, Cl, Br, I, —(CR$^i$R$^i$)$_r$—OR$^c$, SR$^c$, CN, NO$_2$, CF$_3$, OCF$_3$, —CF$_2$CF$_3$, —OCF$_2$CF$_2$H, —OCF$_2$CF$_3$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, Si(Me)$_3$, Si(C$_{1-4}$ alkyl)$_3$, C$_{1-4}$ haloalkyl, C$_{1-4}$ haloalkyloxy-, C$_{1-4}$ alkyloxy-, C$_{1-4}$ alkylthio-, C$_1$-C$_4$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-2 R$^e$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-2 R$^e$;

alternatively, when two R$^{6a}$ groups are attached to adjacent atoms, together with the atoms to which they are attached they form a 5- to 7-membered carbocyclic or heterocyclic ring comprising: carbon atoms and 0-2 heteroatoms selected from N, NR$^{11}$, O, and S(O)$_p$, 0-1 carbonyl and 0-3 ring double bonds, wherein said carbocyclic or heterocyclic ring is substituted with 0-2 R$^b$;

R$^7$, R$^8$, R$^9$ and R$^{10}$ are, independently at each occurrence, F, Cl, Br, I, OCF$_3$, CF$_3$, OR$^c$, SR$^c$, CN, NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-3 R$^b$, or —(CR$^f$R$^f$)$_r$-5- to 10-membered heterocycle comprising: carbon atoms and 1-4 heteroatoms selected from N, NR$^{7b}$, O, and S(O)$_p$, wherein said heterocycle is substituted with 0-3 R$^b$;

alternatively, R$^7$+R$^8$, R$^8$+R$^9$, or R$^7$+R$^{10}$ form a 5- to 7-membered carbocyclic or heterocyclic ring comprising: carbon atoms and 0-3 ring heteroatoms selected from O, N, NR$^{7b}$, and S(O)$_p$, wherein said carbocyclic or heterocyclic ring is substituted with 0-2 R$^{7c}$;

R$^{7b}$ is H, C$_{1-4}$ alkyl, —C(O)(C$_{1-4}$ alkyl), —C(O)phenyl, —C(O)benzyl, or benzyl;

R$^{7c}$ is, independently at each occurrence, H, F, Cl, Br, I, OCF$_3$, CF$_3$, OR$^c$, SR$^c$, CN, NO$_2$, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ alkyl, phenyl substituted with 0-3 R$^b$, or benzyl substituted with 0-3 R$^b$;

R$^{11}$ is, independently at each occurrence, H, C$_{1-4}$ alkoxy, C$_{1-8}$ alkyl substituted with 0-2 R$^a$, C$_{2-4}$ alkenyl substituted with 0-1 R$^a$, C$_{2-4}$ alkynyl substituted with 0-1 R$^a$, —C(O)(C$_{1-6}$ alkyl), —C(O)(CH$_2$)$_n$(C$_{3-6}$ cycloalkyl),
—C(O)(CH$_2$)$_n$(C$_{6-10}$ aryl), —C(O)(CH$_2$)$_n$(5- to 10-membered heteroaryl),
—C(O)O(C$_{1-8}$ alkyl), —C(O)O(CH$_2$)$_n$(C$_{3-6}$ cycloalkyl), —C(O)O(CH$_2$)$_n$(C$_{6-10}$ aryl),
—C(O)O(CH$_2$)$_n$(5- to 10-membered heteroaryl), —C(O)O(CH$_2$)$_{2-4}$(C$_{1-4}$ alkyl),
—C(O)NH(C$_{1-8}$ alkyl), —C(O)NH(CH$_2$)$_n$(C$_{3-6}$ cycloalkyl),
—C(O)NH(CH$_2$)$_n$(C$_{6-10}$ aryl), —C(O)NH(CH$_2$)$_n$(5- to 10-membered heteroaryl),
—S(O)$_2$(C$_{1-8}$ alkyl), —S(O)$_2$(CH$_2$)$_n$(C$_{3-6}$ cycloalkyl), —S(O)$_2$(CH$_2$)$_n$(C$_{6-10}$ aryl),
—S(O)$_2$(CH$_2$)$_n$(5- to 10-membered heteroaryl), —(CR$^f$R$^f$)$_r$—C$_{3-10}$ carbocycle,
or —(CR$^f$R$^f$)$_r$-5- to 10-membered heterocycle; wherein said alkyl, cycloalkyl, phenyl, aryl, and carbocycle are substituted with 0-2 R$^b$, and said heteroaryl and heterocycle are substituted with 0-2 R$^b$ and comprise: carbon atoms and 1-4 heteroatoms selected from N, NR$^f$, O, and S(O)$_p$;

R$^{12}$ is, independently at each occurrence, H, C$_{1-6}$ alkyl, —C(O)(C$_{1-6}$ alkyl), —C(O)(CH$_2$)$_n$(C$_{6-10}$ aryl),
—C(O)(CH$_2$)$_n$(5- to 10-membered heteroaryl), —C(O)O(C$_{1-4}$ alkyl),
—C(O)OCH$_2$(C$_{6-10}$ aryl), —(CH$_2$)$_n$C(O)OCH$_2$(5- to 10-membered heteroaryl),
—(CH$_2$)$_n$OC(O)(C$_{1-4}$ alkyl), —(CH$_2$)$_n$OC(O)(C$_{6-10}$ aryl),
—(CH$_2$)$_n$OC(O)(5- to 10-membered heteroaryl),
—(CH$_2$)$_n$C(O)O(C$_{1-4}$ alkyl),
—(CH$_2$)$_n$C(O)O(C$_{6-10}$ aryl), —(CH$_2$)$_n$C(O)O(5- to 10-membered heteroaryl),
—(CH$_2$)$_n$C(O)NH(C$_{1-6}$ alkyl), —(CH$_2$)$_n$C(O)NH(C$_{6-10}$ aryl),
—(CH$_2$)$_n$C(O)NH(5- to 10-membered heteroaryl),
—(CH$_2$)$_t$OC(O)NH(C$_{1-6}$ alkyl), —(CH$_2$)$_t$OC(O)NH(C$_{6-10}$ aryl),
—(CH$_2$)$_t$OC(O)NH(5- to 10-membered heteroaryl),
—S(O)$_2$(C$_{1-6}$ alkyl),
—S(O)$_2$(CH$_2$)$_n$(C$_{6-10}$ aryl), —S(O)$_2$(CH$_2$)$_n$(5- to 10-membered heteroaryl),
—(CR$^f$R$^f$)$_n$—(C$_{6-10}$ aryl), or —(CR$^f$R$^f$)$_n$-5- to 10-membered heteroaryl; wherein said alkyl, and aryl are substituted with 0-2 R$^g$; and said heteroaryl is substituted with 0-2 R$^g$ and comprises: carbon atoms and 1-4 heteroatoms selected from N, NR$^{11}$, O, and S(O)$_p$;

R$^{13}$ is, independently at each occurrence, H, C$_{1-6}$ alkyl, or —(CH$_2$)$_n$-phenyl;

alternatively, R$^{12}$ and R$^{13}$, when attached to the same nitrogen, combine to form a 5- to 10-membered heterocyclic ring comprising: carbon atoms and 1-2 additional heteroatoms selected from N, NR$^{11}$, O, and S(O)$_p$;

R$^{14}$ is, independently at each occurrence, H, C$_{1-6}$ alkyl substituted with 0-2 R$^{14a}$, C$_{2-6}$ alkenyl substituted with 0-2 R$^{14a}$, C$_{2-6}$ alkynyl substituted with 0-2 R$^{14a}$, —(CH$_2$)$_r$—C$_{3-10}$ carbocycle substituted with 0-3 R$^g$, or —(CH$_2$)$_r$-5- to 10-membered heterocycle comprising: carbon atoms and 1-4 heteroatoms selected from N, NR$^{11}$, O, and S(O)$_p$, wherein said heterocycle is substituted with 0-3 R$^g$;

R$^{14a}$ is, independently at each occurrence, H, C$_{1-4}$ alkyl, OR$^f$, Cl, F, Br, I, =O, CF$_3$, CN, NO$_2$, —C(O)R$^f$, —C(O)OR$^f$, —C(O)NR$^{12}$R$^{13}$, or —S(O)$_p$R$^f$; R$^{16}$ is, independently at each occurrence, H, F, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, or —(CH$_2$)$_r$-phenyl substituted with 0-2 R$^b$;

R$^{17}$ is, independently at each occurrence, H, C$_{1-6}$ alkyl, or —(CH$_2$)$_n$-phenyl;

alternatively, R$^{16}$ and R$^{17}$ combine to form a 3- to 7-membered carbocyclic or heterocyclic ring comprising: carbon atoms and 0-2 heteroatoms selected from N, NR$^{11}$, O, and S(O)$_p$, 0-1 carbonyl, and 0-3 double bonds, wherein said carbocyclic or heterocyclic ring is substituted with 0-2 R$^b$;

R$^{18}$ is, independently at each occurrence, H, F, or C$_{1-6}$ alkyl;

R$^{19}$ is, independently at each occurrence, H, OH, —C(O)OR$^f$, or C$_{1-6}$ alkyl;

R$^a$ is, independently at each occurrence, F, OCF$_3$, CF$_3$, OR$^c$, SR$^c$, CN, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^b$ is, independently at each occurrence, H, =O, F, Cl, Br, I,

—(CH$_2$)$_r$—OR$^c$, SR$^c$, CN, NO$_2$, CF$_3$, OCF$_3$, —(CH$_2$)$_r$—NR$^{12}$R$^{13}$, —C(O)R$^c$,

—(CH$_2$)$_r$—C(O)OR$^c$, —(CH$_2$)$_r$—C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_{1-4}$ haloalkyl, C$_{1-4}$ haloalkyloxy-, C$_{1-4}$ alkyloxy-, C$_{1-4}$ alkylthio-, C$_{1-4}$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^c$ is, independently at each occurrence, H, —OP(O)(OEt)$_2$, C$_{1-8}$ alkyl substituted with 0-2 R$^e$, C$_{2-8}$ alkenyl substituted with 0-2 R$^e$, C$_{2-8}$ alkynyl substituted with 0-2 R$^e$, —(CR$^f$R$^f$)$_r$—C$_{3-8}$ cycloalkyl substituted with 0-2 R$^e$, —(CR$^f$R$^f$)$_r$—C$_{6-10}$ aryl substituted with 0-2 R$^e$, or —(CR$^f$R$^f$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^d$ is, independently at each occurrence, CF$_3$, OH, C$_{1-4}$ alkoxy,

C$_{1-6}$ alkyl, —(CH$_2$)$_r$—C$_{3-10}$ carbocycle substituted with 0-2 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^e$ is, independently at each occurrence, H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—OR$^h$, —(CF$_2$)$_r$CF$_3$, Si(Me)$_3$, Si(Me)$_2$(t-Bu), Si(C$_{1-4}$ alkyl)$_3$, C$_{1-8}$ alkyl substituted with 0-2 R$^g$, C$_{2-8}$ alkenyl substituted with 0-2 R$^g$, C$_{2-8}$ alkynyl substituted with 0-2 R$^g$, —(CH$_2$)$_r$—C$_{3-8}$ cycloalkyl substituted with 0-2 R$^g$, —(CH$_2$)$_r$—C$_{6-10}$ aryl substituted with 0-2 R$^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^g$;

R$^f$ is, independently at each occurrence, H, C$_{1-6}$ alkyl, or —(CH$_2$)$_n$-phenyl;

R$^g$ is, independently at each occurrence, H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, or C$_{2-6}$ alkynyl;

R$^h$ is, independently at each occurrence, C$_{1-6}$ alkyl substituted with 0-2 R$^g$, —(CH$_2$)$_n$-phenyl substituted with 0-2 R$^g$, or —(CH$_2$)$_n$-5- to 10-membered heterocycle comprising: carbon atoms and 1-4 heteroatoms selected from N, NR$^f$, O, and S(O)$_p$, wherein said heterocycle is substituted with 0-2 R$^g$;

R$^i$ is, independently at each occurrence, H, C$_{1-6}$ alkyl substituted with 0-2 R$^g$, —(CH$_2$)$_n$-phenyl substituted with 0-2 R$^g$, or —(CH$_2$)$_n$-5- to 10-membered heterocycle comprising: carbon atoms and 1-4 heteroatoms selected from N, NR$^f$, O, and S(O)$_p$, wherein said heterocycle is substituted with 0-2 R$^g$;

n, at each occurrence, is selected from 0, 1, 2, 3, and 4;

p, at each occurrence, is selected from 0, 1, and 2; and r, at each occurrence, is selected from 0, 1, 2, 3, and 4;

s, at each occurrence, is selected from 0, 1, 2, and 3; and t, at each occurrence, is selected from 1, 2, 3, and 4.

In a twentieth embodiment, the present invention provides a method for treating a thromboembolic disorder, comprising: administering to a patient in need thereof a therapeutically effective amount of a compound of Formula (II), within the scope of the nineteenth embodiment wherein:

X$_2$ is a bond, —CH$_2$—, —CH$_2$CH$_2$—, —CHMe—, —CH$_2$CHMe—, —CH$_2$CO—,

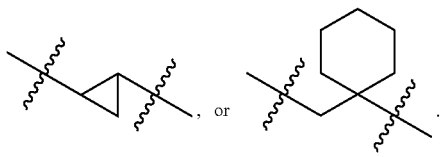

In a twenty first embodiment, the present invention provides a method for treating a thromboembolic disorder, comprising: administering to a patient in need thereof a therapeutically effective amount of a compound of Formula (II), within the scope of the nineteenth embodiment wherein:

Y is O, S, NH, —OCH$_2$—, —OCHMe—, —OCH(CO$_2$Me)—, —CH=CH—, or —CONH—.

In a twenty second embodiment, the present invention provides a method for treating a thromboembolic disorder, comprising: administering to a patient in need thereof a therapeutically effective amount of a compound of Formula (II), within the scope of the sixteenth embodiment wherein:

W is O; and

Y is O, S, or NH.

In a twenty third embodiment, the present invention provides a method for treating a thromboembolic disorder, comprising: administering to a patient in need thereof a therapeutically effective amount of a compound of Formula (II), within the scope of the nineteenth embodiment wherein:

ring A is substituted with 0-5 R$^1$ and selected from: phenyl, pyridinyl, pyrimidinyl, furanyl, isoxazolyl, thiazolyl, thiadiazolyl, benzothiazolyl, indolyl, and benzimidazolyl.

In a twenty fourth embodiment, the present invention provides a method for treating a thromboembolic disorder, comprising: administering to a patient in need thereof a therapeutically effective amount of a compound of Formula (II), within the scope of the nineteenth embodiment wherein:

ring A is substituted with 0-5 $R^1$ and selected from:

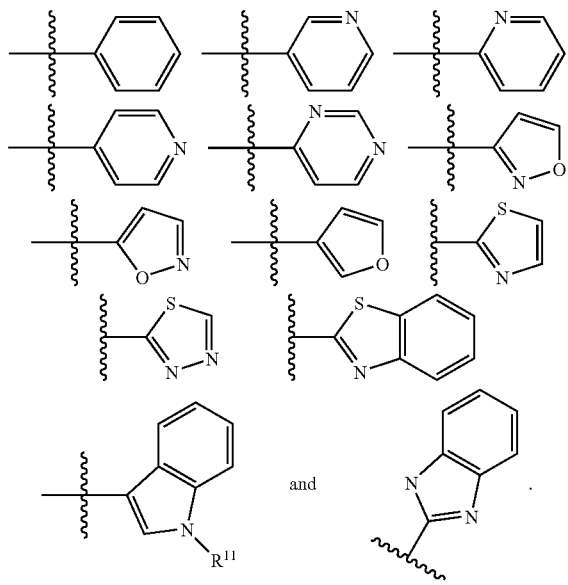

and

In a twenty fifth embodiment, the present invention provides a method for treating a thromboembolic disorder, comprising: administering to a patient in need thereof a therapeutically effective amount of a compound of Formula (II), within the scope of the nineteenth embodiment wherein:
ring B is substituted with 0-3 $R^7$ and selected from:

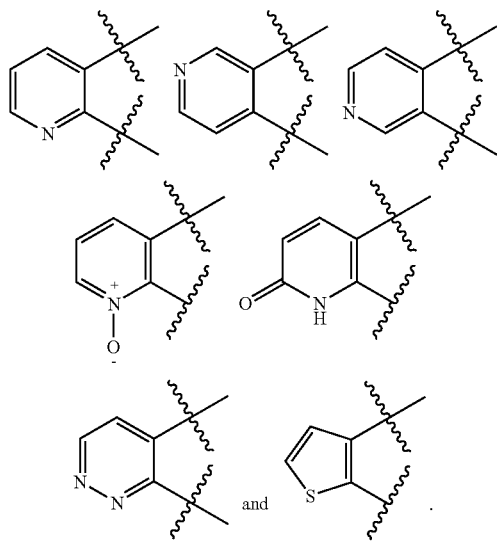

and

In a twenty sixth embodiment, the present invention provides a method for treating a thromboembolic disorder, comprising: administering to a patient in need thereof a therapeutically effective amount of a compound of Formula (II), within the scope of the nineteenth embodiment wherein:
$R^1$ is, independently at each occurrence, F, Cl, Br, I, $CF_3$, $-CF_2CF_3$, $OCF_3$, $-OCF_2CF_2H$, $-OCF_2CF_3$, $SiMe_3$, $-(CR^fR^f)_r-OR^c$, $SR^c$, CN, $NO_2$, $-(CR^fR^f)_r-NR^{12}R^{13}$, $-(CR^fR^f)_r-C(O)R^c$, $-(CR^fR^f)_r-CO_2R^c$, $-(CR^fR^f)_r-C(O)NR^{12}R^{13}$ $-OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-13}$ carbocycle substituted with 0-5 $R^b$, or $-(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;
alternatively, two $R^1$s on two adjacent carbon atoms are combined with the carbon atoms to which they attached, form a 5- to 7-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$.

In a twenty seventh embodiment, the present invention provides a method for treating a thromboembolic disorder, comprising: administering to a patient in need thereof a therapeutically effective amount of a compound of Formula (II), within the scope of the nineteenth embodiment wherein:
$R^6$ is $-(CH_2)_n$-phenyl substituted with 0-3 $R^{6a}$ or $-(CH_2)_n$-pyridyl substituted with 0-3 $R^{6a}$; and
$R^{6a}$ is, independently at each occurrence, F, Cl, Br, I, $-(CR^iR^i)_r-OR^c$, $SR^c$, CN, $CF_3$, $OCF_3$, $-CF_2CF_3$, $-OCF_2CF_2H$, $-OCF_2CF_3$, $-NR^{12}R^{13}$, $-C(O)R^c$, Si$(Me)_3$, Si$(C_{1-4}$ alkyl$)_3$, $C_{1-4}$ haloalkyl, $C_{1-4}$ haloalkyloxy-, $C_{1-4}$ alkyloxy-, $C_{1-4}$ alkylthio-, $C_1$-$C_4$ alkyl-C(O)—, $C_{1-4}$ alkyl-O—C(O)—, $C_{1-4}$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, $-(CR^fR^f)_r-C_{3-10}$ carbocycle substituted with 0-2 $R^e$, or $-(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$;
alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$.

In a twenty eighth embodiment, the present invention provides a method for treating a thromboembolic disorder, comprising: administering to a patient in need thereof a therapeutically effective amount of a compound of Formula (II), within the scope of the nineteenth embodiment wherein:
$R^{11}$ is, independently at each occurrence, H, $C_{1-4}$ alkoxy, $C_{1-8}$ alkyl substituted with 0-2 $R^a$, $-C(O)(C_{1-6}$ alkyl), $-C(O)(CH_2)_n(C_{3-6}$ cycloalkyl), $-C(O)(CH_2)_n$phenyl, $-C(O)O(C_{1-8}$ alkyl), $-C(O)O(CH_2)_n(C_{3-6}$ cycloalkyl), $-C(O)O(CH_2)_n$phenyl, $-C(O)O(CH_2)_{2-4}(C_{1-4}$ alkyl), $-C(O)NH(C_{1-6}$ alkyl), $-S(O)_2(C_{1-6}$ alkyl), $-S(O)_2(CH_2)_n$ phenyl, $-(CR^fR^f)_r-C_{3-10}$ carbocycle, or $-(CR^fR^f)_r$-5- to 10-membered heterocycle; wherein said alkyl, cycloalkyl, phenyl, and carbocycle are substituted with 0-2 $R^b$, and said heterocycle is substituted with 0-2 $R^b$ and comprises: carbon atoms and 1-4 heteroatoms selected from N, $NR^f$, O, and $S(O)_p$.

In a twenty ninth embodiment, the present invention provides a method for treating a thromboembolic disorder, comprising: administering to a patient in need thereof a therapeutically effective amount of a compound of Formula (II), within the scope of the nineteenth embodiment wherein:

ring A is substituted with 0-5 R¹ and selected from:

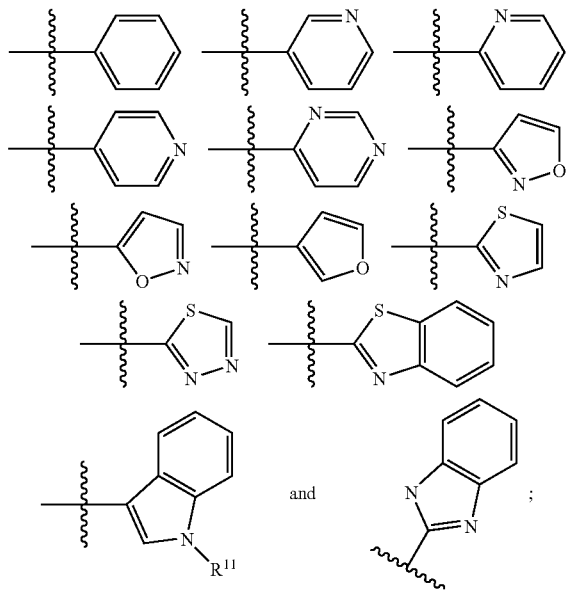

and ring B is substituted with 0-3 R⁷ and selected from:

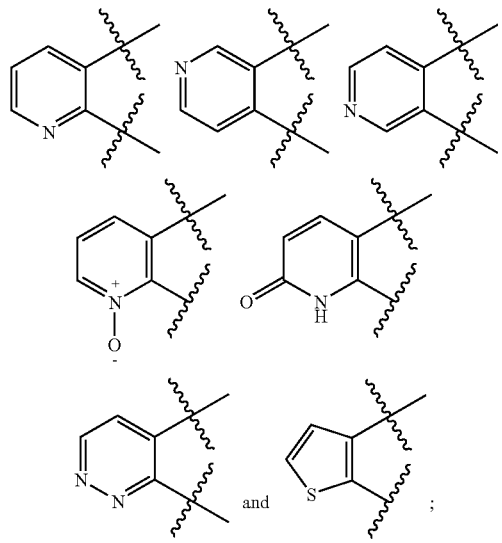

and ;

W is O;

X₂ is a bond, —CH₂—, —CH₂CH₂—, —CHMe—, —CH₂CHMe—, —CH₂CO—,

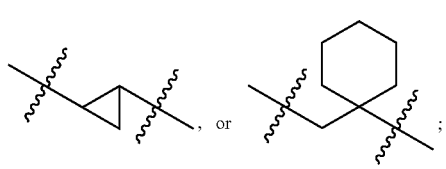

, or ;

Y is O, S, NH, —OCH₂—, —OCHMe—, —OCH(CO₂Me)—, —CH=CH—, or —CONH—;

R¹ is, independently at each occurrence, F, Cl, Br, I, CF₃, —CF₂CF₃, OCF₃, —OCF₂CF₂H, —OCF₂CF₃, SiMe₃, —(CR$^f$R$^f$)$_r$—OR$^c$, SR$^c$, CN, NO₂, —(CR$^f$R$^f$)$_r$—NR$^{12}$R$^{13}$, —(CR$^f$R$^f$)$_r$—C(O)R$^c$, —(CR$^f$R$^f$)$_r$—CO₂R$^c$, —(CR$^f$R$^f$)$_r$—C(O)NR$^{12}$R$^{13}$, —OP(O)(OEt)₂, 4,4,5,5-tetramethyl-1,3,2-dioxaborolanyl, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-13}$ carbocycle substituted with 0-5 R$^b$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-5 R$^b$;

alternatively, two R¹'s on two adjacent carbon atoms are combined with the carbon atoms to which they attached, form a 5- to 7-membered carbocycle or heterocycle comprising: carbon atoms and 0-3 additional heteroatoms selected from N, NR$^{11}$, O, and S(O)$_p$, and 0-2 carbonyl groups, wherein said carbocycle or heterocycle is substituted with 0-4 R$^b$;

R⁶ is —(CH₂)$_n$-phenyl substituted with 0-3 R$^{6a}$ or —(CH₂)$_n$-pyridyl substituted with 0-3 R$^{6a}$;

R$^{6a}$ is, independently at each occurrence, F, Cl, Br, I, —(CR$^f$R$^i$)$_r$—OR$^c$, SR$^c$, CN, CF₃, OCF₃, —NR$^{12}$R$^{13}$, —C(O)R$^c$, Si(Me)₃, Si(C$_{1-4}$ alkyl)₃, C$_{1-4}$ haloalkyl, C$_{1-4}$ haloalkyloxy-, C$_{1-4}$ alkyloxy-, C$_{1-4}$ alkylthio-, C$_1$-C$_4$ alkyl-C(O)—, C$_{1-4}$ alkyl-O—C(O)—, C$_{1-4}$ alkyl-C(O)NH—, C$_{1-8}$ alkyl substituted with 0-2 R$^a$, C$_{2-8}$ alkenyl substituted with 0-2 R$^a$, C$_{2-8}$ alkynyl substituted with 0-2 R$^a$, —(CR$^f$R$^f$)$_r$—C$_{3-10}$ carbocycle substituted with 0-2 R$^e$, or —(CR$^f$R$^f$)$_r$-5- to 10-membered heterocycle comprising: carbon atoms and 1-4 heteroatoms selected from N, NR$^{11}$, O, and S(O)$_p$, wherein said heterocycle is substituted with 0-2 R$^e$;

alternatively, when two R$^{6a}$ groups are attached to adjacent atoms, together with the atoms to which they are attached they form a 5- to 7-membered carbocyclic or heterocyclic ring comprising: carbon atoms and 0-2 heteroatoms selected from N, NR$^{11}$, O, and S(O)$_p$, 0-1 carbonyl and 0-3 ring double bonds, wherein said carbocyclic or heterocyclic ring is substituted with 0-2 R$^b$; and R$^{11}$ is, independently at each occurrence, H, C$_{1-4}$ alkoxy, C$_{1-8}$ alkyl substituted with 0-2 R$^a$, —C(O)(C$_{1-6}$ alkyl), —C(O)(CH₂)$_n$(C$_{3-6}$ cycloalkyl), —C(O)(CH₂)$_n$phenyl, —C(O)O(C$_{1-8}$ alkyl), —C(O)O(CH₂)$_n$(C$_{3-6}$ cycloalkyl), —C(O)O(CH₂)$_n$phenyl, —C(O)O(CH₂)$_{2-4}$(C$_{1-4}$ alkyl), —C(O)NH(C$_{1-6}$ alkyl), —S(O)₂(C$_{1-6}$ alkyl), —S(O)₂(CH₂)$_n$phenyl, —(CR$^f$R$^f$)$_r$—C$_{3-10}$ carbocycle, or —(CR$^f$R$^f$)$_r$-5- to 10-membered heterocycle; wherein said alkyl, cycloalkyl, phenyl, and carbocycle are substituted with 0-2 R$^b$, and said heterocycle is substituted with 0-2 R$^b$ and comprises: carbon atoms and 1-4 heteroatoms selected from N, NR$^f$, O, and S(O)$_p$.

In a thirtieth embodiment, the present invention provides a method for treating a thromboembolic disorder, comprising: administering to a patient in need thereof a therapeutically effective amount of a compound of Formula (Ia):

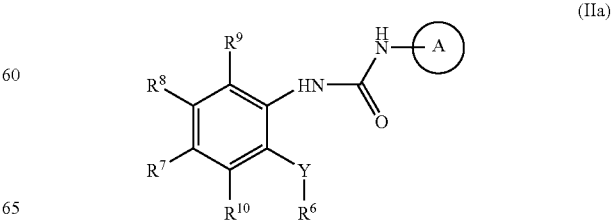

(IIa)

or a stereoisomer or pharmaceutically acceptable salts, solvates, or prodrugs thereof, wherein:

ring A is

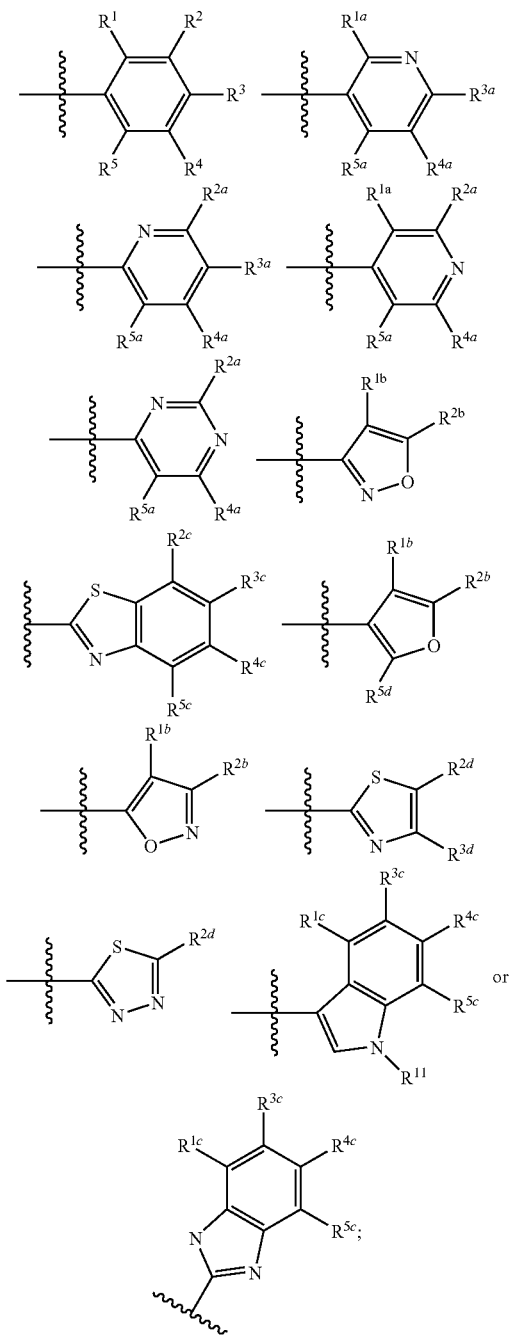

Y is O, S, or NH;

$R^1$, $R^{1a}$, $R^{1b}$, and $R^{1c}$ are, independently at each occurrence, H, F, Cl, Me, or OH;

$R^2$, $R^{2a}$, $R^{2b}$, $R^{2c}$, $R^{2d}$ and $R^{3d}$ are, independently at each occurrence, H, F, Cl, Br, Me, t-Bu, OMe, OBu, pentoxy, isopentoxy, neohexoxy, —O(CH$_2$)$_2$OMe, —O(CH$_2$)$_2$O(i-Pr), —O(CH$_2$)$_8$CO$_2$Me, —O(CH$_2$)$_2$C(Me)$_2$OMe, —O(CH$_2$)$_2$NMe$_2$, —OCH$_2$C(Me)$_2$CH$_2$NMe$_2$, —O(CH$_2$)$_2$OCOMe, —OCH(Et)CH$_2$OMe, —OCH(Me)CH$_2$O(t-Bu), NO$_2$, CF$_3$, OCF$_3$, 2-CH$_2$N(Me)$_2$-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe$_2$-benzoxy, 2-CF$_3$-benzoxy, 3-OCF$_3$-benzoxy, 4-OCF$_3$-benzoxy, 4-CO$_2$Me-benzoxy, 4-NHCOMe-benzoxy, 4-Ph-benzoxy, (2-naphthyl)methoxy, (1-Bn-pyrrolidin-3-yl)oxy, Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl) methoxy, (1H-pyrrol-1-yl)ethoxy, (2-Bu-1H-imidazol-4-yl) methoxy, Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl) ethoxy, or —OCH(Et)(pyridine-4-yl);

$R^3$, $R^{3a}$, $R^{3c}$, $R^4$, $R^{4a}$, $R^{4c}$, $R^5$, $R^{5a}$, $R^{5c}$, and $R^{5d}$, are, independently at each occurrence, H, F, Cl, Br, —OCH(Me)CH$_2$O-t-Bu, CF$_3$, OCHF$_2$, OCF$_3$, —O(CH$_2$)$_2$OMe, —O(CH$_2$)$_3$NMe$_2$, —O(CH$_2$)$_4$NMe$_2$, —OCH(Et)CH$_2$OMe, CN, NH$_2$, NMe$_2$, —CH$_2$NMe$_2$, NEt$_2$, —NHPh, —N(Me)Ph, —NH(4-OMe-Ph), —NH(2-CF$_3$-Ph), —CH(Me)NHCH (Me)Ph, —CH(Me)N(Me)(3-CF$_3$-Bn), —CH(Me)N(Me) (furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH (Me)O(1-Bn-pyrrolidin-3-ylmethyl), —CH(Me)OCH$_2$C (Me)$_2$CH$_2$NMe$_2$, —CH(Me)OBn, —CH(Me)O(4-i-Pr-Bn), —CH(Me)O(4-OPh-Bn), —CH(Me)O(3,5-diCl-Bn), —CH (Me)OCH$_2$(1-Bn-piperidin-4-yl), —CH$_2$NHBn, —CH$_2$NH (4-CF$_3$-Bn), —CH$_2$N(Me)Bn, —CH(Me)NHCH$_2$-pyridin-2-yl, —CH(Me)NHCH$_2$-pyridin-4-yl, —CH(Me)NHCH$_2$(6-Cl-pyridin-3-yl), —CH(Me)N(Me)(i-Bu), —CH(Me)N(Me) Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3,4-diCl-Bn), —CH(Me)N(Me) CH$_2$CH$_2$Ph, —CH(Me)N(Me)CH$_2$-pyridin-2-yl, —CH(Me) N(Me)CH$_2$-pyridin-3-yl, —CH(Me)N(Me)CH$_2$-pyridin-4-yl, —CH(Me)N(Me)CH$_2$-furan-2-yl, —CH(Me)N(Me) CH$_2$-thien-2-yl, —CH(Me)N(Me)CH$_2$-(5-Me-thien-2-yl), —CH(Me)N(Me)CH$_2$-(5-Cl-thien-2-yl), —CH(Me)N(Et) Bn, —CH(Me)N(Et)(4-Me-Bn), —CH(Me)N(Et)(2-Cl-Bn), —CH(Me)N(Bn)CH$_2$CN, —CH(Me)N(Bn)CH$_2$CH$_2$OH, —CH(Me)N(Bn)CH$_2$CO$_2$Me, —CH(Me)N(Bn) CH$_2$CONMe$_2$, —CH(Me)N(Bn)CH$_2$CON(Me)(Bn), —CH (Me)-isoindolin-2-yl, —CH(Me)-(1,2,3,4-tetrahydroisoquinolin-2-yl), —CH(Me)(4-Bn-piperazin-1-yl), —C(CF$_3$)$_2$ OH, —COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$ OMe, —O(CH$_2$)$_2$OCOMe, —OCH$_2$C(Me)$_2$CH$_2$NMe$_2$, Ph, 2-CH$_2$OH-Ph, 2-CH$_2$N(Me)-2-Ph, 3-CH$_2$N(Me)-2-Ph, 4-CH$_2$N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 2-OMe-benzoxy, 3-CN-benzoxy, 4-CN-benzoxy, 3-NMe$_2$-benzoxy, 4-CO$_2$Me-benzoxy, 3-CF$_3$-benzoxy, 3-OCF$_3$-benzoxy, 4-OCF$_3$-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, Bn-pyrrolidin-3-oxy, (1-Bn-pyrrolidin-3-yl)methoxy, (furan-2-yl) methoxy, (furan-3-yl)methoxy, (tetrahydrofuran-3-yl) methoxy, (thien-3-yl)methoxy, thiazol-2-yl, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, Bu-1H-imidazol-4-yl)methoxy, 1H-1,2,4-triazol-1-yl, Ph-1H-1,2,3-triazol-4-yl)methoxy, 2-(1H-pyrrol-1-yl)-ethoxy, 1-piperidinyl, Bn-piperazin-4-yl, (2,2-dimethyl-1,3-dioxolan-4-yl)-methoxy, Bn-piperidin-3-oxy, 1-Bn-piperidin-4- oxy, (1-(i-Bu)-piperidin-4-yl)methoxy, isopentyl-piperidin-4-yl)methoxy, (1-CO₂(t-Bu)-piperidin-4-yl)methoxy, CO₂Bn-piperidin-4-yl)methoxy, (1-Bn-piperidin-4-yl)methoxy, phenethyl-piperidin-4-yl)methoxy, (1-(4-phenylbutyl)-piperidin-4-yl)methoxy, cyclohexylmethyl-piperidin-4-yl) methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl) methoxy, 4,4,5,5-tetramethyl-1,3,2-dioxaborolanyl, —OP(O)(OEt)₂, $C_{1-6}$ alkyl, $C_{1-6}$ alkoxy, or $C_{3-6}$ cycloalkyl optionally substituted with the group selected from: —CO₂Me, —CH₂OH, and —CH₂OMe;

alternatively, $R^1+R^2$, $R^2+R^3$, $R^3+R^4$, $R^4+R^5$, $R^{1a}+R^{2a}$, $R^{2a}+R^{3a}$, $R^{3a}+R^{4a}$, $R^{4a}+R^{5a}$, $R^{1b}+R^{2b}$, $R^{1c}+R^{3c}$, $R^{2c}+R^{3c}$, $R^{2d}+R^{3d}$, $R^{3c}+R^{4c}$, or $R^{4c}+R^{5c}$, combine with the carbon atoms to which they attached, form 5- to 10-membered carbocyclic or heterocyclic ring comprising: carbon atoms and 0-3 heteroatoms selected from N, $NR^{11}$, O, and $S(O)_p$, 0-1 carbonyl group, and additional 0-3 double bonds, wherein said carbocyclic or heterocyclic ring is substituted with 0-2 $R^b$;

$R^6$ is —(CH₂)$_n$-phenyl substituted with 0-3 $R^{6a}$ or —(CH₂)$_n$-pyridyl substituted with 0-3 $R^{6a}$;

$R^{6a}$ is, independently at each occurrence, H, F, Cl, Br, I, CN, —C(Me)₂CN, $C_{1-8}$ alkyl, $C_{2-8}$ alkenyl, OH, SMe, S(i-Pr), —C(Me)₂OMe, —C(Me)₂OEt, —C(Me)₂OPr, —CHMeO(CH₂)₂OMe, —C(Me)₂OBu, —C(Me)₂O(CH₂)₂OMe, —C(Me)(OMe)CH₂OMe, —C(Me)₂O(CH₂)₂N(i-Bu)₂, —C(Me)₂O(CH₂)₂S(i-Bu), —C(Me)₂O(CH₂)₂S(O)(i-Bu), —C(Me)₂O(CH₂)₂S(furan-2-ylmethyl), —C(Me)₂O(CH₂)₂S(pyridin-2-yl), —C(Me)₂O(CH₂)₂S(O)₂(pyridin-2-yl), —C(Me)₂CH₂OSi(Me)₂(t-Bu), —C(Me)₂O(CH₂)₂Si(Me)₂(t-Bu), —C(Et)₂OH, —C(Pr)₂OH, —C(CH₂CH=CH₂)₂OH, —C(CH₂CH=CH₂)₂OMe, —C(Et)₂OMe, —C(Et)₂OEt, —C(Et)₂OPr, COMe, COPh, CO₂Me, CO₂Et, —NH(i-Bu), —CH=CHCO₂(t-Bu), —OCH₂CO₂(t-Bu), CF₃, OCF₃, $C_{1-4}$ alkyloxy, $C_{3-7}$ cycloalkyl, $C_{3-7}$ cycloalkenyl, Ph, Bn, naphthyl, 1-pyrrolidinyl, 5-isoxazolyl, N-morpholinyl, 4-Bn-piperazinyl, 1-piperidinyl, 1-Bn-piperidin-4-yl, 1-i-Bu-piperidin-4-yl, 1-neopentyl-piperidin-4-yl, 1-COPh-piperidin-4-yl, —SiMe₃,

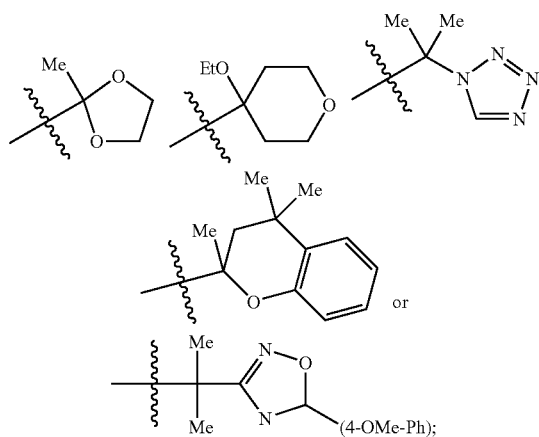

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is H, Me, Cl, Br, CN, OH, OMe, SMe, NHMe, NMe₂, CO₂Me, imidazol-1-yl, or —CH₂NH(CO)H;

$R^8$ is H, Me, Cl, Br, CN, or CF₃;

$R^9$ is H or Me;

$R^{10}$ is H or Me;

$R^{11}$ is, independently at each occurrence, H, $C_{1-6}$ alkyl, OMe, —C(O)($C_{1-6}$ alkyl), —C(O)phenyl, —C(O)benzyl, —C(O)O($C_{1-16}$ alkyl), —C(O)Obenzyl, —S(O)₂($C_{1-6}$ alkyl), —S(O)₂phenyl, —S(O)₂benzyl, cyclohexylmethyl, phenyl, benzyl, phenethyl, phenylpropyl, —CH₂CH(Me)Ph, 1H-pyrrol-2-ylmethyl, Me-pyrrol-2-ylmethyl, thieny-2-ylmethyl, furan-2-ylmethyl, furan-3-ylmethyl, 2-F-Bn, 2-OH-Bn, 2-CN-Bn, 3-CN-Bn, 4-CN-Bn, 4-OMe-Bn, 4-CO₂Me-Bn,

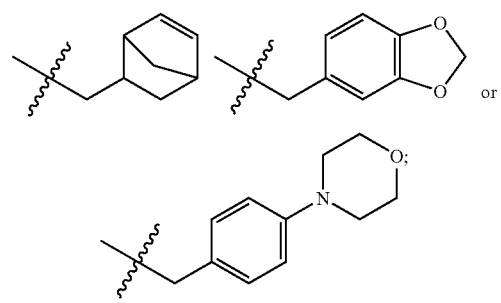

n, at each occurrence, is selected from 0, 1, and 2, and p, at each occurrence, is selected from 0, 1, and 2.

In a thirty first embodiment, the present invention provides a method for treating a thromboembolic disorder, comprising: administering to a patient in need thereof a therapeutically effective amount of a compound of Formula (IIb):

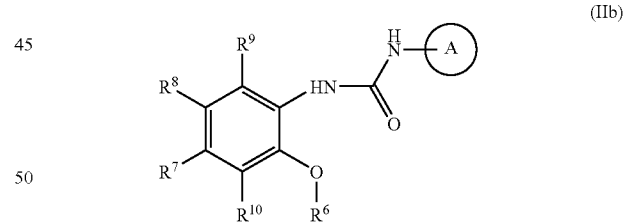

or a stereoisomer or pharmaceutically acceptable salts, solvates, or prodrugs thereof, wherein:

A is

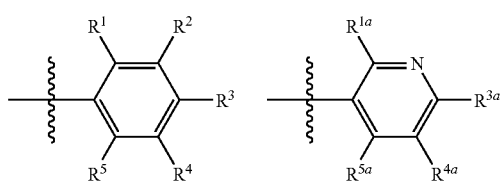

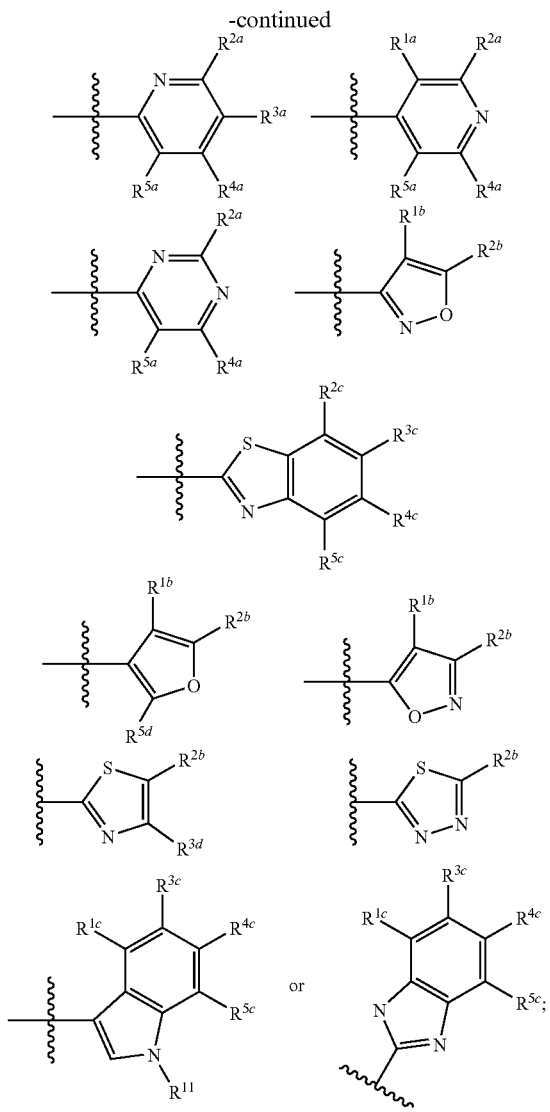

$R^1$, $R^{1a}$, $R^{1b}$, and $R^{1c}$ are, independently at each occurrence, H, F, Cl, or OH;

$R^2$, $R^{2a}$, $R^{2b}$, $R^{2c}$, $R^{2d}$ and $R^{3d}$ are, independently at each occurrence, H, F, Cl, Br, Me, t-Bu, OMe, OBu, pentoxy, isopentoxy, neohexoxy, —O(CH$_2$)$_2$OMe, —O(CH$_2$)$_2$O(i-Pr), —O(CH$_2$)$_8$CO$_2$Me, —O(CH$_2$)$_2$C(Me)$_2$OMe, —O(CH$_2$)$_2$NMe$_2$, —OCH$_2$C(Me)$_2$CH$_2$NMe$_2$, —O(CH$_2$)$_2$OCOMe, —OCH(Et)CH$_2$OMe, —OCH(Me)CH$_2$O(t-Bu), NO$_2$, CF$_3$, OCF$_3$, 2-CH$_2$N(Me)$_2$-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe$_2$-benzoxy, 2-CF$_3$-benzoxy, 3-OCF$_3$-benzoxy, 4-OCF$_3$-benzoxy, 4-CO$_2$Me-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl)ethoxy, or —OCH(Et)(pyridine-4-yl);

$R^3$, $R^{3a}$, $R^{3c}$, $R^4$, $R^{4a}$, $R^{4c}$, $R^5$, $R^{5a}$, $R^{5c}$, and $R^{5d}$, are, independently at each occurrence, H, F, Cl, Br, —OCH(Me)CH$_2$O-t-Bu, CF$_3$, OCHF$_2$, OCF$_3$, —O(CH$_2$)$_2$OMe, —O(CH$_2$)$_3$NMe$_2$, —O(CH$_2$)$_4$NMe$_2$, —OCH(Et)CH$_2$OMe, CN, NH$_2$, NMe$_2$, —CH$_2$NMe$_2$, NEt$_2$, —NHPh, —N(Me)Ph, —NH(4-OMe-Ph), —NH(2-CF$_3$-Ph), —CH(Me)NHCH(Me)Ph, —CH(Me)N(Me)(3-CF$_3$-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH(Me)O(1-Bn-pyrrolidin-3-ylmethyl), —CH(Me)OCH$_2$C(Me)$_2$CH$_2$NMe$_2$, —CH(Me)OBn, —CH(Me)O(4-i-Pr-Bn), —CH(Me)O(4-OPh-Bn), —CH(Me)O(3,5-diCl-Bn), —CH(Me)OCH$_2$(1-Bn-piperidin-4-yl), —CH$_2$NHBn, —CH$_2$NH(4-CF$_3$-Bn), —CH$_2$N(Me)Bn, —CH(Me)NHCH$_2$-pyridin-2-yl, —CH(Me)NHCH$_2$-pyridin-4-yl, —CH(Me)NHCH$_2$(6-Cl-pyridin-3-yl), —CH(Me)N(Me)(i-Bu), —CH(Me)N(Me)Bn, —CH(Me)N(Me)(4-OMe-Bn), —CH(Me)N(Me)(4-F-Bn), —CH(Me)N(Me)(3-Cl-Bn), —CH(Me)N(Me)(4-Cl-Bn), —CH(Me)N(Me)(3,4-diCl-Bn), —CH(Me)N(Me)CH$_2$CH$_2$Ph, —CH(Me)N(Me)CH$_2$-pyridin-2-yl, —CH(Me)N(Me)CH$_2$-pyridin-3-yl, —CH(Me)N(Me)CH$_2$-pyridin-4-yl, —CH(Me)N(Me)CH$_2$-furan-2-yl, —CH(Me)N(Me)CH$_2$-thien-2-yl, —CH(Me)N(Me)CH$_2$-(5-Me-thien-2-yl), —CH(Me)N(Me)CH$_2$-(5-Cl-thien-2-yl), —CH(Me)N(Et)Bn, —CH(Me)N(Et)(4-Me-Bn), —CH(Me)N(Et)(2-Cl-Bn), —CH(Me)N(Bn)CH$_2$CN, —CH(Me)N(Bn)CH$_2$CH$_2$OH, —CH(Me)N(Bn)CH$_2$CO$_2$Me, —CH(Me)N(Bn)CH$_2$CONMe$_2$, —CH(Me)N(Bn)CH$_2$CON(Me)(Bn), —CH(Me)-isoindolin-2-yl, —CH(Me)-(1,2,3,4-tetrahydroisoquinolin-2-yl), —CH(Me)(4-Bn-piperazin-1-yl), —C(CF$_3$)$_2$OH, —COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)-2-Ph, 3-CH$_2$N(Me)-2-Ph, 4-CH$_2$N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 2-OMe-benzoxy, 3-CN-benzoxy, 4-CN-benzoxy, 3-NMe$_2$-benzoxy, 4-CO$_2$Me-benzoxy, 3-CF$_3$-benzoxy, 3-OCF$_3$-benzoxy, 4-OCF$_3$-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO$_2$(t-Bu)-piperidin-4-yl)methoxy, (1-CO$_2$Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 4,4,5,5-tetramethyl-1,3,2-dioxaborolanyl, —OP(O)(OEt)$_2$, C$_{1-6}$ alkyl, C$_{1-6}$ alkoxy, or $C_{3-6}$ cycloalkyl optionally substituted with the group selected from: —$CO_2Me$, —$CH_2OH$, and —$CH_2OMe$;

$R^4$, $R^{4a}$, $R^5$, $R^{5a}$, $R^{5c}$, and $R^{5d}$, are, independently at each occurrence, H, F, Cl, Me, or OMe;

alternatively, $R^1+R^2$, $R^2+R^3$, $R^3+R^4$, $R^4+R^5$, $R^{1a}+R^{2a}$, $R^{2a}+R^{3a}$, $R^{3a}+R^{4a}$, $R^{4a}+R^{5a}$, $R^{1b}+R^{2b}$, $R^{1c}+R^{3c}$, $R^{2c}+R^{3c}$, $R^{2d}+R^{3d}$, $R^{3c}+R^{4c}$, or $R^{4c}+R^{5c}$, combine with the carbon atoms to which they attached, form 5- to 10-membered carbocyclic or heterocyclic ring comprising: carbon atoms and 0-3 heteroatoms selected from N, $NR^{11}$, O, and $S(O)_p$, 0-1 carbonyl group, and additional 0-3 double bonds, wherein said carbocyclic or heterocyclic ring is substituted with 0-2 $R^b$;

$R^6$ is —$(CH_2)_n$-phenyl substituted with 0-3 $R^{6a}$ or —$(CH_2)_n$-pyridyl substituted with 0-3 $R^{6a}$;

$R^{6a}$ is, independently at each occurrence, H, F, Cl, Br, I, CN, —$C(Me)_2CN$, $C_{1-8}$ alkyl, $C_{2-8}$ alkenyl, OH, SMe, S(i-Pr), —$C(Me)_2OMe$, —$C(Me)_2OEt$, —$C(Me)_2OPr$, —$CHMeO(CH_2)_2OMe$, —$C(Me)_2OBu$, —$C(Me)_2O(CH_2)_2OMe$, —$C(Me)(OMe)CH_2OMe$, —$C(Me)_2O(CH_2)_2N(i-Bu)_2$, —$C(Me)_2O(CH_2)_2S(i-Bu)$, —$C(Me)_2O(CH_2)_2S(O)(i-Bu)$, —$C(Me)_2O(CH_2)_2S(furan-2-ylmethyl)$, —$C(Me)_2O(CH_2)_2S(pyridin-2-yl)$, —$C(Me)_2O(CH_2)_2S(O)_2(pyridin-2-yl)$, —$C(Me)_2CH_2OSi(Me)_2(t-Bu)$, —$C(Me)_2O(CH_2)_2Si(Me)_2(t-Bu)$, —$C(Et)_2OH$, —$C(Pr)_2OH$, —$C(CH_2CH=CH_2)_2OH$, —$C(CH_2CH=CH_2)_2OMe$, —$C(Et)_2OMe$, —$C(Et)_2OEt$, —$C(Et)_2OPr$, COMe, COPh, $CO_2Me$, $CO_2Et$, —NH(i-Bu), —CH=$CHCO_2(t-Bu)$, —$OCH_2CO_2(t-Bu)$, $CF_3$, $OCF_3$, $C_{1-4}$ alkyloxy, $C_{3-7}$ cycloalkyl, $C_{3-7}$ cycloalkenyl, Ph, Bn, naphthyl, 1-pyrrolidinyl, 5-isoxazolyl, N-morpholinyl, 4-Bn-piperazinyl, 1-piperidinyl, 1-Bn-piperidin-4-yl, 1-i-Bu-piperidin-4-yl, 1-neopentyl-piperidin-4-yl, 1-COPh-piperidin-4-yl, —$SiMe_3$,

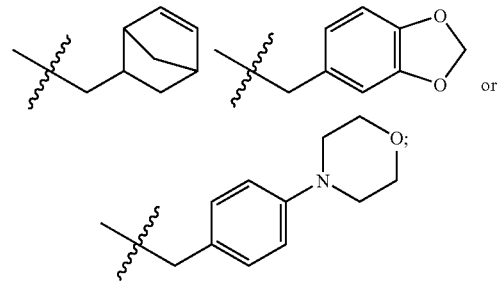

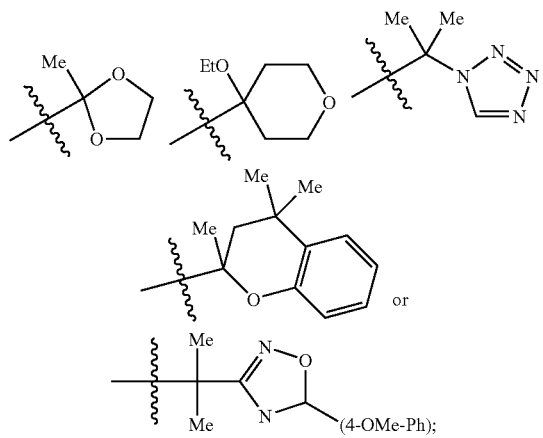

alternatively, when two $R^{6a}$ groups are attached to adjacent atoms, together with the atoms to which they are attached they form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is H, Me, Cl, Br, CN, OH, OMe, SMe, NHMe, $NMe_2$, $CO_2Me$, imidazol-1-yl, or —$CH_2NH(CO)H$;

$R^8$ is H, Me, Cl, Br, CN, or $CF_3$;

$R^9$ is H or Me;

$R^{10}$ is H or Me;

$R^{11}$ is, independently at each occurrence, H, $C_{1-6}$ alkyl, OMe, —$C(O)(C_{1-6}$ alkyl), —$C(O)$phenyl, —$C(O)$benzyl, —$C(O)O(C_{1-16}$ alkyl), —$C(O)O$benzyl, —$S(O)_2(C_{1-6}$ alkyl), —$S(O)_2$phenyl, —$S(O)_2$benzyl, cyclohexylmethyl, phenyl, benzyl, phenethyl, phenylpropyl, —$CH_2CH(Me)Ph$, 1H-pyrrol-2-ylmethyl, 1-Me-pyrrol-2-ylmethyl, thieny-2-ylmethyl, furan-2-ylmethyl, furan-3-ylmethyl, 2-F-Bn, 2-OH-Bn, 2-CN-Bn, 3-CN-Bn, 4-CN-Bn, 4-OMe-Bn, 4-$CO_2$Me-Bn, $R^b$ is, independently at each occurrence, H, F, Cl, Br, $C_{1-4}$ alkyl, OH, $CO_2H$, $NH_2$, $CF_3$, $OCF_3$, $C_{1-4}$ alkyloxy, $C_{3-7}$ cycloalkyl, phenyl, or benzyl;

n, at each occurrence, is selected from 0, 1, and 2; and p, at each occurrence, is selected from 0, 1, and 2.

In a thirty second embodiment, the present invention provides a method for treating a thromboembolic disorder, comprising: administering to a patient in need thereof a therapeutically effective amount of a compound of Formula (IIb), within the scope of the thirty first wherein:

ring A is

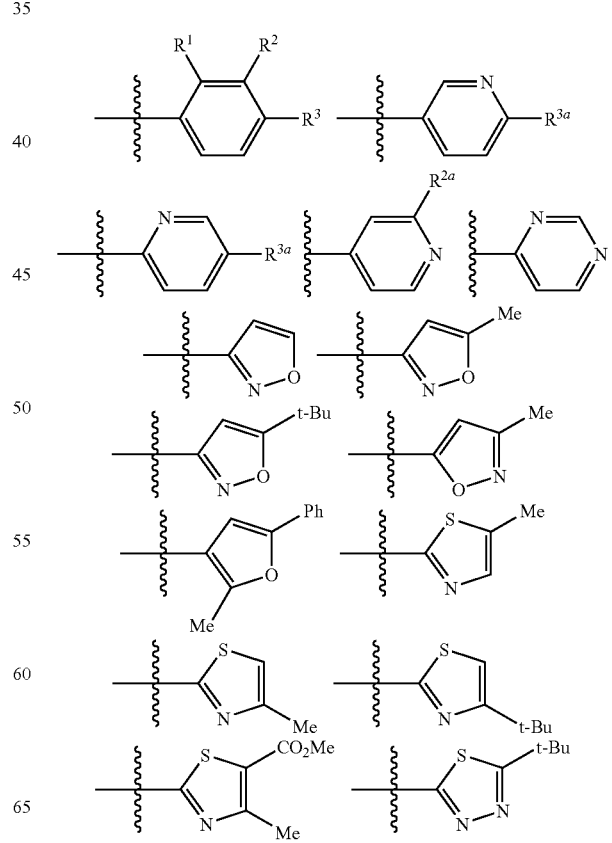

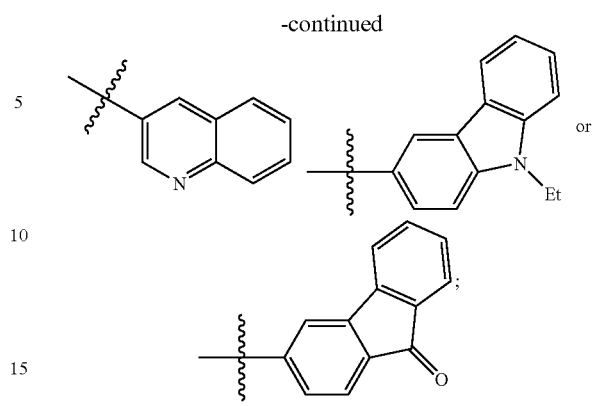

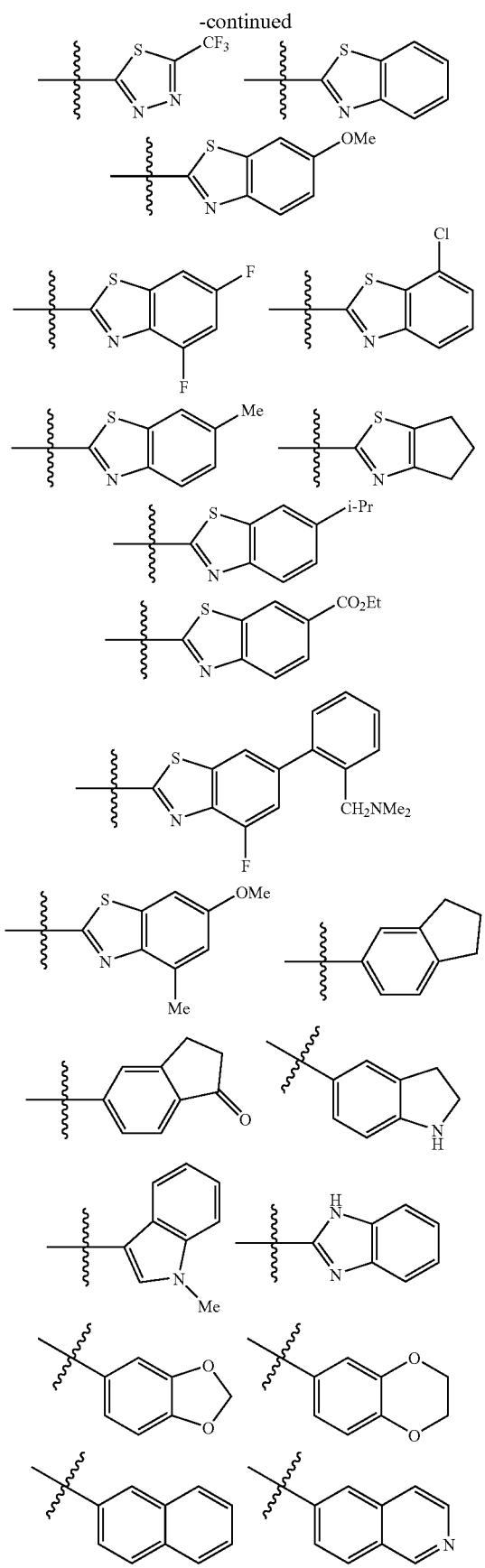

R[1] is H or F;

R[2] is H, F, Cl, Br, Me, t-Bu, OMe, OBu, pentoxy, isopentoxy, neohexoxy, —O(CH$_2$)$_2$OMe, —O(CH$_2$)$_2$O(i-Pr), —O(CH$_2$)$_8$CO$_2$Me, —O(CH$_2$)$_2$C(Me)$_2$OMe, —O(CH$_2$)$_2$NMe$_2$, —OCH$_2$C(Me)$_2$CH$_2$NMe$_2$, —O(CH$_2$)$_2$OCOMe, —OCH(Et)CH$_2$OMe, —OCH(Me)CH$_2$O(t-Bu), NO$_2$, CF$_3$, OCF$_3$, 2-CH$_2$N(Me)$_2$-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe$_2$-benzoxy, 2-CF$_3$-benzoxy, 3-OCF$_3$-benzoxy, 4-OCF$_3$-benzoxy, 4-CO$_2$Me-benzoxy, 4-NHCOMe-benzoxy, 4-Ph-benzoxy, (2-naphthyl)methoxy, Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl)methoxy, (1H-pyrrol-1-yl)ethoxy, (2-Bu-1H-imidazol-4-yl)methoxy, Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl)ethoxy, or —OCH(Et)(pyridine-4-yl);

R[2a] is F, Cl, Br, Me, or t-Bu;

R[3] is H, F, Cl, Br, Me, Et, Pr, Bu, t-Bu, OMe, OEt, OPr, O-i-Pr, OBu, Bu, pentoxy, isopentoxy, neohexoxy, —OCH(Me)CH$_2$O-t-Bu, CF$_3$, OCHF$_2$, OCF$_3$, —O(CH$_2$)$_2$OMe, —O(CH$_2$)$_3$NMe$_2$, —O(CH$_2$)$_4$NMe$_2$, —OCH(Et)CH$_2$OMe, CN, NH$_2$, NMe$_2$, —CH$_2$NMe$_2$, NEt$_2$, —NHPh, —N(Me)Ph, —NH(4-OMe-Ph), —NH(2-CF$_3$-Ph), —CH(Me)NHCH(Me)Ph, —CH(Me)N(Me)(3-CF$_3$-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH(Me)O(1-Bn-pyrrolidin-3-ylmethyl), —C(Me)$_2$OH, —C(Me)$_2$CH$_2$OH, —C(CF$_3$)$_2$OH, —COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)-2-Ph, 3-CH$_2$N(Me)-2-Ph, 4-CH$_2$N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 4-OMe-benzoxy, 3-CN-benzoxy, 4-CN-benzoxy, 3-NMe$_2$-benzoxy, 4-CO$_2$Me-benzoxy, 3-CF$_3$-benzoxy, 3-OCF$_3$-benzoxy, 4-OCF$_3$-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, Bn-pyrrolidin-3-yl)methoxy, (furan-2-yl)methoxy, (furan-3-yl)methoxy, (tetrahydrofuran-3-yl)methoxy, (thien- 3-yl)methoxy, thiazol-2-yl, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, Bn-piperidin-4-oxy, (1-(i-Bu)-piperidin-4-yl)methoxy, isopentyl-piperidin-4-yl)methoxy, (1-CO$_2$(t-Bu)-piperidin-4-yl)methoxy, CO$_2$Bn-piperidin-4-yl)methoxy, (1-Bn-piperidin-4-yl)methoxy, phenethyl-piperidin-4-yl)methoxy, (1-(4-phenylbutyl)-piperidin-4-yl)methoxy, cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 1-CH$_2$OH-cyclopropyl, CO$_2$Me-cyclopropyl, 1-CH$_2$OMe-cyclopropyl, 1-CO$_2$Me-cyclobutyl, CO$_2$Me-cyclopentyl, cyclohexyl, 1-CO$_2$Me-cyclohexyl, 4,4,5,5-tetramethyl-1,3,2-dioxaborolanyl, or —OP(O)(OEt)$_2$;

R$^{3a}$ is Me, Cl, CF$_3$, —NHPh, —NH(2-CF$_3$-Ph), —NH(2-t-Bu-Ph), 2-t-Bu-phenoxy, or 2-CF$_3$-phenoxy;

R$^6$ is 2-Me-Ph, 3-Me-Ph, 2-Et-Ph, 3-Et-Ph, 2-Pr-Ph, 2-i-Pr-Ph, 3-i-Pr-Ph, 2-i-Bu-Ph, 2-t-Bu-Ph, 3-t-Bu-Ph, 2-vinyl-Ph, 2-isopropenyl-Ph, isopropenyl-Ph, 3-Br-Ph, 2-I-Ph, 2-SMe-Ph, 2-S(i-Pr)-Ph, 2-C(Me)$_2$CN-Ph, CF$_3$-Ph, 3-CF$_3$-Ph, 2-OCF$_3$-Ph, 3-OCF$_3$-Ph, 3-Ph-Ph, 2-Bn-Ph, 2-SiMe$_3$-Ph, SiMe$_3$-Ph, 2-C(Me)$_2$OMe-Ph, 2-C(Me)$_2$OEt-Ph, 2-C(Me)$_2$OPr-Ph, CH(Me)O(CH$_2$)$_2$OMe-Ph, 2-C(Me)$_2$O(CH$_2$)$_2$OMe-Ph, 2-C(Et)$_2$OH-Ph, C(Et)$_2$OMe-Ph, 2-C(Et)$_2$OEt-Ph, 2-C(Et)$_2$OPr-Ph, 3-COPh-Ph, 2-CO$_2$Et-Ph, CO$_2$Et-Ph, 2-NH(i-Bu)-Ph, 2-cyclopropyl-Ph, 2-cyclopentyl-Ph, 2,3-dimethoxy-Ph, 2,3-diCl-Ph, 2,6-diMe-Ph, 2-Me-5-F-Ph, 2-i-Pr-5-Me-Ph, 2-t-Bu-4-Me-Ph, 2-t-Bu-5-Me-Ph, 2-t-Bu-6-CN-Ph, 2-F-3-CF$_3$-Ph, 2-F-5-CF$_3$-Ph, 2-Cl-5-CF$_3$-Ph, COMe-3-F-Ph, 2-CO$_2$Me-3-F-Ph, 2-CF$_3$-Bn, 1-naphthyl,

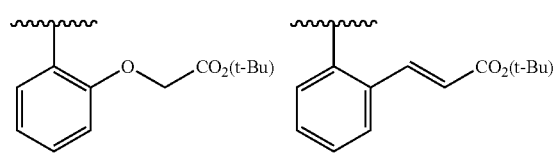

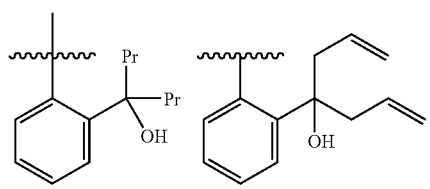

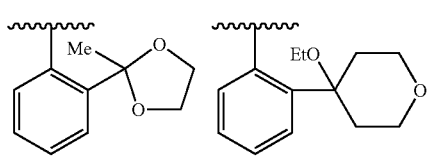

-continued

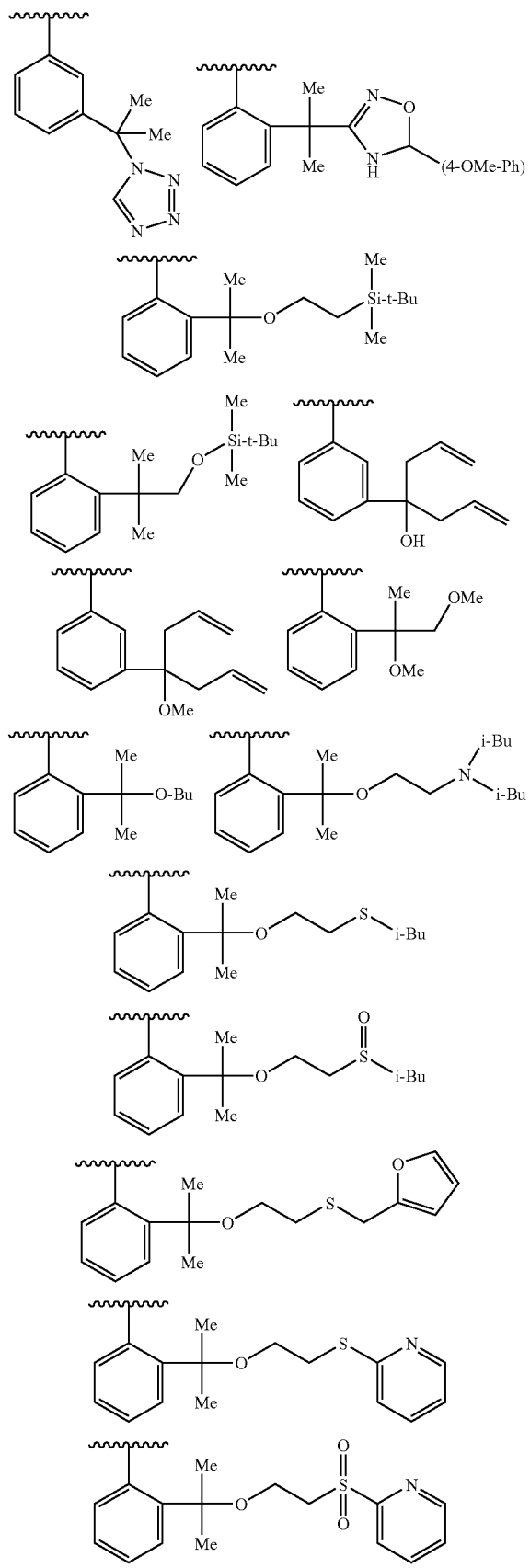

-continued
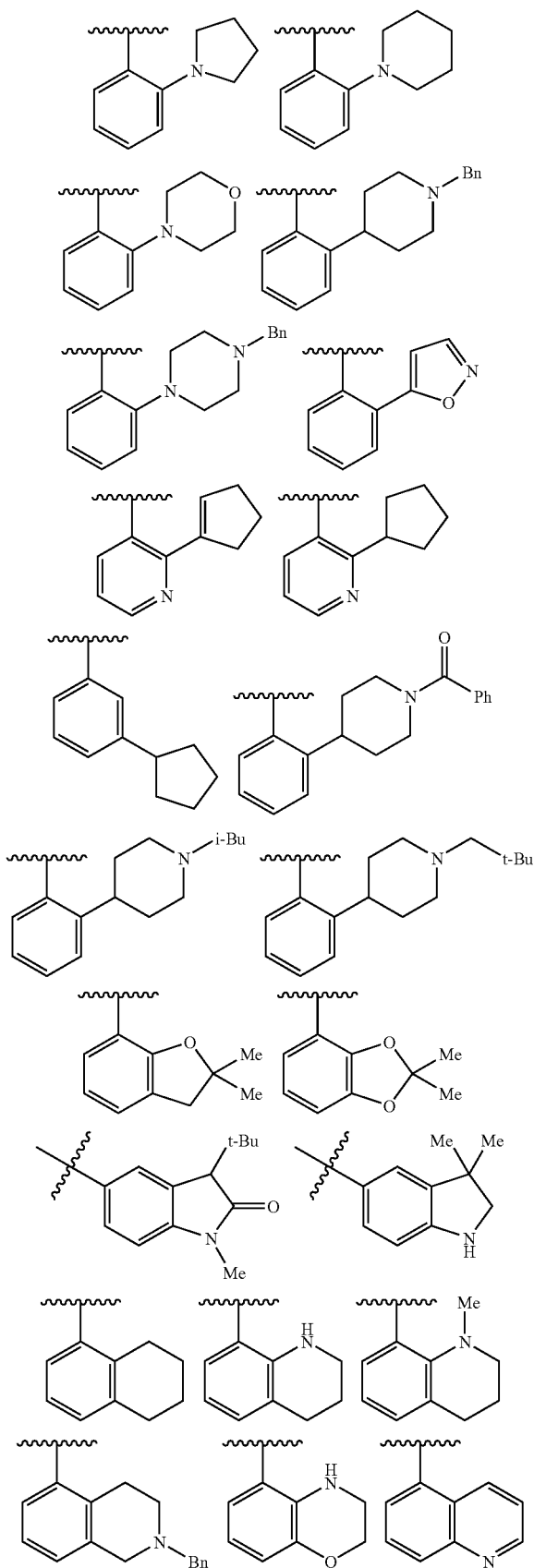
-continued
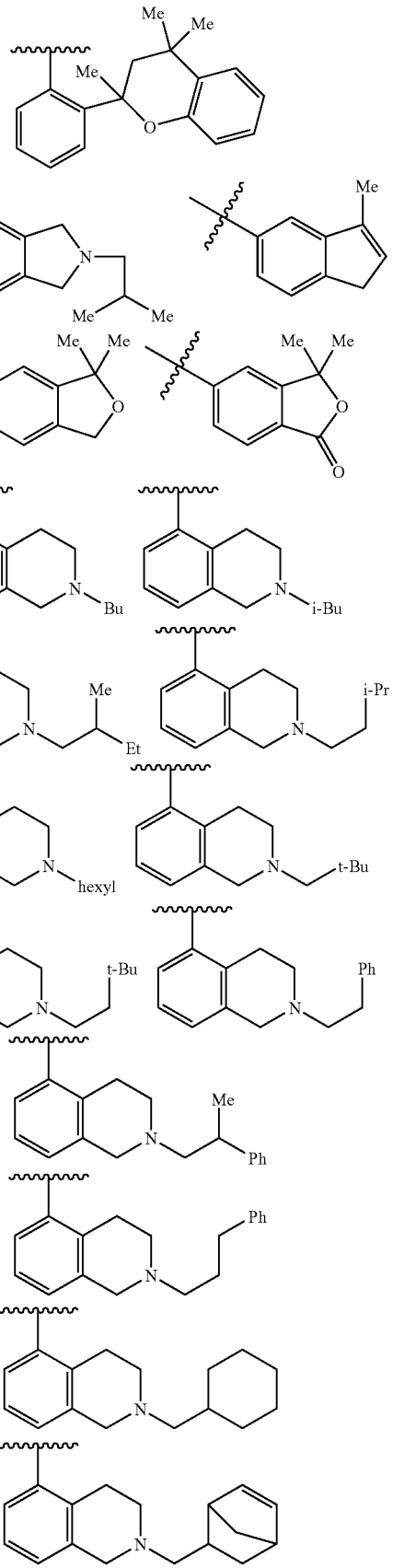

-continued

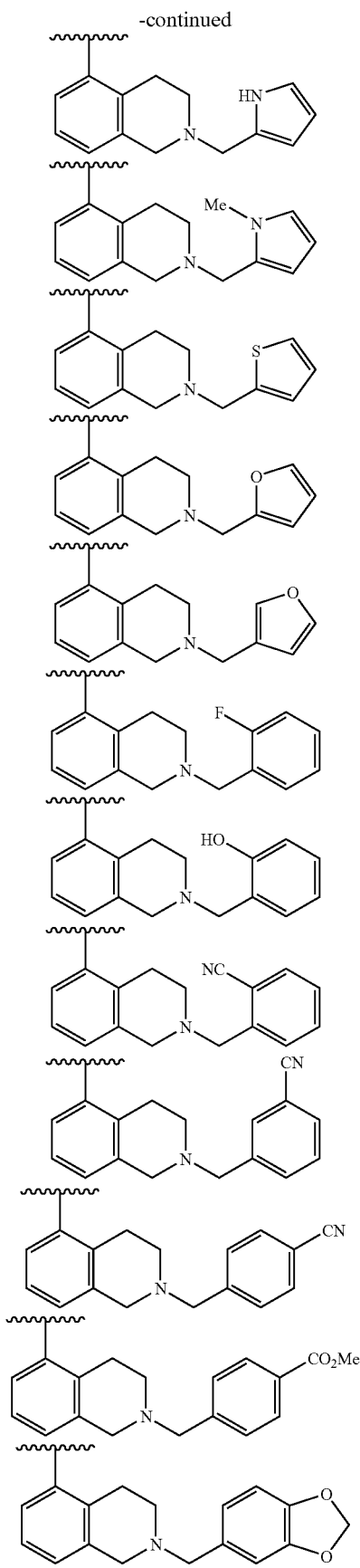

-continued

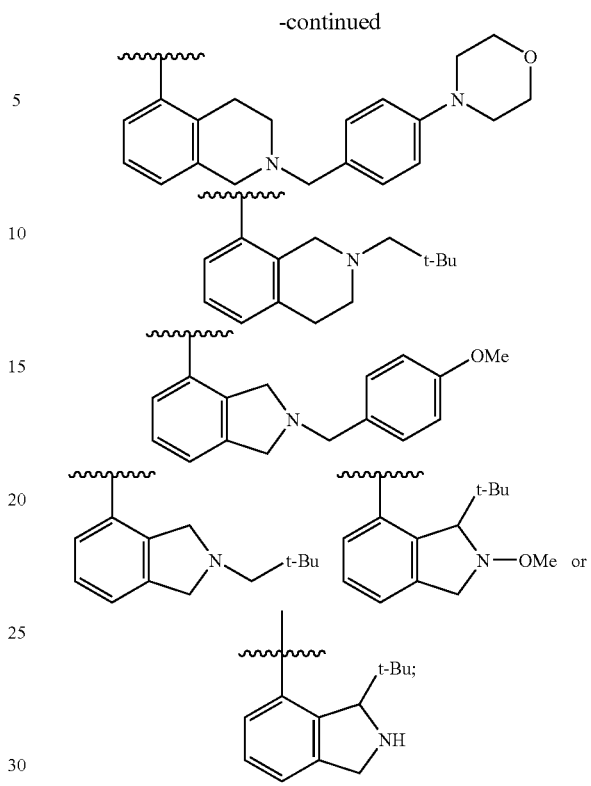

R⁷ is H, Me, Cl, Br, CN, OH, OMe, SMe, NHMe, NMe$_2$, CO$_2$Me, imidazol-1-yl, or —CH$_2$NH(CO)H; and R⁸ is H, Me, Cl, Br, CN, or CF$_3$.

In another embodiment, the present invention provides a compound selected from the exemplified examples of the present invention or a stereoisomer or pharmaceutically acceptable salt, solvate, or prodrug form thereof.

In another embodiment, the present invention provides, inter alia, a method for treating a thromboembolic disorder, comprising: administering to a patient in need thereof a therapeutically effective amount of a compound of Formula (II):

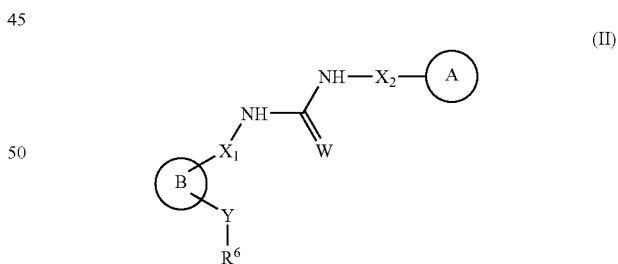

(II)

or a stereoisomer or pharmaceutically acceptable salts, solvates, or prodrugs thereof, wherein:

ring A is C$_{3-13}$ carbocycle substituted with 0-5 R¹, or a 4- to 14-membered heterocycle comprising: carbon atoms and 1-5 ring heteroatoms selected from O, N, NR¹¹, and S(O)$_p$, wherein said heterocycle is substituted with 0-5 R¹;

ring B is phenyl substituted with 0-4 R⁷, naphthyl substituted with 0-5 R⁷, or a 5- to 10-membered heteroaryl comprising: carbon atoms and 1-4 ring heteroatoms selected from N, NR¹¹, S(O)$_p$, and O, wherein said heteroaryl is substituted with 0-5 R⁷;

W is O or S;

$X_1$ and $X_2$ are, independently at each occurrence, —$(CR^{16}R^{17})_s$—, or —$(CR^{16}R^{17})_tC(O)(CR^{16}R^{17})_r$—;

Y is O, S, $NR^{15}$, —$OCR^{18}R^{19}$—, —CH=CH—, or —CONH—;

$R^1$ is, independently at each occurrence, =O, F, Cl, Br, I, $OCF_3$, $CF_3$, —$CF_2CF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—C(O)$NR^{12}R^{13}$, —C(O)$NR^{14}(CR^fR^f)_nN^{12}R^{13}$, —$(CR^fR^f)_r$—$OC(O)NR^{12}R^{13}$, —$(CR^fR^f)_r$—$NR^{14}C(O)NR^{12}R^{13}$, —$(CR^fR^f)_r$—$NR^{14}C(O)R^d$, —$(CR^fR^f)_r$—$NR^{14}C(O)OR^h$, —$NR^{14}(CR^fR^f)_nC(O)R^d$, —$NR^{14}CO(CR^fR^f)_nOR^c$, —$(CH_2)_r$—$CR^{13}(=NOR^c)$, —$S(O)_pNR^{12}R^{13}$, —$(CR^fR^f)_r$—$NR^{14}S(O)_pNR^{12}R^{13}$, —$NR^{14}SO_2CF_3$, —$NR^{14}SO_2R^d$, —$S(O)_2CF_3$, —$S(O)R^d$, —$S(O)_2R^d$, —$OP(O)(OEt)_2$, —$O(CH_2)_2OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 10-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

$R^6$ is —$(CR^fR^f)_n$—$C_{3-10}$ carbocycle substituted with 0-5 $R^{6a}$, or —$(CR^fR^f)_n$-5- to 10-membered heterocycle comprising: carbon atoms and 1-4 heteroatoms selected from N, $NR^{11}$, O, and $S(O)_p$, wherein said heterocycle is substituted with 0-5 $R^{6a}$;

$R^{6a}$ is, independently at each occurrence, =O, F, Cl, Br, I, —$(CR^iR^i)_r$—$OR^c$, $SR^c$, CN, $NO_2$, $CF_3$, $OCF_3$, —$CF_2CF_3$, —$OCF_2CF_2H$, —$OCF_2CF_3$, —$NR^{12}R^{13}$, —C(O)$R^c$, —C(O)$OR^c$, —C(O)$NR^{12}R^{13}$, —$NR^{14}C(O)R^d$, —$S(O)_pNR^{12}R^{13}$, —$S(O)R^d$, —$S(O)_2R^d$, —$Si(C_1-C_4$ alkyl$)_3$, $C_1-C_4$ haloalkyl, $C_1-C_4$ haloalkyloxy-, $C_1-C_4$ alkyloxy-, $C_1-C_4$ alkylthio-, $C_1-C_4$ alkyl-C(O)—, $C_1-C_4$ alkyl-O—C(O)—, $C_1-C_4$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-3 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-3 $R^e$;

alternatively, two $R^{6a}$ groups attached to adjacent atoms, together with the atoms to which they are attached, form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds, wherein said carbocyclic or heterocyclic ring is substituted with 0-2 $R^b$;

$R^7$ is, independently at each occurrence, =O, F, Cl, Br, I, $OCF_3$, $CF_3$, $OR^c$, $SR^c$, CN, $NO_2$, —$NR^{12}R^{13}$, —C(O)$R^c$, —C(O)$OR^c$, —C(O)$NR^{12}R^{13}$, —$NR^{14}C(O)R^d$, —$S(O)_pNR^{12}R^{13}$, —$S(O)R^d$, —$S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-3 $R^b$, or —$(CR^fR^f)_r$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s on two adjacent carbon atoms form a 5- to 7-membered carbocyclic or heterocyclic ring comprising: carbon atoms and 0-3 ring heteroatoms selected from O, N, $NR^{7b}$, and $S(O)_p$, wherein said carbocyclic or heterocyclic ring is substituted with 0-3 $R^{7c}$;

$R^{7b}$ is, independently at each occurrence, H, $C_{1-4}$ alkyl, $(C_{1-4}$ alkyl)C(O)—, phenyl-C(O)—, benzyl-C(O)—, benzyl-$S(O)_2$—, $(C_{1-4}$ alkyl)NHC(O)—, $(C_{1-4}$ alkyl$)_2$NC(O)—, phenyl-NHC(O)—, benzyl-NHC(O)—, $(C_{1-4}$ alkyl)-$S(O)_2$—, phenyl-$S(O)_2$—, phenyl substituted with 0-3 $R^b$, or benzyl substituted with 0-3 $R^b$;

$R^{7c}$ is, independently at each occurrence, H, F, Cl, Br, I, $OCF_3$, $CF_3$, $OR^c$, $SR^c$, CN, $NO_2$, —$NR^{12}R^{13}$, —C(O)$R^c$, —C(O)$OR^c$, —C(O)$NR^{12}R^{13}$, —$NR^{14}C(O)R^d$, —$S(O)_pNR^{12}R^{13}$, —$S(O)R^d$, —$S(O)_2R^d$, $C_{1-4}$ alkyl, phenyl substituted with 0-3 $R^b$, or benzyl substituted with 0-3 $R^b$;

$R^{11}$ is, independently at each occurrence, H, $C_{1-4}$ alkoxy, $C_{1-8}$ alkyl substituted with 0-2 $R^a$, $C_{2-4}$ alkenyl substituted with 0-2 $R^a$, $C_{2-4}$ alkynyl substituted with 0-2 $R^a$, —C(O)$(C_{1-6}$ alkyl), —C(O)$(CH_2)_n(C_{3-6}$ cycloalkyl), —C(O)$(CH_2)_n(C_{6-10}$ aryl), —C(O)$(CH_2)_n$(5- to 10-membered heteroaryl), —C(O)O$(C_{1-8}$ alkyl), —C(O)O$(CH_2)_n(C_{3-6}$ cycloalkyl), —C(O)O$(CH_2)_n(C_{6-10}$ aryl), —C(O)O$(CH_2)_n$(5- to 10-membered heteroaryl), —C(O)O$(CH_2)_{2-4}(C_{1-4}$ alkyl), —C(O)NH$(C_{1-8}$ alkyl), —C(O)NH$(CH_2)_n(C_{3-6}$ cycloalkyl), —C(O)NH$(CH_2)_n(C_{6-10}$ aryl), —C(O)NH$(CH_2)_n$(5- to 10-membered heteroaryl), —$S(O)_2(C_{1-8}$ alkyl), —$S(O)_2(CH_2)_n(C_{3-6}$ cycloalkyl), —$S(O)_2(CH_2)_n(C_{6-10}$ aryl), —$S(O)_2(CH_2)_n$(5- to 10-membered heteroaryl), —$(CR^fR^f)_r$—$C_{3-10}$ carbocycle, or —$(CR^fR^f)_r$-5- to 10-membered heterocycle; wherein said alkyl, cycloalkyl, phenyl, aryl, and carbocycle are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$;

$R^{12}$ is, independently at each occurrence, H, $C_{1-6}$ alkyl, —C(O)$(C_{1-6}$ alkyl), —C(O)$(CH_2)_n(C_{6-10}$ aryl), —C(O)$(CH_2)_n$(5- to 10-membered heteroaryl), —C(O)O$(C_{1-4}$ alkyl), —C(O)O$CH_2(C_{6-10}$ aryl), —$(CH_2)_nC(O)OCH_2$(5- to 10-membered heteroaryl), —$(CH_2)_nOC(O)(C_{1-4}$ alkyl), —$(CH_2)_nOC(O)(C_{6-10}$ aryl), —$(CH_2)_nOC(O)$(5- to 10-membered heteroaryl), —$(CH_2)_nC(O)O(C_{1-4}$ alkyl), —$(CH_2)_nC(O)O(C_{6-10}$ aryl), —$(CH_2)_nC(O)O$(5- to 10-membered heteroaryl), —$(CH_2)_nC(O)NH(C_{1-6}$ alkyl), —$(CH_2)_nC(O)NH(C_{6-10}$ aryl), —$(CH_2)_nC(O)NH$(5- to 10-membered heteroaryl), —$(CH_2)_tOC(O)NH(C_{1-6}$ alkyl), —$(CH_2)_tOC(O)NH(C_{6-10}$ aryl), —$(CH_2)_tOC(O)NH$(5- to 10-membered heteroaryl), —$S(O)_2(C_{1-6}$ alkyl), —$S(O)_2(CH_2)_n(C_{6-10}$ aryl), —$S(O)_2(CH_2)_n$(5- to 10-membered heteroaryl), —$(CH_2)_n$—$(C_{6-10}$ aryl), or —$(CH_2)_n$-5- to 10-membered heteroaryl; wherein said alkyl, and aryl are substituted with 0-2 $R^g$; and said heteroaryl is substituted with 0-2 $R^g$ and comprises: carbon atoms and 1-4 heteroatoms selected from N, $NR^{11}$, O, and $S(O)_p$;

$R^{13}$ is, independently at each occurrence, H, $C_{1-6}$ alkyl, or —$(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^{11}$, O, and $S(O)_p$;

$R^{14}$ is, independently at each occurrence, H, $C_{1-6}$ alkyl substituted with 0-2 $R^{14a}$, $C_{2-6}$ alkenyl substituted with 0-2 $R^{14a}$, $C_{2-6}$ alkynyl substituted with 0-2 $R^{14a}$, —$(CH_2)_r$—$C_{3-10}$ carbocycle substituted with 0-3 $R^g$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^g$;

$R^{14a}$ is, independently at each occurrence, H, $C_{1-4}$ alkyl, $OR^f$, Cl, F, Br, I, =O, $CF_3$, CN, $NO_2$, —C(O)$R^f$, —C(O)$OR^f$, —C(O)$NR^{12}R^{13}$, or —$S(O)_pR^f$;

$R^{15}$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $(C_{1-6}$ alkyl)C(O)—, $(C_{3-6}$ cycloalkyl)$C_{1-3}$ alkyl-C(O)—, $(C_{3-6}$ cycloalkyl)C(O)—, phenyl-C(O)—, benzyl-C(O)—, benzyl-S(O)$_2$—, $(C_{1-6}$ alkyl)NHC(O)—, $(C_{1-6}$ alkyl)$_2$NC(O)—, phenyl-NHC(O)—, benzyl-NHC(O)—, (phenyl)$(C_{1-6}$ alkyl)NC(O)—, (benzyl)$(C_{1-6}$ alkyl)NC(O)—, $(C_{1-6}$ alkyl)-S(O)$_2$—, phenyl-S(O)$_2$—, —(CH$_2$)$_r$—$C_{3-10}$ carbocycle substituted with 0-3 $R^b$, or —(CH$_2$)$_r$-5- to 10-membered heterocycle comprising: carbon atoms and 1-4 heteroatoms selected from N, NR$^{11}$, O, and S(O)$_p$, wherein said heterocycle is substituted with 0-3 $R^b$;

alternatively, $R^{15}$ taken together with an $R^{6a}$ group on $R^6$ forms a 5- to 10-membered carbocyclic or heterocyclic ring comprising: carbon atoms and 0-4 heteroatoms selected from N, NR$^{11}$, O, and S(O)$_p$, 0-1 carbonyl, and 0-3 double bonds, wherein said carbocyclic or heterocyclic ring is substituted with 0-2 $R^b$;

$R^{16}$ is, independently at each occurrence, H, F, Cl, Br, I, OCF$_3$, CF$_3$, —(CH$_2$)$_r$—OR$^c$, SR$^c$, —(CH$_2$)$_r$—NR$^{12}$R$^{13}$, —(CH$_2$)$_r$—C(O)R$^c$, —(CH$_2$)$_r$—CO$_2$R$^c$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —(CH$_2$)$_r$—$C_{3-10}$ carbocycle substituted with 0-3 $R^b$, or —(CH$_2$)$_r$-5- to 10-membered heterocycle comprising: carbon atoms and 1-4 heteroatoms selected from N, NR$^{11}$, O, and S(O)$_p$, wherein said heterocycle is substituted with 0-3 $R^b$;

$R^{17}$ is, independently at each occurrence, H, $C_{1-6}$ alkyl, or —(CH$_2$)$_n$-phenyl;

alternatively, $R^{16}$ and $R^{17}$ on the same carbon atom combine to form a 3- to 7-membered carbocyclic or heterocyclic ring comprising: carbon atoms and 0-2 heteroatoms selected from N, NR$^{11}$, O, and S(O)$_p$, 0-1 carbonyl, and 0-3 double bonds, wherein said carbocyclic or heterocyclic ring is substituted with 0-2 $R^b$;

alternatively, two $R^{16}$ groups on adjacent atoms combine to form a 3- to 7-membered carbocyclic or heterocyclic ring comprising: carbon atoms and 0-2 heteroatoms selected from N, NR$^{11}$, O, and S(O)$_p$, 0-1 carbonyl, and 0-3 double bonds, wherein said carbocyclic or heterocyclic ring is substituted with 0-2 $R^b$;

$R^{18}$ is, independently at each occurrence, H, F, or $C_{1-6}$ alkyl;

$R^{19}$ is, independently at each occurrence, H, OH, —C(O)OR$^f$, or $C_{1-6}$ alkyl;

$R^a$ is, independently at each occurrence, =O, F, OCF$_3$, CF$_3$, OR$^c$, SR$^c$, CN, —NR$^{12}$R$^{13}$, —C(O)R$^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, —(CH$_2$)$_r$—$C_{3-10}$ carbocycle substituted with 0-3 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^b$ is, independently at each occurrence, H, =O, F, Cl, Br, I, —(CH$_2$)$_r$—OR$^c$, SR$^c$, CN, NO$_2$, CF$_3$, OCF$_3$, —NR$^{12}$R$^{13}$, —C(O)R$^c$, —(CH$_2$)$_r$—C(O)OR$^c$, —(CH$_2$)$_r$—C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, $C_1$-$C_4$ alkyl-O—C(O)—, $C_1$-$C_4$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —(CH$_2$)$_r$—$C_{3-10}$ carbocycle substituted with 0-3 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 $R^e$;

$R^c$ is, independently at each occurrence, H, —OP(O)(OEt)$_2$, $C_{1-8}$ alkyl substituted with 0-2 $R^e$, $C_{2-8}$ alkenyl substituted with 0-2 $R^e$, $C_{2-8}$ alkynyl substituted with 0-2 $R^e$, —(CH$_2$)$_r$—$C_{3-8}$ cycloalkyl substituted with 0-2 $R^e$, —(CH$_2$)$_r$—$C_{6-10}$ aryl substituted with 0-2 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 $R^e$;

$R^d$ is, independently at each occurrence, CF$_3$, OH, $C_{1-4}$ alkoxy, $C_{1-6}$ alkyl, —(CH$_2$)$_r$—$C_{3-10}$ carbocycle substituted with 0-2 $R^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 $R^e$;

$R^e$ is, independently at each occurrence, H, =O, —(CH$_2$)$_r$—OR$^f$, F, Cl, Br, I, CN, NO$_2$, —(CH$_2$)$_r$—NR$^{12}$R$^{13}$, —C(O)R$^f$, —(CH$_2$)$_r$—C(O)OR$^f$, —NR$^{14}$C(O)R$^f$, —(CH$_2$)$_r$—C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—$C_{1-4}$ alkyl, —NR$^{14}$SO$_2$CF$_3$, —NR$^{14}$SO$_2$-phenyl, —S(O)$_2$CF$_3$, —S(O)$_p$—OR$^h$, —(CF$_2$)$_r$CF$_3$, Si($C_{1-4}$ alkyl)$_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —(CH$_2$)$_r$—$C_{3-8}$ cycloalkyl substituted with 0-2 $R^g$, —(CH$_2$)$_r$—$C_{6-10}$ aryl substituted with 0-2 $R^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 $R^g$;

$R^f$ is, independently at each occurrence, H, $C_{1-6}$ alkyl, or —(CH$_2$)$_n$-phenyl;

$R^g$ is, independently at each occurrence, H, =O, OR$^f$, F, Cl, Br, I, CN, NO$_2$, —NR$^fR^f$, —C(O)R$^f$, —C(O)OR$^f$, —NR$^fC(O)R^f$, —C(O)NR$^fR^f$, —SO$_2$NR$^fR^f$, —NR$^fSO_2$NR$^fR^f$, —NR$^fSO_2$—$C_{1-4}$ alkyl, —NR$^fSO_2$CF$_3$, —NR$^fSO_2$-phenyl, —S(O)$_2$CF$_3$, —S(O)$_p$—$C_{1-4}$ alkyl, —S(O)$_p$-phenyl, —(CF$_2$)$_r$CF$_3$, $C_{1-6}$ alkyl, $C_{2-6}$ alkenyl, or $C_{2-6}$ alkynyl;

$R^h$ is, independently at each occurrence, $C_{1-6}$ alkyl substituted with 0-2 $R^g$, —(CH$_2$)$_n$-phenyl substituted with 0-2 $R^g$, or —(CH$_2$)$_n$-5- to 10-membered heterocycle comprising: carbon atoms and 1-4 heteroatoms selected from N, NR$^f$, O, and S(O)$_p$, wherein said heterocycle is substituted with 0-2 $R^g$;

$R^i$ is, independently at each occurrence, H, $C_{1-6}$ alkyl substituted with 0-2 $R^g$, —(CH$_2$)$_n$-phenyl substituted with 0-2 $R^g$, or —(CH$_2$)$_n$-5- to 10-membered heterocycle comprising: carbon atoms and 1-4 heteroatoms selected from N, NR$^f$, O, and S(O)$_p$, wherein said heterocycle is substituted with 0-2 $R^g$;

n, at each occurrence, is selected from 0, 1, 2, 3, and 4;

p, at each occurrence, is selected from 0, 1, and 2;

r, at each occurrence, is selected from 0, 1, 2, 3, and 4;

s, at each occurrence, is selected from 0, 1, 2, 3, 4, 5, and 6; and t, at each occurrence, is selected from 1, 2, 3, and 4.

In another embodiment, the present invention provides a method for treating a thromboembolic disorder, comprising: administering to a patient in need thereof a therapeutically effective amount of a compound of Formula (II), or a stereoisomer or pharmaceutically acceptable salts, solvates, or prodrugs thereof, wherein:

X is —(CR$^{16}$R$^{17}$)$_s$—; and s, at each occurrence, is selected from 0, 1, 2, 3, and 4.

In another embodiment, the present invention provides a method for treating a thromboembolic disorder, comprising: administering to a patient in need thereof a therapeutically effective amount of a compound of Formula (IIa):

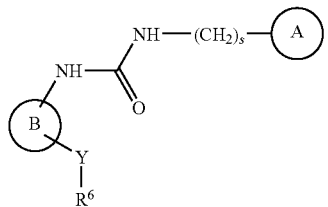

(IIa)

or a stereoisomer or pharmaceutically acceptable salts, solvates, or prodrugs thereof, wherein:

ring A is phenyl substituted with 0-5 $R^1$, naphthyl substituted with 0-5 $R^1$, or a 5- to 10-membered heteroaryl comprising: carbon atoms and 1-4 ring heteroatoms selected from O, N, $NR^{11}$, and $S(O)_p$, wherein said heteroaryl is substituted with 0-5 $R^1$;

ring B is phenyl substituted with 0-4 $R^7$, naphthyl substituted with 0-5 $R^7$, or a 5- to 10-membered heteroaryl comprising: carbon atoms and 1-4 ring heteroatoms selected from N, $NR^{11}$, $S(O)_p$, and O, wherein said heteroaryl is substituted with 0-5 $R^7$;

Y is $NR^{15}$, O, or S;

$R^1$ is, independently at each occurrence, =O, F, Cl, Br, I, $OCF_3$, $CF_3$, —$CF_2CF_3$, —$OCF_2CF_2H$, —$OCF_2CF_3$, $SiMe_3$, —$(CR^fR^f)_r$—$OR^c$, $SR^c$, CN, $NO_2$, —$(CR^fR^f)_r$—$NR^{12}R^{13}$, —$(CR^fR^f)_r$—$C(O)R^c$, —$(CR^fR^f)_r$—$CO_2R^c$, —$(CR^fR^f)_r$—$C(O)NR^{12}R^{13}$, —$C(O)NR^{14}(CR^fR^f)_nN^{12}R^{13}$, —$(CR^fR^f)_r$—$OC(O)NR^{12}R^{13}$, —$(CR^fR^f)_r$—$NR^{14}C(O)NR^{12}R^{13}$, —$(CR^fR^f)_r$—$NR^{14}C(O)R^d$, —$(CR^fR^f)_r$—$NR^{14}C(O)OR^h$, —$NR^{14}(CR^fR^f)_nC(O)R^d$, —$NR^{14}CO(CR^fR^f)_nOR^c$, —$(CH_2)_r$—$CR^{13}(=NOR^c)$, —$S(O)_pNR^{12}R^{13}$, —$(CR^fR^f)_r$—$NR^{14}S(O)_pNR^{12}R^{13}$, —$NR^{14}SO_2CF_3$, —$NR^{14}SO_2R^d$, —$S(O)_2CF_3$, —$S(O)R^d$, —$S(O)_2R^d$, —$OP(O)(OEt)_2$, —$O(CH_2)_2OP(O)(OEt)_2$, 4,4,5,5-tetramethyl-1,3,2-dioxaborolanyl, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-13}$ carbocycle substituted with 0-5 $R^b$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-5 $R^b$;

alternatively, two $R^1$s on two adjacent carbon atoms are combined with the carbon atoms to which they attached, form a 5- to 10-membered carbocycle or heterocycle comprising: carbon atoms and 0-3 additional heteroatoms selected from N, $NR^{11}$, O, and $S(O)_p$, and 0-2 carbonyl groups, wherein said carbocycle or heterocycle is substituted with 0-4 $R^b$;

$R^6$ is —$(CR^fR^f)_n$—$C_{3-10}$ carbocycle substituted with 0-5 $R^{6a}$, or —$(CR^fR^f)_n$-5- to 10-membered heterocycle comprising: carbon atoms and 1-4 heteroatoms selected from N, $NR^{11}$, O, and $S(O)_p$, wherein said heterocycle is substituted with 0-5 $R^{6a}$;

$R^{6a}$ is, independently at each occurrence, =O, F, Cl, Br, I, —$(CR^iR^i)_r$—$OR^c$, $SR^c$, CN, $NO_2$, $CF_3$, $OCF_3$, —$CF_2CF_3$, —$OCF_2CF_2H$, —$OCF_2CF_3$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, —$Si(C_1-C_4$ alkyl$)_3$, $C_1-C_4$ haloalkyl, $C_1-C_4$ haloalkyloxy-, $C_1-C_4$ alkyloxy-, $C_1-C_4$ alkylthio-, $C_1-C_4$ alkyl-C(O)—, $C_1-C_4$ alkyl-O—C(O)—, $C_1-C_4$ alkyl-C(O)NH—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-3 $R^e$, or —$(CR^fR^f)_r$-5- to 10-membered heterocycle comprising: carbon atoms and 1-4 heteroatoms selected from N, $NR^{11}$, O, and $S(O)_p$, wherein said heterocycle is substituted with 0-3 $R^e$;

alternatively, two $R^{6a}$ groups attached to adjacent atoms, together with the atoms to which they are attached, form a 5- to 7-membered carbocyclic or heterocyclic ring comprising: carbon atoms and 0-2 heteroatoms selected from N, $NR^{11}$, O, and $S(O)_p$, 0-1 carbonyl and 0-3 ring double bonds; wherein said carbocyclic or heterocyclic ring is substituted with 0-2 $R^b$;

$R^7$ is, independently at each occurrence, =O, F, Cl, Br, I, $OCF_3$, $CF_3$, $OR^c$, $SR^c$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CR^fR^f)_r$—$C_{3-10}$ carbocycle substituted with 0-3 $R^b$, or —$(CR^fR^f)_r$-5- to 10-membered heterocycle comprising: carbon atoms and 1-4 heteroatoms selected from N, $NR^{7b}$, O, and $S(O)_p$, wherein said heterocycle is substituted with 0-3 $R^b$;

alternatively, two $R^7$s on two adjacent carbon atoms form a 5- to 7-membered carbocyclic or heterocyclic ring comprising: carbon atoms and 0-3 ring heteroatoms selected from O, N, $NR^{7b}$, and $S(O)_p$, wherein said carbocyclic or heterocyclic ring is substituted with 0-3 $R^{7c}$;

$R^{7b}$ is, independently at each occurrence, H, $C_{1-4}$ alkyl, $(C_{1-4}$ alkyl$)C(O)$—, phenyl-C(O)—, benzyl-C(O)—, benzyl-$S(O)_2$—, $(C_{1-4}$ alkyl$)NHC(O)$—, $(C_{1-4}$ alkyl$)_2NC(O)$—, phenyl-NHC(O)—, benzyl-NHC(O)—, $(C_{1-4}$ alkyl$)-S(O)_2$—, phenyl-$S(O)_2$—, phenyl substituted with 0-3 $R^b$, or benzyl substituted with 0-3 $R^b$;

$R^{7c}$ is, independently at each occurrence, H, F, Cl, Br, I, $OCF_3$, $CF_3$, $OR^c$, $SR^c$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-4}$ alkyl, phenyl substituted with 0-3 $R^b$, or benzyl substituted with 0-3 $R^b$;

$R^{11}$ is, independently at each occurrence, H, $C_{1-4}$ alkoxy, $C_{1-8}$ alkyl substituted with 0-2 $R^a$, —$C(O)(CH_2)_n(C_{3-6}$ cycloalkyl), —$C(O)(CH_2)_n$phenyl, —$C(O)O(C_{1-8}$ alkyl), —$C(O)O(CH_2)_n(C_{3-6}$ cycloalkyl), —$C(O)O(CH_2)_n$phenyl, —$C(O)(CH_2)_{2-4}(C_{1-4}$ alkyl), —$C(O)NH(C_{1-6}$ alkyl), —$S(O)_2(C_{1-6}$ alkyl), —$S(O)_2(CH_2)_n$phenyl, —$(CR^fR^f)_r$—$C_{3-10}$ carbocycle, or —$(CR^fR^f)_r$-5- to 10-membered heterocycle; wherein said alkyl, cycloalkyl, phenyl, aryl, and carbocycle are substituted with 0-2 $R^b$, and said heteroaryl and heterocycle are substituted with 0-2 $R^b$ and comprise: carbon atoms and 1-4 heteroatoms selected from N, $NR^f$, O, and $S(O)_p$;

$R^{12}$ is, independently at each occurrence, H, $C_{1-6}$ alkyl, —$C(O)(C_{1-6}$ alkyl), —$C(O)(CH_2)_n$phenyl, —$C(O)(CH_2)_n$(5- to 6-membered heteroaryl), —$C(O)O(C_{1-4}$ alkyl), —$C(O)OCH_2$phenyl, —$(CH_2)_nC(O)OCH_2$(5- to 6-membered heteroaryl), —$(CH_2)_nOC(O)(C_{1-4}$ alkyl), —$(CH_2)_nOC(O)$phenyl, —$(CH_2)_nOC(O)$(5- to 6-membered heteroaryl), —$(CH_2)_nC(O)O(C_{1-4}$ alkyl), —$(CH_2)_nC(O)O$phenyl, —$(CH_2)_nC(O)O$(5- to 6-membered heteroaryl), —$(CH_2)_nC(O)NH(C_{1-6}$ alkyl), —$(CH_2)_nC(O)NH$phenyl, —$(CH_2)_nC(O)NH$(5- to 6-membered heteroaryl), —$(CH_2)_rOC(O)NH(C_{1-6}$ alkyl), —$(CH_2)_rOC(O)NH$phenyl, —$(CH_2)_rOC(O)NH$(5- to 6-membered heteroaryl), —$S(O)_2(C_{1-6}$ alkyl), —$S(O)_2(CH_2)_n$phenyl, —$S(O)_2(CH_2)_n$(5- to 6-membered heteroaryl), —$(CH_2)_n$-phenyl, or —$(CH_2)_n$-5- to 6-membered heteroaryl; wherein said alkyl, and aryl are substituted with 0-2 $R^g$; and said heteroaryl is substituted with 0-2 $R^g$ and comprises: carbon atoms and 1-4 heteroatoms selected from N, $NR^{11}$, O, and $S(O)_p$;

$R^{13}$ is, independently at each occurrence, H, $C_{1-6}$ alkyl, or —$(CH_2)_n$-phenyl;

alternatively, $R^{12}$ and $R^{13}$, when attached to the same nitrogen, combine to form a 5- to 10-membered heterocyclic ring comprising: carbon atoms and 1-2 additional heteroatoms selected from N, $NR^{11}$, O, and $S(O)_p$;

$R^{14}$ is, independently at each occurrence, H, $C_{1-6}$ alkyl substituted with 0-2 $R^{14a}$, $C_{2-6}$ alkenyl substituted with 0-2 $R^{14a}$, $C_{2-6}$ alkynyl substituted with 0-2 $R^{14a}$, —$(CH_2)_r$—$C_{3-10}$ carbocycle substituted with 0-3 $R^g$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^g$;

$R^{14a}$ is, independently at each occurrence, H, $C_{1-4}$ alkyl, $OR^f$, Cl, F, Br, I, =O, $CF_3$, CN, $NO_2$, —$C(O)R^f$, —$C(O)OR^f$, —$C(O)NR^{12}R^{13}$, or —$S(O)_p R^f$;

$R^{15}$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, $(C_{1-6}$ alkyl)$C(O)$—, $(C_{3-6}$ cycloalkyl)$C_{1-3}$ alkyl-$C(O)$—, $(C_{3-6}$ cycloalkyl)$C(O)$—, phenyl-$C(O)$—, benzyl-$C(O)$—, benzyl-$S(O)_2$—, $(C_{1-6}$ alkyl)NHC(O)—, $(C_{1-6}$ alkyl)$_2$NC(O)—, phenyl-NHC(O)—, benzyl-NHC(O)—, (phenyl)$(C_{1-6}$ alkyl)NC(O)—, (benzyl)$(C_{1-6}$ alkyl)NC(O)—, $(C_{1-6}$ alkyl)-$S(O)_2$—, phenyl-$S(O)_2$—, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^b$;

alternatively, $R^{15}$ taken together with an $R^{6a}$ group on $R^6$ forms a 5- to 10-membered carbocyclic or heterocyclic ring comprising: carbon atoms and 0-4 heteroatoms selected from N, $NR^{11}$, O, and $S(O)_p$, 0-1 carbonyl, and 0-3 double bonds, wherein said carbocyclic or heterocyclic ring is substituted with 0-2 $R^b$;

$R^a$ is, independently at each occurrence, =O, F, $OCF_3$, $CF_3$, $OR^c$, $SR^c$, CN, —$NR^{12}R^{13}$, —$C(O)R^c$, —$C(O)OR^c$, —$C(O)NR^{12}R^{13}$, —$NR^{14}C(O)R^d$, —$S(O)_p NR^{12}R^{13}$, —$S(O)R^d$, —$S(O)_2R^d$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^b$ is, independently at each occurrence, H, =O, F, Cl, Br, I, —$(CH_2)_r$—$OR^c$, $SR^c$, CN, $NO_2$, $CF_3$, $OCF_3$, —$NR^{12}R^{13}$, —$C(O)R^c$, —$(CH_2)_r$—$C(O)OR^c$, —$(CH_2)_r$—$C(O)NR^{12}R^{13}$, —$NR^{14}C(O)R^d$, —$S(O)_p NR^{12}R^{13}$, —$S(O)R^d$, —$S(O)_2R^d$, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-$C(O)$—, $C_1$-$C_4$ alkyl-O—$C(O)$—, $C_1$-$C_4$ alkyl-$C(O)NH$—, $C_{1-8}$ alkyl substituted with 0-2 $R^a$, $C_{2-8}$ alkenyl substituted with 0-2 $R^a$, $C_{2-8}$ alkynyl substituted with 0-2 $R^a$, —$(CH_2)_r$—$C_{3-10}$ carbocycle substituted with 0-3 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-3 $R^e$;

$R^c$ is, independently at each occurrence, H, $C_{1-8}$ alkyl substituted with 0-2 $R^e$, $C_{2-8}$ alkenyl substituted with 0-2 $R^e$, $C_{2-8}$ alkynyl substituted with 0-2 $R^e$, —$(CH_2)_r$—$C_{3-8}$ cycloalkyl substituted with 0-2 $R^e$, —$(CH_2)_r$—$C_{6-10}$ aryl substituted with 0-2 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^d$ is, independently at each occurrence, $CF_3$, OH, $C_{1-4}$ alkoxy, $C_{1-6}$ alkyl, —$(CH_2)_r$—$C_{3-10}$ carbocycle substituted with 0-2 $R^e$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^e$;

$R^e$ is, independently at each occurrence, H, =O, —$(CH_2)_r$—$OR^f$, F, Cl, Br, I, CN, $NO_2$, —$(CH_2)_r$—$NR^{12}R^{13}$, —$C(O)R^f$, —$(CH_2)_r$—$C(O)OR^f$, —$NR^{14}C(O)R^f$, —$(CH_2)_r$—$C(O)NR^{12}R^{13}$, —$SO_2NR^{12}R^{13}$, —$NR^{14}SO_2NR^{12}R^{13}$, —$NR^{14}SO_2$—$C_{1-4}$ alkyl, —$NR^{14}SO_2CF_3$, —$NR^{14}SO_2$-phenyl, —$S(O)_2CF_3$, —$S(O)_p$—$OR^h$, —$(CF_2)_r CF_3$, $Si(C_{1-4}$ alkyl)$_3$, $C_{1-8}$ alkyl substituted with 0-2 $R^g$, $C_{2-8}$ alkenyl substituted with 0-2 $R^g$, $C_{2-8}$ alkynyl substituted with 0-2 $R^g$, —$(CH_2)_r$—$C_{3-8}$ cycloalkyl substituted with 0-2 $R^g$, —$(CH_2)_r$—$C_{6-10}$ aryl substituted with 0-2 $R^g$, or —$(CH_2)_r$-5- to 10-membered heterocycle comprising: carbon atoms and 1-4 heteroatoms selected from N, $NR^f$, O, and $S(O)_p$, wherein said heterocycle is substituted with 0-2 $R^g$;

$R^f$ is, independently at each occurrence, H, $C_{1-6}$ alkyl, or —$(CH_2)_n$-phenyl;

$R^g$ is, independently at each occurrence, H, =O, $OR^f$, F, Cl, Br, I, CN, $NO_2$, —$NR^fR^f$, —$C(O)R^f$, —$C(O)OR^f$, —$NR^fC(O)R^f$, —$C(O)NR^fR^f$, —$SO_2NR^fR^f$, —$NR^fSO_2NR^fR^f$, —$NR^fSO_2$—$C_{1-4}$ alkyl, —$NR^fSO_2CF_3$, —$NR^fSO_2$-phenyl, —$S(O)_2CF_3$, —$S(O)_p$—$C_{1-4}$ alkyl, —$S(O)_p$-phenyl, —$(CF_2)_r CF_3$, $C_{1-6}$ alkyl, $C_{2-6}$ alkenyl, or $C_{2-6}$ alkynyl;

$R^h$ is, independently at each occurrence, $C_{1-6}$ alkyl substituted with 0-2 $R^g$, —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

$R^i$ is, independently at each occurrence, H, $C_{1-6}$ alkyl substituted with 0-2 $R^g$, —$(CH_2)_n$-phenyl substituted with 0-2 $R^g$, or —$(CH_2)_n$-5- to 10-membered heterocycle comprising: carbon atoms and 1-4 heteroatoms selected from N, $NR^f$, O, and $S(O)_p$, wherein said heterocycle is substituted with 0-2 $R^g$;

n, at each occurrence, is selected from 0, 1, 2, 3, and 4;

p, at each occurrence, is selected from 0, 1, and 2;

r, at each occurrence, is selected from 0, 1, 2, 3, and 4;

s, at each occurrence, is selected from 0, 1, 2, 3, and 4.

In another embodiment, the present invention provides a method for treating a thromboembolic disorder, comprising: administering to a patient in need thereof a therapeutically effective amount of a compound of Formula (IIb):

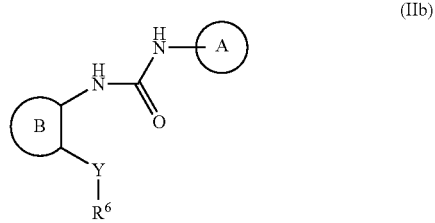

(IIb)

or a stereoisomer or pharmaceutically acceptable salts, solvates, or prodrugs thereof, wherein:

ring A is

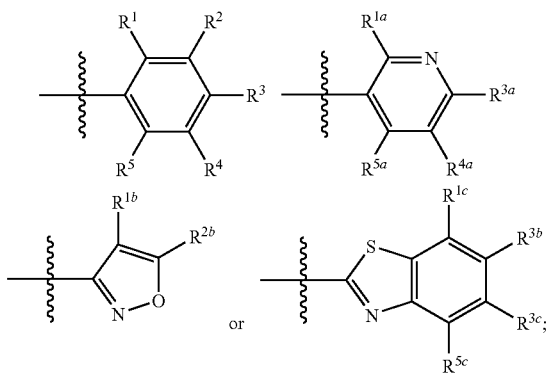

or $R^1$, $R^{1a}$, $R^{1b}$, $R^{1c}$, $R^2$, $R^{2b}$, $R^3$, $R^{3a}$, $R^{3b}$, $R^{3c}$, $R^4$, $R^{4a}$, $R^5$, $R^{5a}$, or $R^{5c}$, are independently at each occurrence, H, F, Cl, Br, I, $OCF_3$, $CF_3$, —$(CH_2)_r$—$OR^c$, $SR^c$, CN, $NO_2$, —$(CH_2)_r$—$NR^{12}R^{13}$, —$C(O)R^c$, —$(CH_2)_r$—$CO_2R^c$, —$(CH_2)_r$—$C(O)NR^{12}R^{13}$, —$(CH_2)_r$—$OC(O)NR^{12}R^{13}$, —$(CH_2)_r$—$NR^{14}C(O)R^d$, —$S(O)_pNR^{12}R^{13}$, —$NR^{14}S(O)_pNR^{12}R^{13}$, —$S(O)R^d$, —$S(O)_2R^d$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^b$;

alternatively, $R^1+R^2$, $R^2+R^3$, $R^3+R^4$, $R^4+R^5$, $R^{4a}+R^{5a}$, $R^{1b}+R^{2b}$, $R^{1c}+R^{3b}$, $R^{3b}+R^{3c}$, or $R^{3c}+R^{5c}$, combine with the carbon atoms to which they attached, form 5-10 membered carbocyclic or heterocyclic ring comprising: carbon atoms and 0-3 heteroatoms selected from N, $NR^{11}$, O, and $S(O)_p$, carbonyl group, and additional 0-2 double bonds, wherein said carbocyclic or heterocyclic ring is substituted with 0-2 $R^b$;

ring B is 5- to 6-membered heteroaryl comprising: carbon atoms and 1-2 ring heteroatoms selected from N, $NR^{11}$, $S(O)_p$, and O, wherein said heteroaryl is substituted with 0-3 $R^7$;

$R^6$ is a phenyl substituted with 0-3 $R^{6a}$, or a 5- to 10-membered heterocycle comprising: carbon atoms and 1-4 heteroatoms selected from N, $NR^{11}$, O, and $S(O)_p$, and substituted with 0-3 $R^{6a}$;

$R^{6a}$ is, independently at each occurrence, H, =O, F, Cl, Br, I, $OR^c$, $SR^c$, CN, $NO_2$, $CF_3$, $OCF_3$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, —$Si(Me)_3$, $C_1$-$C_4$ haloalkyl, $C_1$-$C_4$ haloalkyloxy-, $C_1$-$C_4$ alkyloxy-, $C_1$-$C_4$ alkylthio-, $C_1$-$C_4$ alkyl-C(O)—, $C_1$-$C_4$ alkyl-O—C(O)—, $C_1$-$C_4$ alkyl-C(O)NH—, $C_{1-8}$ alkyl substituted with 0-1 $R^a$, $C_{2-8}$ alkenyl substituted with 0-1 $R^a$, $C_{2-8}$ alkynyl substituted with 0-1 $R^a$, —$(CH_2)_r$—$C_{3-10}$ carbocycle substituted with 0-2 $R^e$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-2 $R^e$;

$R^7$ is, independently at each occurrence, H, =O, F, Cl, Br, I, $OCF_3$, $CF_3$, $OR^e$, $SR^e$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, $NR^{7b}$, O, and $S(O)_p$, and substituted with 0-3 $R^b$;

alternatively, two $R^7$s on the two adjacent carbon atoms are combined to form a 5- to 7-membered carbocyclic or heterocyclic ring comprising: carbon atoms and 0-3 ring heteroatoms selected from O, N, $NR^{7b}$, and $S(O)_p$, and said carbocyclic or heterocyclic ring is substituted with 0-2 $R^{7c}$;

$R^{7b}$ is, independently at each occurrence, H, $C_{1-4}$ alkyl, ($C_{1-4}$ alkyl)C(O)—, phenyl-C(O)—, benzyl-C(O)—, or benzyl;

$R^{7c}$ is, independently at each occurrence, H, F, Cl, Br, I, $OCF_3$, $CF_3$, $OR^c$, $SR^c$, CN, $NO_2$, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, —$S(O)_2R^d$, $C_{1-4}$ alkyl, phenyl substituted with 0-2 $R^b$, or benzyl substituted with 0-2 $R^b$;

$R^{11}$ is, independently at each occurrence, H, $C_{1-4}$ alkyl substituted with 0-1 $R^a$, $C_{2-4}$ alkenyl substituted with 0-1 $R^a$, $C_{2-4}$ alkynyl substituted with 0-1 $R^a$, ($C_{1-4}$ alkyl)C(O)—, ($C_{3-6}$ cycloalkyl)$C_{1-3}$ alkyl-C(O)—, ($C_{3-6}$ cycloalkyl)C(O)—, phenyl-C(O)—, benzyl-C(O)—, benzyl-S(O)$_2$—, ($C_{1-6}$ alkyl)-S(O)$_2$—, phenyl-S(O)$_2$—, —$(CH_2)_r$—$C_{3-7}$ cycloalkyl substituted with 0-2 $R^b$, —$(CH_2)_r$-phenyl substituted with 0-2 $R^b$, or —$(CH_2)_r$-5- to 6-membered heterocycle comprising: carbon atoms and 1-4 heteroatoms selected from N, $NR^f$, O, and $S(O)_p$, wherein said heterocycle is substituted with 0-2 $R^b$;

$R^{12}$ is, independently at each occurrence, H, $C_{1-4}$ alkyl, ($C_{1-4}$ alkyl)C(O)—, —$(CH_2)_n$-phenyl, phenyl-C(O)—, benzyl-C(O)—, ($C_{1-4}$ alkyl)-NHC(O)—, phenyl-NHC(O)—, (5- to 10-membered heteroaryl)-NHC(O)—, (5- to 10-membered heteroaryl)-C(O)—, ($C_{1-4}$ alkyl)-S(O)$_2$—, phenyl-S(O)$_2$—, (5- to 10-membered heteroaryl)-S(O)$_2$—, or benzyl-S(O)$_2$—, wherein said phenyl, aryl and heteroaryl are substituted with 0-2 $R^g$;

$R^{13}$ is, independently at each occurrence, H, $C_{1-4}$ alkyl, phenyl, or benzyl;

alternatively, $R^{12}$ and $R^{13}$, when attached to the same nitrogen, together with the nitrogen atom form a 5- to 6-membered heterocyclic ring comprising carbon atoms and 0-2 additional heteroatoms selected from N, $NR^{11}$, O, and $S(O)_p$;

$R^{14}$ is, independently at each occurrence, H, $C_{1-4}$ alkyl, phenyl, or benzyl;

Y is $NR^{15}$, O, or S;

$R^{15}$ is H, $C_{1-6}$ alkyl substituted with 0-2 $R^a$, $C_{2-6}$ alkenyl substituted with 0-2 $R^a$, $C_{2-6}$ alkynyl substituted with 0-2 $R^a$, ($C_{1-6}$ alkyl)C(O)—, ($C_{3-6}$ cycloalkyl)$C_{1-3}$ alkyl-C(O)—, ($C_{3-6}$ cycloalkyl)C(O)—, phenyl-C(O)—, benzyl-C(O)—, benzyl-S(O)$_2$—, ($C_{1-6}$ alkyl)NHC(O)—, ($C_{1-6}$ alkyl)$_2$NC(O)—, phenyl-NHC(O)—, benzyl-NHC(O)—, (phenyl)($C_{1-6}$ alkyl)NC(O)—, (benzyl)($C_{1-6}$ alkyl)NC(O)—, ($C_{1-6}$ alkyl)-S(O)$_2$—, phenyl-S(O)$_2$—, —$(CH_2)_r$—$C_{3-10}$ carbocycle substituted with 0-3 $R^b$, or —$(CH_2)_r$-5- to 10-membered heterocycle comprising: carbon atoms and 1-4 heteroatoms selected from N, $NR^{11}$, O, and $S(O)_p$, wherein said heterocycle is substituted with 0-3 $R^b$;

alternatively, $R^{15}$ taken together with an $R^{6a}$ group on $R^6$, form a 5- to 10-membered carbocyclic or heterocyclic ring comprising: carbon atoms and 0-4 heteroatoms selected from N, $NR^{11}$, O, and $S(O)_p$, 0-1 carbonyl, and 0-3 double bonds, wherein said heterocycle is substituted with 0-2 $R^b$;

$R^a$ is, independently at each occurrence, H, =O, F, $OCF_3$, $CF_3$, $OR^c$, $SR^c$, CN, —$NR^{12}R^{13}$, —$C(O)R^c$, —$C(O)OR^c$, —$C(O)NR^{12}R^{13}$, —$NR^{14}C(O)R^d$, —$S(O)_pNR^{12}R^{13}$, —$S(O)R^d$, or —$S(O)_2R^d$;

$R^b$ is, independently at each occurrence, H, =O, F, Cl, Br, I, $OR^c$, $SR^c$, CN, $NO_2$, $CF_3$, $OCF_3$, —$NR^{12}R^{13}$, —$C(O)R^c$, —C(O)OR$^c$, —C(O)NR$^{12}$R$^{13}$, —NR$^{14}$C(O)R$^d$, —S(O)$_p$NR$^{12}$R$^{13}$, —S(O)R$^d$, —S(O)$_2$R$^d$, C$_1$-C$_4$ haloalkyl, C$_1$-C$_4$ haloalkyloxy-, C$_1$-C$_4$ alkyloxy-, C$_1$-C$_4$ alkylthio-, C$_1$-C$_4$ alkyl-C(O)—, C$_1$-C$_4$ alkyl-O—C(O)—, C$_1$-C$_4$ alkyl-C(O)NH—, C$_{1-6}$ alkyl substituted with 0-2 R$^a$, C$_{2-6}$ alkenyl substituted with 0-2 R$^a$, C$_{2-6}$ alkynyl substituted with 0-2 R$^a$, —(CH$_2$)$_r$—C$_{3-10}$ carbocycle substituted with 0-3 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-3 R$^e$;

R$^c$ is, independently at each occurrence, H, C$_{1-6}$ alkyl substituted with 0-2 R$^e$, C$_{2-6}$ alkenyl substituted with 0-2 R$^e$, C$_{2-6}$ alkynyl substituted with 0-2 R$^e$, —(CH$_2$)$_r$—C$_{3-8}$ cycloalkyl substituted with 0-2 R$^e$, —(CH$_2$)$_r$—C$_{6-10}$ aryl substituted with 0-2 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^d$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^e$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^e$;

R$^e$ is, independently at each occurrence, H, =O, OR$^f$, F, Cl, Br, I, CN, NO$_2$, —NR$^{12}$R$^{13}$, —C(O)R$^f$, —C(O)OR$^f$, —NR$^{14}$C(O)R$^f$, —C(O)NR$^{12}$R$^{13}$, —SO$_2$NR$^{12}$R$^{13}$, —NR$^{14}$SO$_2$NR$^{12}$R$^{13}$, —NR$^{14}$SO$_2$—C$_{1-4}$ alkyl, —NR$^{14}$SO$_2$CF$_3$, —NR$^{14}$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^g$, C$_{2-6}$ alkenyl substituted with 0-2 R$^g$, C$_{2-6}$ alkynyl substituted with 0-2 R$^g$, —(CH$_2$)$_r$—C$_{3-8}$ cycloalkyl substituted with 0-2 R$^g$, —(CH$_2$)$_r$—C$_{6-10}$ aryl substituted with 0-2 R$^g$, or —(CH$_2$)$_r$-5- to 10-membered heterocycle comprising: carbon atoms and 1-4 heteroatoms selected from N, NR$^f$, O, and S(O)$_p$, wherein said heterocycle is substituted with 0-2 R$^g$;

R$^f$ is, independently at each occurrence, H, C$_{1-6}$ alkyl, or —(CH$_2$)$_n$-phenyl;

R$^g$ is, independently at each occurrence, H, =O, OR$^f$, F, Cl, Br, I, CN, NO$_2$, —NR$^f$R$^f$, —C(O)R$^f$, —C(O)OR$^f$, —NR$^f$C(O)R$^f$, —C(O)NR$^f$R$^f$, —SO$_2$NR$^f$R$^f$, —NR$^f$SO$_2$NR$^f$R$^f$, —NR$^f$SO$_2$—C$_{1-4}$ alkyl, —NR$^f$SO$_2$CF$_3$, —NR$^f$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl, C$_{2-6}$ alkenyl, or C$_{2-6}$ alkynyl;

n, at each occurrence, is selected from 0, 1, 2, 3, and 4;

p, at each occurrence, is selected from 0, 1, and 2; and r, at each occurrence, is selected from 0, 1, 2, 3, and 4.

In another embodiment, the present invention includes compounds of Formula (Ia), or a stereoisomer or pharmaceutically acceptable salts, solvates, or prodrugs thereof, wherein:

ring A is

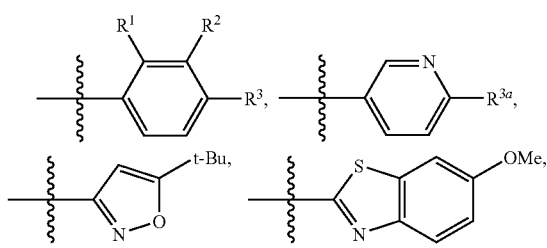

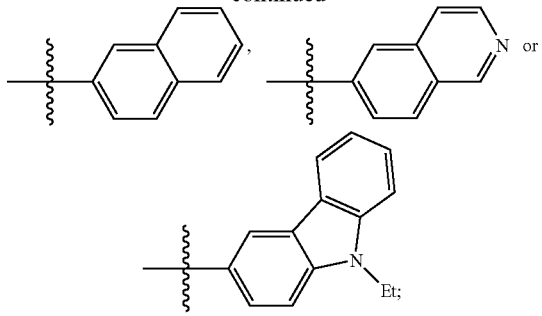

R$^1$ is H or F;

R$^2$ is H, F, Cl, or CF$_3$;

R$^3$ is H, F, Cl, Me, Et, Pr, Bu, t-Bu, OMe, OEt, OPr, O-i-Pr, OBu,

Bu, isopentoxy, neohexoxy, —OCH(Me)CH$_2$O-t-Bu, CF$_3$, OCF$_3$, NMe$_2$, NEt$_2$, —NHPh, —CH$_2$CO$_2$Me, —C(Me)$_2$CO$_2$Me, —OCH$_2$C(Me)$_2$CH$_2$NMe$_2$, cyclohexyl, Ph, 2-N(Me)$_2$CH$_2$-Ph, phenoxy, Bn, 3-OMe-benzoxy, 4-OCF$_3$-benzoxy, 2,4-diF-benzoxy, cyclohexylethoxy, cyclopentoxy, 3-Me-cyclopentoxy, N-morpholinyl, 3-CO$_2$Et-5-Me-1H-pyrazolyl, 1-Bn-piperazin-4-yl, 1-piperidinyl, Bn-piperidin-4-yl-methoxy, 1-CO$_2$Me-cyclopropyl, 1-CH$_2$OMe-cyclopropyl, CO$_2$Me-cyclobutyl, 1-CO$_2$Me-cyclopentyl, or 1-CO$_2$Me-cyclohexyl;

R$^{3a}$ is CF$_3$, —NHPh, —NH(2-CF$_3$-Ph), —NH(2-t-Bu-Ph), 2-t-Bu-phenoxy, or 2-CF$_3$-phenoxy;

R$^6$ is 2-Pr-Ph, 2-i-Pr-Ph, 3-i-Pr-Ph, 3-Et-Ph, 2-t-Bu-Ph, 3-t-Bu-Ph, CF$_3$-Ph, 3-CF$_3$-Ph, 2-OCF$_3$-Ph, 3-Ph-Ph, 2-SiMe$_3$-Ph, 2-cyclopentyl-Ph,

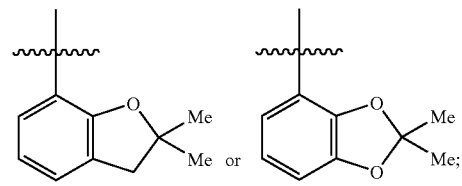

ring B is

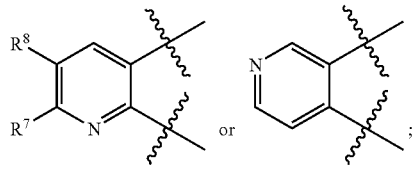

R$^7$ is H, Me, Cl, Br, CN, OMe, SMe, or NHMe;

R$^8$ is H, Me, Cl, or CN; and

Y is O, S, or NH.

In another embodiment, the present invention includes compounds of Formula (Ia), or a stereoisomer or pharmaceutically acceptable salts, solvates, or prodrugs thereof, wherein:

ring A is

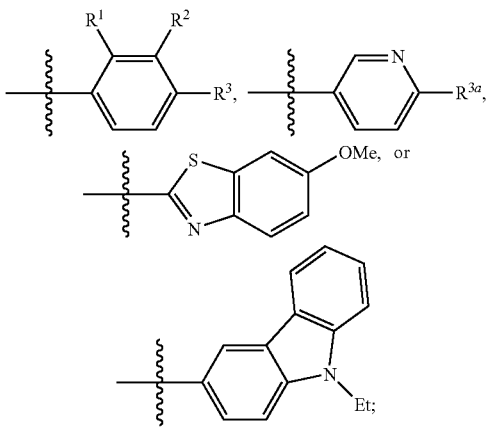

R¹ is H or F;
R² is H, or F;
R³ is H, F, Cl, Me, t-Bu, OMe, OEt, OPr, O-i-Pr, OBu, O-t-Bu, isopentoxy, neohexoxy, —OCH(Me)CH₂O-t-Bu, OCF₃, NMe₂, NEt₂, —CH₂CO₂Me, —C(Me)₂CO₂Me, —OCH₂C(Me)₂CH₂NMe₂, cyclohexyl, Ph, 2-N(Me)₂CH₂-Ph, phenoxy, Bn, 3-OMe-benzoxy, 4-OCF₃-benzoxy, 2,4-diF-benzoxy, cyclohexylethoxy, cyclopentoxy, 3-Me-cyclopentoxy, N-morpholinyl, 3-CO₂Et-5-Me-1H-pyrazolyl, N-Bn-piperazin-4-yl, N-piperidinyl, N-Bn-piperidin-4-yl-methoxy, 1-CO₂Me-cyclopropyl, 1-CH₂OMe-cyclopropyl, CO₂Me-cyclobutyl, 1-CO₂Me-cyclopentyl, or 1-CO₂Me-cyclohexyl;
R³ᵃ is —NH(2-CF₃-Ph), —NH(2-t-Bu-Ph), 2-t-Bu-phenoxy, or 2-CF₃-phenoxy;
R⁶ is 2-i-Pr-Ph, 3-i-Pr-Ph, 2-t-Bu-Ph, 2-CF₃-Ph, 2-OCF₃-Ph, 2-SiMe₃-Ph,
2-cyclopentyl-Ph,

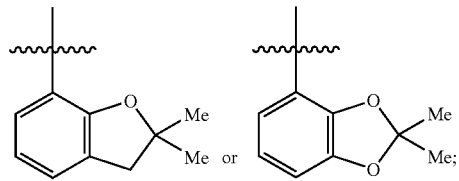

ring B is

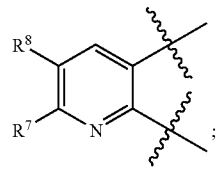

R⁷ is H, Cl, CN, OMe, or NHMe;
R⁸ is H, Me, Cl, or CN; and
Y is O or NH.

In another embodiment, the present invention includes compounds of Formula (Ia), or a stereoisomer or pharmaceutically acceptable salts, solvates, or prodrugs thereof, wherein:

ring A is

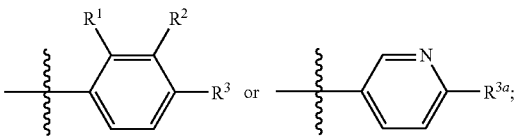

R¹ is H or F;
R² is H, or F;
R³ is Cl, Me, t-Bu, OPr, O-i-Pr, OBu, O-t-Bu, OCF₃, isopentoxy, neohexoxy, 3-Me-cyclopentoxy, cyclohexylethoxy, NMe₂, Ph, 2-N(Me)₂CH₂-Ph, 2,4-diF-benzoxy, —OCH(Me)CH₂O-t-Bu, —OCH₂C(Me)₂CH₂NMe₂,
3-CO₂Et-5-Me-1H-pyrazolyl, N-Bn-piperazin-4-yl, N-piperidinyl,
N-Bn-piperidin-4-yl-methoxy, 1-CO₂Me-cyclopropyl, 1-CH₂OMe-cyclopropyl,
CO₂Me-cyclobutyl, 1-CO₂Me-cyclopentyl, or 1-CO₂Me-cyclohexyl;
R³ᵃ is —NH(2-CF₃-Ph), —NH(2-t-Bu-Ph), 2-t-Bu-phenoxy, or
2-CF₃-phenoxy;
R⁶ is 2-i-Pr-Ph, 3-i-Pr-Ph, 2-t-Bu-Ph, 2-SiMe₃-Ph, 2-cyclopentyl-Ph,

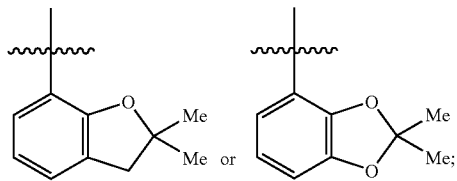

ring B is

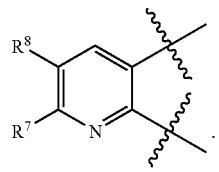

R⁷ is H, Cl, or CN;
R⁸ is H, Me, Cl, or CN; and
Y is O.

In another embodiment, the present invention includes compounds wherein: Y is O.

In another embodiment, the present invention includes compounds wherein: ring B is

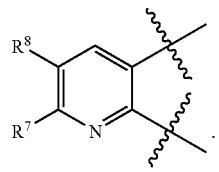

In another embodiment, the present invention includes compounds wherein: ring A is

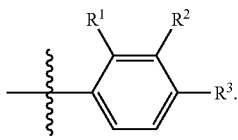

In another embodiment, the present invention provides a pharmaceutical composition comprising a pharmaceutically acceptable carrier and a therapeutically effective amount of at least one of the compounds of the present invention or a pharmaceutically acceptable salt, solvate, or prodrug form thereof.

In another embodiment, the present invention provides a novel process for making a compound of the present invention or a stereoisomer or pharmaceutically acceptable salt, solvate or prodrug form thereof.

In another embodiment, the present invention provides a novel intermediate for making a compound of the present invention or a stereoisomer or pharmaceutically acceptable salt, solvate or prodrug form thereof.

In another embodiment, the present invention provides a pharmaceutical composition further comprising additional therapeutic agent(s) selected from potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other kallikrein inhibitors, factor VIIa inhibitors and factor Xa inhibitors, and antiplatelet agents selected from GPIIb/IIIa blockers, other P2Y$_1$ antagonists, P2Y$_{12}$ antagonists, thromboxane receptor antagonists, and aspirin, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment, the present invention provides a method for modulation of platelet reactivity comprising administering to a patient in need of such treatment a therapeutically effective amount of at least one of the compounds of the present invention or a pharmaceutically acceptable salt, solvate, or prodrug form thereof.

In another embodiment, the present invention provides a method for treating thromboembolic disorders comprising: administering to a patient in need of such treatment a therapeutically effective amount of at least one of the compounds of the present invention or a pharmaceutically acceptable salt, solvate, or prodrug form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt, solvate, or prodrug form thereof in an amount effective to treat a thromboembolic disorder.

In another embodiment, the present invention provides a method for treating a thromboembolic disorder, comprising: administering to a patient in need thereof a therapeutically effective amount of a first and additional therapeutic agent(s), wherein the first therapeutic agent is a compound of present invention or a pharmaceutically acceptable salt thereof and the additional therapeutic agent(s) are selected from potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a method for treating a thromboembolic disorder, comprising: administering to a patient in need thereof a therapeutically effective amount of a first and additional therapeutic agent(s), wherein the first therapeutic agent is a compound of present invention or a pharmaceutically acceptable salt thereof and the additional therapeutic agent(s) are selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent, or a combination thereof.

In another embodiment, the present invention provides a method for treating a thromboembolic disorder, wherein the additional therapeutic agent(s) are selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, a combination thereof.

In another embodiment, the present invention provides a method for treating a thromboembolic disorder, wherein the additional therapeutic agent(s) are selected from an antihypertensive agent selected from ACE inhibitors, AT-1 receptor antagonists, ET receptor antagonists, dual ET/AII receptor antagonists, and vasopepsidase inhibitors, or an antithrombotic agent selected from an antiplatelet agent selected from GPIIb/IIIa blockers, $P2Y_1$ and $P2Y_{12}$ antagonists, thromboxane receptor antagonists, and aspirin, a combination thereof.

In another embodiment, the present invention provides a method for treating a thromboembolic disorder, wherein the additional therapeutic agent(s) are an anti-platelet agent or a combination thereof.

In another embodiment, the present invention provides a method for treating a thromboembolic disorder, wherein the additional therapeutic agent(s) are the anti-platelet agent(s) clopidogrel and/or aspirin.

In another embodiment, the present invention provides a novel method, comprising: administering a compound of the present invention or a pharmaceutically acceptable salt form thereof in an amount effective to treat a thromboembolic disorder.

In another embodiment, the present invention provides a compound of the present invention for use in therapy.

In another embodiment, the present invention also provides the use of a compound of the present invention for the manufacture of a medicament for the treatment of a thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising: (d) a second container; wherein components (a) and (b) are located within the second container and component (c) is located within or outside of the second container.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The following are definitions of terms used in this specification. The initial definition provided for a group or term herein applies to that group or term throughout the present specification, individually or as part of another group, unless otherwise indicated.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbon atom of the carbonyl group or one carbon atom of the double bond be part of (i.e., within) the ring. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

When any variable (e.g., $R^{2b}$, $R^{8b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

"Alkoxy" or "alkyloxy" represents an alkyl group as defined above with the indicated number of carbon atoms attached through an oxygen bridge. For example, "$C_1$-$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluoroethoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, naphthyl, and indanyl. When the term "carbocycle" is used, it is intended to include "aryl".

As used herein, the term "bicyclic carbocycle" or "bicyclic carbocyclic group" is intended to mean a stable 9- or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

As used herein, the term "aryl", "$C_6$-$C_{10}$ aryl" or "aromatic residue", is intended to mean an aromatic moiety containing, if specified, the specified number of carbon atoms; for example phenyl or naphthyl. Unless otherwise specified, "aryl", "$C_6$-$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3, 4, 5, 6, or 7-membered monocyclic or bicyclic or 7, 8, 9, 10, 11, 12, 13, or 14-membered bicyclic or tricyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

As used herein, the term "aromatic heterocyclic group" or "heteroaryl" is intended to mean a stable monocyclic and polycyclic aromatic hydrocarbon that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-5-oxide, 2,3-dihydrobenzothienyl-5-dioxide, benzoxazolin-2-on-yl, indolinyl, benzodioxolanyl, benzodioxane, and the like. Heteroaryl groups can be substituted or unsubstituted.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5 or 6-membered monocyclic aromatic ring comprising a 5 membered heteroaryl ring, a 6-membered heteroaryl ring or a benzo ring, each fused to a second ring. The second ring is a 5 or 6 membered monocyclic ring which is saturated, partially unsaturated, or unsaturated, and comprises a 5 membered heterocycle, a 6 membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinoline, 2,3-dihydrobenzofuranyl, chromanyl, 1,2,3,4-tetrahydro-quinoxaline, and 1,2,3,4-tetrahydro-quinazoline.

Also included are fused ring and spiro compounds containing, for example, the above carbocycles or heterocycles.

Bridged rings are also included in the definition of carbocycle or heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 112, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield compounds of the present invention per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Therapeutically effective amount" is intended to include an amount of a compound of the present invention that is effective when administered alone or in combination to inhibit $P2Y_1$. "Therapeutically effective amount" is also intended to include an amount of the combination of compounds claimed that is effective to inhibit $P2Y_1$. The combination of compounds is preferably a synergistic combination. Synergy, as described, for example, by Chou and Talalay, *Adv. Enzyme Regul.* 1984, 22:27-55, occurs when the effect (in this case, inhibition of $P2Y_1$) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and nonaqueous liquid media, as well as a variety of solid and semisolid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "M" for molar, "mmol" for millimole or millimoles, "min" for minute or minutes, "h" for hour or hours, "rt" for room temperature, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, "tlc" for thin layer chromatography, and "α", "β", "R", "S", "E", and "Z" are stereochemical designations familiar to one skilled in the art.

Me methyl
Et ethyl
MeOH methanol
EtOH ethanol
i-PrOH isopropanol
Ph phenyl
Bn benzyl
t-Bu tertiary butyl
AcOH acetic acid
EtOAc ethyl acetate
2MeS-ADP 2 methylthio adenosine diphosphate
cDNA complimentary DNA
DMEM Dulbecco's modified Eagle media
DMF dimethyl formamide
DMSO dimethyl sulfoxide
DCE 1,2 dichloroethane
DCM dichloromethane
DCC dicyclohexylcarbodiimide
DIC or DIPCDI diisopropylcarbodiimide
DIEA diethylpropyl amine
EDTA ethylenediaminetetraacetic acid
FBS Fetal Bovine Serum
HEPES 4-(2-hydroxyethyl)piperaxine-1-ethanesulfonic acid
D-PBS Dulbecco's Phosphate Buffered Saline
Pd/C palladium on carbon
SCX Strong Cation Exchanger
THF tetrahydrofuran
TFA trifluoroacetic acid
TRIS tris (hydroxymethyl)aminomethane
EDC (or EDC.HCl) or EDCI (or EDCI.HCl) or EDAC
3-ethyl-3'-(dimethylamino)propyl-carbodiimide hydrochloride (or 1-(3-dimethylaminopropyl)-3-ethylcarbodiimide hydrochloride)

Solution ratios express a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C. *Comprehensive Organic Transformations*, VCH: New York, 1989. Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Schemes 1-7 describe synthetic routes of making compounds of the invention. Schemes 1 and 2 describe preparations of compounds of the invention from a key amine intermediate 1 or an isocyanate intermediate 4. Scheme 3 describes a preparation of the key isocyanate intermediate 4 from the corresponding amine 1. Schemes 4, 5 and 6 describe a preparation of the amines from commercially available starting materials. Scheme 6 elaborates further functionalization of ureas.

Scheme 1 describes a one-step preparation of substituted ureas and thioureas, from the key amine intermediate 1. Substituted isocyanates and isothiocyanates are commercially available or can readily be prepared from commercially available materials by methods known to one skilled in the art of organic synthesis. Reaction of an iso(thio)cyanate 2 with key amine 1 typically occurs at temperatures between 20° C. and 80° C. in a variety of solvents such as tetrahydrofuran, dichloroethane or dioxane.

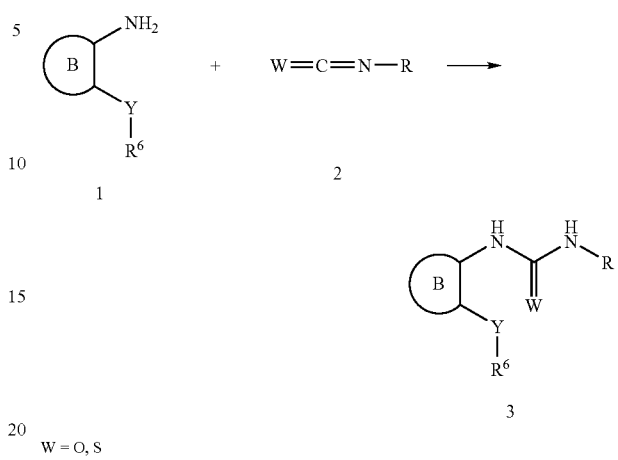

Scheme 2 describes a preparation of substituted ureas from the key iso(thio)cyanate intermediate 4. Substituted anilines and amino substituted heteroaromatics are commercially available or can readily be prepared from commercially available materials by methods known to one skilled in the art of organic synthesis. Reaction of the isocyanate 4 with aniline 5 typically occurs at temperatures between 20° C. and 80° C. in a variety of solvents such as tetrahydrofuran, dichloroethane or dioxane.

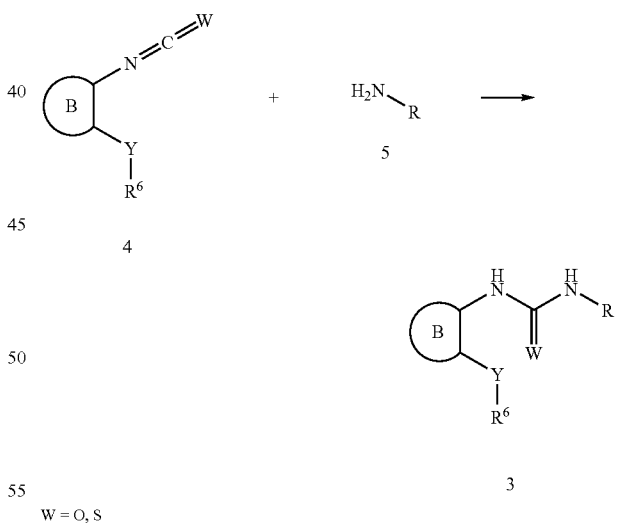

Scheme 3 outlines a preparation of the key iso(thio)cyanate intermediate 4. Anilines 1, prepared according to Schemes 4, 5 and 6 can be treated with a phosgene equivalent in an organic solvent such as $CH_2Cl_2$, dichloroethane or toluene, to produce the corresponding iso(thio)cyanate. (Thio)phosgene equivalents include diphosgene, triphosgene, carbonyl diimidazole, thiocarbonyldiimidazole, trichloromethyl chloroformate, and disuccinimidyl carbonate.

Scheme 3

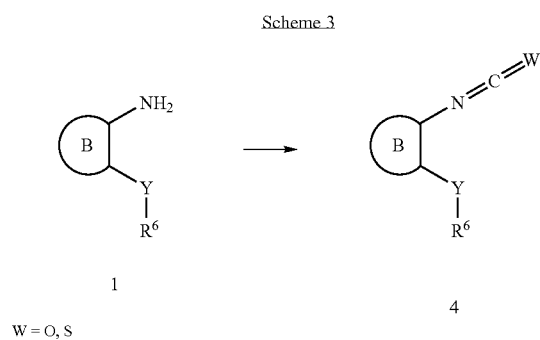

W = O, S

Typical conditions include hydrogenation in the presence of a metal catalyst such as palladium or platinum. Other conditions include treatment with reducing agents such as $SnCl_2$ or Zinc powder with ammonium chloride.

Scheme 4

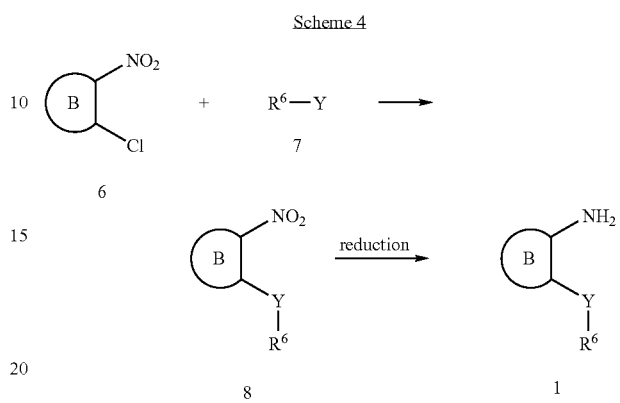

Scheme 4 outlines one possible preparation of amino derivatives 1, which proceeds by aromatic nucleophilic substitution followed by reduction. Nitroaryl derivatives or nitroheteroaryl derivatives 6, substituted in the ortho position with a halogen (such as chlorine, fluorine or bromine), are commercially available or can readily be prepared by one skilled in the art of organic synthesis. They can be reacted with nucleophiles such as substituted alcohols, substituted amines, or substituted thiols to provide the corresponding ether, amine or thioether, respectively. Typical reaction conditions involve the reaction of a nucleophile and a halo nitro derivative in an organic solvent such as THF, DMF, toluene, dioxane or n-butanol, in the presence of a base such as potassium carbonate, cesium carbonate, triethylamine, or DIEA. The reaction temperature is usually between room temperature and reflux condition. Sometimes microwave irradiation can be used to accelerate the rate of reaction. The preferred synthesis of diaryl ethers proceeds by an ortho chloro-nitroaryl derivative with a substituted phenol and cesium carbonate at 80° C. in DMF. Diaryl amines are preferably obtained by reacting an ortho chloro-nitroaryl derivative with a substituted aniline and triethylamine in butanol at 210° C. using microwave irradiation.

Following aromatic nucleophilic substitution, the resulting nitro derivative 8 can be reduced to the corresponding aniline.

Preparation of substituted pyridine amines such as 10, 11, 12, or 13 is shown in Scheme 5. The pyridine aniline 9 prepared as described in Scheme 4 can be brominated or chlorinated using agents such as N-bromosuccinimide or N-chlorosuccinimide in an organic solvent such as DMF. The resulting aromatic bromide can be converted to the corresponding nitrile by metal catalyzed cyanation. For example, reaction of the bromide 10 (X=Br) with copper (I) cyanide, tris-(dibenzylideneaceteone)-bispalladium, diphenylphosphine ferrocene and tetrabutylammonium cyanide affords the corresponding nitrile 11. The resulting nitrile can be hydrolyzed to the corresponding carboxylic acid using methods know in the art of organic synthesis such as treatment with aqueous sodium hydroxide. Conversion of the corresponding carboxylic acid to the methyl ester can be accomplished by treatment with trimethylsilyl diazomethane or with hydrochloric acid in methanol. Alternatively, the nitrile 11 can be converted to the corresponding ester 12 and amide 13 by acidic or basic hydrolysis.

Scheme 5

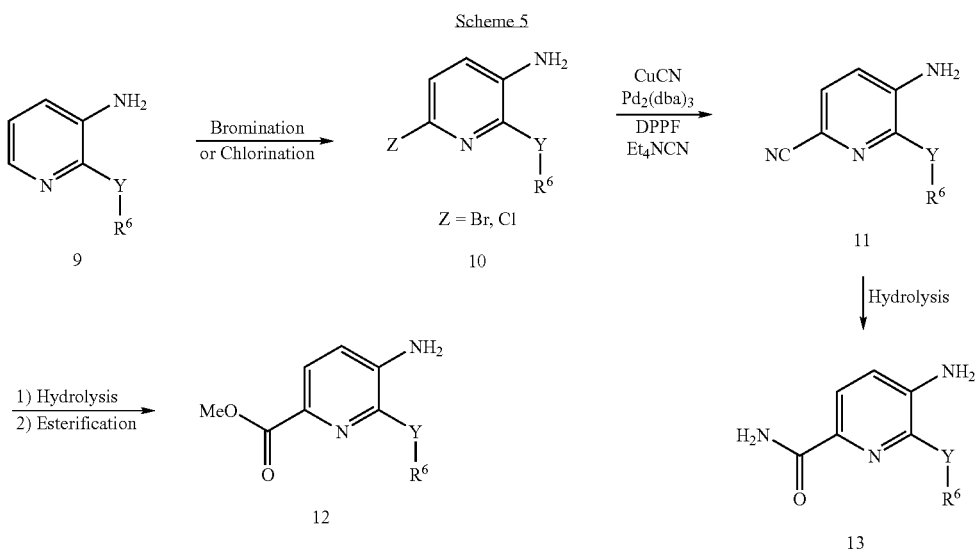

Preparation of substituted pyridine amines such as 16, 17, 18 or 19 is shown in Scheme 6. The nitrochloro pyridine 14 can be prepared as described above for Scheme 4. The resulting aromatic bromide can be converted to the corresponding nitrile by metal catalyzed cyanation. For example, reaction of the bromide 16 (Z=Br) with copper (I) cyanide, tris-(dibenzylideneaceteone)-bispalladium, diphenylphosphine ferrocene and tetrabutylammonium cyanide affords the corresponding nitrile 17. The resulting nitrile can be hydrolyzed to the corresponding carboxylic acid using methods know in the art of organic synthesis such as treatment with aqueous sodium hydroxide. Conversion of the corresponding carboxylic acid to the methyl ester 18 can be accomplished by treatment with trimethylsilyl diazomethane or with hydrochloric acid in methanol. Alternatively, the nitrile 17 can be converted to the corresponding amide 19 by acidic or basic hydrolysis.

Scheme 7

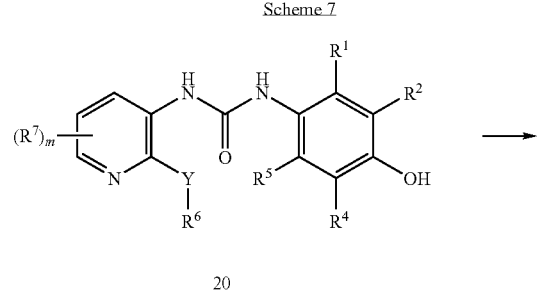

20

Scheme 6

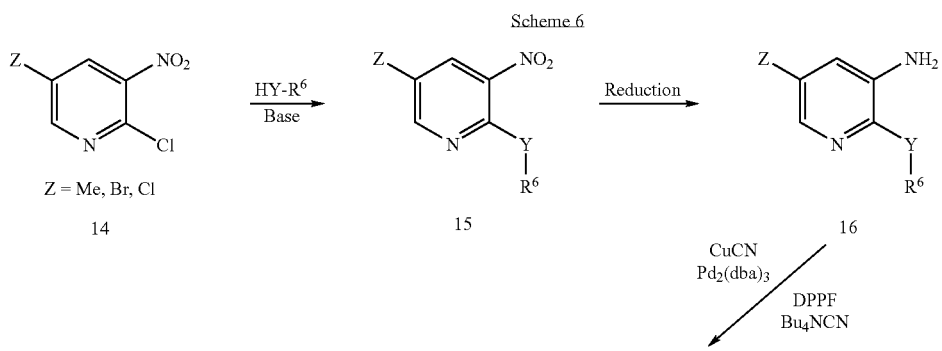

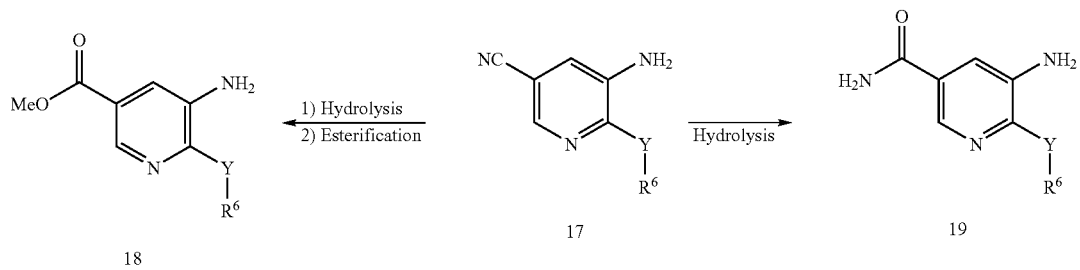

Scheme 7 describes further functionalization of urea 20 by alkylation with alcohols via Mitsunobu chemistry or by direct reaction with alkyl halides. The preferred conditions for the alkylation of such phenols involve treatment with an excess of a primary or secondary alcohol in the presence of an azodicarboxylate equivalent such as diethyl, diisopropyl or di-tert-butyl azodicarboxylate and in the presence of triphenylphosphine or polystyrene bound triphenylphosphine. The reactions can be run in a solvents such as tetrahydrofuran, toluene or dichloromethane and from 0° C. to 50° C.

-continued

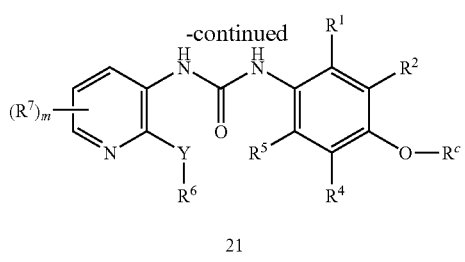

21 m = 0-3

Alternatively, when Y is O, synthesis of compounds of the present invention with variations of $R^6$ can be prepared as demonstrated below in Schemes 8-13.
Scheme 8
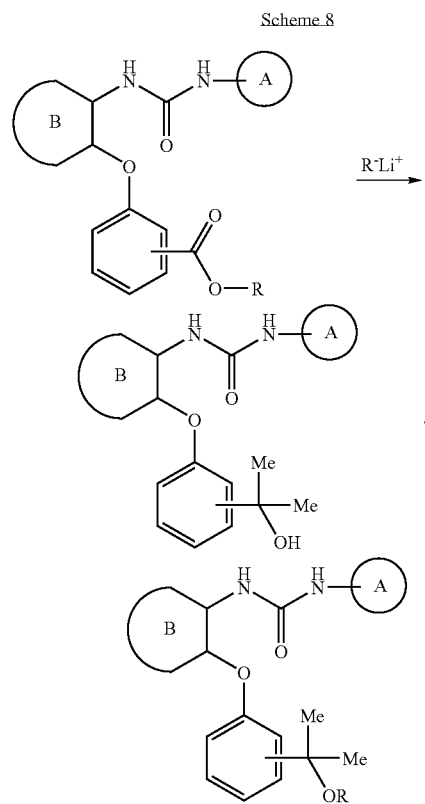
-continued
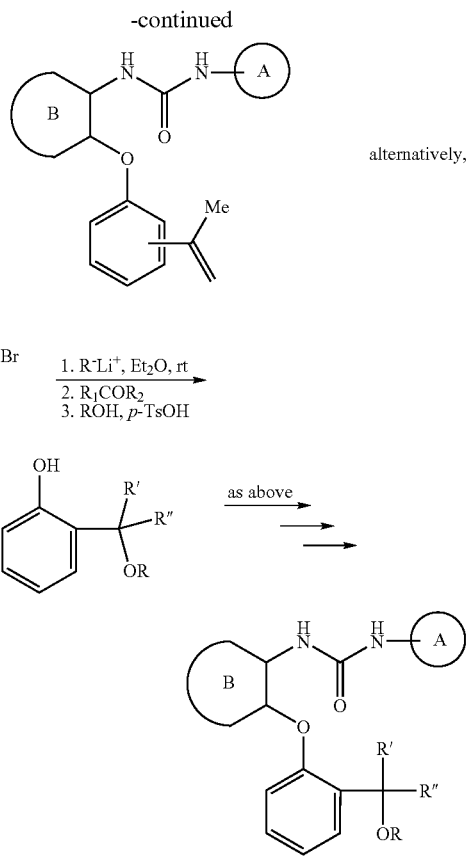
Scheme 9
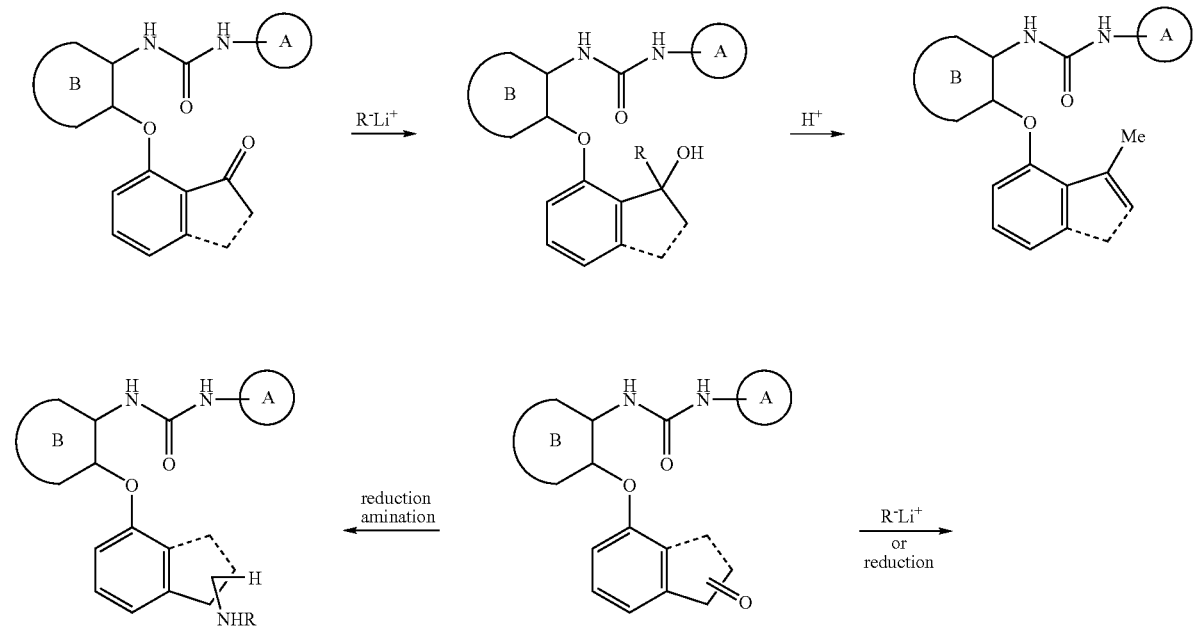

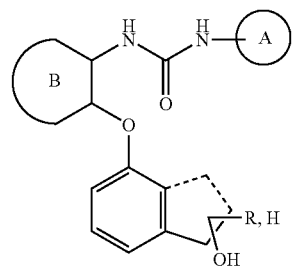
Scheme 10
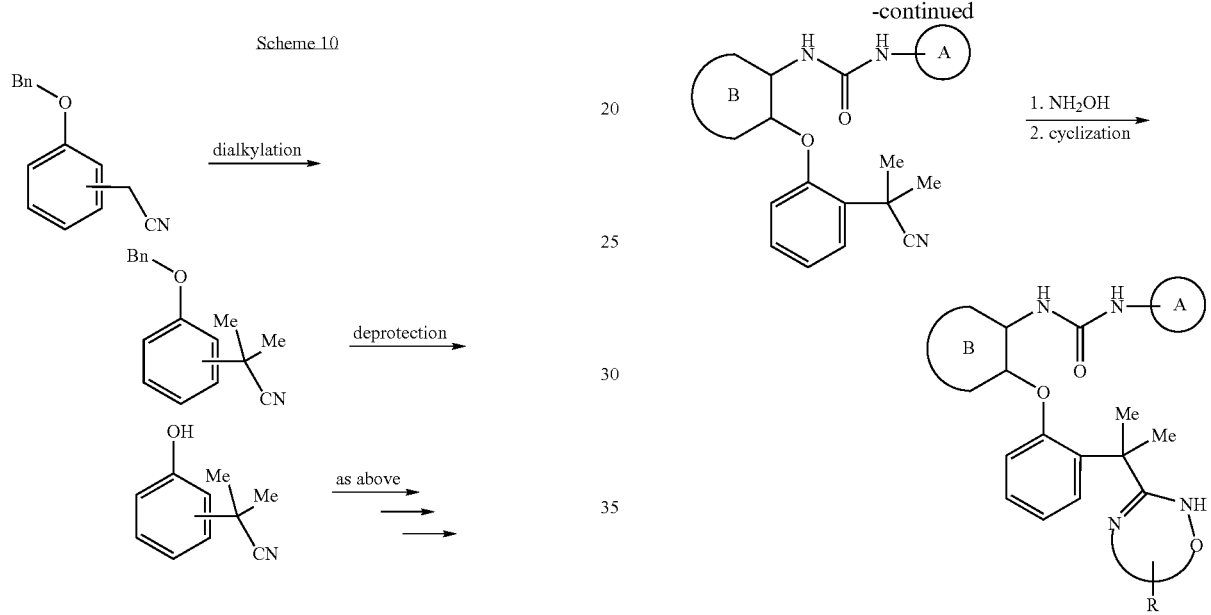
Scheme 11
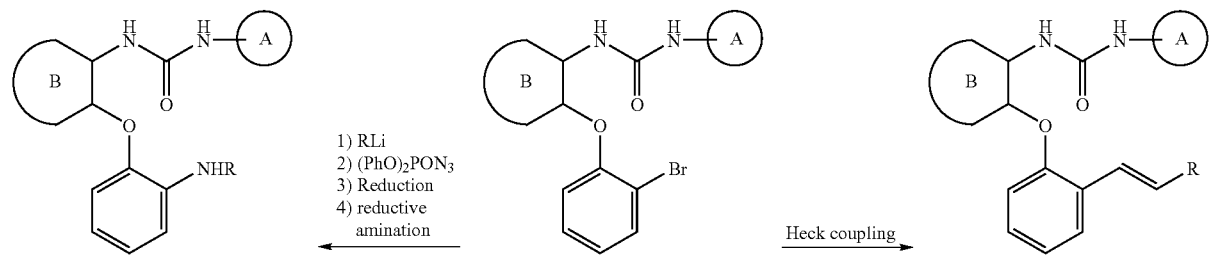

-continued
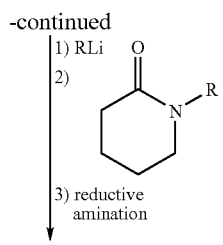
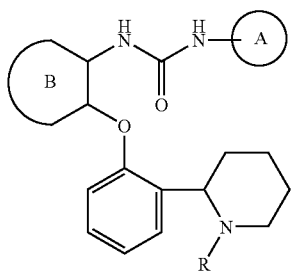
25
Scheme 12
Scheme 13
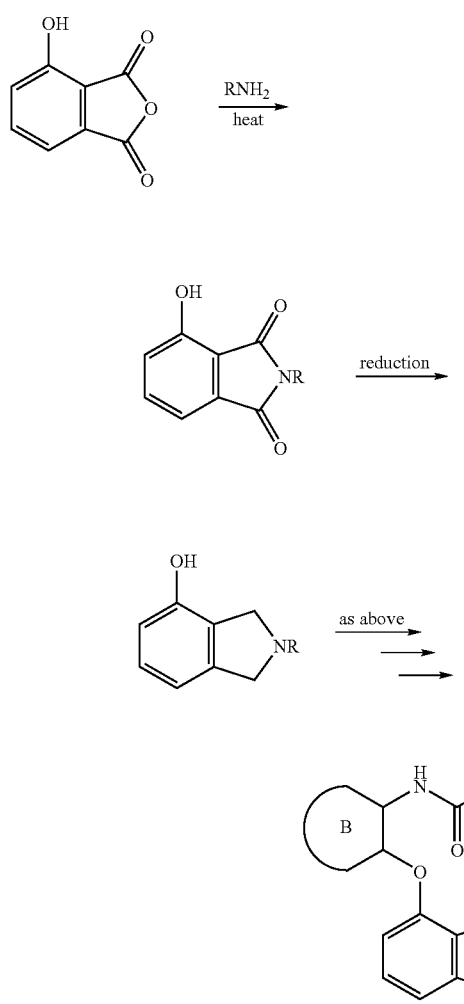
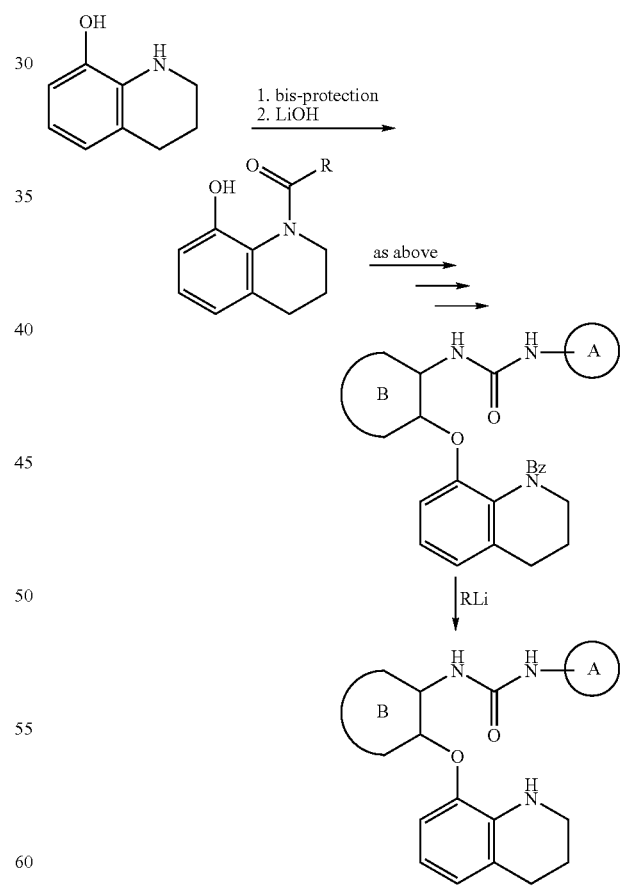
In an alternative synthesis of the compounds of the present invention, the side chain functionalization can be achieved as depicted in Scheme 14. Compound 22 prepared according to one of the previous methods, is transformed to compounds 23 either by classical reductive amination procedure or by a two step reaction sequence that involves the formation of the intermediate halogen compound 24. This compound is reacted with the appropriated nucleophile to yield the expected derivatives 25.

Scheme 14

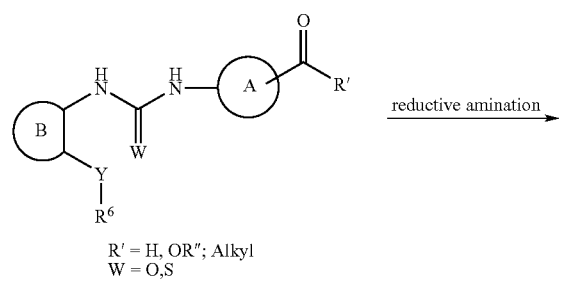

R' = H, OR''; Alkyl
W = O,S

22

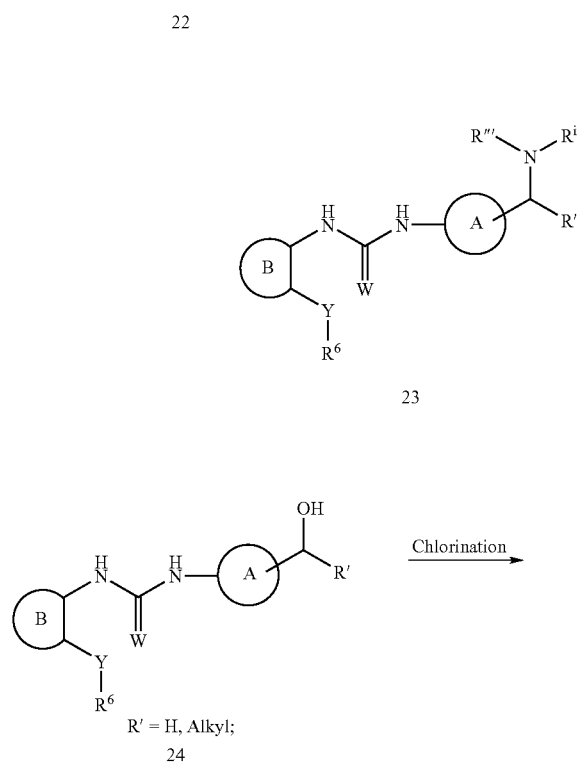

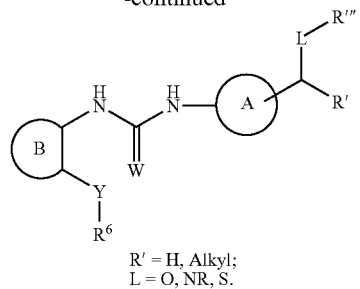

R' = H, Alkyl;
L = O, NR, S.

26

Products were analyzed by reverse phase analytical HPLC carried out on a Shimadzu Analytical HPLC system running DiscoveryVP software using Method A: Phenominex Luna C18 column (4.6×50 mm) eluted at 4 mL/min with a 4 min gradient from 100% A to 100% B (A: 10% methanol, 89.9% water, 0.1% TFA; B: 10% water, 89.9% methanol, 0.1% TFA, UV 220 nm), Method B: Phenominex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm), or Method C: Zorbax SB C18 column (4.6×75 mm) eluted at 2.5 mL/min with methanol/water with 0.2% $H_3PO_4$ as a gradient of 10% to 90% methanol over 8 min followed by holding at 90% methanol for 3 min (UV 220 nm). Purification of intermediates and final products was carried out via either normal or reverse phase chromatography. Normal phase chromatography was carried out on an ISCO CombiFlash™ System Sq16x using prepacked $SiO_2$ cartridges eluted with gradients of hexanes and ethyl acetate. Reverse phase preparative HPLC was carried out using a Shimadzu Preparative HPLC system running DiscoveryVP software on a Shim-PackVP-ODS column (50 L×20 mm) at 20 mL/min, 6 min gradient 100% A to 100% B with the solvent system used for the analytical. LCMS were obtained on a Shimadzu HPLC system running DiscoveryVP software, coupled with a Waters Model PlatformLC mass spectrometer running MassLynx version 3.5 software using the same column and conditions as utilized for analytical described above.

EXAMPLES

The following Examples have been prepared, isolated and characterized using the methods disclosed herein. The following Examples demonstrate a partial scope of the invention and are not meant to limit the scope of the invention.

Example 1

1-(4-tert-Butylphenyl)-3-(2-(3-isopropylphenoxy)pyridin-3-yl)urea 1a. 2-(3-Isopropylphenoxy)-3-nitropyridine: To a solution of meta-isopropylphenol (214 mg, 1.57 mmol) in dry DMF (3 mL) was added cesium carbonate (587 mg, 1.8 mmol) followed by 2-chloro-3-nitropyridine (237 mg, 1.5 mmol). The mixture was heated at 180° C. for 700 s in a Personal Chemistry microwave. The mixture was diluted with water (3 mL) and extracted with ethyl acetate (2×4 mL). The combined organic layers were washed with 5% aqueous LiCl solution (2×1.5 mL), saturated $Na_2CO_3$ (2×1.5 mL), water (1×1.5 mL), and then dried over $Na_2SO_4$. The solvent was removed in vacuo to yield 1a (338 mg, 87% yield) as a dark brown oil; HPLC purity: 90%, 2.89 min (Method B).

1b. 2-(3-Isopropylphenoxy)pyridin-3-amine: 1a (338 mg, 1.3 mmol) was dissolved in 1:1 methanol/ethyl acetate (5 mL) and a small spatula of 10% Pd/C was added. The mixture was hydrogenated at 40 Psi for 3.5 h. The catalyst was removed by filtering through a pad of Celite®. Solvent removal afforded 1b (267 mg, 90% yield) as a brown oil; HPLC purity: 81%, 2.89 min (Method B); [M+H]$^+$: 229.52.

Example 1: To 1b (33 mg, 0.14 mmol) was added a solution of p-tert-butylphenylisocyanate (12 mg, 0.15 mmol) in dry THF (0.75 mL). The mixture was heated with stirring at 80° C. for 1 h. Following solvent removal, the crude product was dissolved in DMF (0.15 mL) and methanol (1.55 mL) and purified by preparative HPLC to afford Example 1 (21 mg, 30% yield) as fine colorless crystals; HPLC purity: 95%; 4.38 min (Method A); [M+H]$^+$: 404.67.

Example 2

1-(2-(2-tert-Butylphenoxy)pyridin-3-yl)-3-(4-(trifluoromethoxy)phenyl)urea 2a. 2-(2-tert-Butylphenoxy)-3-nitropyridine: A solution of 2-chloro-3-nitropyridine (21.1 g, 133 mmol) in DMF (100 mL) was treated with 2-tert-butylphenol (23.5 mL, 153 mmol) and cesium carbonate (130 g, 398 mmol). The mixture was heated at 80° C. for 30 h. The reaction was cooled to rt and the mixture was poured into water (IL) with stirring. The resulting yellow precipitate was filtered, washed with water, and recrystallized from ethanol to afford 2a (32.8 g, 90% yield) as beige crystals; HPLC purity: 92%, 3.66 min (Method A); $^1$H NMR (400 MHz, CD$_3$OD) δ ppm 1.34 (s, 9H), 6.93 (m, 1H), 7.22 (m, 3H), 7.47 (m, 1H), 8.31 (dd, J=4.82, 1.75 Hz, 1H), 8.46 (dd, J=7.89, 1.75 Hz, 1H).

2b. 2-(2-tert-Butylphenoxy)pyridin-3-ylamine: 2a (7.2 g, 27 mmol) was dissolved in a 1:1 mixture of methanol and ethyl acetate (160 mL). Palladium on charcoal (10%, 360 mg, 0.33 mmol) was added and the mixture was stirred overnight under hydrogen atmosphere (40 Psi). The reaction mixture was filtered over Celite® and concentrated to afford 2b (7.2 g, 100% yield) as a white powder; HPLC purity: 100%, 2.87 min (Method A); [M+H]$^+$=243.3.

Example 2: To a solution of 2b (2.42 g, 10 mmol) in anhydrous THF (30 mL) was added dropwise a solution of 4-trifluoromethoxy phenylisocyanate (2.21 g, 11 mmol) of THF (20 mL). The reaction mixture was stirred at rt for 18 h. The solvent was evaporated and the crude product was dissolved in CH$_2$Cl$_2$ and purified by silica gel chromatography (120 g cartridge). Solvent removal afforded Example 2 (4 g, 90% yield) as a white powder; HPLC purity: 100%, 4.03 min (Method A); [M+H]$^+$=446.12; $^1$H NMR (500 MHz, CD$_3$OD) δ ppm 1.41 (s, 9H) 7.09 (d, J=9.35 Hz, 1H) 7.21 (d, J=8.80 Hz, 2H) 7.34 (m, 2H) 7.43 (dd, J=8.25, 5.50 Hz, 1H) 7.60 (m, 3H) 7.81 (d, J=5.50 Hz, 1H) 9.06 (d, J=8.25 Hz, 1H).

Example 3

1-(2-(2-tert-Butylphenoxy)pyridin-3-yl)-3-(4-cyclohexylphenyl)urea 3a. 2-(2-tert-Butylphenoxy)-3-isocyanatopyridine: To a solution of 2b (7 g, 29 mmol) and diphosgene (4.7 g, 24 mmol) in CH$_2$Cl$_2$ (200 mL) at 0° C. was added dropwise a solution of 1,8-bis[dimethylamino]naphthalene (proton sponge, 12.6 g, 57 mmol) in CH$_2$Cl$_2$ (50 mL). After stirring for 1 h, the reaction mixture was allowed to warm to rt. The organic phase was washed with 0.5 N aqueous HCl (3×), 1N aqueous sodium hydroxide and saturated aqueous ammonium chloride. The organic phase was dried over magnesium sulfate and concentrated in vacuo to afford 3a (7.8 g, 100%) as a beige solid which was used without further purification; $^1$H NMR (400 MHz, CDCl$_3$) δ ppm 1.38 (s, 9H) 6.92 (m, 2H) 7.22 (m, 2H) 7.40 (dd, J=7.83, 1.77 Hz, 1H) 7.48 (dd, J=7.83, 2.02 Hz, 1H) 7.95 (dd, J=4.93, 1.64 Hz, 1H).

Example 3: A solution of 3a (100 mg, 0.36 mmol) and 4-cyclohexylaniline (72 mg, 0.41 mmol) in THF was heated at 60° C. for 18 h. The reaction mixture was concentrated, and the residue was triturated with ethanol and filtered to afford Example 3 (120 mg, 72% yield) as white crystals; HPLC purity: 100%, 2.17 min (Method A); [M+H]$^+$=444.19.

Example 4

1-(4-tert-Butoxyphenyl)-3-(2-(2-tert-butylphenoxy)pyridin-3-yl)urea 4a. 1-tert-Butoxy-4-nitrobenzene: 1-Fluoro-4-nitrobenzene (4.2 mL, 40 mmol) was added to a suspension of potassium tert-butoxide (6.7 g, 59 mmol) in DMF (90 mL). The solution turned dark brown and warmed up instantly. After 1 h at rt, the reaction mixture was poured into water (400 mL) and extracted with diethyl ether:heptane (1:1, 3×100 mL). The combined organic phases were washed with brine (100 mL) and dried over sodium sulfate. Removal of solvent afforded 4a (7.75 g, 100% yield) as an orange oil; HPLC purity 94%, 3.38 min (Method A). Compound used without further purification.

4b. 4-tert-Butoxybenzenamine: Prepared from 4a (7.75 g, 39 mmol) as described previously for 2b to afford 4b (6.35 g, 99% yield) as a yellow oil; HPLC purity 89% pure, 1.60 min (Method A); [M+H]$^+$=166.1. 4b was used without further purification.

Example 4: Prepared from 4b and 3a as described previously for Example 3 to afford Example 4 (58 mg, 72% yield) as a white powder; HPLC purity 100%, 4.02 min (Method A); [M+H]$^+$=434.38.

Examples 5-43

Examples 5-43 listed in Table 1 below were prepared as previously described for Examples 1-4 above depending on whether the requisite isocyanate was commercially available.

Example 44

Methyl 2-(4-(3-(2-(2-tert-butylphenoxy)pyridin-3-yl)ureido)phenyl)acetate

44a. Methyl 2-(4-nitrophenyl)acetate: To a solution of 2-(4-nitrophenyl)acetic (1.14 g, 6.2 mmol) in methanol (5 mL) was added chlorotrimethylsilane (1.7 mL, 13.6 mmol) and resulting reaction mixture was stirred overnight at rt. The solvent was removed and the oily residue was purified by SiO$_2$ chromatography (40 g) using a gradient of ethyl acetate in hexane to afford 44a (1.06 g, 87% yield) was obtained as a white solid; HPLC purity 100%, 2.38 min (Method A), [M+H]$^+$=196.97.

44b. Methyl 2-(4-aminophenyl)acetate: 44a (124 mg, 0.64 mmol) was dissolved in a 1:1 mixture of methanol and ethyl acetate (2 mL). Palladium on charcoal (10%, 80 mg, 0.075 mmol) was added and the mixture was stirred 1 hour under hydrogen atmosphere (40 psi). The reaction mixture was filtered over Celite® and concentrated to afford 44b (104 mg, 100% yield) as a brown oil; HPLC purity 100%, 0.80 min (Method A), [M+H]⁺=166.05.

Example 44: Prepared from 44b and 3a as previously described for Example 3 to afford Example 44 (22 mg, 37% yield) as an off-white solid; HPLC purity 99%, 3.69 min (Method A); [M+H]⁺=434.29.

Example 45

Methyl 2-(4-(3-(2-(2-tert-butylphenoxy)pyridin-3-yl)ureido)phenyl)-2-methylpropanoate 45a. 2-Methyl-2-(4-nitrophenyl)propanoic acid: To a solution of 45a (645 mg, 3.3 mmol) in dry THF (4 mL) was added dropwise into a stirred suspension of sodium hydride (400 mg, 60%, 9.9 mmol) in dry THF (12 mL). To the resulting dark rose colored suspension was added dropwise iodomethane (0.5 mL, 8.3 mmol) and the reaction was stirred under nitrogen at rt overnight. Florisil (300 mg) was added to the brown reaction mixture and the solids were filtered through Celite® and washed with methanol (200 mL). The filtrate was concentrated to afford a yellow solid which was redissolved in methanol (100 mL) and filtered again. Concentration of the filtrate afforded a yellow solid which purified by SiO₂ chromatography (12 g) using a gradient of methanol in dichloromethane to afford 45a (100 mg, 14% yield) as a yellow solid; HPLC purity 100%, 2.74 min (Method A).

45b. Methyl 2-methyl-2-(4-nitrophenyl)propanoate: Prepared from 45a as described previously for 44a to afford 45b (478 mg, 88% yield) as a white solid; HPLC purity 100%, 3.26 min (Method A).

45c. Methyl 2-(4-aminophenyl)-2-methylpropanoate: Prepared from 45a as described previously for 44b to afford 44c (399 mg, 100% yield) as a light pink solid; HPLC purity 100%, 2.13 min (Method A); [M+H]⁺=194.16.

Example 45: Prepared from 45c and 3a as previously described for Example 3 to afford Example 45 (15 mg, 56% yield) as white crystals; HPLC purity 100%, 4.01 min (Method A); [M+H]⁺=462.25.

Example 46

1-(2-(2-tert-Butylphenoxy)pyridin-3-yl)-3-(6-(2-tert-butylphenoxy)pyridin-3-yl)urea 46a. 2-(2-tert-Butylphenoxy)-5-nitropyridine: To a solution of the 2-chloro-5-nitropyridine (2.54 g, 10 mmol) and 2-tert-butyl phenol (1.5 g, 10 mmol) in anhydrous DMF (30 mL) under argon was added cesium carbonate (3.9 g, 12 mmol). The resulting mixture was refluxed for 3 h, allowed to cool to rt and diluted with H₂O. After extracting with EtOAc and washing with 1 M HCl and brine, the crude product was purified by SiO₂ chromatography (120 g) eluting with hexanes/EtOAc gradient over 40 min to afford 46a (1.91 g, 70% yield) as a brown oil which was used immediately in the next step.

46b. 6-(2-tert-Butylphenoxy)pyridin-3-amine: To a solution of 46a (1.9 g, 7.0 mmol) in MeOH:THF (40 mL of 4:1) was added 200 mg of 10% Pd—C. The resulting mixture was hydrogenated at rt with a hydrogen pressure of 14 psi for 14 h. The catalyst was removed by filtration through a bed of Celite® and 7 mL of a 2 N solution of HCl in ether was added. Concentration afforded the HCl salt of 46b (1.8 g, 93% yield) as a white solid; HPLC purity 94%, 3.38 min (Method A); [M+H]⁺=243.17.

Example 46: A solution of 3a (28 mg, 0.1 mmol), 46b (34 mg 0.12 mmol) and diisopropylethylamine (0.12 mmol) in anhydrous THF (1 mL) was stirred at rt for 14 h. The reaction mixture was diluted with MeOH to 2 mL total volume and purified by preparative HPLC to afford the TFA salt of Example 46 (42 mg, 67% yield) as a colorless oil, HPLC purity 94%, 4.50 min (Method A); [M+H]⁺=511.43; ¹H NMR (500 MHz, CD₃OD) δ ppm 1.38 (d, 18H) 6.88 (m, 3H) 7.06 (dd, J=7.70, 4.95 Hz, 1H) 7.18 (m, 4H) 7.47 (t, J=7.42 Hz, 2H) 7.68 (d, J=4.95 Hz, 1H) 8.03 (dd, J=9.35, 2.75 Hz, 1H) 8.35 (d, J=2.20 Hz, 1H) 8.57 (d, J=7.70 Hz, 1H).

Example 47

1-(2-(2-tert-Butylphenoxy)pyridin-3-yl)-3-(6-(2-(trifluoromethyl)phenoxy)pyridin-3-yl)urea 47a. 5-Nitro-2-(2-(trifluoromethyl)phenoxy)pyridine: Prepared from 2-chloro-5-nitropyridine (0.82 g, 5.2 mmol) and 2-fluoromethyl phenol (0.81 g, 5 mmol) as described previously for 46a to afford 47a (0.66 g, 46% yield) as a colorless oil which was used immediately in the next step.

47b. 6-(2-(Trifluoromethyl)phenoxy)pyridin-3-amine: Prepared from 47a (0.66 g, 2.3 mmol) as described previously for 46b to afford the HCl salt of 47b (0.54 g, 83% yield) as an off-white solid; HPLC purity 99%, 2.86 min (Method A); [M+H]⁺=255.21.

Example 47: Prepared from 3a (28 mg, 0.1 mmol) and 47b (34 mg, 0.12 mmol) as described previously for Example 46 to afford the TFA salt of Example 47 (29 mg, 67% yield) as a white solid; HPLC purity 98%, 4.31 min (Method A); [M+H]⁺=522.29; ¹H NMR (500 MHz, CDCl₃) δ ppm 1.3 (s, 9H) 6.82 (m, 2H) 6.97 (m, 3H) 7.16 (m, 3H) 7.28 (m, 2H) 7.36 (m, 1H) 7.42 (m, 2H) 7.66 (m, 1H) 7.79 (m, 1H) 8.59 (m, 1H).

Example 48

1-(2-(2-tert-Butylphenoxy)pyridin-3-yl)-3-(6-(2-tert-butylphenylamino)pyridin-3-yl)urea 48a. N-(2-tert-Butylphenyl)-5-nitropyridin-2-amine: To a solution of the 2-chloro-5-nitropyridine (2.54 g, 10 mmol) and N-(2-tert-butylphenyl)formamide (2.3 g, 13 mmol) in anhydrous DMF (50 mL) under argon was added potassium tert-butoxide (1.8 g, 16 mmol). The resulting mixture was refluxed for 3 h, allowed to cool to rt and diluted with H₂O. After extracting with EtOAc and washing with 1 N HCl and brine, the crude product was purified by SiO₂ chromatography (120 g) eluted with EtOAc/hexane gradient (0-100% EtOAc in 30 min) to afford 48a (1.13 g, 42% yield) as an off white solid which was used immediately in the next step.

48b. N2-(2-tert-Butylphenyl)pyridine-2,5-diamine: Prepared from 48a (1.13 g, 4.1 mmol) as described previously for 46b to afford the HCl salt of 48b (1.05 g, 92% yield) as an off-white solid; HPLC purity 92%, 3.17 min (Method A); [M+H]⁺=242.16.

Example 48: Prepared from 3a (28 mg, 0.1 mmol) and 48b (34 mg, 0.12 mmol) as described previously for Example 46 to afford the TFA salt of Example 48 (34 mg, 54% yield) as brown oil; HPLC purity 98%, 4.34 min (Method A); [M+H]⁺= 510.39; ¹H NMR (500 MHz, CD₃OD) δ ppm 1.39 (d, 18H) 6.86 (m, 1H) 7.05 (m, 1H) 7.15 (m, 2H) 7.21 (m, 1H) 7.28 (m, 1H) 7.44 (m, 3H) 7.68 (m, 2H) 7.92 (m, 1H) 8.33 (m, 1H) 8.52 (m, 1H).

Example 49

1-(2-(2-tert-butylphenoxy)pyridin-3-yl)-3-(6-(2-(trifluoromethyl)phenylamino)pyridin-3-yl)urea 49a. N-(2-(Trifluoromethyl)phenyl)formamide: A solution of 2-trifluoromethyl aniline (26 g, 62 mmol) in formic acid (50 mL) was refluxed for 1 h, poured onto ice, and extracted with ether to give 49a (28.9 g, 95% yield) as a white solid which was used immediately in the next step.

49b. 5-Nitro-N-(2-(trifluoromethyl)phenyl)pyridin-2-amine: Prepared from 49a (1.14 g, 6 mmol) and 2-chloro-5-nitropyridine (2.54 g 10 mmol) as described previously for 48a to afford 49b (0.6 g, 42% yield) as a yellow solid which was used immediately in the next step.

49c. N2-(2-(Trifluoromethyl)phenyl)pyridine-2,5-diamine: Prepared from 49b (0.6 g, 4.2 mmol) as described previously for 46b to afford a crude HCl salt. Recrystallization from MeOH/diethyl ether afforded the HCl salt of 49c (0.42 g, 69% yield) as an off-white solid; HPLC purity 95%, 2.74 min (Method A); [M+H]$^+$=254.09.

Example 49: Prepared from 3a and 49c as described previously for Example 46 to afford the TFA salt of Example 49 (40 mg, 63% yield) as a brown oil; HPLC purity 94%, 4.10 min (Method A); [M+H]$^+$=522.31; $^1$H NMR (500 MHz, CD$_3$OD) δ ppm 1.39 (s, 9H) 6.84 (m, 1H) 7.04 (m, 1H) 7.18 (m, 4H) 7.48 (m, 1H) 7.62 (m, 2H) 7.70 (m, 1H) 7.80 (m, 1H) 7.93 (m, 2H) 8.37 (m, 1H) 8.55 (m, 1H).

Example 50

1-(2-(2-tert-Butylphenoxy)pyridin-3-yl)-3-(6-(phenylamino)pyridin-3-yl)urea 50a. 5-Nitro-N-phenylpyridin-2-amine: A solution of the 2-chloro-5-nitropyridine (2.54 g 10 mmol), aniline (1.0 g, 11 mmol) and triethyl amine (1.1 g, 11 mmol) in anhydrous DMF (20 mL) under argon was refluxed for 14 h. The DMF was removed in vacuo. The residue was then taken up in EtOAc and washed with 1 N HCl and brine. The crude product was then purified by SiO$_2$ chromatography (120 g) eluted with EtOAc/hexane (0-70% EtOAc in 25 min) to afford 50a (1.8 g, 42% yield) as a yellow solid.

50b. N2-phenylpyridine-2,5-diamine: Prepared from 50a (1.5 g, 7 mmol) as described previously for 49c to afford the HCl salt of 50b (1.27 g, 80% yield) as a brown solid; HPLC purity 93%, 2.10 min (Method A); [M+H]$^+$=186.23.

Example 50: Prepared from 3a (28 mg, 0.1 mmol) and 50b (34 mg, 0.12 mmol) as described previously for Example 46 to afford the TFA salt of Example 50 (26 mg, 46% yield) as a brown oil; HPLC purity 94%, 3.93 min (Method A); [M+H]$^+$= 454.17; $^1$H NMR (500 MHz, CD$_3$OD) δ ppm 1.34 (s, 9H) 6.68 (m, 1H) 6.92 (m, 1H) 6.99 (m, 1H) 7.06 (m, 2H) 7.12 (m, 2H) 7.25 (m, 2H) 7.36 (m, 3H) 7.73 (m, 1H) 7.96 (m, 2H) 8.17 (m, 1H) 8.47 (m, 1H) 9.48 (m, 1H) 10.21 (m, 1H).

Example 51

1-(5-tert-Butylisoxazol-3-yl)-3-(2-(2-tert-butylphenoxy)pyridin-3-yl)urea

Prepared from 3a (28 mg, 1 mmol) and 5-tert-butylisoxazol-3-amine (21 mg, 1.5 mmol) as previously described for Example 3. Purification of the crude product by preparative HPLC afforded Example 51 (9.5 mg, 24% yield) as a white solid; HPLC purity 98%, 4.23 min (Method A); [M+H]$^+$= 409.18; $^1$H NMR (500 MHz, CDCl$_3$) δ ppm 1.29 (s 9H) 1.37 (s, 9H) 6.01 (m, 8H) 6.82 (m, 14H) 6.92 (m, 15H) 7.23 (m, 2H) 7.48 (m, 1H) 7.81 (m, 1H) 7.96 (m, 1H) 8.65 (m, 1H) 9.52 (m, 1H).

Example 52

1-(2-(2-tert-Butylphenoxy)pyridin-3-yl)-3-(6-(trifluoromethyl)pyridin-3-yl)urea

Prepared from 3a (28 mg, 1 mmol) and 6-(trifluoromethyl) pyridin-3-amine (24 mg, 1.5 mmol) as previously described for Example 3. Purification of the crude product by preparative HPLC afforded Example 52 (18 mg, 41% yield) as a foam; HPLC purity 97%, 3.97 min (Method A); [M+H]$^+$= 431.14; $^1$H NMR (500 MHz, CDCl$_3$) δ ppm 1.29 (s, 9H) 6.81 (m, 1H) 7.01 (m, 1H) 7.15 (m, 2H) 7.41 (m, 1H) 7.62 (m, 1H) 7.77 (m, 2H) 8.29 (m, 1H) 8.39 (m, 1H) 8.52 (m, 1H) 8.60 (m, 1H).

Example 53

Ethyl 1-(3-(3-(2-(2-tert-butylphenoxy)pyridin-3-yl) ureido)phenyl)-5-methyl-1H-pyrazole-3-carboxylate 53a. Ethyl 1-(3-aminophenyl)-5-methyl-1H-pyrazole-3-carboxylate: Ethyl 5-methyl-1-(3-nitrophenyl)-1H-pyrazole-3-carboxylate was prepared as described in Example 169 (p 64) in U.S. Pat. No. 6,020,357. To a solution of ethyl 5-methyl-1-(3-nitrophenyl)-1H-pyrazole-3-carboxylate (275 mg, 1.0 mmol) in methanol (5 mL) was added stannous chloride dihydrate (900 mg, 4.0 mmol) and the resulting reaction mixture was refluxed for 3 h. The reaction was cooled to ambient temperature and saturated sodium bicarbonate (5 mL) was added. The suspension was allowed to stir for 1 h, filtered through number 2 filter paper on a Büchner funnel, and the filtrate extracted twice with ethyl acetate (15 mL). The combined ethyl acetate extracts were washed successively with saturated sodium bicarbonate (10 mL), water (10 mL), and brine (10 mL), dried over sodium sulfate, filtered and evaporated to give 53a (209 mg, 85% yield) as a light tan glassine solid; HPLC purity 93%, 1.99 min (Method C); [M+H]$^+$=246.17.

Example 53: Prepared from 3a and 53a as described previously for Example 3. Product was purified by preparative HPLC to provide Example 53 (36 mg, 71% yield) as a beige solid; HPLC purity 99% (Method B), 8.48 min (Method C); [M+H]$^+$=514.34.

Example 54

1-(2-(2-tert-Butylphenoxy)pyridin-3-yl)-3-(2-fluoro-(2'-N,N-dimethylaminomethylphenyl))urea 54a. 4-(2'-N,N-Dimethylaminomethylphenyl)-2-fluoroaniline: To a solution of 2-formylphenylboronic acid (5 g, 33 mmol) in THF (80 mL) was added 4-bromo-2-fluoroaniline (4.2 g, 22 mmol) and sodium carbonate (2 M, 80 mL) and then was bubbled with nitrogen for 10 min. After Pd(PPh$_3$)$_4$ (1.54 g, 1.33 mmol) was added, the resulting mixture was refluxed under nitrogen for 4 h. The THF layer was separated and filtered through a pad of silica gel. The pad was washed with THF to give an 80 mL solution of 4(2'-formylphenyl)-2-fluoroaniline in THF. To the filtrate (15 mL from total 80 mL) was added Me$_2$NH·HCl (0.68 g, 8.3 mmol) and the resulting mixture was refluxed for 2 h. The mixture was cooled to rt and MeOH (5 mL) was added followed by NaBH$_4$ (0.32 g, 8.3 mmoL). After being stirred at 50° C. for 1 hour, the mixture was cooled to rt and quenched with 1 N HCl to pH 1. The aqueous layer was separated, neutralized with 50% NaOH to pH 12, and extracted with EtOAc. The EtOAc layer was dried over MgSO$_4$, concentrated, and purified by SiO$_2$ chromatography eluted with EtOAc to give 54a (0.89 g, 88% yield); [M+H]$^+$=245.2; $^1$H NMR (CDCl$_3$) δ 7.49 (dd, J=8.8 Hz, J=1.8 Hz, 1H), 7.31-7.21 (m, 3H), 7.14 (dd, J=12.1 Hz, J=1.8 Hz, 1H), 6.97 (dd, J=8.1 Hz, J=1.5 Hz, 1H), 6.80 (t, J=8.8 Hz, 1H), 3.76 (bs, 2H), 3.34 (s, 2H), 2.17 (s, 6H); $^{19}$F NMR (CDCl$_3$) δ −136.19. This material was converted to the bis-HCl salt by dissolving a sample in a minimum volume of methanol and adding 2.2 equivalents of 1.0 M HCl in diethyl ether followed by removal of the solvent under reduced pressure.

Example 54: Prepared from 3a and 54a with the addition of 4 equivalents of triethylamine as described previously for Example 53 to provide Example 54 (16 mg, 26% yield) as a colorless solid; HPLC purity 99%, 7.32 min (Method C); $[M+H]^+=513.28$.

Example 55

1-(2-(2-tert-Butylphenoxy)pyridin-3-yl)-3-(2-fluoro-4-morpholinophenyl)urea 55a. 4-(3-Fluoro-4-nitrophenyl)morpholine: A solution of 2,4-difluoronitrobenzene (10.0 mL, 91 mmol) and morpholine (17.4 mL, 200 mmol) in THF (100 mL) was stirred at RT under nitrogen for 2 h. The solvent was removed and the residue was partitioned between EtOAc and water. The organic layer was washed brine, dried over $MgSO_4$, and concentrated. The resulting solid was purified by $SiO_2$ chromatography with 20-50% EtOAc in hexane to give 4-fluoro-2-morpholinonitrobenzene (18.1 g) and 55a (1.81 g, 8% yield); $[M+H]^+=227.10$.

55b. 2-Fluoro-4-morpholinobenzenamine: To a solution of 55a (1.8 g, 8 mmol) in MeOH (100 mL) was added 10% Pd/C (94 mg). The mixture was placed under hydrogen atmosphere (45 psi) for 2.5 h. The mixture was filtered through Celite®, rinsing with MeOH and concentrated to afford 55b (1.51 g, 97% yield) as a solid; $[M+H]^+=197.10$.

Example 55: Prepared from 3a and 55b as previously described for Example 53 to provide Example 55 (34 mg, 58% yield) as a tan solid; HPLC purity 98%, 8.04 min (Method C); $[M+H]^+=465.33$.

Example 56

1-(4-tert-Butoxyphenyl)-3-(2-(2-tert-butylphenoxy)-6-chloropyridin-3-yl)urea 56a. 2-(2-tert-Butylphenoxy)-6-chloropyridin-3-ylamine: A solution of N-chlorosuccinimide (556 mg, 4.2 mmol) in DMF (10 mL) was added to a solution of 2b (960 mg, 4.0 mmol) in DMF (15 mL) at rt. The reaction was heated at 40° C. for 30 min. The reaction mixture was cooled to rt and quenched with saturated aqueous sodium thiosulfate ($Na_2S_2O_3$) solution (100 mL). The mixture was extracted with ethyl acetate (3×20 mL) and the organic layers were washed with aqueous sodium thiosulfate solution, brine and were dried over sodium sulfate. The solvents were removed under reduced pressure and the dark red oil was purified by $SiO_2$ chromatography (continuous gradient 0 to 40% Hexane/ethyl acetate) to give 56a (746 mg, 68% yield) as an off-white solid; HPLC purity 100%, 3.52 min (Method A); $[M+H]^+=277.11$; $^1H$ NMR (500 MHz, $CDCl_3$): 7.41 (d, 1H, J=7.4 Hz), 7.20 (t, 1H, J=7.4 Hz), 7.11 (t, 1H, J=7.4 Hz), 7.01 (d, 1H, J=8.1 Hz), 6.93 (d, 1H, J=8.1 Hz), 6.85 (d, 1H, J=8.1 Hz), 3.91 (s, 1H), 1.39 (s, 9H).

56b. 1-tert-Butoxy-4-isocyanatobenzene: To a solution of 56a (3.16 g, 19.1 mmol) and trichloromethyl chloroformate (1.8 mL, 15.3 mmol) in $CH_2Cl_2$ (90 mL) at 0° C. was added 1,8-bis[dimethylamino]naphthalene (proton sponge, 8.20 g, 38.2 mmol) in $CH_2Cl_2$ (65 mL) via an additional funnel. After addition was complete, the yellow solution was stirred for 1 h at 0° C. The reaction mixture was washed with 0.5 N HCl (2×100 mL), sat. $NH_4Cl$ solution (100 mL) and the organic layer was dried over sodium sulfate. Solvent removal provided an amber colored mixture of product as a liquid and residual proton sponge as a solid. The solid was removed by filtration using dry diethyl ether to complete filtration. Concentration afforded 56b (3.0 g, 82% yield) as an amber colored oil; HPLC purity >95%.

Example 56: 56a (25 mg, 0.091 mmol) and 56b (26 mg, 0.14 mmol) in THF (0.2 ml) in a 1 dram vial were heated to 80° C. for 2 h. The solvent was removed under reduced pressure and the residual oil was purified by $SiO_2$ chromatography (12 g) eluting with a gradient of ethyl acetate in hexanes to afford Example 56 (33 mg, 78% yield) as a white solid; HPLC purity 100%, 4.25 min (Method A); $[M+H]^+=468.33$; $^1H$ NMR (500 MHz, $CD_3OD$) δ ppm 1.31 (s, 9H) 1.38 (s, 9H) 6.87 (dd, J=7.97, 1.65 Hz, 1H) 6.94 (d, J=8.20 Hz, 2H) 7.04 (d, J=8.25 Hz, 1H) 7.19 (m, 2H) 7.34 (d, J=9.10 Hz, 2H) 7.47 (dd, J=8.25, 1.65 Hz, 1H) 8.53 (d, J=9.10 Hz, 1H); $^{13}C$ (500 MHz, $CD_3OD$) δ (ppm) 153.69, 152.56, 152.39, 150.74, 141.53, 139.71, 134.58, 129.91, 127.20, 126.95, 124.91, 124.53, 123.94, 123.15, 120.02, 118.18, 78.32, 34.30, 29.97, 27.89.

Example 57

1-(4-tert-Butoxyphenyl)-3-(2-(2-tert-butylphenoxy)-6-cyanopyridin-3-yl)urea 57a. 6-Bromo-2-(2-tert-butylphenoxy)pyridin-3-amine: A solution of N-bromosuccinimide (2.32 g, 13.0 mmol) in DMF (20 mL) was added to solution of 2b (2.76 g, 11.4 mmol) in DMF (25 mL) at −20° C. The reaction rapidly turned dark red. HPLC analysis after 5 min indicated the reaction was complete. The reaction was quenched with a freshly prepared solution of sodium thiosulfate (40 mL, 10% aqueous). The heterogeneous mixture was warmed to rt and diluted with water (60 mL). The solid was filtered, washed with water and dried overnight under reduced pressure to give 57a (3.82 g, 96% yield) as brown solid; HPLC purity 100%, 3.60 min (Method A); $[M+H]^+=321.14$; $^1H$ NMR (500 MHz, $CDCl_3$) δ ppm 1.40 (s, 9H), 3.91 (s, 2H), 6.93 (m, 2H), 7.00 (d, J=8.07 Hz, 1H), 7.12 (t, J=7.73 Hz, 1H), 7.20 (t, J=7.73 Hz, 1H), 7.41 (d, J=8.07 Hz, 1H).

57b. 6-Cyano-2-(2-tert-butylphenoxy)pyridin-3-amine: A mixture of 57a (1.0 g, 3.1 mmol), copper cyanide (1.12 g, 12.5 mmol), tris(dibenzylideneacetone)dipalladium(0) (114 mg, 0.12 mmol), 1,1'-bis (diphenylphosphino)ferrocene (276 mg, 0.5 mmol) and tetraethylammonium cyanide (486 mg, 3.1 mmol) in dioxane (16 mL) was heated at 105° C. for 4.5 h. The mixture was cooled to rt, diluted with ether (50 mL), filtered over Celite® and concentrated to give 1.35 g of yellow foam. The foam was recrystallized from 30% ethyl acetate in heptane to give 57b (754 mg, 91% yield) as a brown powder; HPLC purity 98%, 3.4 min (Method A); $[M+H]^+=268.13$; $^1H$ NMR (500 MHz, $CDCl_3$) δ ppm 1.36 (s, 9H), 4.53 (s, 2H), 6.96 (dd, J=7.97, 4.12 Hz, 2H), 7.17 (t, J=7.42 Hz, 1H), 7.24 (m, 2H), 7.44 (d, J=7.70 Hz, 1H).

Example 57: Prepared from 57b and 56b as described previously for Example 56 to afford Example 57 (18 mg, 36% yield) as a white solid; HPLC purity 100%, 4.11 min (Method A); $[M+H]^+=459.38$; $^1H$ NMR (500 MHz, $CD_3OD$) δ ppm 1.31 (s, 9H) 1.38 (s, 9H) 6.92 (dd, J=7.97, 1.37 Hz, 1H) 6.95 (d, J=8.80 Hz, 2H) 7.24 (m, 2H) 7.38 (d, J=8.80 Hz, 2H) 7.51 (d, J=8.25 Hz, 2H) 8.76 (d, J=8.25 Hz, 1H); $^{13}C$ NMR (500 MHz, $CD_3OD$) δ ppm 154.56, 154.43, 153.50, 152.47, 143.19, 135.75, 131.10, 128.87, 128.59, 126.83, 126.65, 126.47, 126.00, 125.07, 122.04, 121.41, 118.44, 79.78, 35.76, 31.45, 29.30.

Example 58

1-[2-(2-tert-Butylphenoxy)-6-methoxypyridin-3-yl]-3-(4-trifluoromethoxy-phenyl)urea 58a. 2-(2-tert-Butylphenoxy)-6-methoxy-3-nitropyridine: Prepared from 2-chloro-6-methoxy-3-nitropyridine (5.2 g, 28 mmol) and 2-tert-butylphenol (4.9 mL, 32 mmol) as described previously for 2a to afford 58a (6.7 g, 80% yield) as brown crystals; HPLC purity 96%, 3.85 min (Method A); $[M+H]^+=303.2$.

58b. 2-(2-tert-Butylphenoxy)-6-methoxypyridin-3-ylamine: To a solution of 58a (580 mg, 1.9 mmol) in a 1:1 mixture of ethyl acetate and methanol (6 mL) was added palladium on charcoal (10% wt, 300 mg, 0.28 mmol). The mixture was stirred under an atmosphere of hydrogen (40 psi). After 30 min, the solution was filtered over Celite® and the resulting solution was concentrated to afford 58b (500 mg, 96% yield) as a dark oil. The compound was used in the next step without any further purification; $[M+H]^+=273.21$. $^1H$ NMR (500 MHz, $CD_3OD$) δ ppm 1.43 (m, 9H), 3.58 (m, 3H), 6.33 (d, J=8.25 Hz, 1H), 6.93 (d, J=8.25 Hz, 1H), 7.09 (m, 2H), 7.17 (t, J=7.70 Hz, 1H), 7.41 (d, J=8.25 Hz, 1H).

Example 58: Prepared from 58b and 4-trifluoromethoxy phenylisocyanate as described previously for Example 56 to afford Example 58 (50 mg, 65% yield) as a white solid; HPLC purity 88%, 4.27 min (Method A); $[M+H]^+=476.20$; $^1H$ NMR (500 MHz, $CDCl_3$) δ ppm 1.30 (s, 9H) 3.54 (s, 3H) 6.43 (d, J=8.74 Hz, 1H) 6.68 (s, 1H) 6.84 (m, 2H) 7.12 (m, 4H) 7.30 (d, J=8.74 Hz, 2H) 7.39 (d, J=8.07 Hz, 1H) 8.22 (d, J=8.74 Hz, 1H).

Example 59

1-(2-(2-tert-Butylphenoxy)-6-(methylthio)pyridin-3-yl)-3-(4-tert-butylphenyl)urea 59a. 6-(2-tert-Butyl-phenoxy)-5-nitro-pyridin-2-ol: Sodium iodide (10.6 g, 71 mmol) was added to a green solution of 58a (4.26 g, 14 mmol) in acetonitrile (80 mL) in a vessel covered with aluminum foil to protect from light, followed by chlorotrimethylsilane (8.9 mL, 71 mmol) and water (0.4 mL, 21 mmol). The yellow-orange mixture was refluxed overnight in the dark. HPLC analysis showed that although some starting pyridine was still present, decomposition also appeared to be occurring. The reaction was quenched with saturated sodium thiosulfate solution (30 mL). The resulting mixture was extracted with ethyl acetate (3×50 mL). The combined organic layer was washed with brine (30 mL), dried over sodium sulfate, and concentrated to give a yellow oil. The oil was purified by $SiO_2$ chromatography (120 g), loaded with $CH_2Cl_2$ and eluted using a gradient of ethyl acetate in hexanes to afford 59a (2.34 g, 58% yield) as a yellow waxy solid, HPLC purity 100%, 3.66 min (Method A); $[M+H]^+=289.17$; $^1H$ NMR (500 MHz, $CDCl_3$) δ ppm 8.42 (d, 1H, J=5.0 Hz), 7.48 (m, 1H), 7.18 (m, 2H), 6.92 (m, 1H), 6.33 (d, 1H, J=10.0 Hz), 1.37 (s, 9H); $^{13}C$ (125 MHz, $CDCl_3$) δ (ppm), 163.87, 155.70, 150.61, 142.05, 139.87, 127.86, 126.83, 125.98, 122.98, 104.62, 34.68, 30.17.

59b. 2-(2-tert-Butylphenoxy)-6-chloro-3-nitropyridine: 2,4,6-Trimethylpyridine (1.6 mL) was added dropwise into 59a (2.32 g, 8.0 mmol) in phosphorus oxychloride (3.2 mL) at 0° C. The reaction mixture was heated at 130° C. for 20 h. The reaction was stopped at ~70% conversion as determined by HPLC. The dark brown solution was poured into water (40 mL) with stirring, and stirred for 15 min. The brown precipitate was filtered, air dried, and purified by $SiO_2$ chromatography (120 g), loaded with a $CH_2Cl_2$ and eluted using a gradient of ethyl acetate in hexanes to afford 59b (1.91 g, 77% yield) as an amber colored oil; HPLC purity 100%, 3.95 min (Method A); $^1H$ NMR (500 MHz, $CDCl_3$) δ ppm 8.36 (d, 1H, J=10.0 Hz), 7.47 (d, 1H, J=5.0 Hz), 7.23 (m, 2H), 7.16 (d, 1H, J=10.0 Hz), 6.95 (d, 1H, J=10.0 Hz), 1.36 (s, 9H); $^{13}C$ (125 MHz, $CDCl_3$) δ (ppm), 155.30, 153.23, 150.87, 141.45, 137.72, 133.22, 127.59, 126.91, 125.79, 123.04, 118.39, 34.60, 30.25.

59c. 2-(2-tert-Butylphenoxy)-6-methylsulfanyl-3-nitropyridine: 59b (146 mg, 0.48 mmol) in $CH_2Cl_2$ (1.0 mL) was treated with sodium thiomethoxide (27 mg, 0.38 mmol) and stirred at rt for 72 h. HPLC indicated ~40% 59b remained. Another 0.5 eq. of sodium thiomethoxide (18 mg, 0.24 mmol) was added. After additional 4 h at rt, another 0.5 eq of sodium thiomethoxide (18 mg, 0.24 mmol) was added and the reaction was stirred at rt overnight. The reaction mixture was directly purified by $SiO_2$ chromatography (12 g) eluted with a gradient of ethyl acetate in hexanes to afford 59c (110 mg, 72% yield) as a brown oil, HPLC purity 100%, 4.15 min (Method A); $^1H$ NMR (500 MHz, $CDCl_3$) δ ppm 8.26 (d, 1H, J=10.0 Hz), 7.44 (dd, 1H, J=10.0 Hz, J=1.7 Hz), 7.18 (m, 2H), 6.96 (dd, 1H, J=5.0 Hz, J=1.7 Hz), 6.93 (d, 1H, J=10.0 Hz), 2.09 (s, 3H), 1.36 (s, 9H); $^{13}C$ (125 MHz, $CDCl_3$) δ (ppm), 165.69, 155.72, 151.15, 141.71, 135.18, 129.53, 127.25, 126.34, 125.35, 124.01, 115.28, 34.62, 30.33, 13.12.

59d. 2-(2-tert-Butylphenoxy)-6-(methylthio)pyridin-3-amine: Prepared from 59c (110 mg, 0.346 mmol) as described previously for 58b to afford to afford 59d (92 mg, 92% yield) as a red solid; HPLC purity 100%, 3.49 min (Method A); $[M+H]^+=289.2$; $^1H$ NMR (500 MHz, $CDCl_3$) δ ppm 7.41 (d, 1H, J=5.0 Hz), 7.17 (m, 1H), 7.09 (m, 1H), 6.96 (d, 2H, J=10.0 Hz), 6.77 (d, 1H, J=5.0 Hz), 3.77 (br, 2H), 2.19 (s, 3H), 1.36 (s, 9H); $^{13}C$ (125 MHz, $CDCl_3$) δ (ppm), 152.71, 151.43, 143.61, 141.02, 127.94, 126.85, 126.36, 123.89, 123.81, 123.02, 116.80, 34.62, 30.45, 13.77.

Example 59: Prepared from 59d and 4-tert-butylphenylisocyanate as described previously for Example 56 to afford Example 59 (56 mg, 95% yield) as a light brown solid; HPLC purity 96%, 4.55 min (Method A); $[M+H]^+=464.37$.

Example 60

1-(2-(2-tert-Butylphenoxy)-6-(methylamino)pyridin-3-yl)-3-(4-(trifluoromethoxy)phenyl)urea 60a. 6-(2-tert-Butylphenoxy)-N-methyl-5-nitropyridin-2-amine: Methylamine (280 μL, 0.56 mmol) was added into a solution of 59b (157 mg, 0.51 mmol) in 1,4-dioxane at 0° C. (1 mL) over 1 h and the resulting reaction mixture was stirred at rt. After 72 h, 40% of the starting chloride remained by HPLC. Another 1.1 eq. of methylamine was added at −10° C. over 30 min. The reaction was allowed to warm to rt, stir for 30 min and was then diluted with water (1 mL) and extracted with ethyl acetate (3×1 mL). The combined organic layer was washed with brine (1 mL), dried over sodium sulfate, and concentrated to give a yellow oil. The oil was purified by $SiO_2$ chromatography (12 g) using a gradient of ethyl acetate in hexanes to afford 60a (94 mg, 61% yield) as a yellow oil; HPLC purity 100%, 3.76 min (Method A); $[M+H]^+=302.24$.

60b. 6-(2-tert-Butylphenoxy)-N2-methylpyridine-2,5-diamine: Prepared from 60a as previously described for 58b to afford 60b (85 mg, 89% yield) as a pink solid; HPLC purity 89%, 2.71 min (Method A); [M+H]$^+$=272.2; $^1$H NMR (500 MHz, CDCl$_3$) δ ppm 1.42 (s, 9H) 2.71 (s, 3H) 6.01 (d, J=8.25 Hz, 1H) 6.91 (d, J=8.25 Hz, 1H) 7.06 (m, 2H) 7.14 (t, J=7.15 Hz, 1H) 7.39 (d, J=7.70 Hz, 1H); $^{13}$C NMR (500 MHz, CDCl$_3$) δ ppm 153.34, 152.02, 150.34, 140.56, 127.67, 126.93, 126.52, 123.39, 121.89, 99.47, 34.68, 30.37, 29.84.

Example 60: Prepared from 60b and 4-trifluoromethoxy phenylisocyanate as described previously for Example 56 except that following solvent removal the residue was dissolved in warm methanol (0.5 ml) and cooled at 4° C. in the refrigerator overnight. Example 60 (14 mg, 27% yield) was isolated by filtration as an off-white solid; HPLC purity 94%, 3.99 min (Method A); [M+H]$^+$=475.32; $^1$H NMR (500 MHz, DMSO-d$_6$) δ ppm 1.33 (s, 9H) 3.33 (s, 3H) 6.09 (d, J=8.80 Hz, 1H) 6.22 (m, J=4.95 Hz, 1H) 6.84 (dd, J=8.25, 1.10 Hz, 1H) 7.06 (td, J=7.42, 1.65 Hz, 1H) 7.18 (td, J=7.42, 1.65 Hz, 1H) 7.24 (d, J=8.80 Hz, 2H) 7.35 (dd, J=7.70, 1.65 Hz, 1H) 7.51 (d, J=9.35 Hz, 2H) 7.89 (d, J=9.35 Hz, 1H) 7.89 (s, 1H) 9.17 (s, 1H).

Example 61

1-(4-tert-Butoxyphenyl)-3-(2-(2-tert-butylphenoxy)-5-methylpyridin-3-yl)urea 61a. 2-Chloro-5-methyl-3-nitropyridine: Phosphorus pentachloride (2.4 g, 11 mmol) was added to a hot (45-60° C.) solution of 2-hydroxy-5-methyl-3-nitropyridine (2.2 g, 14 mmol) in phosphorus oxychloride (5 mL) in a screw cap vial. The vial was capped and the mixture was heated at 125° C. overnight. The reaction was cooled to rt and the volatiles were removed under reduced pressure. The paste was quenched with ice (~4 g) and chloroform (6 mL). The black precipitate was filtered and the mixture was extracted with chloroform (5×6 mL) and the chloroform extracts were dried with magnesium sulfate, filtered through silica gel (10 g) with chloroform and ethyl acetate/chloroform (5%) and concentrated to give 61a (1.8 g, 72% yield) as an orange solid; HPLC purity 93%, 2.21 min (Method A). $^1$H NMR (CDCl$_3$) δ (ppm) 2.47 (s, 3H) 8.05 (d, J=1.65 Hz, 1H) 8.45 (d, J=1.65 Hz, 1H) and $^{13}$C NMR (125 MHz, CDCl$_3$) δ (ppm), 17.49, 133.82, 134.39, 140.49, 144.17, 152.71. The oil was used immediately.

61b. 2-(2-tert-Butylphenoxy)-5-methyl-3-nitropyridine: A mixture of 61a (500 mg, 2.9 mmol), potassium carbonate (940 mg, 6.8 mmol) and 2-tert-butylphenol (700 μL, 4.6 mmol) was stirred in dioxane (5 mL) at 105° C. for 3 days. The mixture was cooled to rt, water (10 mL) was added and the mixture was extracted with heptane (5 mL) and ethyl acetate (2×5 mL). The combined organic layers were washed with water (5 mL) and brine (5 mL), dried with magnesium sulfate, filtered through silica gel (10 g, eluted with 20% ethyl acetate in heptane) and concentrated to give 1.08 g of yellow oil. The oil was purified by SiO$_2$ chromatography (40 g) using a gradient of ethyl acetate in hexanes to afford 61b (565 mg, 68% yield) as a yellow oil; HPLC purity 96%, 3.85 min (Method A); $^1$H NMR (500 MHz, CDCl$_3$) δ ppm 1.38 (s, 9H) 2.38 (s, 3H) 6.92 (dd, J=7.70, 1.65 Hz, 1H) 7.21 (m, 2H) 7.47 (dd, J=7.70, 1.65 Hz, 1H) 8.18 (dd, J=9.90, 1.65 Hz, 2H); $^{13}$C (125 MHz, CDCl$_3$) δ (ppm), 154.12, 151.94, 151.45, 141.61, 135.56, 134.37, 128.14, 127.55, 126.83, 125.39, 123.12, 34.62, 30.19, 17.15.

61c. 2-(2-tert-Butylphenoxy)-5-methylpyridin-3-amine: Prepared from 61b (199 mg, 0.695 mmol) as described previously for 58b to afford 61c (169 mg, 95% yield) as a white solid; HPLC purity 100% pure, 3.04 min (Method A); [M+H]$^+$=257.18. $^1$H NMR (500 MHz, CDCl$_3$) δ ppm 7.41 (m, 2H), 7.18 (m, 1H), 7.08 (m, 1H), 6.88 (m, 2H), 3.86 (br, 2H), 2.21 (s, 3H), 1.41 (s, 9H); $^{13}$C (125 MHz, CDCl$_3$) δ (ppm), 153.21, 150.08, 140.76, 135.88, 131.60, 128.71, 127.23, 126.87, 123.89, 123.19, 121.85, 34.68, 30.39, 17.63.

Example 61: Prepared from 61c as described previously for Example 56 to afford Example 61 (28 mg, 81% yield) as a colorless solid; HPLC purity 99%, 4.24 min (Method A); [M+H]$^+$=460.28; $^1$H NMR (500 MHz, CD$_3$OD) δ ppm 1.40 (s, 9H) 2.29 (s, 3H) 6.82 (dd, J=7.70, 1.65 Hz, 1H) 7.14 (m, 1H) 7.20 (m, 3H) 7.47 (dd, J=7.97, 1.92 Hz, 1H) 7.51 (d, J=1.65 Hz, 1H) 7.54 (d, J=9.35 Hz, 2H) 8.45 (d, J=1.65 Hz, 1H); $^{13}$C NMR (500 MHz, CD$_3$OD) δ ppm 155.14, 154.86, 153.26, 145.84, 143.23, 140.32, 139.94, 130.49, 130.35, 128.87, 128.65, 126.41, 126.16, 124.41, 123.15, 121.47, 35.98, 31.51, 18.18.

Example 62

1-(2-(2-tert-Butylphenoxy)-5-chloropyridin-3-yl)-3-(4-(trifluoromethoxy)phenyl)urea 62a. 2,5-Dichloro-3-nitropyridine: Prepared from 2-hydroxy-5-chloro-3-nitropyridine (2.5 g, 14 mmol) as previously described for 61a to give 62a (1.83 g, 66% yield) as a yellow solid; HPLC purity 94%, 2.41 min (Method A); $^1$H NMR (500 MHz, CDCl$_3$) δ (ppm) 8.25 (d, J=2.20 Hz, 1H) 8.61 (d, J=2.20 Hz, 1H); $^{13}$C NMR (125 MHz, CDCl$_3$) δ (ppm), 133.82, 138.19, 141.45, 146.02, 151.23.

62b. 2-(2-tert-Butylphenoxy)-5-chloro-3-nitropyridine: Prepared from 62a (500 mg, 2.6 mmol) as previously described for 61b to give 62b (748 mg, 94% yield) as a yellow oil; HPLC purity 87%, 4.06 min (Method A); $^1$H NMR (500 MHz, CDCl$_3$) δ ppm 1.37 (s, 9H) 6.92 (m, 1H) 7.23 (m, 2H) 7.49 (m, 1H) 8.30 (d, J=2.20 Hz, 1H) 8.38 (d, J=2.20 Hz, 1H); $^{13}$C (125 MHz, CDCl$_3$) δ (ppm), 154.43, 151.01, 150.52, 141.67, 134.95, 134.35, 127.74, 126.97, 125.92, 124.94, 123.14, 34.62, 30.23.

62c. 2-(2-tert-Butylphenoxy)-5-chloropyridin-3-amine: Zinc dust (2.4 g, 36.7 mmol) was added to a mixture of 62b (557 mg, 1.8 mmol) and ammonium chloride (490 mg, 9.2 mmol) in methanol (15 mL). The mixture warmed slightly and appeared to form some white solids among the zinc particles. The mixture was stirred for 5 h and then filtered through Celite®, which was washed with methanol to complete filtration. The solvent was removed to afford a grey solid (489 mg) which was suspended in CH$_2$Cl$_2$ (10 mL) and filtered through a 0.45 μm glass fiber filter to remove any residual Zn. After removal of the solvent 62c (451 mg, 90% yield) was obtained as a beige solid; HPLC purity 99%, 3.69 min (Method A); [M+H]$^+$=277.20; $^1$H NMR (500 MHz, CDCl$_3$) δ ppm 1.39 (s, 9H) 4.05 (s, 2H) 6.92 (dd, J=7.97, 1.37 Hz, 1H) 7.02 (d, J=2.20 Hz, 1H) 7.14 (td, J=7.56, 1.37 Hz, 1H) 7.21 (td, J=7.70, 1.65 Hz, 1H) 7.44 (dd, J=7.70, 1.65 Hz, 1H) 7.49 (d, J=2.20 Hz, 1H); $^{13}$C NMR (125 MHz, CDCl$_3$) δ ppm 152.38, 150.32, 141.10, 133.60, 132.71, 127.37, 126.93, 125.94, 124.64, 122.64, 121.08, 34.64, 30.43.

Example 62: Prepared from 62c as described previously for Example 56 to afford Example 62 (20 mg, 53% yield); HPLC purity 98%, 4.53 min (Method A); [M+H]$^+$=480.2; $^1$H NMR (400 MHz, CD$_3$OD) δ ppm 1.20 (s, 9H) 6.68 (d, J=7.51 Hz, 1H) 7.01 (m, 4H) 7.30 (d, J=7.51 Hz, 1H) 7.36 (d, J=8.54 Hz, 2H) 7.45 (s, 1H) 8.50 (s, 1H).

Example 63

1-(2-(2-tert-Butylphenoxy)-5-cyanopyridin-3-yl)-3-(4-tert-butylphenyl)urea 63a. 5-Bromo-2-chloro-3-nitropyridine: Prepared from 5-bromo-2-hydroxy-3-nitropyridine (3.13 g, 14 mmol) as previously described for 61a to give 63a (2.22 g, 65% yield) as a dark solid; HPLC purity 91%, 2.54 min (Method A); $^1$H NMR (500 MHz, CDCl$_3$) δ (ppm) 8.38 (d, J=2.20 Hz, 1H) 8.70 (d, J=2.20 Hz, 1H); $^{13}$C NMR (125 MHz, CDCl$_3$) δ(ppm) 118.8, 136.51, 138.21, 142.11, 153.46.

63b. 5-Bromo-2-(2-tert-butylphenoxy)-3-nitropyridine: Prepared from 63a (1.0 g, 4.2 mmol) as described previously for 61b to afford 63b (1.42 g, 96% yield) as a yellow oil; HPLC purity 80%, 4.1 min (Method A); $^1$H NMR (500 MHz, CDCl$_3$) δ (ppm) 1.36 (s, 9H) 6.92 (dd, J=7.42, 1.92 Hz, 1H) 7.24 (m, 2H) 7.49 (dd, J=6.87, 2.47 Hz, 1H) 8.38 (d, J=2.20 Hz, 1H) 8.50 (d, J=2.20 Hz, 1H); $^{13}$C (125 MHz, CDCl$_3$) δ (ppm) 154.85, 152.75, 150.95, 141.67, 137.58, 127.74, 126.97, 125.94, 123.12, 120.54, 111.90, 34.64, 30.23.

63c. 5-Bromo-2-(2-tert-butylphenoxy)pyridin-3-amine: Prepared from 63b (902 mg, 2.6 mmol) as described previously for 62c to afford 63c (737 mg, 89% yield) as a beige solid; HPLC purity 91%, 3.75 min (Method A); [M+H]$^+$=321.17; $^1$H NMR (500 MHz, CDCl$_3$) δ ppm 1.38 (s, 9H) 4.03 (s, 2H) 6.91 (d, J=7.70 Hz, 1H) 7.14 (m, 2H) 7.21 (m, 1H) 7.43 (dd, J=7.70, 1.65 Hz, 1H) 7.59 (s, 1H); $^{13}$C (125 MHz, CDCl$_3$) δ ppm 152.28, 150.73, 141.08, 135.94, 134.63, 133.11, 127.41, 126.95, 124.68, 123.75, 122.64, 34.66, 30.43.

63d. 5-Amino-6-(2-tert-butylphenoxy)nicotinonitrile: A mixture of 63c (676 mg, 2.1 mmol), copper (I) cyanide (755 mg, 8.4 mmol), tris(dibenzilideneacetone)dipalladium(0) (77 mg, 0.08 mmol), bis(diphenylphosphino)ferrocene (187 mg, 0.34 mmol) and tetraethylammonium cyanide (330 mg, 2.1 mmol) in dioxane (11 mL) was heated at 105° C. overnight. The mixture was cooled to rt, diluted with ether (50 mL), filtered through Celite® and silica (3 g) and concentrated to give a brown solid (883 mg). The solid was purified by SiO$_2$ chromatography (40 g) to afford 63d (472 mg. 84% yield) as a yellow solid; HPLC purity 95%, 3.37 min (Method A); [M+H]$^+$=268.15; $^1$H NMR (CDCl$_3$) δ ppm: 1.35 (s, 9H) 4.26 (s, 2H) 6.95 (d, J=7.70 Hz, 1H) 7.15 (s, 1H) 7.20 (t, J=7.70 Hz, 1H) 7.25 (t, J=7.42 Hz, 1H) 7.47 (d, J=7.70 Hz, 1H) 7.82 (s, 1H); $^{13}$C NMR (CDCl$_3$) δ ppm: 154.22, 151.27, 141.40, 139.75, 131.98, 127.57, 127.03, 125.53, 123.53, 121.69, 117.38, 104.08, 34.60, 30.47.

Example 63: Prepared from 63d and 4-tert-butylphenylisocyanate as described previously for Example 56 to afford Example 63 (3 mg, 11% yield) HPLC purity 100%, 4.43 min (Method A); [M+H]$^+$=443.3; $^1$H NMR (400 MHz, CD$_3$OD) δ ppm 1.12 (s, 9H) 1.17 (s, 9H) 6.74 (d, J=6.83 Hz, 1H) 7.05 (m, 2H) 7.18 (m, 4H) 7.32 (d, J=7.51 Hz, 1H) 7.82 (s, 1H) 8.71 (s, 1H).

Examples 64-75

Examples 64-75 listed in Table 3 below were prepared in a similar manner to Examples 56-63.

Example 76

1-(2-(2,2-Dimethyl-2,3-dihydrobenzofuran-7-yloxy) pyridin-3-yl)-3-(4-(trifluoromethoxy)phenyl)urea 76a. 2-(2,2-Dimethyl-2,3-dihydrobenzofuran-7-yloxy)-3-nitropyridine: Prepared as described previously for 2a from 2-chloro-3-nitropyridine (4.9 g, 31 mmol) and 2,2-dimethyl-2,3-dihydrobenzofuran-7-ol (5.3 mL, 46 mmol) to afford 76a (6.5 g, 73% yield) as brown crystals; HPLC purity 96%, 3.13 min (Method A); [M+H]$^+$=287.16. $^1$H NMR (500 MHz, CDCl$_3$) δ ppm 8.38 (dd, 1H, J=1.7 Hz, J=5.0 Hz), 8.31 (dd, 1H, J=5.0 Hz, J=1.7 Hz), 7.12 (dd, 1H, J=10.0 Hz, J=5.0 Hz), 7.05 (d, 1H, J=5.0 Hz), 7.00 (d, 1H, J=10.0 Hz), 6.86 (t, 1H, J=10.0 Hz), 3.05 (s, 2H), 1.39 (s, 6H); $^{13}$C (125 MHz, CDCl$_3$) δ (ppm), 155.42, 151.76, 150.16, 136.03, 135.40, 134.04, 129.76, 122.60, 121.06, 120.37, 118.07, 88.40, 43.07, 27.98.

76b. 2-(2,2-Dimethyl-2,3-dihydrobenzofuran-7-yloxy)pyridin-3-amine: Prepared as described previously for 58b from 76a (3.27 g, 11.4 mmol) to afford 76b (2.78 g, 97% yield) as an off-white solid; HPLC purity 100%, 2.29 min (Method A); [M+H]$^+$=257.17; $^1$H NMR (500 MHz, CDCl$_3$) δ ppm 7.53 (d, 1H, J=5.0 Hz), 6.97 (d, 2H, J=10.0 Hz), 6.95 (d, 1H, J=5.0 Hz), 6.80 (m, 2H), 3.97 (br, 2H), 3.05 (s, 2H), 1.44 (s, 6H); $^{13}$C (125 MHz, CDCl$_3$) δ (ppm), 151.60, 150.18, 137.70, 135.60, 131.52, 129.47, 121.77, 121.30, 120.96, 120.27, 119.02, 87.80, 43.19, 28.08.

Example 76: Prepared from 76b as described previously for Example 56 to afford Example 76 (52 mg, 89% yield) as a white solid, HPLC purity 96%, 3.94 min (Method A); [M+H]$^+$=460.24; $^1$H NMR (500 MHz, CD$_3$OD) δ ppm 1.38 (s, 6H) 3.07 (s, 2H) 6.85 (t, J=7.70 Hz, 1H) 6.96 (d, J=7.70 Hz, 1H) 7.03 (m, 2H) 7.18 (d, J=8.80 Hz, 2H) 7.53 (d, J=8.80 Hz, 2H) 7.62 (dd, J=4.95, 1.65 Hz, 1H) 8.56 (dd, J=7.70, 1.65 Hz, 1H); $^{13}$C NMR (500 MHz, CD$_3$OD) δ ppm 154.51, 153.28, 151.16, 145.21, 139.33, 139.23, 137.97, 131.02, 127.90, 125.54, 122.97, 122.56, 122.24, 121.47, 120.87, 119.79, 89.18, 43.80, 28.19.

Example 77

1-(2-(2,2-Dimethylbenzo[d][1,3]dioxol-4-yloxy) pyridin-3-yl)-3-(4-(trifluoromethoxy)phenyl)urea 77a. 2-(2,2-Dimethylbenzo[d][1,3]dioxol-4-yloxy)-3-nitropyridine: A solution of 2-chloro-3-nitropyridine (1.25 g, 7.9 mmol) in DMF (15 mL) was treated with 2,2-dimethylbenzo[d][1,3]dioxol-4-ol (1.5 g, 9.0 mmol) and cesium carbonate (7.68 g, 23.6 mmol). The mixture was heated at 80° C. for 10 h. The reaction was cooled to rt, and the mixture was poured in water (200 mL) with stirring. No precipitate was formed. The resulting brown solution was extracted with ethyl acetate (3×80 mL). The combined organic phase was washed with brine (50 mL), dried over sodium sulfate, and concentrated to give a dark brown solid. The dark brown solid was purified by SiO$_2$ chromatography (40 g) using a gradient of ethyl acetate in hexanes. The separation was incomplete. Compound 77a (772 mg, 34% yield) was obtained as a light brown solid. The still impure compound was used in the next step without further purification; HPLC purity 84%, 3.34 min (Method A); $^1$H NMR (500 MHz, CDCl$_3$) δ ppm 8.38 (dd, 1H, J=1.7 Hz, J=10.0 Hz), 8.35 (dd, 1H, J=5.0 Hz, J=1.7 Hz), 7.16 (dd, 1H, J=10.0 Hz, J=5.0 Hz), 6.83 (t, 1H, J=8.0 Hz), 6.70 (t, 2H, J=8.3 Hz), 1.64 (s, 6H); $^{13}$C (125 MHz, CDCl$_3$) δ (ppm), 154.89, 151.78, 149.25, 138.78, 135.56, 134.99, 134.06, 121.20, 119.38, 118.49, 115.20, 106.34, 25.76.

77b. 2-(2,2-Dimethylbenzo[d][1,3]dioxol-4-yloxy)pyridin-3-amine: Prepared from 77a (772 mg, 2.68 mmol) as described previously for 58b to afford 77b (650 mg, 77% pure) as a gray solid; HPLC purity 84%, 2.40 min (Method A); [M+H]$^+$=259.13; $^1$H NMR (500 MHz, CDCl$_3$) δ ppm 7.55 (d, 1H, J=5.0 Hz), 7.01 (d, 1H, J=10.0 Hz), 6.82 (m, 2H), 6.67 (d, 1H, J=10.0 Hz), 6.62 (d, 1H, J=10.0 Hz), 3.96 (br, 2H), 1.66 (s, 6H); $^{13}$C (125 MHz, CDCl$_3$) δ (ppm), 151.05, 149.13, 138.61, 136.71, 135.62, 131.29, 122.01, 121.04, 119.36, 118.82, 115.22, 105.23, 25.78.

Example 77: Prepared from 77b as described previously for Example 58 to afford Example 77 (24 mg, 64% yield) as a light yellow solid; HPLC purity 88%, 4.95 min (Method A); [M+H]$^+$=462.26; $^1$H NMR (500 MHz, CD$_3$OD) δ ppm 1.60 (s, 6H) 6.67 (d, J=12.65 Hz, 1H) 6.69 (d, J=13.19 Hz, 1H) 6.83 (t, J=8.25 Hz, 1H) 7.06 (dd, J=8.25, 4.95 Hz, 1H) 7.21 (d, J=8.80 Hz, 2H) 7.55 (d, J=8.80 Hz, 2H) 7.65 (dd, J=4.95, 1.65 Hz, 1H) 8.57 (dd, J=8.25, 1.65 Hz, 1H); $^{13}$C NMR (500 MHz, CD$_3$OD) δ ppm 154.47, 152.88, 150.67, 145.29, 139.87, 139.53, 139.43, 137.37, 128.15, 125.58, 122.63, 122.20, 120.87, 120.20, 120.16, 116.46, 106.47, 25.62.

Examples 78-82

Examples 78-82 listed in Table 3 below were prepared in a similar manner to Examples 76 and 77.

Example 83

1-(4-tert-Butylphenyl)-3-(2-(2-tert-butylphenylamino)pyridin-3-yl)urea

83a. N-(2-tert-Butylphenyl)-3-nitropyridin-2-amine: A suspension of 2-chloropyridine (500 mg, 3.2 mmol) and 2-tert butylaniline (471 mg, 3.2 mmol) in n-butanol (5 mL) was heated to 210° C. for 1 h using a microwave reactor. After removal of solvent, the crude product was purified by SiO$_2$ chromatography (40 g) eluted with EtOAc/hexane (0-50% EtOAc in 30 min) to afford 83a (800 mg, 94% yield) as a yellow solid; HPLC purity 99%, 3.84 min (Method A); [M+H]$^+$=272.13.

83b. N2-(2-tert-Butylphenyl)pyridine-2,3-diamine: To 83a (500 mg, 1.84 mmol) in methanol (50 mL) was added 100 mg of 10% Pd—C. The resulting mixture was hydrogenated at rt under hydrogen pressure (15 psi) for 14 h. The catalyst was removed by filtration through a bed of Celite®. Concentration afforded 83b (450 mg, 100% yield) as a tan solid; HPLC purity 95%, 2.79 min (Method A); [M+H]$^+$=242.16.

Example 83: An anhydrous THF solution (0.8 mL) containing 83b (25 mg, 0.1 mmol) and 4-tert-butylphenylisocyanate (19.3 mg 0.11 mmol) was stirred at rt for 3 h, diluted with MeOH to 2 mL total volume, and purified by preparative HPLC to afford Example 83 (18 mg, 35% yield) as a TFA salt; HPLC purity 98%, 4.15 min (Method A); [M+H]$^+$=417.36.

Example 84

1-(4-(2-tert-Butylphenoxy)pyridin-3-yl)-3-(4-(trifluoromethoxy)phenyl)urea 84a. 4-Chloro-3-nitropyridine: Prepared from 4-hydroxy-3-nitropyridine (2 g, 14.3 mmol) as previously described for 61a to afford 84a (1.29 g, 57% yield) as a pale yellow oil which solidifies upon cooling; HPLC purity >47%, 1.73 min (Method A); $^1$H NMR (CDCl$_3$) (500 MHz, Solvent) δ ppm 7.56 (d, J=5.27 Hz, 1H) 8.70 (d, J=5.27 Hz, 1H) 9.13 (s, 1H).

84b. 4-(2-tert-Butylphenoxy)-3-nitropyridine: A mixture of 84a (1.29 g, 8.17 mmol), potassium carbonate (1.70 g, 12.3 mmol) and 2-tert-butylphenol (1.30 mL, 8.46 mmol) were stirred in dioxane (8 mL) at 105° C. for 3 days. The mixture was cooled to rt, water (15 mL) was added and the resulting heterogeneous mixture was extracted with ether (3×30 mL), washed with brine (15 mL) dried with magnesium sulfate, filtered and concentrated to give 3.64 g of yellow oil. The oil was purified by SiO$_2$ chromatography (120 g) using a gradient of ethyl acetate in hexanes to afford 84b (1.33 g, 59% yield) as a yellow oil; HPLC purity 100%, 3.69 min (Method A); $^1$H NMR (500 MHz, CDCl$_3$) δ ppm 1.37 (s, 9H) 6.78 (d, J=6.05 Hz, 1H) 6.92 (m, J=9.41 Hz, 1H) 7.27 (m, 2H) 7.51 (m, 1H) 8.54 (d, J=6.05 Hz, 1H) 9.15 (s, 1H); $^{13}$C (125 MHz, CDCl$_3$) δ (ppm), 30.17, 34.72, 112.29, 121.65, 126.48, 127.74, 128.32, 137.14, 142.36, 147.47, 151.56, 154.43, 158.17.

84c. 4-(2-tert-Butylphenoxy)pyridin-3-amine: Prepared from 84b (1.33 g, 4.9 mmol) as previously described for 58b to afford 84c (1.16 g, 98% yield) as a white solid; HPLC purity 100%, 2.45 min (Method A); [M+H]$^+$=243.17; $^1$H NMR (500 MHz, CDCl$_3$) δ ppm 8.07 (s, 1H), 7.75 (d, 1H, J=5.0 Hz), 7.32 (d, 1H, J=10.0 Hz), 7.03 (m, 2H), 6.77 (d, 1H, J=5.0 Hz), 6.41 (d, 1H, J=5.0 Hz), 4.26 (br, 2H), 1.27 (s, 9H); $^{13}$C (125 MHz, CDCl$_3$) δ (ppm), 152.89, 150.65, 140.96, 139.93, 137.42, 134.21, 127.13, 126.93, 124.22, 120.56, 110.45, 34.19, 29.86.

Example 84: Prepared from 84c as described previously for Example 56 to afford Example 84 (9 mg, 23% yield) as an off-white solid; HPLC purity 96%, 3.44 min (Method A); [M+H]$^+$=446.27; $^1$H NMR (500 MHz, DMSO-d$_6$) δ ppm 1.32 (s, 9H) 6.49 (d, J=5.50 Hz, 1H) 7.01 (d, J=8.25 Hz, 1H) 7.24 (t, J=7.70 Hz, 1H) 7.30 (m, J=9.35, 9.35 Hz, 3H) 7.49 (dd, J=7.70, 1.65 Hz, 1H) 7.57 (d, J=9.35 Hz, 2H) 8.08 (d, J=5.50 Hz, 1H) 8.63 (d, J=2.75 Hz, 1H) 9.25 (d, J=4.40 Hz, 1H) 9.67 (d, J=4.40 Hz, 1H). $^{13}$C NMR (500 MHz, DMSO-d$_6$) δ ppm 153.73, 153.65, 152.64, 152.37, 152.29, 152.21, 144.55, 142.75, 142.10, 141.98, 141.44, 138.77, 138.66, 128.03, 127.85, 126.67, 126.59, 125.62, 122.25, 121.82, 119.31, 119.23, 110.33, 34.42, 30.38.

Example 85

1-(4-(2-tert-Butylphenoxy)pyridin-3-yl)-3-(4-tert-butylphenyl)urea

Prepared from 84c as described previously for Example 56 to afford Example 85 (18 mg, 47% yield) as an white solid; HPLC purity 90%, 3.59 min (Method A); [M+H]$^+$=418.41.

Example 86

1-(4-Butoxyphenyl)-3-(2-(2-tert-butylphenoxy)pyridin-3-yl)urea 86a. 1-(2-(2-tert-Butylphenoxy)pyridin-3-yl)-3-(4-hydroxyphenyl)urea: A solution of 3a (2.0 g, 7.4 mmol) and 4-aminophenol (0.895 g, 8.2 mmol) in THF (40 mL) was stirred at 60° C. for 18 h. The mixture was concentrated and the resulting residue was triturated with ethanol and filtered. The resulting powder was triturated with ether, filtered and dried in vacuo to afford 86a (2.0 g, 71% yield) as a white powder; HPLC purity 90%, 3.35 min (Method A); [M+H]$^+$=378.10.

Example 86: To a suspension of 86a (50 mg, 0.13 mmol) and triphenylphosphine resin (200 mg of 3 mmol/g, 0.6 mmol) in anhydrous THF (2 mL) was added n-butanol (12 mg, 0.16 mmol) followed by diisobutylazodicarboxylate (50 mg, 0.21 mmol). The mixture was stirred overnight at rt. The mixture was concentrated and the residue was purified by prep HPLC to afford Example 86 (28 mg, 50% yield) as beige crystals; HPLC purity 100%, 4.25 min (Method A); [M+H]$^+$=434.17.

Examples 87-97 listed in Table 2 below were prepared in a similar manner to Example 86. Examples 98-108 and 113-131, 133-136 and 138-152 listed in Table 1 below were prepared similarly as previously described for Examples 1-4. Examples 109-111 listed in Table 2 were prepared in a similar manner as to Example 86. Example 112 listed in Table 2 was prepared as previously described for Examples 1-4.

Example 132

1-(2-(2-(4-hydroxyheptan-4-yl)phenoxy)pyridin-3-yl)-3-(4-(trifluoromethoxy)phenyl)urea Example 132: Prepared according to the procedure described below for 153a. (M+H)=504. $^1$H NMR (400 MHz, DMSO-d6) δppm 0.58 (t, J=7.6 Hz, 6H), 0.90 (m, 2H), 1.25 (m, 2H), 1.58 (m, 2H), 1.74 (m, 2H), 4.55 (s, 1H), 7.01 (dd, J=8.1, 1.2 Hz, 1H), 7.05 (dd, J=8.1, 4.8 Hz, 1H), 7.18 (td, J=7.9, 1.2 Hz, 1H), 7.25 (td, J=7.8, 1.3 Hz, 1H), 7.32 (d, J=8.3 Hz, 2H), 7.58 (m, 2H), 7.66 (dd, J=8.0, 1.8 Hz, 1H), 7.70 (dd, J=4.8, 1.8 Hz, 1H), 8.43 (dd, J=8.0, 1.7 Hz), 8.56 (s, 1H), 9.60 (s, 1H).

Example 137

1-(2-(2-(4-hydroxyhepta-1,6-dien-4-yl)phenoxy)pyridin-3-yl)-3-(4-(trifluoromethoxy)phenyl)urea Example 137: Prepared according to the procedure described below for 153a using allyl magnesium bromide instead of methyllithium. (M+H)=500. $^1$H NMR (400 MHz, DMSO-d6) δppm 2.57 (m, 4H), 4.86 (m, 4H), 4.88 (s, 1H), 5.64 (m, 2H), 7.00 (dd, J=8.1, 1.3 Hz, 1H), 7.09 (dd, J=8.1, 4.8 Hz, 1H), 7.18 (td, J=7.9, 1.1 Hz, 1H), 7.26 (td, J=7.6, 1.5 Hz, 1H), 7.31 (d, J=8.6 Hz, 2H), 7.58 (m, 2H), 7.66 (dd, J=7.9, 1.8 Hz, 1H), 7.71 (dd, J=4.8, 1.8 Hz, 1H), 8.43 (dd, J=8.0, 1.7 Hz), 8.56 (s, 1H), 9.60 (s, 1H).

Example 153

1-(2-(2-(2-ethoxypropan-2-yl)phenoxy)pyridin-3-yl)-3-(4-(trifluoromethoxy)-phenyl)urea 153a. 1-(2-(2-(2-hydroxypropan-2-yl)phenoxy)pyridin-3-yl)-3-(4(trifluoromethoxy)-phenyl)urea: Methyllithium (1.6 M in ether, 5.5 mL, 8.8 mmol) was added to a solution of methyl 2-(3-(3-(4-(trifluoromethoxy)phenyl)ureido)pyridin-2-yloxy)benzoate (500 mg, 1.11 mmol) in THF (5.0 mL). The mixture was stirred at −78° C. for 2.5 h and quenched with a saturated solution of ammonium chloride (30 mL). Ethyl acetate was added and the separated aqueous layer was extracted with ethyl acetate (3×50 mL). The combined organic layers were dried (anhydrous sodium sulfate), filtered and evaporated and the residue was purified by reverse phase HPLC. M−H=447. $^1$H NMR (400 MHz, CDCl$_3$) δppm 1.72 (s, 6H), 7.05 (td, J=8.3, 1.1 Hz, 1H), 7.11 (m, 4H), 7.23 (br. t, J=8.1 Hz), 7.38 (m, 3H), 7.66 (s, 1H), 7.88 (dd, J=4.8, 1.8 Hz), 8.54 (s, 1H), 8.63 (dd, J=8.1, 1.7 Hz, 1H). The reaction also affords 1-(2-(2-acetylphenoxy)pyridin-3-yl)-3-(4-(trifluoromethoxy)phenyl)urea. (M+H)=432.

153b. Methyl 2-(3-(3-(4-(trifluoromethoxy)phenyl)ureido)pyridin-2-yloxy)benzoate: 153b was prepared from methyl 2-(3-aminopyridin-2-yloxy)benzoate and p-trifluoromethoxyphenyl isocyanate according to the procedure described for Example 2. (M+H)$^+$=448. $^1$H NMR (400 MHz, DMSO-d$_6$) δppm 3.57 (s, 3H), 7.05 (dd, J=8.0, 4.8 Hz, 1H), 7.33 (d, J=8.6 Hz, 2H), 7.42 (m, 1H), 7.59 (m, 3H), 7.73 (td, J=8.1, 1.7 Hz, 1H), 7.95 (dd, J=7.7, 1.7 Hz, 1H), 8.55 (dd, J=8.0, 1.6 Hz, 1H), 8.72 (s, 1H), 9.62 (s, 1H).

153c. methyl 2-(3-aminopyridin-2-yloxy)benzoate: Prepared according to the procedures described for 2a and 2b using methyl salicylate and 2-cholor-3-nitro pyridine in the first step. (M+H)$^+$=245.

Example 153: To a solution of 153a (46 mg, 0.1 mmol) in ethanol (3.0 mL) at rt, was added one drop of concentrated sulfuric acid. The mixture was heated to 45° C. for 72 h after which time it was allowed to cool to rt. Saturated sodium bicarbonate was added and the solvent was evaporated under reduced pressure. The residue was dissolved in dichloromethane and the separated aqueous layer was extracted with dichloromethane (2×15 mL). The combined organic layers were dried (anhydrous sodium sulfate), filtered and evaporated and the residue was purified by reversed phase HPLC. (M-EtOH)=430. $^1$H NMR (400 MHz, CDCl$_3$) δ ppm 1.30 (t, J=7.07 Hz, 3H), 1.59 (s, 6H), 3.48 (q, J=7.07 Hz, 2H), 7.07 (dd, J=7.96, 4.93 Hz, 1H), 7.16-7.24 (m, 3H), 7.37-7.46 (m, 2H), 7.52 (d, J=9.09 Hz, 1H), 9.26 (s, 1H). The reaction also affords 1-(2-(2-acetylphenoxy)pyridin-3-yl)-3-(4-(trifluoromethoxy)phenyl)urea. (M+H)=432.

Example 154

1-(2-(2-(3-ethoxypentan-3-yl)phenoxy)pyridin-3-yl)-3-(4-(trifluoromethoxy)phenyl)urea Example 154: Prepared according to the procedure described for Example 153 using 1-(2-(2-(3-hydroxypentan-3-yl)phenoxy)pyridin-3-yl)-3-(4-(trifluoromethoxy)phenyl)urea. (M−H)=502. $^1$H NMR (400 MHz, CDCl$_3$) δ ppm 0.82 (t, J=7.2 Hz, 6H), 1.32 (t, J=7.0 Hz, 3H), 2.06 (q, J=7.2 Hz, 4H), 3.43 (q, J=7.0 Hz, 2H), 7.07 (dd, J=8.1, 4.8 Hz, 1H), 7.24 (m, 4H), 7.34 (dd, J=8.1, 1.8 Hz, 1H), 7.44 (dd, J=8.3, 1.8 Hz, 1H), 7.51 (m, 2H), 7.84 (dd, J=5.1, 1.8 Hz, 1H), 8.35 (dd, J=8.4, 1.2 Hz, 1H), 8.58 (dd, J=7.8, 1.7 Hz, 1H), 9.43 (s, 1H).

Example 155

1-(2-(2-(2-methoxypropan-2-yl)phenoxy)pyridin-3-yl)-3-(4-(trifluoromethoxy)phenyl)urea Example 155 was prepared using the similar procedure as described in Example 153. (M−H)=460.

Example 156

1-(2-(2-(3-methoxypentan-3-yl)phenoxy)pyridin-3-yl)-3-(4-(trifluoromethoxy)phenyl)urea Example 156: Prepared according to the procedure described for Example 153 using 1-(2-(2-(3-hydroxypentan-3-yl)phenoxy)pyridin-3-yl)-3-(4-(trifluoromethoxy)phenyl)urea. (M−H)=488. $^1$H NMR (400 MHz, CHLOROFORM-D) δ ppm 0.85 (t, J=7.2 Hz, 6H), 2.13 (q, J=7.2 Hz, 4H), 3.21 (s, 3H), 7.08 (dd, J=7.8, 5.0 Hz, 1H), 7.14-7.51 (m, 7H), 7.86 (dd, J=5.1, 1.7 Hz, 1H), 8.39 (dd, J=8.4, 1.2 Hz, 1H), 8.58 (dd, J=7.8, 1.7 Hz, 1H), 9.46 (s, 1H).

Example 157

1-(2-(2-(2-propoxypropan-2-yl)phenoxy)pyridin-3-yl)-3-(4-(trifluoromethoxy)phenyl)urea 157a. 2-(1-Methyl-1-propoxy-ethyl)-phenol: A mixture of 2-(1-hydroxy-1-methyl-ethyl)-phenol (30 mg, 0.2 mmol) in 1-propanol (6 mL) was treated with p-TsOH (1 mg) at rt and stirred 17 h at 30° C. The mixture was then treated with sodium acetate (0.22 mmol) and the solvent was removed under reduced pressure. The residue was purified by flash chromatography on silica gel using a mixture of toluene-hexane (1:1) to give 16 mg (41% yield) of 157a as an off white solid. ¹H NMR (400 MHz, CDCl₃) δppm 0.91 (t, J=7.50 Hz, 3H), 1.59-1.69 (m, 2H), 1.61 (s, 3H), 3.28 (t, J=7.09 Hz, 2H), 6.81-6.87 (m, 2H), 7.06 (m, 1H), 7.18 (m, 1H), 8.82 (s, 1H).

157b. 2-[2-(1-Methyl-1-propoxy-ethyl)-phenoxy]-3-nitro-pyridine:

A mixture of 157a (16 mg, 0.08 mmol) in DMF (1 mL) was treated with 2-chloro-3-nitro-pyridine (15 mg, 0.09 mmol) and cesium carbonate (90 mg, 0.28 mmol) at rt and then stirred 2 h at rt. The mixture was diluted with dichloromethane and water and the organic layer was separated, dried (sodium sulfate) and filtered. The filtrate was concentrated under vacuum. The residue was purified by flash chromatography on silica gel using a mixture of ethyl acetate-toluene (1:33) to give 20 mg (80% yield) of 157b as a colorless oil. (M-C₃H₇O)⁺=257. ¹H NMR (400 MHz, CDCl₃) δppm 0.76 (t, J=7.24 Hz, 3H), 1.24 (dq, J=7.07 Hz, J=7.24 Hz, 2H), 1.59 (s, 3H), 3.15 (t, J=7.07 Hz, 2H), 7.01 (m, 1H), 7.14 (m, 1H), 7.24-7.32 (m, 2H), 7.59 (m, 1H), 8.33 (m, 1H), 8.38 (m 1H).

157c. 2-[2-(1-Methyl-1-propoxy-ethyl)-phenoxy]-pyridin-3-ylamine: A mixture of 157b (20 mg, 0.06 mmol) in ethyl acetate (2.2 mL) was treated with 10% Pd/C (2 mg) and stirred 17 h under H₂ (1 atm). The mixture was retreated with 10% Pd/C (2 mg) and stirred 17 h at rt and 24 h at 30° C. The mixture was filtered through a glass microfiber paper and the filtrate was concentrated under vacuum to give 17 mg (100% yield) of 157c as a solid. (M-C₃H₇O)⁺=227. ¹H NMR (400 MHz, CDCl₃) δppm 0.84 (t, J=7.23 Hz, 3H), 1.46 (dq, J=7.09 Hz, J=7.23 Hz, 2H), 1.60 (s, 3H), 3.21 (t, J=7.09 Hz, 2H), 4.01 (s (br), 2H), 6.81 (m, 1H), 7.02 (m, 1H), 7.13-7.18 (m, 2H), 7.28 (m, 1H), 7.51-7.55 (m, 2H).

Example 157: A mixture of 157c (17 mg, 0.06 mmol) in DMF (1 mL) was treated with 4-(trifluoromethoxy)phenyl isocyanate (18 mg, 0.09 mmol) and stirred 17 h at rt. The mixture was retreated with 4-(trifluoromethoxy)phenyl isocyanate and stirred 2 h at rt. The mixture was diluted with dichloromethane and a solution of sodium hydrogen carbonate (sat.) and the organic layer was separated, dried (sodium sulfate) and filtered. The residue was purified by preparative LC on YMC Pack C-18 using a gradient of acetonitrile in sodium acetate buffer (0.05%) to give 15 mg (52% yield of Example 157 as a light yellow sticky oil. (M−H)⁻=488. ¹H NMR (400 MHz, CDCl₃) δppm 0.88 (t, J=7.33 Hz, 3H), 1.64-1.70 (m, 2H), 1.68 (s, 3H), 3.31 (t, J=7.67 Hz, 2H), 7.04 (m, 1H), 7.10 (s(br), 1H), 7.15-7.20 (m, 2H), 7.36-7.46 (m, 2H), 7.48 (m, 2H), 7.83 (m, 1H), 8.23 (m, 1H), 8.56 (m, 1H), 9.20 (s(br), 1H).

Example 158

1-(2-(3-(2-ethoxypropan-2-yl)phenoxy)pyridin-3-yl)-3-(4-(trifluoromethoxy)phenyl)urea 158a. 1-(2-(3-(2-hydroxypropan-2-yl)phenoxy)pyridin-3-yl)-3-(4-(trifluoromethoxy)phenyl)urea: 158a was prepared according to the procedure described for 153a using ethyl 3-(3-(3-(4-(trifluoromethoxy)phenyl)ureido)pyridin-2-yloxy)benzoate and methyl magnesium bromide instead of methyllithium. (M+H)=448.

Example 158: Prepared from 158a and p-toluenesulfonic acid (1.1 equiv.) according to the procedure described for Example 153. (M+H)⁺=476. ¹H NMR (rotamers) (400 MHz, DMSO-D6) δ ppm 1.04 (3H, t, J=6.95 Hz), 1.44 (5H, s), 3.18 (2H, q, J=7.07 Hz), 7.04 (1H, dd, J=7.96, 1.64 Hz), 7.07-7.11 (1H, m), 7.16 (1H, t), 7.21-7.26 (1H, m, J=8.08 Hz), 7.30 (2H, d, J=8.84 Hz), 7.36-7.43 (2H, m), 7.52-7.58 (2H, m), 7.69 (1H, td, J=4.29, 1.77 Hz), 8.54 (1H, dt, J=7.89, 1.86 Hz), 8.70-8.74 (1H, m), 9.51-9.57 (1H, m).

Example 159

1-2-{2-[1-(2-Methoxy-ethoxy)-1-methyl-ethyl]-phenoxy}-pyridin-3-yl)-3-(4-trifluoromethoxy-phenyl)-urea A mixture of 1-{2 [2-(1-hydroxy-1-1-methyl-ethyl)-phenoxy]-pyridin-3-yl}-3-(4-trifluoromethoxy-phenyl)-urea (20 mg, 0.45 mmol) in dichloromethane (DCM) (1 mL) was treated at rt with trichloroacetonitrile (17 mg, 0.11 mmol) and cesium carbonate (2 mg, 0.0045 mmol). The mixture was stirred at rt for 17 h and retreated with cesium carbonate (15 mg, 0.045 mmol). The mixture was stirred for 7 h at rt and treated an other time with cesium carbonate (15 mg, 0.045 mmol). The mixture was stirred for 17 h at rt, diluted with DCM, and filtered through a microfiber paper. The filtrate was concentrated under vacuum. The residue was dissolved in DCM and the mixture was diluted with cyclohexane until the mixture became cloudy. The mixture was treated at rt with 2-methoxyethanol (10 mg, 0.135 mmol) and trifluoromethanesulfonic acid (1.4 mg, 0.018 mmol and then stirred for 24 h at rt. The mixture was treated with pyridine (7 mg, 0.090 mmol), diluted with DCM and washed with water. The aqueous layer was re-extracted with DCM and the combined organic layer was dried (sodium sulfate), filtered and concentrated under vacuum. The residue was purified by flash chromatography using a gradient of ethyl acetate in toluene (5 to 10%) to give 4 mg (17% yield) of Example 159 as a colorless sticky oil. (M+H)⁺=506; ¹H NMR (400 MHz, CDCl₃) δppm 1.54 (s, 6H), 3.36 (s, 3H), 3.46 (t, J=4.21 Hz, 2H), 3.79 (dd, J=4.21 Hz, 2H), 7.00 (m, 1H), 7.15-7.22 (m, 3H), 7.36-7.44 (m, 2H), 7.51-7.53 (m, 2H), 7.65 (m, 1H), 7.74 (m, 1H), 8.42 (s, br), 1H), 8.65 (s (br), 1H), 8.70 (m, 1H).

Example 160

1-(2-(2-(1-(2-methoxyethoxy)ethyl)phenoxy)pyridin-3-yl)-3-(4-(trifluoromethoxy)phenyl)urea Example 160 was prepared according to the procedure described for Example 159. (M+H)=492. ¹H NMR (400 MHz, DMSO-D₆) δ ppm 1.29 (d, J=6.32 Hz, 3H), 3.18 (s, 3H), 3.59 (m, 2H), 3.34 (m, 2H), 4.56 (q, J=6.32 Hz, 1H), 7.06-7.14 (m, 2H), 7.29-7.38 (m, 4H), 7.51 (dd, J=7.33, 1.77 Hz, 1H), 7.56-7.66 (m, 3H), 8.55 (dd, J=7.83, 1.52 Hz, 1H), 8.76 (s, 1H), 9.58 (s, 1H).

Example 161

1-(2-(2-(2-cyanopropan-2-yl)phenoxy)pyridin-3-yl)-3-(4-(trifluoromethoxy)phenyl)urea 161a. 2-(2-(benzyloxy)phenyl)-2-methylpropanenitrile: A mixture of 2-benzyloxyphenyl acetonitrile (2 g, 8.9 mmol), sodium hydride (60% oil, 900 mg, 22.4 mmol) and iodomethane (1.2 mL, 19.7 mmol) in DMF (40 mL) was stirred at rt for 48 h and quenched with saturated solution of ammonium chloride (30 mL). The mixture was diluted with water (300 mL) and extracted with diethyl ether (3×150 mL). The combined organic layers were dried (anh. sodium sulfate), filtered and evaporated. Flash-chromatography (ethyl acetate:hexanes/1:10) yielded 2.8 g of 161a. (M+H)⁺=252; ¹H NMR (400 MHz, CDCl₃) δppm 1.82 (s, 6H), 5.23 (s, 2H), 6.90-7.56 (m, 9H).

161b. 2-(2-hydroxyphenyl)-2-methylpropanenitrile: A mixture of 161a (2.2. g, 8.8 mmol) and palladium 10% on charcoal (200 mg) in ethyl acetate (8 mL) was stirred at rt under one atmosphere of hydrogen for 18 h, filtered through Celite and evaporated. The resulting compound was used directly in the next step.

161c. 2-Methyl-2-(2-(3-nitropyridin-2-yloxy)phenyl)propanenitrile: 161c was prepared from 161b and 2-chloro-3-nitro pyridine according to the procedure described for 2a. $(M+H)^+=284$; $^1H$ NMR (400 MHz, $CDCl_3$) δppm 1.87 (s, 6H), 7.21 (m, 2H), 7.32 (m, 1H), 7.42 (m, 1H), 7.53 (dd, J=7.8, 1.5 Hz, 1H), 8.38 (dd, J=4.8, 1.8 Hz, 1H), 8.47 (dd, J=8.1, 1.8 Hz, 1H).

161d. 2-(2-(3-aminopyridin-2-yloxy)phenyl)-2-methylpropanenitrile: 161d was prepared according to the procedure described for Example 2b. $(M+H)^+=254$; $^1H$ NMR (400 MHz, DMSO-$d_6$) δppm 1.73 (s, 6H), 6.93 (dd, J=7.6, 4.8 Hz, 1H), 7.03 (dd, J=8.0, 1.5 Hz, 1H), 7.15 (dd, J=7.7, 1.5 Hz, 1H), 7.23 (t, J=7.6 Hz, 1H), 7.37 (m, 2H), 7.49 (dd, J=8.0, 1.5 Hz, 2H).

Example 161: Prepared from 161d and p-trifluoromethoxyphenyl isocyanate according to the procedure described for Example 2. $(M+H)^+=457$; $^1H$ NMR (400 MHz, DMSO-$d_6$) δppm 1.76 (s, 6H), 7.10 (m, 1H), 7.31 (m, 2H), 7.43 (dd, J=7.6, 1.5 Hz, 1H), 7.57 (m, 3H), 7.68 (dd, J=4.4, 1.7 Hz, 1H), 8.52 (dd, J=8.0, 1.5 Hz, 1H), 8.60 (s, 1H), 9.56 (s, 1H).

Example 162

1-(4-(trifluoromethoxy)phenyl)-3-(2-(2-vinylphenoxy)pyridin-3-yl)urea 162a. 2-(2-bromophenoxy)-3-nitropyridine: A mixture of 2-bromophenol (10 g, 57 mmol), 2-chloro-2-nitropyridine (9.16 g, 57 mmol) and cesium carbonate (18.6 g, 57 mmol) in DMF (50 mL) was stirred at 23° C. for 48 h. Water (300 mL) was added and mixture was stirred at 0° C. for 1 h. The solid was filtered and dried in vacuo to afford 15.7 g (93%) of 162a. $(M+H)^+=296$.

162b. 2-(2-bromophenoxy)pyridin-3-amine: A mixture of 162a (5 g, 16.9 mmol), 5% Palladium on charcoal (600 mg) in 75 mL of ethyl acetate was stirred at 23° C. for 18 h under 1 atm of hydrogen. The hydrogen was removed and the solution was filtered over a pad of Celite™ and the filtrate was concentrated in vacuo to give 4.07 g (91%) of 162b. $(M+H)^+=266$.

162c. 1-(2-(2-bromophenoxy)pyridin-3-yl)-3-(4-(trifluoromethoxy)-phenyl)urea: To 162b (3 g, 11.3 mmol) in 22 mL of THF was added 1-isocyanato-4-(trifluoromethoxy)benzene (1.7 mL, 11.3 mmol) and the mixture was stirred at 23° C. for 16 h. The mixture was concentrated in vacuo and the residue was purified by flash chromatography (Biotage™, silica, 25% $CH_3CN$/methylene chloride gradient) providing 3.46 g (66%) of 162c as a tan oil. $(M+H)^+=468$. $^1H$ NMR (400 MHz, DMSO-D6) δ ppm 7.08 (dd, J=7.96, 4.93 Hz, 1H) 7.20-7.27 (m, 1H) 7.30 (d, J=8.59 Hz, 2H) 7.34-7.39 (m, 1H) 7.43-7.53 (m, 1H) 7.54-7.59 (m, 2H) 7.63 (dd, J=4.80, 1.52 Hz, 1H) 7.71-7.77 (m, 1H) 8.55 (dd, J=7.96, 1.64 Hz, 1H) 8.78 (s, 1H) 9.57 (s, 1H).

Example 162: A 10-mL oven-dried flask capped with a rubber septum was evacuated and backfilled with argon. The flask was charged with 162c (125 mg, 0.27 mmol), tetraethylammonium chloride (45 mg, 0.27 mmol), and evacuated and backfilled with Argon. DMF (2.6 mL), tributyl(vinyl)stannane (101 mL, 0.35 mmol) were added and argon was bubbled through the mixture for 20 min. $Pd(PPh_3)_4$ (11.2 mg, 0.016 mmol) was added, the septum was replaced with a Teflon® screwcap, the flask was sealed and the mixture was heated at 80° C. for 72 h. The mixture was cooled to rt, a solution of KF in water (1.1 eq./1 mL of water) was added and the mixture was stirred for 30 min then filtered through Celite®. The residue was partitioned between water and ethyl acetate, organic layer was washed with water, dried over $Na_2SO_4$, filtered and concentrated in vacuo. The residue was purified by preparative HPLC (solvent A: 10% acetonitrile-90% water+0.1% TFA; solvent B: 90% acetonitrile-10% water+0.1% TFA, with 20% B to 100% in 7 min gradient. Column: YMC Pack C-18 20×100 mm. Flow rate=20 mL/min.) to yield 70 mg (64%, TFA salt) of Example 162. $(M+H)^+=416$. $^1H$ NMR (400 MHz, DMSO-D6) δ ppm 5.28 (d, J=11.87 Hz, 1H) 5.85 (d, J=16.93 Hz, 1H) 6.73 (dd, J=17.81, 11.24 Hz, 1H) 7.06 (dd, J=7.83, 4.80 Hz, 1H) 7.13 (d, J=8.08 Hz, 1H) 7.26-7.36 (m, 4H) 7.56 (d, J=9.09 Hz, 2H) 7.62 (dd, J=4.80, 1.52 Hz, 1H) 7.74 (dd, J=7.83, 1.52 Hz, 1H) 8.54 (dd, J=7.96, 1.64 Hz, 1H) 8.81 (s, 1H) 9.54 (s, 1H).

Example 163 listed in Table 1 was prepared similarly as described in Example 162.

Example 164

1-(2-(2-cyclopropylphenoxy)pyridin-3-yl)-3-(4-(trifluoromethoxy)-phenyl)urea

A 15-mL oven-dried resealable flask capped with a rubber septum was evacuated and backfilled with argon. The flask was charged with Example 162 (58 mg, 0.14 mmol), methylene chloride (1.4 mL) and at −10° C., the diethyl zinc solution in toluene (1.1 M, 634 µL, 0.59 mmol) followed by the diiodomethane (55 µL, 0.59 mmol) were added. The mixture was stirred at 23° C. for 16 h and aqueous solution of $NH_4Cl$ (sat) was added and extracted with methylene chloride. The organic layer was dried over $Na_2SO_4$, filtered and concentrated in vacuo. The residue was purified by preparative HPLC (solvent A: 10% acetonitrile-90% water+0.1% TFA; solvent B: 90% acetonitrile-10% water+0.1% TFA, with 20% B to 100% in 25 min gradient. Column: YMC Pack C-18 20×250 mm. Flow rate=20 mL/min.) to yield 30 mg (50%, TFA salt) of Example 164. $(M+H)^+=430$. $^1H$ NMR (400 MHz, DMSO-D6) δ ppm 0.56-0.62 (m, 2H) 0.73-0.78 (m, 2H) 1.79-1.86 (m, 1H) 7.00 (dd, J=7.58, 1.52 Hz, 1H) 7.05 (dd, J=7.96, 4.93 Hz, 1H) 7.08 (dd, J=7.71, 1.39 Hz, 1H) 7.14-7.23 (m, 2H) 7.30 (d, J=8.59 Hz, 2H) 7.53-7.58 (m, 2H) 7.63 (dd, J=4.93, 1.64 Hz, 1H) 8.54 (dd, J=7.96, 1.64 Hz, 1H) 8.80 (s, 1H) 9.58 (s, 1H).

Example 165

(E)-tert-butyl 3-(2-(3-(3-(4-(trifluoromethoxy)phenyl)ureido)pyridin-2-yloxy)phenyl)acrylate A 10-mL oven-dried flask capped with a rubber septum was evacuated and backfilled with argon. The flask was charged with 163c (200 mg, 0.43 mmol), DMF (2.2 mL), tert-butyl acrylate (125 µL, 0.95 mmol), triethylamine (120 µL, 0.95 mmol) and $Pd(PPh_3)_4$ (25 mg, 0.021 mmol). The septum was replaced with a Teflon® screwcap, the flask was sealed and the mixture was heated at 140° C. for 16 h. The mixture was cooled to rt, partitioned between a saturated aqueous solution of ammonium chloride and ethyl acetate, layers were separated and organic layer was dried over $Na_2SO_4$, filtered and concentrated in vacuo. The residue was purified by preparative HPLC (solvent A: 10% acetonitrile-90% water+0.1% TFA; solvent B: 90% acetonitrile-10% water+0.1% TFA, with 20% B to 100% in 7 min gradient.

Column: YMC Pack C-18 20×100 mm. Flow rate=20 mL/min.) to yield 50 mg (23%, TFA salt) of Example 165. (M+H)$^+$=516. $^1$H NMR (400 MHz, DMSO-D6) δ ppm 1.38 (s, 10H) 7.11 (dd, J=7.96, 4.93 Hz, 1H) 7.19 (d, J=8.08 Hz, 1H) 7.27-7.33 (m, 3H) 7.45-7.51 (m, 1H) 7.54-7.62 (m, 3H) 7.64 (dd, J=4.93, 1.64 Hz, 1H) 7.94 (dd, J=7.83, 1.26 Hz, 1H) 8.59 (dd, J=8.08, 1.52 Hz, 1H) 8.85 (s, 1H) 9.51 (s, 1H).

Examples 166-212 and 217 listed in Table 2 below were prepared similarly as previously described for Example 86.

Example 213

1-(4-acetylphenyl)-3-(2-(2-tert-butylphenoxy)pyridin-3-yl)urea 213a. 1-(4-acetylphenyl)-3-(2-(2-tert-butylphenoxy)pyridin-3-yl)urea: 2-(2-tert-Butylphenoxy)pyridin-3-amine (484.6 mg, 2 mmol) was dissolved in 7 mL of CH$_2$Cl$_2$. To this solution cooled to −20° C. were added 0.4 mL of TEA followed by 363 mg (2 mmol) of 1-(4-isocyanatophenyl)ethanone portion wise. The stirring continued while the temperature was allowed to increase to ambient. After 1 night stirring at rt, volatiles were evaporated to dryness and the dark oily residue triturated with petroleum ether/ether to yield 658.6 mg (82% yield) of 213a as a grey powder. HPLC purity 90%, 3.762 min (Method A: HPLC: 90% pure, Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$ & B=90% MeOH, 10% H2O, 0.2% H$_3$PO$_4$). [M+H]$^+$=404.2; $^1$H NMR (400 MHz, CDCl$_3$) δ ppm 1.31 (s, 9H), 2.48 (s, 3H), 6.82 (dd, J=7.9 Hz and J=1.8 Hz, 2H), 6.98 (q, J=8.4 Hz and J=5.3 Hz, 1H), 7.16 (m, 2H), 7.41 (dd, J=7.9 Hz, and J=1.8 Hz, 1H), 7.46 (d, J=8.8 Hz, 2H), 7.76 (s, 1H); 7.81 (dd, J=4.8 Hz and J=1.8 Hz, 1H); 7.85 (d, J=8.4 Hz, 2H); 7.92 (s, 1H); 8.58 (dd, J=8.4 Hz and J=1.8 Hz, 1H).

213b. 1-(2-(2-tert-butylphenoxy)pyridin-3-yl)-3-(4-(1-hydroxyethyl)phenyl)urea: 213a (568 mg, 1.41 mmol) was dissolved in 7 mL of isopropanol. To this solution were added 53.3 mg (1.41 mmol) of NaBH$_4$ and the mixture was stirred at rt for the night. Volatiles were evaporated, 10 mL of CH$_2$Cl$_2$ added and the solution washed twice with 2 mL of water. The organic phase was dried over MgSO$_4$ filtered and concentrated to yield a viscous oil. Trituration of the crude material with methanol yield 213b in a white powder (142 mg, HPLC purity 96.4%, 3.583 min (Method A); [M+H]$^+$=406.12; $^1$H NMR (500 MHz, DMSO_d$_6$) δ ppm 1.28 (d, J=6.6 Hz, 3H); 1.32 (s, 9H); 4.65 (m, 1H); 5.04 (d, J=4.95 Hz, 1H); 6.91 (dd, J=7.8 Hz and J=1.4 Hz, 2H), 7.05 (q, J=7.7 Hz and J=4.95 Hz, 1H), 7.15 (m, 2H), 7.22 (dd, J=7.9 Hz, and J=1.4 Hz, 1H), 7.24 (d, J=8.8 Hz, 2H), 7.38 (d, J=8.8 Hz, 2H); 7.42 (dd, J=8.3 Hz and J=1.7 Hz, 1H); 7.65 (dd, J=4.95 Hz and J=1.9 Hz, 2H); 8.55 (dd, J=7.7 Hz and J=1.9 Hz, 1H); 8.56 (s, 1H); 9.37 (s, 1H). A second crop of 229 mg was isolated from the mother liquors (65% yield).

Example 213: To 22.9 mg (0.0565 mmol) of 213b in 1.5 mL of CH$_2$Cl$_2$ was added 4 drops of SOCl$_2$ (excess). The solution was stirred for 2 h and concentrated to dryness. 54 mg (0.285 mmol) of N-methyl(3-(trifluoromethyl)phenyl)methanamine was added and the mixture stirred for 1 h at rt. Volatiles were evaporated. 3 mL of CH$_2$Cl$_2$ were added and the mixture washed twice with 1 mL of water. The organic phase was dried over MgSO$_4$ and concentrated to yield an oily residue purified by preparative HPLC (Method B (Shimadzu Phenomenex Luna 5u 21.2×100; flow rate 20 ml/min; detection at 220 nM; Gradient elution 0% to 100% B over 20 min; (A=10% MeOH, 90% H$_2$O, 0.1% TFA& B=90% MeOH, 10% H$_2$O, 0.1% TFA)); to yield the desired product. HPLC purity 98.5%). HRMS (ESI) m/z calcd for C$_{33}$H$_{36}$N$_4$O$_2$F$_3$ [M+H]$^+$ 577.2790, found 577.2773.

Example 222

1-(2-(2-tert-butylphenoxy)pyridine-3-yl)-3-(2-fluoro-4-((1-isobutylpiperidin-4-yl)methoxy)phenyl)urea 222a. 1-(2-(2-tert-butylphenoxy)pyridine-3-yl)-3-(2-fluoro-4-(piperidin-4-ylmethoxy)phenyl)urea: To a solution of 4-((1-benzylpiperidin-4-yl)methoxy)-2-fluorophenyl)-3-(2-(2-tert-butylphenoxy)pyridine-3-yl)urea (200 mg, 0.343 mmol) in MeOH (5 ml) was added 10% Pd/C (20 mg, 10%). The reaction mixture was stirred at rt under H$_2$ for 16 h. The mixture was filtered and washed with MeOH (10 mL). The solvent was evaporated under reduced pressure and striped with toluene to afford 222a (160 mg, 95%) as a off-white powder. LC-MS ESI 493 [M+H]$^+$.

222b. 1-(2-(2-tert-butylphenoxy)pyridine-3-yl)-3-(2-fluoro-4-((1-isobutylpiperidin-4-yl)methoxy)phenyl)urea: To a solution of the product of 222a (100 mg, 0.203 mmol) in MeOH (2 ml) was add NaBH$_4$CN (28 mg, 0.44 mmol), conc. HCl (10 µL), follow by isobutyraldehyde (32 µL, 0.507 mmol). The reaction mixture was stirred at rt for 16 h. The solvent was evaporated under reduced pressure and suspended in EtOAc. It was filtered and washed with H$_2$O. The filter cake was re-dissolved in MeOH and treated with 1 eq. of TFA. The MeOH was evaporated and pump to dryness to afford Example 222 (72 mg, 65%). LC-MS ESI 549 [M+H]$^+$.

Example 223 listed in Table 2 below was prepared similarly as described for Example 222. Example 224-231 listed in Table 2 below and Example 233 listed in Table 3 below were prepared similarly as described for Examples 1-4. Example 232 listed in Table 3 was prepared similarly as described for Examples 56-63.

Example 234

1-(2-(1,2,3,4-tetrahydroquinolin-8-yloxy)pyridin-3-yl)-3-(4-(trifluoromethoxy)phenyl)urea 234a. (8-hydroxy-3,4-dihydroquinolin-1(2H)-yl)(phenyl)methanone: A mixture of 1,2,3,4-tetrahydroquinolin-8-ol (250 mg, 1.68 mmol), diisopropylethyl-amine (594 µL, 3.36 mmol) and benzoyl chloride (388 µL, 3.36 mmol) in DCM (5 mL) was stirred at rt for 3 h. The mixture was evaporated and diluted with THF (5 mL). A solution of lithium hydroxide monohydrate (830 mg, 16.8 mmol) in water (2 mL) was added and mixture was stirred for 18 h. The mixture was dissolved in EtOAc, washed with water, dried (MgSO$_4$), filtered and evaporated to give the crude 234a (425 mg). (M+H)$^+$=254.

234b. (8-(3-nitropyridin-2-yloxy)-3,4-dihydroquinolin-1(2H)-yl)(phenyl)methanone: A mixture of 1-benzoyl-3-[2-(2-tert-butyl-phenoxy)-pyridin-3-yl]-thiourea (425 mg, 1.68 mmol), 2-chloro-2-nitropyridine (303 mg, 1.91 mmol) and cesium carbonate (622 mg, 1.91 mmol) in DMF (5 mL) was stirred at rt for 18 h. Water (25 mL) was added and mixture was stirred for 1 h. The solid formed was isolated by filtration and dried in vacuo to yield 234b (630 mg). (M+H)$^+$=376.

234c. (8-(3-aminopyridin-2-yloxy)-3,4-dihydroquinolin-1(2H)-yl)(phenyl)-methanone: A mixture of 234b (500 mg, 1.33 mmol), 5% Palladium on charcoal (50 mg) in ethyl acetate (20 mL) was stirred at rt for 18 h under 1 atm of hydrogen. The solution was filtered over a pad of Celite™ and evaporated in vacuo to afford 234c (460 mg). (M+H)+=346.

234d. 1-(2-(1-benzoyl-1,2,3,4-tetrahydroquinolin-8-yloxy)pyridin-3-yl)-3-(4-(trifluoromethoxy)phenyl)urea: A mixture of 234c (500 mg, 1.33 mmol), 1-isocyanato-4-(trifluoromethoxy)benzene (200 µL, 1.33 mmol) in DMF (5 mL) was stirred at rt for 24 h. The solution was directly purified using preparative HPLC to afford 234d (320 mg). (M+H)+=549.

Example 234: 234d (227 mg, 0.41 mmol) was diluted in THF (10 mL) and cooled to −78° C. Butyllithium (1.6 M/hexanes, 2.48 mmol) was added and the reaction mixture was stirred for 2 h. A saturated solution of ammonium chloride was added, the solution was warmed to rt and extracted twice using ethyl acetate. Organic phase were combined, dried using $MgSO_4$ and evaporated. 180 mg of crude material was obtained from which 30 mg was directly purified using preparative HPLC to afford Example 234 as a TFA salt (6.5 mg). (M+H)+=445. $^1$H NMR (400 MHz, DMSO $d_6$) δ ppm 1.80 (m, 2H), 2.73 (t broad, J=6.32 Hz, 2H), 3.17 (m, 2H), 6.44 (t, J=7.83 Hz, 1H), 6.70 (d, J=8.09 Hz, 1H), 6.77 (d, J=6.57 Hz, 1H), 7.01 (dd, J=7.83, 4.80 Hz, 1H), 7.30 (d, J=8.59 Hz, 2H), 7.56 (d, J=9.09 Hz, 2H), 7.64 (dd, J=4.80, 1.77, 1H), 8.46 (dd, J=7.83, 1.51 Hz, 1H), 8.62 (s, 1H), 9.61 (s, 1H).

Example 235

1-(2-(1-methyl-1,2,3,4-tetrahydroquinolin-8-yloxy) pyridin-3-yl)-3-(4-(trifluoromethoxy)phenyl)urea A mixture of Example 234 (140 mg, 0.32 mmol), cesium carbonate (104 mg, 0.32 mmol) and methyliodide (20 µL, 0.32 mmol) in acetone (10 mL) was stirred for 18 h. The solution was directly purified using preparative HPLC to afford Example 235 as a TFA salt (7 mg). (M+H)+=459. $^1$H NMR (400 MHz, DMSO $d_6$) δ ppm 1.78 (m, 2H), 2.75 (m, 2H), 2.79 (s, 3H), 2.99 (m, 2H), 6.78 (m, 2H), 6.88 (m, 1H), 7.03 (dd, J=7.83, 5.05 Hz, 1H), 7.30 (d, J=8.84 Hz, 2H), 7.56 (d, J=8.84 Hz, 2H), 7.64 (d, J=6.06 Hz, 1H), 8.52 (d, J=8.09 Hz, 1H), 8.74 (s, 1H), 9.58 (s, 1H).

Example 236

1-(2-(3,3-dimethylindolin-4-yloxy)pyridin-3-yl)-3-(4-(trifluoromethoxy)phenyl)urea 236a. 4-bromoindolin-2-one: A mixture of 4-bromoindoline-2,3-dione (5 g, 22.12 mmol) and hydrazine hydrate (22 mL) was heated at 80° C. for 18 h. The mixture was cooled down to rt and diluted with water. The solid formed was isolated by filtration, washed with water and dried in vacuo to give 236a (3.65 g). (M+H)+=214.

236b. 4-bromo-3,3-dimethylindolin-2-one: A mixture of 236a (3.65 g, 17.2 mmol) was diluted in THF (100 mL) and cooled to −78° C. Lithium hexamethyldisilazane (1.0 M/THF, 64.5 mL) and iodomethane (2.68 mL, 43 mmol) were added. The reaction mixture was warmed to rt and stirred for 3 h. A saturated solution of ammonium chloride was added and extracted twice using ethyl acetate. Organic phases were combined, dried using $MgSO_4$ and evaporated. The crude material was purified using flash chromatography (silica, 25-50% EtOAc/hexane gradient) to afford 236b (0.93 g). (M+H)+=240.

236c. 4-hydroxy-3,3-dimethylindolin-2-one: 236b (930 mg, 3.87 mmol) was diluted in THF (20 mL) and cooled to −78° C. Methyllithium (1.6 M/Et$_2$O, 3.87 mmol) was added followed by the addition of tert-butyllithium (1.7M/pentane, 7.74 mmol) and the reaction mixture was stirred for 15 min. Triisopropylborate (893 µL, 3.87 mmol) was added and the reaction mixture was stirred for 2 h. Peracetic acid was added (32% wt/acetic acid, 919 µL, 3.87 mmol) and reaction mixture was stirred for 2 h. A solution of sodium thiosulfate (1 M) was then added and the mixture was stirred for 30 min, a solution of sodium hydroxide (1 M) was added and the aqueous phase was washed twice using ethyl acetate. The organic phase was acidified using 4N HCl and extracted twice using ethyl acetate. The organic phase were combined, dried using $MgSO_4$ and evaporated to afford 236c (54 mg). (M+H)+=178.

236d. 3,3-dimethyl-4-(3-nitropyridin-2-yloxy)indolin-2-one: A mixture of 236c (54 mg, 0.30 mmol), 2-chloro-2-nitropyridine (72 mg, 0.46 mmol) and cesium carbonate (150 mg, 0.46 mmol) in DMF (4 mL) was stirred at rt for 2 h. The solution was filtered and directly purified using preparative HPLC to afford a crude product directly used in the next step. (M+H)+=300.

236e. 4-(3-aminopyridin-2-yloxy)-3,3-dimethylindolin-2-one: A mixture of crude 236e (50 mg), Zinc (75 mg) and ammonium chloride (50 mg) in EtOH (4 mL) and ethyl acetate (4 mL) was heated to reflux for 18 h. The solution was cooled to rt, filtered over Celite™ and directly used in the next step. (M+H)+=270.

236f. 1-(2-(3,3-dimethyl-2-oxoindolin-4-yloxy)pyridin-3-yl)-3-(4-(trifluoromethoxy)phenyl)urea: A crude mixture of 236e (81 mg, 0.3 mmol), 1-isocyanato-4-(trifluoromethoxy)benzene (68 µL, 0.45 mmol) in DMF (2 mL) was stirred at rt for 18 h. The solution was directly purified using preparative HPLC to afford 236f as a TFA salt (30 mg). (M+H)+=473.

Example 236: 236f (10 mg, 0.02 mmol) was diluted in THF at rt and lithium aluminium hydride (20 mg) was added and the mixture was stirred at rt for 4 h. Sodium sulfate decahydrate was added and solution was stirred for 30 min and filtered over Celite™. The solution was evaporated and directly purified using preparative HPLC to afford Example 236 as a TFA salt (3 mg). (M+H)+=459. $^1$H NMR (400 MHz, DMSO $d_6$) δ ppm 1.18 (s, 6H), 3.18 (s, 2H), 6.31 (m, 1H), 6.46 (m, 1H), 7.00 (m, 1H), 7.03 (dd, J=8.08, 4.80 Hz, 1H), 7.30 (d, J=9.10 Hz, 2H), 7.56 (d, J=9.09 Hz, 2H), 7.66 (dd, J=4.80, 1.52 Hz, 1H), 8.52 (dd, J=9.35, 1.52 Hz, 1H), 8.66 (s, 1H), 9.62 (s, 1H).

Example 237

1-(2-(3-tert-butyl-1-methyl-2-oxoindolin-4-yloxy) pyridin-3-yl)-3-(4-(trifluoromethoxy)phenyl)urea Example 237 was prepared using similar procedures as described in Example 236. (M+H)+=515.

Example 238

1-(2-(2-benzyl-1,2,3,4-tetrahydroisoquinolin-5-yloxy)pyridin-3-yl)-3-(4-(trifluoromethoxy)phenyl) urea 238a. 5-amino-3,4-dihydroisoquinolin-2(1H)-yl)(phenyl) methanone: A mixture of 1,2,3,4-tetrahydroisoquinolin-5-amine (5 g, 33.7 mmol), diisopropylethylamine (6.55 mL, 37 mmol) and benzoyl chloride (3.92 mL, 33.7 mmol) in DCM (50 mL) was stirred at r.t. for 18 h. The mixture was dissolved in EtOAc, washed with a saturated solution of sodium bicarbonate, dried (MgSO$_4$), filtered and evaporated to give the crude 238a (6.74 g containing 36% of N-(2-benzoyl-1,2,3,4-tetrahydroisoquinolin-5-yl)benzamide). (M+H)+=253.

238b. (5-hydroxy-3,4-dihydroisoquinolin-2(1H)-yl)(phenyl)methanone: A mixture of 238a (1.85 g, 7.33 mmol) was suspended in water (20 mL) and sulfuric acid (5 mL) and was stirred at 0° C. A solution of sodium nitrite (1.01 g, 14.66 mmol) in water (10 mL) was added dropwise. The reaction mixture was stirred at 0° C. for 1 h and heated at 60° C. for 1 h. The reaction mixture was extracted twice using ethyl acetate. Organic phases were combined, dried (MgSO$_4$) and evaporated in vacuo. Crude material was purified using flash chromatography (50 to 100% ethyl acetate/hexanes) to yield 238b (650 mg). (M+H)$^+$=254.

238c. (5-(3-nitropyridin-2-yloxy)-3,4-dihydroisoquinolin-2(1H)-yl)(phenyl)methanone: A mixture of 238b (650 mg, 2.57 mmol), 2-chloro-2-nitropyridine (407 mg, 2.57 mmol) and cesium carbonate (837 mg, 2.57 mmol) in DMF (15 mL) was stirred at r.t. for 18 h. Water was added and mixture was extracted twice using ethyl acetate. Organic phases were combined, dried (MgSO$_4$) and evaporated in vacuo to yield the crude 238c still containing DMF, which was directly used in the next step. (M+H)$^+$=376.

238d. (5-(3-aminopyridin-2-yloxy)-3,4-dihydroisoquinolin-2(1H)-yl)(phenyl)-methanone: A mixture of 238c (965 mg, 2.57 mmol), zinc (840 mg, 12.9 mmol) and ammonium chloride (687 mg, 12.9 mmol) in ethanol (20 mL) was heated to reflux for 2 h. The solution was filtered over a pad of Celite™ and evaporated in vacuo. Crude material was purified using flash chromatography (25 to 50% ethyl acetate/hexanes) to yield the crude 238d still containing DMF. (M+H)$^+$=346.

238e. 1-(2-(2-benzoyl-1,2,3,4-tetrahydroisoquinolin-5-yloxy)pyridin-3-yl)-3-(4-(trifluoromethoxy)phenyl)urea: A mixture of 238d (443 mg, 1.29 mmol), 1-isocyanato-4-(trifluoromethoxy)benzene (292 µL, 1.94 mmol) in DMF (10 mL) was stirred at rt for 18 h. Water was added and the solid formed was isolated by filtration (660 mg). (M+H)$^+$=549.

238f. 1-(2-(1,2,3,4-tetrahydroisoquinolin-5-yloxy)pyridin-3-yl)-3-(4-(trifluoromethoxy)phenyl)urea: 238e (660 mg, 1.2 mmol) was diluted in THF (10 mL) and cooled to −78° C. Butyllithium (1.6 M/hexanes, 6 mmol) is added and the reaction mixture is stirred for 15 min. A saturated solution of ammonium chloride is added, the solution is warmed to rt and extracted twice using ethyl acetate. Organic phases were combined, dried using MgSO$_4$ and evaporated. Crude material was directly purified using preparative HPLC to afford 238f as 2 TFA salt (100 mg). (M+H)$^+$=445.

Example 238: A mixture of 238f (40 mg, 0.06 mmol), benzyl bromide (7 µL, 0.06 mmol) and cesium carbonate (58 mg, 0.18 mmol) in acetone (2 mL) was stirred at rt for 18 h. Crude mixture was directly purified using preparative HPLC to afford Example 238 as a TFA salt (23 mg). (M+H)$^+$=535. $^1$H NMR (400 MHz, DMSO-D6) δ ppm 2.87-2.98 (m, 1H), 3.24-3.35 (m, 1H), 3.59-3.70 (m, 1H), 4.37-4.48 (m, J=17.43 Hz, 4H), 7.09 (dd, J=7.96, 4.93 Hz, 1H), 7.16 (t, J=7.07 Hz, 2H), 7.31 (d, J=8.59 Hz, 2H), 7.35 (t, J=7.83 Hz, 1H), 7.47-7.54 (m, 5H), 7.56 (d, J=9.09 Hz, 2H), 7.63 (dd, J=4.80, 1.77 Hz, 1H), 8.53 (dd, J=7.96, 1.64 Hz, 1H), 8.77 (s, 1H), 9.54 (s, 1H), 10.20 (s, 1H).

Example 239

1-(2-(1,2,3,4-tetrahydroquinolin-5-yloxy)pyridin-3-yl)-3-(4-(trifluoromethoxy)phenyl)urea 239a. 1-benzoyl-1,2,3,4-tetrahydroquinolin-5-yl benzoate: A mixture of quinolin-5-ol (540 mg, 3.72 mmol), 10% palladium on charcoal (Degussa 50% wet, 100 mg) were diluted in ethyl acetate and hydrogenated at 1 atm for 18 h. Mixture was filtered over Celite™ and evaporated in vacuo. The crude material was diluted in dichloromethane. Benzoyl chloride (906 µL, 7.8 mmol) and diisopropylethylamine (1.97 mL, 11.2 mmol) were added and mixture was stirred at rt for 3 h. The mixture was dissolved in EtOAc, washed with a saturated solution of ammonium chloride and a 1N HCl solution, dried (MgSO$_4$), filtered and evaporated to afford the crude 239a (1.31 g). (M+H)$^+$=358.

239b. (5-hydroxy-3,4-dihydroquinolin-1(2H)-yl)(phenyl) methanone: 239a (1.31 g, 3.66 mmol) was diluted in THF (20 mL). A solution of lithium hydroxide monohydrate (769 mg, 18.3 mmol) in water (10 mL) was added and mixture was stirred for 18 h. The mixture was dissolved in EtOAc, washed with a saturated solution of sodium bicarbonate, dried (MgSO$_4$), filtered and evaporated to afford the crude 239b (560 mg). (M+H)$^+$=254.

239c. (5-(3-nitropyridin-2-yloxy)-3,4-dihydroquinolin-1(2H)-yl)(phenyl)methanone: A mixture of 239b (560 mg, 2.21 mmol), 2-chloro-2-nitropyridine (525 mg, 3.31 mmol) and cesium carbonate (1.08 g, 3.31 mmol) in DMF (10 mL) was stirred at rt for 18 h. Water (25 mL) was added and mixture was extracted twice using ethyl acetate. The organic phases was dried (MgSO$_4$), filtered and evaporated to afford the crude 239c (800 mg). (M+H)$^+$=376.

239d. (5-(3-aminopyridin-2-yloxy)-3,4-dihydroquinolin-1(2H)-yl)(phenyl)methanone: A mixture of 239c (800 mg, 2.13 mmol), zinc (697 mg, 10.7 mmol) and ammonium chloride (572 mg, 10.7 mmol) in ethanol (20 mL) was heated to reflux for 24 h. The solution was filtered over a pad of Celite™ and evaporated in vacuo to afford the crude 239d. The crude material was directly used in the next step. (M+H)$^+$=346.

239e. 1-(2-(1-benzoyl-1,2,3,4-tetrahydroquinolin-5-yloxy)pyridin-3-yl)-3-(4-(trifluoromethoxy)phenyl)urea: A mixture of 239d (400 mg, 1.13 mmol), 1-isocyanato-4-(trifluoromethoxy)benzene (256 µL, 1.7 mmol) in DMF (5 mL) was stirred at rt for 3 h. The solution was directly purified using preparative HPLC to afford 239e as a TFA salt (272 mg). (M+H)$^+$=549.

Example 239: 239e (246 mg, 0.38 mmol) was diluted in THF (10 mL) and cooled to −78° C. Butyllithium (1.6 M/hexanes, 2.28 mmol) was added and the reaction mixture was stirred for 2 h. A saturated solution of ammonium chloride was added. The solution was warmed to rt and extracted twice using ethyl acetate. Organic phase were combined, dried (MgSO$_4$) and evaporated. The crude material was directly purified using preparative HPLC to afford Example 239 as a TFA salt (100 mg). (M+H)$^+$=445. $^1$H NMR (400 MHz, DMSO-D6) δ ppm 1.68-1.78 (m, 2H), 2.40 (t, J=6.06 Hz, 3H), 3.09-3.18 (m, 2H), 6.29-6.38 (m, 1H), 6.40-6.50 (m, 1H), 6.91-6.99 (m, 1H), 7.03 (dd, J=7.83, 4.80 Hz, 1H), 7.30 (d, J=9.09 Hz, 2H), 7.55 (d, J=9.09 Hz, 2H), 7.63 (dd, J=4.80, 1.52 Hz, 1H), 8.51 (d, J=8.08 Hz, 1H), 8.73 (s, 1H), 9.54 (s, 1H).

Example 240

1-(2-(3,4-dihydro-2H-benzo[b][1,4]oxazin-5-yloxy)pyridin-3-yl)-3-(4-(trifluoromethoxy)phenyl)urea Example 240 was prepared using similar procedures as described for Example 239. (M+H)$^+$=447.

Example 241

1-(3-(2-tert-butylphenoxy)pyridazin-4-yl)-3-(4-(trifluoromethoxy)-phenyl)urea 241a. 3-(2-tert-butylphenoxy)-6-chloropyridazine: In a pressure tube at rt was combined a solution of 3,6-dichloropyridazine (3.0 g, 20.3 mmol), 2-tert-butylphenol (3.09 g, 2.06 mmol), potassium carbonate (2.94 g, 22.2 mmol) and (dioxane (10 mL). Reaction vessel was fitted with a stir bar, degassed with nitrogen for 5 min, sealed and heated at 130° C. overnight (~18 h). The reaction mixture was extracted with ethyl acetate and washed twice with 1N NaOH. The aqueous washings were back extracted once with ethyl acetate. The combined organic extracts were dried over $MgSO_4$, filtered and concentrated. Purification by flash chromatography (120 g ISCO silica gel column, 0-15% ethyl acetate/hexane, 30 min. gradient, 10 min. hold at 15%, 50 ml/min) provided 241a as a white solid (0.73 g). $[M+H]^+$=263.2, 265.3 chlorine isotopes.

241b. 3-(2-tert-butyl-6-chlorophenoxy)-4,6-dichloropyridazine: 241a (0.73 g, 2.8 mmol) was taken up in $POCl_3$ (5 mL). An exotherm was noted by significant heating of the flask. The reaction was cooled to rt and chlorine gas was bubbled through the reaction mixture for 3 h. Solvents were removed under vacuum. The residue was taken up in dichloromethane (15 mL) and water was added dropwise with vigorous stirring. Extract in to EtOAc (100 mL) and wash once with water and twice with brine. Dry organics over $MgSO_4$, filter and concentrate. Purify by flash chromatography (40 g ISCO silica gel cartridge, 0% then 10% ethyl acetate/hexane) gave 241b (380 mg). $[M+H]^+$=331.1, 333.2 chlorine isotopic pattern.

241c. 4-azido-3-(2-tert-butyl-6-chlorophenoxy)-6-chloropyridazine: To a solution of 241b (380 mg, 1.14 mmol) in DMF (4 ml) at rt was added sodium azide (148 mg, 2.28 mmol). The reaction was heated to 80° C. for 30 min. Extract into ethyl acetate (50 mL) and wash once with brine. Dry organics over $MgSO_4$, filter and concentrate. Purification by flash chromatography (40 g ISCO silica gel cartridge, 0-15% ethyl acetate/hexane, 40 min. gradient, 10 min hold, 30 mL/min) provided 241c (360 mg). $[M+H]^+$=338.1.

Example 241: To a solution of 241c (330 mg, 0.98 mmol) in THF:MeOH (10 ml, 1:2) at rt was added $iPr_2Net$ (1 mL) and 5% Pd/C (50 mg). With vigorous stirring the vessel was carefully evacuated with a vacuum until mild bubbling of solvent was observed. The reaction vessel was then filled with hydrogen gas (1 atm) and the reaction was stirred at rt for ~4 h. The reaction was filtered through celite and the pad was washed with THF:MeOH (10 ml, 1:2) to provide an inseparable mixture of 3-(2-tert-butylphenoxy)pyridazin-4-amine and 3-(2-tert-butyl-6-chlorophenoxy)pyridazin-4-amine. Solvent was removed to dryness and the residue was taken up in dichloromethane (3 mL) and 4-tert-butylphenylisocyanate (250 mg) was added and the reaction was stirred at rt for 3 h. Hexane (3 mL) was added and the mixture was loaded to silica gel for purification by flash chromatography (40 g AnaLogix RS-40 silica gel cartridge, 20%-50% ethyl acetate/hexane, 40 min gradient, 10 min. hold, 30 mL/min) to provide Example 241 (47 mg)-$[M+H]^+$=419, $^1$H NMR (400 MHz, $CD_3OD$) δ ppm 1.31 (s, 9H), 1.40 (s, 9H), 6.97 (dd, J=7.48, 1.76, 1H), 7.23 (m, 2H), 7.38 (dd, J=17.16, 8.80 Hz, 4H), 7.51 (dd, J=7.48, 1.76 Hz, 1H), 8.48 (d, J=5.72, 1H), 8.65 (d, J=5.72, 1H)— and 1-(3-(2-tert-butyl-6-chlorophenoxy)pyridazin-4-yl)-3-(4-(trifluoromethoxy)phenyl)urea (70 mg)-$[M+H]^+$=453.2 & 455.2, $^1$H NMR (400 MHz, $CD_3OD$) δ ppm 1.28 (s, 9H), 1.35 (s, 9H), 6.97 (d, J=8.8, 1H), 7.18 (dd, J=8.8, 2.64 Hz, 1H), 7.34 (m, 4H), 7.42 (d, J=2.64 Hz, 1H), 8.44 (d, J=5.72, 1H), 8.60 (d, J=5.72, 1H).

Examples 242-262 listed in Table 5 were prepared similarly as previously described for Examples 1-4. Examples 263-275 listed in Table 6 were prepared similarly according to the previously described experimental procedures.

Example 276

(E)-1-(2-(4-fluorostyryl)phenyl)-3-(4-(trifluoromethoxy)phenyl)urea 276a. 1-(2-bromophenyl)-3-(4-(trifluoromethoxy)phenyl)urea: A mixture of 2-bromobenzenamine (2.75 g, 16.7 mmol) and 1-isocyanato-4-(trifluoromethoxy)benzene (3.25 g, 16.7 mmol) in DMF (32 mL) was stirred at 23° C. for 5 days. The solution was concentrated in vacuo and the residue was purified by flash chromatography (Biotage™, silica, 25% Hexanes/methylene chloride gradient) to provide 5.05 g (84%) of 276a as an grey solid. $(M+H)^+$=376.

Example 276: A 1 dram vial with a Teflon™ cap was evacuated and backfilled with argon. The flask was charged with 276a (30 mg, 0.08 mmol), (E)-4-fluorostyrylboronic acid (16 mg, 0.095 mmol), degassed DME (1 mL), degassed 2M $Na_2CO_3$ (80 μL, 0.16 mmol), $Pd(PPh_3)_4$ (4.5 mg, 0.004 mmol) and the mixture was heated at 90° C. for 30 h. The mixture was cooled to room temperature, filtered through a 0.45 μm PTFE filter with glass microfiber and concentrated in vacuo. The residue was purified by preparative HPLC (solvent A: 10% acetonitrile-90% water+0.1% TFA; solvent B: 90% acetonitrile-10% water+0.1% TFA, with 20% B to 100% in 7 min gradient. Column: YMC Pack C-18 20×100 mm. Flow rate=20 mL/min) to yield 4 mg (12%) of Example 276. $(M+H)^+$=417.

Examples 277-279 listed in Table 6 were prepared using similar methods as described in Example 276.

Examples 280-364 and Examples 367-412 listed in Table 1 were prepared similarly as previously described for Examples 1-4.

Example 365

1-(2-(2-bromopyridin-3-yloxy)pyridin-3-yl)-3-(4-(trifluoromethoxy)phenyl)urea 365a. 2-bromo-3-(3-nitropyridin-2-yloxy)pyridine: A mixture of 2-fluoro-3-nitropyridine (2.7 g, 19.0 mmol), 2-bromo-3-hydroxypyridine (3.4 g, 19.5 mmol) and potassium carbonate (4.3 g, 32 mmol) in dioxane (20 mL) in a pressure vessel fitted with a stir bar was heated to 100° C. overnight (~16 h). The reaction was cooled to rt and mixture was transferred to a separatory funnel with ethyl acetate (150 mL). The organic extract was washed twice with sat'd $NaHCO_3$ (~150 mL) and the washings were back extracted once with ethyl acetate. The combined organic extracts were dried over $MgSO_4$, filtered and concentrated to give a yellow solid. Triturate with ethyl acetate and then add small portion of hexane. Collect solid and rinse with small portion of 50% ethyl acetate in hexane to give 365a (4.8 g). $(M+H)^+$=298.0.

365b. 2-(2-bromopyridin-3-yloxy)pyridin-3-amine: Under nitrogen 365a (4.66 g, 15.6 mmol) was taken up in methanol (50 mL) and acetic acid (15 mL). Powdered iron (6.4 g) and a large stir bar was added. The reaction vessel was fitted with a reflux condenser and the reaction was then heated to 80° C. for 2 h. The reaction was cooled to rt, filtered through a pad of Celite and the pad was liberally washed with methanol. Solvent was removed under vacuum. The residue was taken up in dichloromethane, solids were removed and rinsed with a minimum of dichloromethane and solids were discarded. Solvent was removed under vacuum. Residue was taken up in ethyl acetate and washed twice with water. Aqueous washings were back extracted once with ethyl acetate. The combined organics were dried over MgSO$_4$, filtered and concentrated to give 365b (4.2 g). (M+H)$^+$=266 & 268, bromine isotopic pattern.

365c. 1-(2-(2-bromopyridin-3-yloxy)pyridin-3-yl)-3-(4-(trifluoromethoxy)-phenyl)urea: To a solution of 365b (496 mg, 1.86 mmol) in dichloromethane (3 mL) at rt was added 4-trifluoromethoxyphenyl isocyanate (416 mg, 2.05 mmol). The reaction was stirred at rt overnight. The reaction was diluted with hexane (~3 mL) and the mixture was loaded to a silica gel cartridge for flash chromatography (40 g Analogix, 0-40% ethyl acetate in hexane gradient over 35 min, 5 min. hold, 40 mL/min) to provide 365c (656 mg). (M+H)$^+$=469 & 471, bromine isotopic pattern.

Example 365: A mixture of 365c (70 mg, 0.150 mmol), cyclopentenylboronic acid (21 mg, 0.185 mmol), sodium carbonate (60 mg), toluene (1 mL), methanol (0.25 mL) and water (0.05 mL) was degassed with nitrogen for 10 minutes. Pd(PPh$_3$)$_4$ (5 mg) was added and the reaction was degassed with nitrogen for an additional 5 min. The reaction was capped and heated at 80° C. overnight. Ethyl acetate was added (2 mL), the reaction was filtered and concentrated. Purification by prep. HPLC (28 mm×100 mm C18, 20-100% B solvent, 10 min grad, 2 min hold, 25 ml/min., A solvent=10% MeOH/Water+0.1% TFA, B solvent=90% MeOH/Water+0.1% TFA) provided the title compound (~10 mg). (M+H)$^+$=457.1.

Example 366

1-(2-(2-cyclopentylpyridin-3-yloxy)pyridin-3-yl)-3-(4-(trifluoromethoxy)phenyl)urea To a solution of Example 365 (~5 mg) in methanol (2 ml) was added 5% Pd/C. The vessel was evacuated with a mild vacuum until solvent bubbled gently. Hydrogen gas was then added and bubbled through solution for 5 min. The reaction was then stirred under hydrogen for 30 min. It was filtered through Celite and rinse THF:methanol (1:1, 2×10 ml). Solvent was removed. Purification by prep. HPLC (20 mm×100 mm C18, 20-100% B solvent, 10 min. grad, 2 min. hold, 20 ml/min., A solvent=10% MeOH/Water+0.1% TFA, B solvent=90% MeOH/Water+0.1% TFA) provided the title compound (4.5 mg). (M+H)$^+$=459.1.

Example 413

1-(4-Trifluoromethoxy-phenyl)-3-{2-[2,4,4-trimethyl-1-benzopyran-2-yl]-phenoxy}-pyridin-3-yl}-urea 413a. 2-[2,4,4-Trimethyl-1-benzopyran-2-yl]-phenol: A mixture of 2-(1-hydroxy-1-methyl-ethyl)-phenol (60 mg, 0.39 mmol) in 2,2,2-trifluoroethanol (3 ml) was treated with p-TsOH (1 mg) at rt and stirred 3 h at 30° C. The mixture was then treated with sodium acetate (2 mg) and the solvent was removed under reduced pressure. The residue was purified by flash chromatography on silica gel using a gradient of toluene in hexane (50 to 52%)) to give 42 mg (40% yield) of 413a as a white solid. (M−H)=267. $^1$H NMR (400 MHz, CDCl$_3$) δppm 1.19 (s, 3H), 1.45 (s, 3H), 1.72 (s, 3H), 2.10 (d, J=14.1 Hz, 1H), 2.60 (d, J=14.1 Hz, 1H), 6.82-6.86 (m, 2H), 6.94 (m, 1H), 6.98 (m, 1H), 7.12-7.18 (m, 2H), 7.26-7.30 (m, 2H), 8.15 (s(br), 1H).

413b. 3-Nitro-2-[2-(2,4,4-trimethyl-1-benzopyran-2-yl)-phenoxy]-pyridine: 413b was prepared from 413a and 2-chloro-3-nitro pyridine according to the procedure described for Example 2a. (M+H)$^+$=391. $^1$H NMR (400 MHz, CDCl$_3$) δppm 0.85 (s, 3H), 1.32 (s, 3H), 1.64 (s, 3H), 2.11 (d, J=14.1 Hz, 1H), 2.94 (d, J=14.1 Hz, 1H), 6.90 (m, 1H), 7.11-7.13 (m, 2H), 7.15-7.18 (m, 2H), 7.20-7.26 (m, 3H), 7.57 (m, 1H), 8.40-8.44 (m 2H).

413c. 2-[2-(2,4,4-Trimethyl-1-benzopyran-2-yl)-phenoxy]-pyridin-3-ylamine: A mixture of 413b (49 mg, 0.12 mmol) in ethyl acetate (5.1 ml) was treated with 10% Pd/C (10 mg) and stirred 17 h at 35° C. under H$_2$ (1 atm). The mixture was retreated with 10% Pd/C (10 mg) and stirred 1 h at 40° C. under H$_2$ (1 atm). The mixture was filtered through a glass microfiber paper and the filtrate was concentrated under vacuum to give 35 mg (100% yield) of 413c. (M+H)$^+$=361. $^1$H NMR (400 MHz, CDCl$_3$) δppm 0.87 (s, 3H), 1.28 (s, 3H), 1.75 (s, 3H), 2.12 (d, J=14.2 Hz, 1H), 2.82 (d, J=14.2 Hz, 1H) 3.92 (s (br), 2H), 6.87-6.92 (m, 3H), 6.99-7.08 (m, 2H), 7.10 (m, 1H), 7.13-7.20 (m, 3H), 7.50 (m, 1H), 7.62 (m, 1H).

Example 413: Prepared from 413c and p-trifluoromethoxyphenyl isocyanate according to the procedure described for Example 2. (M+H)$^+$=564. $^1$H NMR (400 MHz, CDCl$_3$) δppm 0.88 (s, 3H), 1.26 (s, 3H), 1.68 (s, 3H), 2.03 (d, J=14.2 Hz, 1H), 2.53 (d, J=14.2 Hz, 1H), 6.55 (s(br), 1H), 6.90-6.97 (m, 3H), 7.05-7.26 (m, 8H), 7.37-7.39 (m, 2H), 7.53 (m, 1H), 7.87 (m, 1H), 8.53 (m, 1H).

Example 414

1-(2-(2-(2-methyl-1,3-dioxolan-2-yl)phenoxy)pyridin-3-yl)-3-(4-(trifluoromethoxy)phenyl)urea 1-(2-(2-acetylphenoxy)pyridin-3-yl)-3-(4-(trifluoromethoxy)phenyl)urea (25 mg, 0.057 mmol) was placed in 600 μL of ethylene glycol then triethylorthoformate (11 μL, 0.64 mmol) followed by tetrabutylammonium tribromide (3 mg, 0.0057 mmol) and the mixture was heated at 95° C. for 5 h. The reaction mixture was cooled to 23° C. methanol was added and purified by preparative HPLC (solvent A: 10% acetonitrile-90% water+0.05% NH$_4$OAc; solvent B: 90% acetonitrile-10% water+0.05% NH$_4$OAc, with 20% B to 100% in 7 minute gradient. Column: YMC Pack C-18 20×100 mm. Flow rate=20 mL/min.) giving 10 mg (38%) of Example 414. (M+H)$^+$=476. $^1$H NMR (400 MHz, DMSO-D$_6$) δ ppm 1.67 (3H, s), 3.52 (2H, t, J=6.82 Hz), 3.70-3.76 (2H, m), 6.99 (1H, dd, J=7.83, 4.80 Hz), 7.14 (1H, dd, J=8.08, 1.01 Hz), 7.25 (1H, td, J=7.52, 1.14 Hz), 7.30 (2H, d, J=8.59 Hz), 7.39 (1H, td, J=7.64, 1.64 Hz), 7.53 (1H, dd, J=7.71, 1.64 Hz), 7.56 (2H, d), 7.59 (1H, dd, J=4.80, 1.77 Hz), 8.50 (1H, dd, J=7.83, 1.77 Hz), 8.61 (1H, s), 9.64 (1H, s).

Example 415 and Example 416

1-(2-(3-(2-(1H-tetrazol-1-yl)propan-2-yl)phenoxy)pyridin-3-yl)-3-(4-(trifluoromethoxy)phenyl)urea and 1-(2-(3-(prop-1-en-2-yl)phenoxy)pyridin-3-yl)-3-(4-(trifluoromethoxy)-phenyl)urea 1-(2-(3-(2-hydroxypropan-2-yl)phenoxy)pyridin-3-yl)-3-(4-trifluoromethoxy)phenyl)urea (Example 418) (37 mg, 0.083 mmol) and di-tert-butyl diethylphosphoramidite (27 μL, 0.083 mmol) were placed in 1 mL of THF and the tetrazole was added (17 mg, 0.248 mmol). Since the reaction didn't proceed, the mixture was heated at 60° C. for 16 h. Then the reaction mixture was cooled to −40° C. and the m-CPBA (36 mg, 0.218 mmol) was added and stirred for 16 h at 23° C. An aqueous solution of 10% sodium hydrogensulfite (2 mL) was added and stirred for 10 min. Ethyl acetate was added, layers were separated. The organic layer was washed with an aqueous solution of 10% sodium hydrogensulfite, 0.5 N of sodium hydroxide, dried over $Na_2SO_4$, filtered and concentrated in vacuo. The residue was purified by preparative HPLC (solvent A: 10% acetonitrile-90% water+ 0.1% TFA; solvent B: 90% acetonitrile-10% water+0.1% TFA, with 20% B to 100% in 7 minute gradient. Column: YMC Pack C-18 20×100 mm. Flow rate=20 mL/min.) affording 8 mg (16%) of Example 415 and 5 mg (11%) of Example 416. Example 415: (M−H)+=498. $^1$H NMR (400 MHz, DMSO-D6) δ ppm 2.13 (6H, s), 6.84-6.87 (1H, m), 6.92 (1H, t, J=2.02 Hz), 7.08-7.11 (2H, m, J=5.05, 5.05, 2.78 Hz), 7.30 (2H, d, J=8.59 Hz), 7.38 (1H, t, J=8.08 Hz), 7.52-7.56 (2H, m), 7.67 (1H, dd, J=4.67, 1.64 Hz), 8.53 (1H, dd, J=7.96, 1.64 Hz), 8.68 (1H, s), 9.03 (1H, s), 9.50 (1H, s). Example 416: (M+H)+=430. $^1$H NMR (400 MHz, DMSO-D6) δ ppm 2.10 (3H, s), 5.12-5.14 (1H, m, J=1.52 Hz), 5.47 (1H, s), 7.07-7.12 (2H, m), 7.28-7.33 (3H, m), 7.35-7.43 (2H, m), 7.51-7.59 (2H, m), 7.65-7.74 (1H, m), 8.54 (1H, dd, J=7.83, 1.77 Hz), 8.73 (1H, s), 9.55 (1H, s).

Example 417

1-(2-(2-(4-ethoxy-tetrahydro-2H-pyran-4-yl)phenoxy)pyridin-3-yl)-3-(4-(trifluoromethoxy)phenyl)urea 417a. 4-(2-hydroxyphenyl)-tetrahydro-2H-pyran-4-ol: At 0° C., a solution of n-butyllithium in hexanes (1.6M in hexanes, 4.95 mL, 7.9 mmol) was added to a solution of 2-bromophenol (0.4 mL, 3.45 mmol) in diethyl ether (10 mL). The mixture was warmed to rt and stirred for 2 h, after which it was cooled to −78° C. for the addition of tetrahydro-4H-pyran-4-one (448 uL, 1.3 mmol). The mixture was stirred at 0° C. for 2 h and a saturated solution of ammonium chloride (30 mL) was added. Ethyl acetate was added and the separated aqueous layer was extracted with ethyl acetate (3×50 mL). The combined organic layers were dried (anh. sodium sulfate), filtered and evaporated and the residue was purified by reverse phase HPLC. (M−H)=193.

417b. 2-(4-ethoxy-tetrahydro-2H-pyran-4-yl)phenol: p-Toluenesulphonic acid (10 mg, 0.05 mmol) was added to a solution of 417a (60 mg, 0.3 mmol) in ethanol (3 mL) at rt. The mixture was stirred at room temperature for 16 h, and a saturated solution of sodium bicarbonate was added. The solvent was evaporated under reduced pressure and the residue was extracted with dichloromethane (3×25 mL). The combined organic layers were dried (anh. sodium sulfate), filtered and evaporated and the residue was purified by reverse phase HPLC. (M−H)=222.

417c. 2-(2-(4-ethoxy-tetrahydro-2H-pyran-4-yl)phenoxy)pyridin-3-amine: 417c was prepared from 417b following the procedures for 2a and 2b. (M+H)=315.

Example 417: Prepared from 417c and p-trifluoromethoxyphenyl isocyanate according to the procedure described for Example 2. (M−H)=516. $^1$H NMR (400 MHz, DMSO-d6) δppm 0.79 (t, J=7.1 Hz, 3H), 2.12 (m, 4H), 3.08 (q, J=7.1 Hz, 2H), 3.61 (m, 4H), 7.05 (dd, J=8.1, 1.3 Hz, 1H), 7.06 (dd, J=8.1, 4.8 Hz, 1H), 7.32 (m, 4H), 7.51 (dd, J=7.8, 1.8 Hz, 1H), 7.58 (m, 4H), 7.67 (dd, J=4.8, 1.7 Hz, 1H), 8.51 (dd, J=8.0, 1.7 Hz), 8.60 (s, 1H), 9.58 (s, 1H).

Example 418

1-(2-(2-(3-hydroxypentan-3-yl)phenoxy)pyridin-3-yl)-3-(4-(trifluoromethoxy)phenyl)urea Example 418 was prepared using similar procedures as those described for Example 132. (M−H)+=474.

Examples 419-503 listed in Table 2 were prepared similarly according to the previously described experimental procedures for Example 86 and 46-52. Examples 504-580 in Table 3 were prepared similarly according to the procedures described for Examples 56-63 and 76-77.

Example 581

1-(6-cyano-2-(2-(2-ethoxypropan-2-yl)phenoxy)pyridin-3-yl)-3-(4-(trifluoromethoxy)phenyl)urea 581a. 2-(2-ethoxypropan-2-yl)phenol: Prepared from 2-(1-hydroxy-1-methyl-ethyl)phenol (J. Am. Chem. Soc. 1940, 62, 771), p-toluenesulphonic acid and ethanol according to the procedure described for 417b.

581b. 2-(2-(2-ethoxypropan-2-yl)phenoxy)pyridin-3-amine: Prepared from 581a following the procedures for 2a and 2b.

581c. 6-bromo-2-(2-(2-ethoxypropan-2-yl)phenoxy)pyridin-3-amine: Prepared using the method described in Scheme 5. (M-EtO)=305, 307.

581d. 5-amino-6-(2-(2-ethoxypropan-2-yl)phenoxy)picolinonitrile: Prepared using the method described in Scheme 5. (M−H)=296.

Example 581: Prepared from 581d and p-trifluoromethoxyphenyl isocyanate according to the procedure described for Example 2. (M−H)=499. $^1$H NMR (400 MHz, DMSO-d6) δppm 0.75 (t, J=7.0 Hz, 3H), 1.53 (s, 6H), 3.18 (q, J=7.0 Hz, 2H), 7.20 (dd, J=8.0, 1.2 Hz, 1H), 7.35 (m, 5H), 7.58 (m, 4H), 7.73 (d, J=8.3 Hz, 1H), 8.70 (d, J=8.3 Hz, 1H), 9.14 (s, 1H), 9.81 (s, 1H).

Example 582

1-(6-bromo-2-(2-(2-ethoxypropan-2-yl)phenoxy)pyridin-3-yl)-3-(4-(trifluoromethoxy)phenyl)urea Example 582 was prepared from 6-bromo-2-(2-(2-ethoxypropan-2-yl)phenoxy)pyridin-3-amine and p-trifluoromethoxyphenyl isocyanate according to the procedure described for Example 2. (M-EtO)=508, 510. $^1$H NMR (400 MHz, DMSO-d6) δppm 0.82 (t, J=7.0 Hz, 3H), 1.53 (s, 6H), 3.21 (q, J=7.0 Hz, 2H), 7.21 (dd, J=8.1, 1.3 Hz, 1H), 7.30 (m, 6H), 7.56 (m, 4H), 8.49 (d, J=8.4 Hz, 1H), 8.73 (s, 1H), 9.61 (s, 1H).

Examples 583-594 listed in Table 4 were prepared similarly as described for Examples 84-85. Examples 595-612 and Examples 614-616 listed in Table 5 and Examples 617-624 listed in Table 6, Example 625 listed in Table 1 and Examples 626-627 listed in Table 3 were prepared similarly as previously described for Examples 1-4.

Example 628

1-(2-(2-tert-butylphenoxy)pyridin-3-yl)-3-(4-(1-((R)-1-phenylethylamino)ethyl)phenyl)urea 20.2 mg (0.05 mmol) of 1-(4-acetylphenyl)-3-(2-(2-tert-butylphenoxy)pyridin-3-yl)urea (213a) was dissolved in 2 mL of dry toluene. R(+) α-methylbenzylamine (12.1 mg, 0.1 mmol, 2 eq) and TEA (10.1 μL, 0.072 mmol, 1.44 eq) were added. To this mixture was then added 28 μL, (0.56 eq) of TiCl4 (IV) in toluene (1M solution) so that the temperature of the reaction mixture stays below 60° C. The mixture was stirred at rt overnight. 2 mL of AcOEt was added and the mixture washed with 1N NaOH solution (2×2 mL). The organic phase was dried over MgSO4 and concentrated to yield 41.5 mg of an oil. The crude Schiff base was mixed with 3 mL of MeOH without any purification and reduced in the presence of Raney Ni to yield, after further purification with preparative HPLC (Method B) the desired Example 628. $C_{32}H_{36}N_4O_2$ [M+H]+ 509.32 1H NMR (400 MHz, MeOD) δ ppm 1.40 (s, 9H); 1.59 (d, J=6.6 Hz, 6H); 4.0-4.11 (m, 2H); 6.87 (dd, J=7.9 Hz and J=1.3 Hz, 1H); 7.09 (q, J=7.9 Hz and J=4.8 Hz, 1H), 7.15-7.26 (m, 4H), 7.3-7.35 (m, 2H), 7.45-7.53 (m, 4H), 7.58 (d, J=8.8 Hz, 2H), 7.69 (dd, J=4.8 Hz and J=1.76 Hz, 1H); 8.58 (dd, J=8.1 Hz and J=1.5 Hz, 1H).

According to the procedures in Example 213 or Example 628 and using the appropriated nucleophiles, Examples 214-216 and 218-221 listed in Table 2 were prepared and resolved according to the known enantiomer separation procedures.

Example 214A (S)-1-(2-(2-tert-butylphenoxy)pyridin-3-yl)-3-(4-(1-(methyl(thiophen-2-ylmethyl)amino)ethyl)phenyl) urea Example 214B (R)-1-(2-(2-tert-butylphenoxy)pyridin-3-yl)-3-(4-(1-(methyl(thiophen-2-ylmethyl)amino)ethyl)phenyl) urea Example 629

1-(2-(3,3-dimethyl-1,3-dihydroisobenzofuran-4-yloxy)pyridin-3-yl)-3-(4-(trifluoromethoxy)phenyl) urea 629a. 2-(2-(hydroxymethyl)-6-(methoxymethoxy)phenyl)propan-2-ol: 7-(methoxymethoxy)isobenzofuran-1(3H)-one (Tetrahedron 2003, 59, 3201-3217) (1 g, 5.15 mmol) in THF (20 mL) was stirred at −78° C. Methylmagnesium bromide (3.0 M in Et$_2$O, 6.9 mL, 20.5 mmol) was added and mixture was warmed to rt and stirred for 30 min. A saturated solution of ammonium chloride was added and the solution was warmed to rt and extracted twice using ethyl acetate. Organic phases were combined, dried using MgSO$_4$ and evaporated. Crude material was purified using flash chromatography (25 to 50% ethyl acetate/hexanes) to yield the desired material (160 mg).

629b. 3,3-dimethyl-1,3-dihydroisobenzofuran-4-ol: A mixture of 629a (160 mg, 0.71 mmol), triphenylphosphine (185 mg, 0.71 mmol) in CCl$_4$ (2 mL) was stirred at 80° C. for 6 h. The mixture was evaporated and purified on preparative HPLC to give the desired material (65 mg). (M−H)$^-$=163.

629c. 2-(3,3-dimethyl-1,3-dihydroisobenzofuran-4-yloxy)-3-nitropyridine: A mixture of 629b (65 mg, 0.4 mmol), 2-chloro-2-nitropyridine (94 mg, 0.6 mmol) and cesium carbonate (195 mg, 0.6 mmol) in DMF (4 mL) was stirred at 80° C. for 2 h. The mixture directly purified on preparative HPLC to give the desired material (115 mg). (M+H)$^+$=287.

629d. 2-(3,3-dimethyl-1,3-dihydroisobenzofuran-4-yloxy)pyridin-3-amine: A mixture of 629c (115 mg, 0.4 mmol), zinc (261 mg, 4 mmol) and ammonium chloride (214 mg, 4 mmol) in ethanol (10 mL) was heated to reflux for 2 h. The solution was filtered over a pad of Celite™ and evaporated in vacuo. Crude material was directly use in the next step. (M+H)$^+$=257.

Example 629: A mixture of 629d (103 mg, 0.4 mmol), 1-isocyanato-4-(trifluoromethoxy)benzene (90 µL, 0.6 mmol) in THF (5 mL) was stirred at rt for 72 h. The mixture was evaporated and purified on preparative HPLC (132 mg). (M+H)$^+$=460. 1H NMR (400 MHz, DMSO-D6) δ ppm 1.35 (s, 6H), 5.00 (s, 2H), 6.98 (d, J=8.08 Hz, 1H), 7.07 (dd, J=7.96, 4.93 Hz, 1H), 7.14 (d, J=7.07 Hz, 1H), 7.27-7.35 (m, J=8.08, 7.83, 7.71, 7.71 Hz, 3H), 7.52-7.58 (m, 3H), 7.66 (dd, J=4.80, 1.52 Hz, 1H), 8.54 (dd, J=7.83, 1.52 Hz, 1H), 8.70 (s, 1H), 8.94 (s, 1H), 9.59 (s, 1H).

Example 630 methyl 2-fluoro-6-(3-(3-(4-(trifluoromethoxy)phenyl)ureido)pyridin-2-yloxy)benzoate 630a. methyl 2-fluoro-6-hydroxybenzoate: A mixture of methyl 2-fluoro-6-(methoxymethoxy)benzoate (European Journal of Organic Chemistry 2001, 15, 2911-2915) (0.92 g, 4.29 mmol) and bromotrimethylsilane (567 µL, 4.29 mmol) in CH$_2$Cl$_2$ (20 mL) was stirred at 20° C. for 5 days. Bromotrimethylsilane (567 µL, 4.29 mmol) was added again and stirring was continued for 18 h. Iodotrimethylsilane (700 µL, 4.29 mmol) was added and stirring was continued for 2 h. Methanol (20 mL) and 1 N citric acid solution were added and the reaction mixture was stirred for 1 h. The reaction mixture was extracted twice using ethyl acetate. Organic phases were combined, dried using MgSO$_4$ and evaporated to yield the desired material (780 mg).

630b. methyl 2-fluoro-6-(3-nitropyridin-2-yloxy)benzoate: A mixture of 630a (714 mg, 4.2 mmol), 2-chloro-2-nitropyridine (1.09 g, 6.9 mmol) and cesium carbonate (2.25 g, 6.9 mmol) in DMF (10 mL) was stirred at 80° C. for 2 h. Water was added and the mixture was extracted twice using ethyl acetate. Organic phases were combined, dried (MgSO$_4$) and evaporated in vacuo to yield final product. The crude material was directly use in the next step. (M+H)$^+$=293.

630c. methyl 2-(3-aminopyridin-2-yloxy)-6-fluorobenzoate: A mixture of 630b (1.22 g, 4.2 mmol), zinc (2.74 g, 42 mmol) and ammonium chloride (2.24 g, 42 mmol) in ethanol (20 mL) was heated to reflux for 2 h. The solution was filtered over a pad of Celite™ and evaporated in vacuo. Crude material was directly use in the next step. (M+H)$^+$=263.

Example 630: A mixture of 630c (1.1 g, 4.2 mmol), 1-isocyanato-4-(trifluoromethoxy)benzene (1.04 mL, 6.9 mmol) in THF (20 mL) was stirred at rt for 72 h. The mixture was evaporated and purified on flash chromatography (20 to 40% ethyl acetate/hexanes) (1.1 g). (M+H)=466. 1H NMR (400 MHz, DMSO-D6) δ ppm 3.57 (s, 3H), 7.06-7.12 (m, 1H), 7.22 (d, J=8.34 Hz, 1H), 7.29 (td, J=8.84, 5.05 Hz, 3H), 7.52-7.59 (m, 2H), 7.61-7.69 (m, 2H), 8.54 (dd, J=7.96, 1.64 Hz, 1H), 8.67 (s, 1H), 9.57 (s, 1H).

Example 631

1-(2-(2-acetyl-3-fluorophenoxy)pyridin-3-yl)-3-(4-(trifluoromethoxy)phenyl)urea

Methyl 2-fluoro-6-(3-(3-(4-(trifluoromethoxy)phenyl)ureido)pyridin-2-yloxy)benzoate (250 mg, 0.54 mmol) was diluted in THF (10 mL) and cooled to −78° C. Methylmagnesiumbromide (3.0 M in Et$_2$O, 1.07 mL, 3.22 mmol) was added and mixture was warmed to rt and stirred for 18 h. Sodium sulfate decahydrate was added and stirring was continued for 30 min. The solution was filtered over a pad of Celite® and washed using ethyl acetate. The organic phase was evaporated and crude material was purified using preparative HPLC to yield the desired material (20 mg) (M+H)$^+$=450. $^1$H NMR (400 MHz, Acetone) δ ppm 2.33-2.40 (m, J=1.77 Hz, 3H), 7.07-7.18 (m, 3H), 7.27 (d, J=8.84 Hz, 2H), 7.56 (td, J=8.34, 6.57 Hz, 1H), 7.63-7.70 (m, 3H), 8.20 (s, 1H), 8.67 (dd, J=7.96, 1.64 Hz, 1H), 8.91 (s, 1H).

Example 632

1-(2-(2-(cyclohexylmethyl)-1,2,3,4-tetrahydroisoquinolin-5-yloxy)pyridin-3-yl)-3-(4-(trifluoromethoxy)phenyl)urea A mixture of 1-(2-(1,2,3,4-tetrahydroisoquinolin-5-yloxy)pyridin-3-yl)-3-(4-(trifluoromethoxy)phenyl)urea (238f, 15 mg, 0.034 mmol), cyclohexanecarboxaldehyde (38 mg, 034 mmol), acetic acid (50 µL) were added to NMP (0.75 mL) and trimethylorthoformate (0.5 mL) and stirred at rt for 2.5 h. Triacetoxyborohydride (36 mg) was added and stirring was continued for 18 h. A solution of acetic acid in methanol (50% v/v, 0.5 mL) was added and reaction mixture was directly purified on preparative HPLC to yield the desired material (5.4 mg). (M+H)$^+$=541. 1H NMR (400 MHz, DMSO-D6) δ ppm 1.6-1.9 (m, 10H), 2.32 (m, 1H), 3.04-3.06 (m, 2H), 3.66-3.75 (m, 2H), 4.31-4.43 (m, 2H), 4.60-4.70 (m, 2H), 7.11 (dd, J=7.83, 4.80 Hz, 1H), 7.18 (t, J=7.83 Hz, 2H), 7.33 (d, J=8.08 Hz, 2H), 7.39 (t, J=7.83 Hz, 1H), 7.56 (d, J=9.09 Hz, 2H), 7.65 (dd, J=4.80, 1.76 Hz, 1H), 8.53 (d, J=7.84 Hz, 1H), 8.78 (s, 1H), 9.54 (s, 1H).

Example 633

1-(2-(2-(1-benzoylpiperidin-4-yl)phenoxy)pyridin-3-yl)-3-(4-(trifluoromethoxy)phenyl)urea 633a. (4-hydroxy-4-(2-(methoxymethoxy)phenyl)piperidin-1-yl)(phenyl)methanone: 1-iodo-2-(methoxymethoxy)benzene (Tetrahedron Asymmetry 1999, 10 (6), 1069-1078) (2 g, 7.6 mmol) in THF (20 mL) was cooled to 0° C. Isopropylmagnesiumbromide (2.0 M in Et$_2$O, 3.8 mL, 7.6 mmol) was added and mixture was stirred for 30 min at 0° C. and cooled to −78° C. A solution of 1-benzoylpiperidin-4-one (1.7 g, 8.36 mmol) in THF (10 mL) was added and stirring was continued for 30 min. A saturated solution of ammonium chloride was added and the solution was warmed to rt and extracted twice using ethyl acetate. Organic phases were combined, dried using MgSO$_4$ and evaporated. The crude product was directly use in the next step (2.43 g). (M+H)$^+$=342, (M+H—H$_2$O)$^+$=324.

633b. (4-(2-hydroxyphenyl)piperidin-1-yl)(phenyl)methanone: A mixture of 633a (2.43 g, 7.1 mmol), triethylsilane (3.4 mL, 21.3 mmol) in trifluoroacetic acid (10 mL) was stirred at 60° C. for 3 h. The mixture was partially evaporated and purified using a silica gel pad (100% hexanes to 100% ethylacetate). The ethylacetate portion was evaporated and product was diluted in MeOH (20 mL) and 4N HCl (2 mL) and stirred for 3 days. The solid formed was collected by filtration and air dried to give the desired material (340 mg). (M+H)$^+$=282.

633c. (4-(2-(3-nitropyridin-2-yloxy)phenyl)piperidin-1-yl)(phenyl)methanone: A mixture of 633b (340 mg, 1.2 mmol), 2-chloro-2-nitropyridine (313 mg, 1.97 mmol) and cesium carbonate (642 mg, 1.97 mmol) in DMF (10 mL) was stirred at 20° C. for 18 h. The mixture directly filtered through a pad of silica gel using ethyl acetate. The crude product was directly used in the next step. (M+H)$^+$=404.

633d. (4-(2-(3-aminopyridin-2-yloxy)phenyl)piperidin-1-yl)(phenyl)methanone: A mixture of 633c (528 mg, 1.31 mmol), zinc (856 mg, 13.1 mmol) and ammonium chloride (700 mg, 13.1 mmol) in ethanol (20 mL) was heated to reflux for 2 h. The solution was filtered over a pad of Celite™ and evaporated in vacuo. The crude material was directly used in the next step. (M+H)+=374.

Example 633: A mixture of 633d (489 mg, 1.31 mmol), 1-isocyanato-4-(trifluoromethoxy)benzene (257 µL, 1.7 mmol) in DMF (10 mL) was stirred at rt for 2 h. The mixture was evaporated and purified on preparative HPLC (550 mg). (M+H)$^+$=577. 1H NMR (400 MHz, DMSO-D6) δ ppm 1.63 (s, 2H), 1.73-1.81 (m, 1H), 2.92-3.03 (m, 2H), 3.39-3.50 (m, 2H), 3.53-3.59 (m, 1H), 4.49-4.61 (m, 1H), 7.01-7.09 (m, 2H), 7.21-7.32 (m, 5H), 7.33-7.42 (m, 5H), 7.46 (dd, J=7.33, 2.02 Hz, 1H), 7.51-7.59 (m, 3H), 7.64 (dd, J=4.80, 1.77 Hz, 1H), 8.53 (dd, J=7.96, 1.64 Hz, 1H), 8.76 (s, 1H), 9.55 (s, 1H).

Example 634

1-(2-(2-(1-neopentylpiperidin-4-yl)phenoxy)pyridin-3-yl)-3-(4-(trifluoromethoxy)phenyl)urea 634a. 1-(2-(2-(piperidin-4-yl)phenoxy)pyridin-3-yl)-3-(4-(trifluoromethoxy)phenyl)urea: Example 633 (500 mg, 0.87 mmol) was diluted in THF (10 mL) and cooled to −78° C. n-Butyllithium (1.6 M/hexanes, 2.7 mL, 4.33 mmol) is added and the reaction mixture is stirred for 15 min. A saturated solution of ammonium chloride is added, the solution is warmed to rt and extracted twice using ethyl acetate. Organic phases were combined, dried using MgSO$_4$ and evaporated. The crude material was directly purified using solid phase extraction (SCX resin) (300 mg). (M+H)$^+$=473.

Example 634

634a (20 mg, 0.042 mmol), trimethyacetaldehyde (49 µL, 0.42 mmol), acetic acid (50 µL) were added to NMP (0.75 mL) and trimethylorthoformate (0.5 mL) and stirred at rt for 2 h. Triacetoxyborohydride (44 mg) was added and stirring was continued for 18 h. A solution of acetic acid in methanol (50% v/v, 0.5 mL) was added and reaction mixture was directly purified on preparative HPLC to yield the desired material (15 mg). (M+H)$^+$=543. 1H NMR (400 MHz, DMSO-D6) δ ppm 0.98-1.03 (m, 9H), 1.82-1.90 (m, 2H), 2.09 (d, J=12.63 Hz, 2H), 2.91 (d, J=4.04 Hz, 2H), 2.94-3.04 (m, 2H), 3.07-3.16 (m, 2H), 3.20 (s, 1H), 7.04-7.11 (m, 2H), 7.27-7.37 (m, 3H), 7.53-7.59 (m, 2H), 7.64-7.68 (m, 1H), 8.23 (s, 1H), 8.54 (dt, J=7.89, 1.99 Hz, 1H), 8.72-8.80 (m, 1H), 9.57 (s, 1H).

Example 635

1-(2-(2-(4-methoxybenzyl)isoindolin-4-yloxy)pyridin-3-yl)-3-(4-(trifluoromethoxy)phenyl)urea 635a. 2-(4-methoxybenzyl)-4-hydroxyisoindoline-1,3-dione: A mixture of 4-hydroxyisobenzofuran-1,3-dione (1 g, 6.09 mmol), 4-methoxybenzylamine (1.45 mL, 12.18 mmol) in toluene (20 mL) was stirred at reflux in a Dean-Stark apparatus for 18 h. The mixture was cooled down and the solid formed was collected by filtration and air dried. (1.33 g) (M−H)$^-$=282.

635b. 2-(4-methoxybenzyl)isoindolin-4-ol: A mixture of 635a (1.33 g, 4.70 mmol), lithium aluminium hydride (713 mg, 18.8 mmol) in THF (20 mL) was stirred at rt for 18 h. Sodium sulfate decahydrate was added and mixture was stirred for 30 min. The reaction mixture was filtered over a pad of Celite® and washed with ethylacetate. The organic phase was evaporated and the crude material obtained was directly used in the next step (686 mg) (M+H)$^+$=256.

635c. 2-(4-methoxybenzyl)-4-(3-nitropyridin-2-yloxy) isoindoline: A mixture of 635b (686 mg, 2.69 mmol), 2-chloro-2-nitropyridine (853 mg, 5.38 mmol) and cesium carbonate (853 mg, 8.07 mmol) in DMF (10 mL) was stirred at 80° C. for 3 h. Water was added and mixture was extracted twice using ethyl acetate. The organic phases was dried (MgSO$_4$), filtered and evaporated to afford the crude product (260 mg). (M+H)$^+$=378.

635d. 2-(2-(4-methoxybenzyl)isoindolin-4-yloxy)pyridin-3-amine: A mixture of 635c (260 mg, 0.69 mmol), zinc (451 mg, 6.9 mmol) and ammonium chloride (369 mg, 6.9 mmol) in ethanol (20 mL) was heated to reflux for 2 h. The solution was filtered over a pad of Celite® and evaporated in vacuo. The crude material was directly used in the next step. (M+H)$^+$=348.

Example 635: A mixture of 635d (240 mg, 069 mmol), 1-isocyanato-4-(trifluoromethoxy)benzene (157 μL, 1.04 mmol) in THF (10 mL) was stirred at rt for 2 h. The mixture was evaporated and purified on preparative HPLC (164 mg). (M+H)$^+$=551. 1H NMR (400 MHz, DMSO-D6) δ ppm 3.67-3.78 (m, 4H), 4.39 (s, 2H), 6.84-6.94 (m, 1H), 7.00 (d, J=8.34 Hz, 1H), 7.15 (dd, J=7.96, 4.93 Hz, 1H), 7.24 (dd, J=8.59, 2.53 Hz, 2H), 7.29 (s, 1H), 7.31 (d, J=8.59 Hz, 1H), 7.40-7.51 (m, 3H), 7.53-7.59 (m, 2H), 7.70 (dd, J=4.80, 1.52 Hz, 1H), 8.54 (dd, J=7.83, 1.52 Hz, 1H), 8.73 (s, 1H), 9.55 (s, 1H).

Example 636

1-(2-(2-neopentylisoindolin-4-yloxy)pyridin-3-yl)-3-(4-(trifluoromethoxy)phenyl)urea 636a. 1-(2-(isoindolin-4-yloxy)pyridin-3-yl)-3-(4-(trifluoromethoxy)phenyl)urea: A mixture of Example 635 (144 mg, 0.26 mmol), 1-chloroethylchloroformate (700 μL, 6.5 mmol) in CH$_2$Cl$_2$ (10 mL) was refluxed for 18 h. MeOH was added and refluxing was continued for 2 h. Saturated sodium bicarbonate solution was added and the mixture was extracted twice using ethylacetate. The organic phases was dried (MgSO$_4$), filtered and evaporated. The crude material was purified on preparative HPLC (41 mg). (M+H)$^+$=431.

Example 636: 636a (15 mg, 0.035 mmol), trimethyacetaldehyde (38 μL, 0.35 mmol), acetic acid (50 μL) were added to NMP (0.75 mL) and trimethylorthoformate (0.5 mL) and stirred at rt for 2 h. Triacetoxyborohydride (35 mg) was added and stirring was continued for 18 h. A solution of acetic acid in methanol (50% v/v, 0.5 mL) was added and reaction mixture was directly purified on preparative HPLC to yield the desired material (9.4 mg). (M+H)$^+$=501. 1H NMR (400 MHz, Acetone) δ ppm 0.85-0.94 (m, 9H), 2.44-2.55 (m, 2H), 3.81-3.92 (m, 2H), 4.10-4.19 (m, 2H), 6.96 (d, J=7.83 Hz, 1H), 7.04-7.13 (m, 2H), 7.21-7.29 (m, 3H), 7.62-7.69 (m, 3H), 8.26 (s, 1H), 8.67 (dd, J=7.96, 1.64 Hz, 1H), 8.92 (s, 1H).

Example 637

1-(2-(2-neopentyl-1,2,3,4-tetrahydroisoquinolin-8-yloxy)pyridin-3-yl)-3-(4-(trifluoromethoxy)phenyl)urea 637a. tert-butyl 2-bromo-5-methoxyphenethylcarbamate: A mixture of 2-(3-methoxyphenyl)ethanamine (10 g, 66.13 mmol), and ditertbutyldicarbonate (14.4 g, 66.13 mmol) in THF (100 mL) was stirred at rt for 2 h. The reaction mixture was evaporated and the crude material was diluted in acetone (150 mL) and cooled to 0° C. N-bromosuccinimide (11.77 g, 66.13 mmol) was added and the reaction mixture was stirred for 2 h. The reaction mixture was partially evaporated, hexanes was added until a precipitate was formed. The solution was cooled to 0° C. for 30 min and the solid was removed by filtration. The organic phase was evaporated to yield the desired material (23.33 g). (M+H)$^+$=330, 332 (bromine pattern).

637b. 3-(2-aminoethyl)-4-bromophenol hydrobromide: 637a (10 g, 30.3 mmol) in CH$_2$Cl$_2$ (200 mL) was stirred at −78° C. Boron tribromide (1.0 M in CH$_2$Cl$_2$, 60.6 mL, 60.6 mmol) was added and mixture was warmed to rt and stirred for 30 min. Water was added and the solid formed was isolated by filtration and dried under vacuo (13.2 g, contains water). (M+H)$^+$=216, 218 (bromide pattern).

637c. 5-bromo-1,2,3,4-tetrahydroisoquinolin-8-ol: A mixture of 637b (2.5 g, 8.42 mmol), and paraformaldehyde (37% wt/v, 1.19 mL) in 0.05N HCl (13 mL) was stirred at 90° C. for 2 h. The reaction mixture was cooled down to 20° C. A saturated solution of sodium bicarbonate was added and the solid formed was isolated by filtration and dried under vacuo (1.02 g). (M+H)$^+$=228, 230 (bromide pattern).

637d. 1,2,3,4-tetrahydroisoquinolin-8-ol: 637c (680 mg, 2.98 mmol) in THF (25 mL) was stirred at −78° C. Tert-butyllithium (1.7 M in pentane, 7 mL, 11.9 mmol) was added and mixture was stirred for 30 min. A saturated solution of sodium bicarbonate is added, the solution is warmed to rt and extracted twice using ethyl acetate. Organic phases were combined, dried using MgSO$_4$ and evaporated. The crude material was directly purified used in the next step (220 mg).

637e. (8-hydroxy-3,4-dihydroisoquinolin-2(1H)-yl)(phenyl)methanone: A mixture of 637d (220 mg, 1.48 mmol), benzoyl chloride (343 μL, 2.96 mmol) and diisopropylethylamine (323 μL, 2.96 mmol) were added to CH$_2$Cl$_2$ and mixture was stirred at rt for 3 h. The mixture was evaporated in vacuo and diluted in ethanol/water (2/1, 20 mL). Lithium hydroxide monohydrate (1.5 g, 30 mmol) was added and mixture was stirred for 18 h. The mixture was dissolved in EtOAc, washed with a saturated solution of sodium bicarbonate, dried (MgSO$_4$), filtered and evaporated to afford the crude product (480 mg). (M+H)$^+$=254.

637f. (8-(3-nitropyridin-2-yloxy)-3,4-dihydroisoquinolin-2(1H)-yl)(phenyl)methanone: A mixture of (8-hydroxy-3,4-dihydroisoquinolin-2(1H)-yl)(phenyl)methanone (374 mg, 1.48 mmol), 2-chloro-2-nitropyridine (235 mg, 1.48 mmol) and cesium carbonate (482 mg, 1.48 mmol) in DMF (10 mL) was stirred at 20° C. for 18 h. Water was added and mixture was extracted twice using ethyl acetate. The organic phases was dried (MgSO$_4$), filtered and evaporated to afford the crude product. (M+H)$^+$=376.

637g. (8-(3-aminopyridin-2-yloxy)-3,4-dihydroisoquinolin-2(1H)-yl)(phenyl)methanone: A mixture of 637f (556 mg, 1.48 mmol), zinc (968 mg, 14.8 mmol) and ammonium chloride (792 mg, 14.8 mmol) in ethanol (30 mL) was heated to reflux for 2 h. The solution was filtered over a pad of Celite™ and evaporated in vacuo. The crude material was directly used in the next step. (M+H)$^+$=257.

637h. 1-(2-(2-benzoyl-1,2,3,4-tetrahydroisoquinolin-8-yloxy)pyridin-3-yl)-3-(4-(trifluoromethoxy)phenyl)urea: A mixture of 637g (511 mg, 1.48 mmol), 1-isocyanato-4-(trifluoromethoxy)benzene (335 μL, 2.22 mmol) in THF (10 mL) was stirred at rt for 18 h. The mixture was evaporated and purified on preparative HPLC (120 mg). (M+H)$^+$=549.

637i. 1-(2-(1,2,3,4-tetrahydroisoquinolin-8-yloxy)pyridin-3-yl)-3-(4-(trifluoromethoxy)phenyl)urea: 637h (100 mg, 0.18 mmol) was diluted in THF (5 mL) and cooled to −78° C. n-Butyllithium (1.6 M/hexanes, 563 μL, 0.9 mmol) was added and the reaction mixture was stirred for 2 h. A saturated solution of ammonium chloride was added. The solution was warmed to r.t. and extracted twice using ethyl acetate. Organic phase were combined, dried (MgSO$_4$) and evaporated. The crude material was directly purified using preparative HPLC to afford the final product as TFA salt (7.9 mg). (M+H)$^+$=445.

Example 637

637i (7.9 mg, 0.018 mmol), trimethyacetaldehyde (19 μL, 0.18 mmol), acetic acid (50 μL) were added to NMP (0.75 mL) and trimethylorthoformate (0.5 mL) and stirred at rt for 2 h. Triacetoxyborohydride (9.3 mg) was added and stirring was continued for 18 h. A solution of acetic acid in methanol (50% v/v, 0.5 mL) was added and reaction mixture was directly purified on preparative HPLC to yield the desired material (2.9 mg). (M+H)$^+$=515. $^1$H NMR (400 MHz, Acetone) δ ppm 1.22-1.28 (m, 9H), 3.05 (s, 6H), 3.41 (s, 2H), 6.66 (d, J=8.08 Hz, 1H), 6.98 (d, J=7.83 Hz, 1H), 7.18-7.26 (m, 4H), 7.60 (ddd, J=9.35, 2.78, 2.53 Hz, 2H), 7.87 (dd, J=4.67, 1.64 Hz, 1H), 8.44 (s, 1H), 8.78 (dd, J=8.08, 1.77 Hz, 1H), 9.58 (s, 1H).

Example 638

1-(2-(3-tert-butyl-2-methoxyisoindolin-4-yloxy)pyridin-3-yl)-3-(4-(trifluoromethoxy)phenyl)urea 638a. 3-(methoxymethoxy)benzoic acid: Ethyl 3-hydroxybenzoate (25 g, 150.4 mmol) was added to THF (250 mL) and cooled to 0° C. Sodium hydride (60% in mineral oil, 6.6 g, 165.5 mmol) was added portion wise. Methoxymethylether (11.5 mL, 150.4 mmol) was added to the solution and the reaction mixture was stirred at 20° C. for 18 h. The solvent was evaporated in vacuo and EtOH (250 mL), water (250 mL) and lithium hydroxide monohydrate (25.2 g, 0.6 mole) was added. The reaction mixture was stirred for 2 h at 20° C. The reaction mixture was washed twice using ethyl acetate. The aqueous phase was acidified using 4N HCl and extracted twice using ethyl acetate. The organic phases were combined, dried using MgSO$_4$ and evaporated to yield the desired material (22 g).

638b. N-methoxy-3-(methoxymethoxy)benzamide: 638a (5 g, 27.4 mmol) was added to CH$_2$Cl$_2$ (100 mL) and DMF (0.5 mL) at 20° C. Oxalyl chloride (2.35 mL, 27.4 mmol) was added and reaction mixture was stirred at 20° C. for 30 min. Methoxylamine hydrochloride (2.30 g, 27.4 mmol) was added and the reaction mixture was stirred for 1 h. The reaction mixture was washed using a saturated solution of ammonium chloride following by a saturated solution of sodium bicarbonate. The organic phases was dried using MgSO$_4$ and evaporated. The crude material was purified by flash chromatography on silica gel (50 to 100% ethyl acetate/hexanes) (1.67 g).

638c. 3-tert-butyl-3-hydroxy-2-methoxy-4-(methoxymethoxy)isoindolin-1-one: 638b (1 g, 4.73 mmol) in THF (20 mL) was stirred at 0° C. n-Butyllithium (1.6 M in hexanes, 5.91 mL, 9.46 mmol) was added and mixture was stirred for 1 h. Trimethylacetylchloride (593 μL, 4.73 mmol) was added and stirring was continued for 30 min. A saturated solution of ammonium chloride was added and the solution was warmed to rt and extracted twice using ethyl acetate. Organic phases were combined, dried using MgSO$_4$ and evaporated. The crude material was directly used in the next step (410 mg).

638d. 3-tert-butyl-4-hydroxy-2-methoxyisoindolin-1-one: A mixture of 638c (410 mg, 1.39 mmol), triethylsilane (443 μL, 2.77 mmol) in trifluoroacetic acid (5 mL) and CH$_2$Cl$_2$ was stirred at 20° C. for 18 h. The solvent evaporated in vacuo and the crude material was directly used in the next step.

638e. 3-tert-butyl-2-methoxyisoindolin-4-ol: A mixture of 638d (327 mg, 1.39 mmol), lithium aluminium hydride (158 mg, 4.17 mmol) in THF (10 mL) was stirred at rt for 18 h. Sodium sulfate decahydrate was added and mixture was stirred for 30 min. The reaction mixture was filtered over a pad of Celite® and washed with ethylacetate. The organic phase was evaporated and the crude product was purified using preparative HPLC (140 mg). (M+H)$^+$=222.

638f. 2-(3,3-dimethyl-1,3-dihydroisobenzofuran-4-yloxy)-3-nitropyridine: A mixture of 638e (140 mg, 0.63 mmol), 2-chloro-2-nitropyridine (150 mg, 0.95 mmol) and cesium carbonate (615 mg, 1.82 mmol) in DMF (4 mL) was stirred at 60° C. for 2 h. The mixture directly purified on preparative HPLC to give the desired material (136 mg). (M+H)$^+$=344.

638g. 2-(3-tert-butyl-2-methoxyisoindolin-4-yloxy)pyridin-3-amine: A mixture of 638f (136 mg, 0.4 mmol), zinc (261 mg, 4 mmol) and ammonium chloride (214 mg, 4 mmol) in ethanol (20 mL) was heated to reflux for 2 h. The solution was allowed to cool and filtered over a pad of Celite® and evaporated in vacuo. The crude material was purified using preparative HPLC (100 mg). (M+H)$^+$=314.

Example 638: A mixture of 638f (100 mg, 0.32 mmol), 1-isocyanato-4-(trifluoromethoxy)benzene (72 μL, 0.48 mmol) in THF (10 mL) was stirred at reflux for 2 h. The mixture was evaporated and purified on preparative HPLC (32 mg). (M+H)$^+$=517. 1H NMR (400 MHz, DMSO-D6) δ ppm 0.84 (s, 9H), 3.45 (s, 3H), 4.16 (d, J=17.68 Hz, 1H), 4.30 (s, 1H), 4.41 (d, J=17.68 Hz, 1H), 6.97 (d, J=8.08 Hz, 1H), 7.08 (dd, J=7.83, 4.80 Hz, 1H), 7.14 (d, J=7.33 Hz, 1H), 7.26-7.35 (m, J=8.34, 8.34 Hz, 3H), 7.56 (d, J=8.84 Hz, 2H), 7.70 (dd, J=4.80, 1.52 Hz, 1H), 8.54 (dd, J=7.83, 1.52 Hz, 1H), 8.62 (s, 1H), 9.59 (s, 1H).

Example 639

1-(2-(3-tert-butylisoindolin-4-yloxy)pyridin-3-yl)-3-(4-(trifluoromethoxy)phenyl)urea A mixture of Example 638 (24 mg, 0.046 mmol), zinc (30 mg, 0.46 mmol) and ammonium chloride (25 mg, 0.46 mmol) in ethanol (5 mL) was heated to reflux for 6 h. The solution was filtered over a pad of Celite® and evaporated in vacuo. The crude material was purified using preparative HPLC (7 mg). (M+H)$^+$=487. $^1$H NMR (400 MHz, DMSO-D6) δ ppm 0.97 (s, 9H), 4.54-4.66 (m, 3H), 7.14 (dd, J=7.83, 4.80 Hz, 1H), 7.19 (d, J=8.08 Hz, 1H), 7.25-7.35 (m, J=7.83, 7.83 Hz, 3H), 7.47-7.58 (m, 3H), 7.63-7.73 (m, 1H), 8.51 (dd, J=7.83, 1.26 Hz, 1H), 8.64 (s, 2H), 9.56 (s, 1H), 10.13 (s, 1H).

Example 640

1-(2-(3-(4-hydroxyhepta-1,6-dien-4-yl)phenoxy)pyridin-3-yl)-3-(4-(trifluoromethoxy)phenyl)urea Example 640 was prepared according to the procedure described for Example 137 in Table 1 using ethyl 3-(3-(3-(4-(trifluoromethoxy)phenyl)ureido)pyridin-2-yloxy)benzoate. (M+H)$^+$=500; $^1$H NMR (400 MHz, DMSO-d$_6$) δppm 2.51 (m, 4H), 4.95 (m, 4H), 5.66 (m, 2H), 7.00 (dd, J=9.2, 1.5 Hz), 7.09 (dd, J=7.9, 4.9 Hz, 1H), 7.22 (m, 2H), 7.34 (m, 3H), 7.57

(d, J=9.1 Hz, 2H), 7.70 (dd, J=4.8, 1.8 Hz, 1H), 8.56 (dd, J=7.8, 1.6 Hz, 1H), 8.73 (s, 1H), 9.58 (s, 1H).

Example 641 ethyl 3-(3-(3-(4-(trifluoromethoxy)phenyl)ureido)pyridin-2-yloxy)benzoate

Example 641 was prepared according to the procedure described for 153b using ethyl 3-(3-aminopyridin-2-yloxy)benzoate which, in turn, was made according to the procedure described for Example 2. (M+H)$^+$=462; $^1$H NMR (400 MHz, DMSO-d$_6$) δppm 1.32 (t, J=7.0 Hz, 3H), 4.33 (q, J=7.0 Hz, 2H), 7.15 (dd, J=7.8, 4.8 Hz, 1H), 7.32 (d, J=8.6 Hz, 2H), 7.58 (m, 4H), 7.72 (m, 2H), 7.85 (d, J=7.9 Hz, 1H), 8.59 (dd, J=7.9, 1.6 Hz, 1H), 8.76 (s, 1H), 9.54 (s, 1H).

Example 642

1-(2-(3-(4-methoxyhepta-1,6-dien-4-yl)phenoxy)pyridin-3-yl)-3-(4-(trifluoromethoxy)phenyl)urea To a solution of Example 640 (120 mg, 0.24 mmol) in dry methanol (15 mL) was added concentrated sulfuric acid (2 mL) at rt. The mixture was heated to 100° C. for 72 h and cooled down to rt. A saturated solution of sodium bicarbonate was slowly added and the mixture was extracted with dichloromethane. Evaporation afforded a residue which was purified by reverse phase preparative HPLC. (M+H)$^+$=514. $^1$H NMR (400 MHz, DMSO-d$_6$) δppm 2.62 (m, 4H), 3.08 (s, 3H), 5.03 (m, 4H), 5.55 (m, 2H), 7.31 (m, 7H), 7.57 (d, 2H, J=9.1 Hz), 7.70 (dd, J=5.0, 1.7 Hz, 1H), 8.55 (dd, J=7.8, 1.5 Hz, 1H), 8.72 (s, 1H), 9.56 (s, 1H).

Example 643

1-(2-(3-cyclopentylphenoxy)pyridin-3-yl)-3-(4-(trifluoromethoxy)phenyl)urea 643a. 1-(2-(3-(1-hydroxycyclopent-3-enyl)phenoxy)pyridin-3-yl)-3-(4-(trifluoromethoxy)phenyl)urea: A mixture of Example 640 (125 mg, 0.25 mmol) and Grubb's second generation catalyst (70 mg) in dichloromethane (70 mL) was stirred at rt for 16 h. An additional 1.0 mg of Grubb's second generation catalyst was added and the mixture was stirred at rt for an additional 17 h. Evaporation under reduced pressure afforded a residue which was filtered and purified using reverse-phase preparative HPLC. (M+H)$^+$=472.

Example 643: A mixture of 643a (14 mg, 0.03 mmol) and 10% palladium on charcoal (8 mg) in ethyl acetate was stirred under one atmosphere of hydrogen for 16 h. The mixture was filtered through Celite® and evaporated. The residue was purified by reverse phase preparative HPLC. (M+H)$^+$=458; $^1$H NMR (400 MHz, DMSO-d$_6$) δppm 1.65 (m, 6H), 2.01 (m, 2H), 3.01 (m, 1H), 6.98 (dd, J=7.9, 1.8 Hz, 1H), 7.09 (m, 3H), 7.33 (m, 3H), 7.57 (d, J=9.1 Hz, 2H), 7.70 (dd, J=4.8, 1.7 Hz, 1H), 8.55 (dd, J=8.1, 1.8 Hz, 1H), 8.71 (s, 1H), 9.55 (s, 1H).

Example 644

1-(2-(2-(1,2-dimethoxypropan-2-yl)phenoxy)pyridin-3-yl)-3-(4-(trifluoromethoxy)phenyl)urea 644a. 2-(2-hydroxy-1-methoxypropan-2-yl)phenol was prepared according to the procedure described for 417a using 2-bromophenol (400 μL, 3.4 mmol), n-butyllithium in hexanes (1.6 M, 5.0 mL, 7.9 mmol) and methoxyacetone (412 uL, 4.48 mmol). $^1$H NMR (400 MHz, CDCl$_3$) δppm 1.64 (s, 3H), 3.45 (d, J=9.3 Hz, 1H), 3.47 (s, 3H), 3.77 (d, J=9.3 Hz, 1H), 6.85 (m, 1H), 6.90 (m, 1H), 7.04 (m, 1H), 7.20 (m, 1H), 9.22 (s, 1H).

644b. 2-(1,2-dimethoxypropan-2-yl)phenol was prepared according to the procedure described for 157a using 644a (230 mg, 1.26 mmol), p-TsOH (6 mg) and methanol (8 mL) instead of propanol. $^1$H NMR (400 MHz, CDCl$_3$) δppm 1.70 (s, 3H), 3.30 (s, 3H), 3.39 (s, 3H), 3.49 (d, J=10.1 Hz, 1H), 3.73 (d, J=10.1 Hz, 1H), 6.89 (m, 2H), 7.08 (m, 1H), 7.24 (m, 1H), 8.69 (s, 1H).

644c. 2-(2-(1,2-dimethoxypropan-2-yl)phenoxy)-3-nitropyridine was prepared from 644b (43 mg, 0.20 mmol) and 2-chloro-3-nitropyridine (44 mg, 0.28 mmol) as described in 2a. (MH$^+$-MeOH)=287.

644d. 2-(2-(1,2-dimethoxypropan-2-yl)phenoxy)pyridin-3-amine was prepared from 644c (50 mg, 0.15 mmol), zinc dust (200 mg, 3.0 mmol) and ammonium chloride (166 mg, 3.0 mmol) in methanol-ethyl acetate (1:1) as described in 62c. (M+H)$^+$=289.

Example 644 was prepared according to the procedure described for Example 2 using 644d (45 mg, 0.15 mmol) and 4-trifluoromethoxy phenylisocyanate (30 μL, 0.20 mmol). (M+H)$^+$=492. $^1$H NMR (400 MHz, DMSO-d$_6$) δppm 1.47 (s, 3H), 2.98 (s, 3H), 3.17 (s, 3H), 3.53 (d, J=10.1 Hz, 1H), 3.63 (d, J=10.1 Hz, 1H), 7.06 (m, 2H), 7.27 (m, 1H), 7.33 (m, 2H), 7.53 (dd, J=8.1, 1.8 Hz, 1H), 7.58 (m, 2H), 7.68 (dd, J=4.8, 1.7 Hz, 1H), 8.52 (dd, J=8.0, 1.6 Hz, 1H), 8.64 (s, 1H), 9.63 (s, 1H).

Example 645

1-(2-(3,3-dimethyl-1-oxo-1,3-dihydroisobenzofuran-4-yloxy)pyridin-3-yl)-3-(4-(trifluoromethoxy)phenyl)urea 645a. 4-hydroxy-3,3-dimethylisobenzofuran-1(3H)-one: At −78° C., methylmagnesium bromide (3M in ether, 1.5 mL, 4.48 mmol) was added to a solution of 3-hydroxy phthalic anhydride (210 mg, 1.28 mmol, Fluka) in THF (5.0 mL). The mixture was stirred at −78° C. for 3.5 h and a 10% HCl solution and ethyl acetate was added. The separated aqueous solution was extracted twice with ethyl acetate and the combined organic layers were dried (anh. sodium sulfate), filtered and evaporated to afford a residue which was purified by reverse-phase HPLC. Two isomeric products were obtained and the structure was confirmed with nOe nmr experiments. The isomers formed were 4-hydroxy-3,3-dimethylisobenzofuran-1(3H)-one and 7-hydroxy-3,3-dimethylisobenzofuran-1(3H)-one and the ratio was (1:3). 4-hydroxy-3,3-dimethylisobenzofuran-1(3H)-one: $^1$H NMR (400 MHz, DMSO-d$_6$) δppm 1.64 (s, 6H), 7.13 (d, J=7.4 Hz, 1H), 7.23 (d, J=6.9 Hz, 1H), 7.38 (t, J=7.9 Hz, 1H), 10.15 (br. s, 1H). 7-hydroxy-3,3-dimethylisobenzofuran-1(3H)-one: $^1$H NMR (400 MHz, DMSO-d$_6$) δppm 1.55 (s, 6H), 6.86 (d, J=7.6 Hz, 1H), 7.01 (d, J=6.8 Hz, 1H), 7.51 (t, J=7.7 Hz, 1H), 10.10 (br. s, 1H).

645b. 3,3-dimethyl-4-(3-nitropyridin-2-yloxy)isobenzofuran-1(3H)-one was prepared from 645a (70 mg, 0.39 mmol) and 2-chloro-3-nitropyridine (80 mg, 0.51 mmol) as described in 2a. (M+H)$^+$=301.

645c. 4-(3-aminopyridin-2-yloxy)-3,3-dimethylisobenzofuran-1(3H)-one was prepared from 645b (43 mg, 0.14 mmol), zinc dust (182 mg, 2.8 mmol) and ammonium chloride (152 mg, 2.8 mmol) in methanol-ethyl acetate (1:1) as described in 62c. (M+H)$^+$=271.

Example 645 was prepared according to the procedure described for Example 2 using 645c (34 mg, 0.12 mmol) and 4-trifluoromethoxy phenylisocyanate (25 μL, 0.16 mmol). (M+H)⁺=474. ¹H NMR (400 MHz, DMSO-d₆) δppm 1.60 (s, 6H), 7.17 (dd, J=8.0, 4.8 Hz, 1H), 7.32 (d, J=8.6 Hz, 2H), 7.58 (m, 3H), 7.68 (t, J=7.7 Hz, 1H), 7.73 (m, 2H), 8.58 (dd, J=8.1, 1.8 Hz, 1H), 8.80 (s, 1H), 9.60 (s, 1H).

Example 646

1-(2-(2-(1-(tert-butyldimethylsilyloxy)-2-methylpropan-2-yl)phenoxy)pyridin-3-yl)-3-(4-(trifluoromethoxy)phenyl)urea 646a. 3,3-dimethylbenzofuran-2(3H)-one: To benzofuran-2(3H)-one (500 mg, 3.7 mmol) in THF (19 mL) at 0° C. was added the iodomethane (1.16 mL, 18.5 mmol) followed by the NaH (60%, 372 mg, 9.31 mmol). The mixture was allowed to reach 23° C. and stirred for 64 hours. The mixture was partitioned between 1N HCl and ethyl acetate, layers were separated. The aqueous layer was extracted twice with ethyl acetate. Combined organic layers were washed with NaHCO₃ sat, brine, dried over Na₂SO₄, filtered and concentrated in vacuo. The residue was purified by flash chromatography (Biotage™, silica, 15% ethyl acetate/85% hexanes). ¹H NMR (400 MHz, DMSO-d₆) δ ppm 7.44-7.47 (m, 1H), 7.30-7.35 (m, 1H), 7.20-7.23 (m, 1H), 7.16-7.20 (m, 1H), 1.43 (s, 6H).

646b. 2-(1-hydroxy-2-methylpropan-2-yl)phenol: To a solution of 646a (681 mg, 4.2 mmol) in THF (14 mL) at 0° C. was added lithium aluminium hydride (239 mg, 6.3 mmol). The mixture was allowed to reach 23° C. and stirred for 16 hours. The mixture was neutralized with Rochelle's salt, stirred for 30 min and extracted with ethyl acetate (3×). Combined organic layers were washed with water, brine, dried over Na₂SO₄, filtered and concentrated in vacuo. 1H NMR (400 MHz, DMSO-D6) δ ppm 1.25 (6H, s), 3.60 (2H, d, J=4.55 Hz), 4.71 (1H, t, J=5.05 Hz), 6.69 (1H, td, J=7.45, 1.26 Hz), 6.72 (1H, dd, J=7.83, 1.26 Hz), 6.97 (1H, td, J=7.58, 1.52 Hz), 7.12 (1H, dd, J=7.71, 1.64 Hz), 9.36 (1H, s).

646c. 2-(1-(tert-butyldimethylsilyloxy)-2-methylpropan-2-yl)phenol: To a solution of 646b (680 mg, 4.8 mmol) in DMF (5 mL) was added imidazole (696 mg, 10.2 mmol). Tert-butylchlorodimethylsilane (770 mg, 5.11 mmol) was added and stirred at 23° C. for 2 h. The mixture was partitioned between water and ethyl acetate, layers were separated. The aqueous layer was extracted twice with ethyl acetate. Combined organic layers were washed with water, brine, dried over Na₂SO₄, filtered and concentrated in vacuo. The residue was purified by flash chromatography (Biotage™, silica, 5% ethyl acetate/95% hexanes). 1H NMR (400 MHz, DMSO-d₆) δ ppm –0.09 (6H, s), 0.78 (9H, s), 1.27 (6H, s), 3.78 (2H, s), 6.68 (1H, td, J=7.45, 1.26 Hz), 6.73 (1H, dd, J=8.08, 1.26 Hz), 6.98 (1H, td, J=7.58, 1.52 Hz), 7.11 (1H, dd, J=7.83, 1.52 Hz), 9.28 (1H, s).

646d. 2-(2-(1-(tert-butyldimethylsilyloxy)-2-methylpropan-2-yl)phenoxy)-3-nitropyridine was prepared according to the procedures described for 2a using 646c (801 mg, 2.96 mmol), 2-chloro-3-nitro pyridine (453 mg, 2.96 mmol) and cesium carbonate (930 mg, 2.96 mmol). (M+H)⁺=403. 1H NMR (400 MHz, DMSO-d₆) δ ppm –0.13 (6H, s), 0.74 (9H, s), 1.23 (6H, s), 3.71 (2H, s), 7.03 (1H, dd, J=7.96, 1.39 Hz), 7.18 (1H, td, J=7.52, 1.39 Hz), 7.25 (1H, td, J=7.64, 1.64 Hz), 7.37 (1H, dd, J=7.83, 4.80 Hz), 7.42 (1H, dd, J=7.83, 1.77 Hz), 8.42 (1H, dd, J=4.80, 1.77 Hz), 8.58 (1H, dd, J=8.08, 1.77 Hz).

646e. 2-(2-(1-(tert-butyldimethylsilyloxy)-2-methylpropan-2-yl)phenoxy)pyridin-3-amine was prepared according to the procedure described for 2b using 646d (319 mg, 0.79 mmol). (M+H)⁺=403. 1H NMR (400 MHz, DMSO-d₆) δ ppm –0.12 (6H, s), 0.74 (9H, s), 1.23 (6H, s), 3.71 (2H, s), 7.03 (1H, dd, J=7.96, 1.39 Hz), 7.18 (1H, td, J=7.52, 1.39 Hz), 7.25 (1H, td, J=7.64, 1.64 Hz), 7.37 (1H, dd, J=7.83, 4.80 Hz), 7.42 (1H, dd, J=7.83, 1.77 Hz), 8.42 (1H, dd, J=4.80, 1.77 Hz), 8.58 (1H, dd, J=8.08, 1.77 Hz).

Example 646 was prepared according to the procedure described for Example 2 using 646e (200 mg, 0.54 mmol). (M+H)⁺=576. ¹H NMR (400 MHz, DMSO-d₆) δppm –0.09 (s, 6H), 0.78 (s, 9H), 1.29 (s, 6H), 3.69 (s, 2H), 6.95 (dd, J=8.1, 1.4 Hz, 1H), 7.09 (dd, J=7.8, 4.8 Hz, 1H), 7.18 (m, 1H), 7.27 (m, 1H), 7.32 (d, J=8.6 Hz, 2H), 7.47 (dd, J=7.8, 1.5 Hz, 1H), 7.57 (d, J=8.6 Hz, 2H), 7.70 (dd, J=4.8, 1.8 Hz, 1H), 8.52 (dd, J=8.0, 1.7 Hz, 1H), 8.69 (s, 1H), 9.61 (s, 1H).

Example 647

1-[2-(2-{1-[2-(tert-Butyl-dimethyl-silanyloxy)-ethoxy]-1-methyl-ethyl}-phenoxy)-pyridin-3-yl]-3-(4-trifluoromethoxy-phenyl)-urea 647a. 2-[1-(2-Hydroxy-ethoxy)-1-methyl-ethyl]-phenol was prepared according to the procedure described for 157a using ethylene glycol. (M–H)⁻=195; ¹H NMR (400 MHz, CDCl₃) δppm 1.65 (s, 6H), 1.82 (m, 1H), 3.46 (t, J=4.52 Hz, 2H), 3.78 (m, 2H), 6.83-6.88 (m, 2H), 7.08 (m, 1H), 7.20 (m, 1H), 8.45 (s, 1H).

647b. 2-{1-[2-(tert-Butyl-dimethyl-silanyloxy)-ethoxy]-1-methyl-ethyl}-phenol: A solution of 647a (242 mg, 1.23 mmol) in dichloromethane (5 ml) at 0° C. was treated with tert-butyl-dimethylsilyl chloride (204 mg, 1.35 mmol) and then with triethylamine (498 mg, 4.92 mmol) dropwise. The mixture was warmed to rt, stirred 17 h at rt and then concentrated under reduced pressure. The residue was diluted with dichloromethane and water, the organic layer was separated, dried (Na₂SO₄), filtered and concentrated under reduced pressure. The residue was purified by flash chromatography using a gradient of toluene in hexane (50 to 52%) to give 131 mg (34% yield) of 647b as a colorless oil. (M–H)⁻=309; ¹H NMR (400 MHz, CDCl₃) δppm 0.07 (s, 6H), 0.90 (s, 9H), 1.62 (s, 6H), 3.39 (t, J=4.9 Hz, 2H), 3.76 (t, J=4.9 Hz, 2H), 6.80-6.87 (m, 2H), 7.06 (m, 1H), 7.16 (m, 1H), 8.49 (s, 1H).

647c. 2-(2-{1-[2-(tert-Butyl-dimethyl-silanyloxy)-ethoxy]-1-methyl-ethyl}-phenoxy)-3-nitro-pyridine was prepared according to the procedure described for 157b using 647b. (M+H)⁺=433; ¹H NMR (400 MHz, CDCl₃) δppm 0.02 (s, 6H), 0.88 (s, 9H), 1.59 (s, 6H), 3.33 (t, J=5.7 Hz, 2H), 3.50 (t, J=5.7 Hz, 2H), 7.0 (m, 1H), 7.13 (m, 1H), 7.26-7.31 (m, 2H), 7.70 (m, 1H), 8.33 (m, 1H), 8.38 (m, 1H).

647d. 2-(2-{1-[2-(tert-Butyl-dimethyl-silanyloxy)-ethoxy]-1-methyl-ethyl}-phenoxy)-pyridin-3-ylamine was prepared according to the procedure described for Example 157c using 647c. (M+H)⁺=403; ¹H NMR (400 MHz, CDCl₃) δppm 0.04 (s, 6H), 0.89 (s, 9H), 1.60 (s, 6H), 3.37 (t, J=5.6 Hz, 2H), 3.65 (t, J=5.6 Hz, 2H), 6.82 (m, 1H), 7.02 (m, 1H), 7.10 (m, 1H), 7.16 (m, 1H), 7.28 (m 1H), 7.54 (m, 1H), 7.61 (m, 1H).

Example 647 was prepared according to the procedure described for Example 157 using 647d. (M–H)⁻=605; ¹H NMR (400 MHz, CDCl₃) δppm 0.00 (s, 6H), 0.82 (s, 9H), 1.53 (s, 6H), 3.39 (t, J=4.0 Hz, 2H), 3.98 (t, J=4.0 Hz, 2H), 6.82 (m, 1H), 7.01 (m, 1H), 7.16-7.21 (m, 3H), 7.38 (m, 1H), 7.42 (m 1H), 8.03 (s, 1H), 8.61 (m, 1H), 8.75 (s, 1H).

Example 648

Toluene-4-sulfonic acid 2-[1-methyl-1-(2-{3-[3-(4-trifluoromethoxy-phenyl)-ureido]-pyridin-2-yloxy}-phenyl)-ethoxy]-ethylester 648a. 1-(2-{2-[1-(2-Hydroxy-ethoxy)-1-methyl-ethyl]-phenoxy}-pyridin-3-yl)-3-(4-trifluoromethoxy-phenyl)-urea: A solution of 1-[2-(2-{1-{2-(tert-Butyl-dimethyl-silanyloxy)-ethoxy}-1-methyl}-phenoxy)-pyridin-3-yl]-3-(4-trifluoromethoxy-phenyl)-urea (173 mg, 0.29 mmol) in THF at rt was treated with a solution of tetrabutylammonium fluoride (1M) in tetrahydrofuran (0.435 ml, 0.43 mmol) and stirred at rt for 3 h. The mixture was diluted with ether and water, the organic layer was separated, dried (Na$_2$SO$_4$), filtered and concentrated under vacuum. The residue was purified by flash chromatography on silica gel using a gradient of ethyl acetate in toluene (18 and 19%) to give 133 mg (86% yield) of the title compound as a white foamy solid. (M–H)$^-$=490; $^1$H NMR (400 MHz, CDCl$_3$) δppm 1.58 (s, 6H), 2.62 (s(br), 1H) 3.42 (t, J=4.0 Hz, 2H), 3.94 (m, 2H), 7.1 (m, 1H), 7.14-7.20 (m, 3H), 7.29 (m, 1H), 7.37 (m, 2H), 7.51 (m 2H), 7.76 (m, 1H), 8.29 (s, 1H), 8.50 (s, 1H), 8.69 (m, 1H).

Example 648: A solution of 648a (67 mg, 0.14 mmol) in dichloromethane at rt was treated with triethylamine (21 mg, 0.21 mmol) and then with p-toluenesulfonylchloride (29 mg, 0.15 mmol). The mixture was stirred 30 min at 10° to 35° C. and retreated with trietylamine (29 mg, 0.29 mmol) and p-toluenesulfonyl chloride (40 mg, 0.21 mmol). The mixture was stirred 1 h at 35° C. and 2 days at rt. The mixture was purified directly by flash chromatography on silica gel using a gradient of ethyl acetate in toluene (15 to 17%) to give 76 mg (84% yield) of Example 647 as a white foamy solid. (M–H)$^-$=645; $^1$H NMR (400 MHz, CDCl$_3$) δppm 1.58 (s, 6H), 2.37 (s, 3H) 3.44 (m, 2H), 4.23 (m, 2H), 7.01 (m, 1H), 7.15-7.19 (m, 5H), 7.33-7.41 (m, 3H), 7.41-7.56 (m, 4H), 7.63 (m 2H), 7.77 (m, 1H), 8.02 (s, 1H), 8.56 (m, 1H).

Example 649

1-{2-[2-(1-Methyl-1-butoxy-ethyl)-phenoxy]pyridin-3-yl}-3-(4-trifluoromethoxy-phenyl)urea Example 649 was prepared using a similar procedure as described in Example 157. (M–H)$^-$=502; $^1$H NMR (400 MHz, CDCl$_3$) δppm 0.82 (t, J=7.6 Hz, 3H), 1.30 (m, 2H), 1.58-1.65 (m, 2H), 1.67 (s, 6H), 3.35 (t, J=7.3 Hz, 2H), 7.04 (m, 1H), 7.10 (s, 1H), 7.15-7.20 (m, 3H), 7.36-7.49 (m, 4H), 7.82 (m, 1H), 8.20 (m, 1H), 8.55 (m, 1H), 9.17 (s, 1H).

Example 650

1-(2-{2-[1-(2-Diisobutylamino-ethoxy)-1-methyl-ethyl]-phenoxy}-pyridin-3-yl)-3-(4-trifluoromethoxy-phenyl)-urea 650a. 1-(2-{2-[1-methyl-1-(2-morpholin-4-yl-ethoxy)-ethyl]-phenoxy}-pyridin-3-yl)-3-(4-trifluoromethoxy-phenyl)-urea: A solution of Example 648 (20 mg, 0.03 mmol) in dimethylformamide at rt was treated with triethylamine (5 mg, 0.045 mmol) and with morpholine (4 mg, 0.045 mmol). The mixture was stirred 4 days at 45° C., cooled to rt, treated with acetic acid (0.050 mL) and purified by preparative LC on YMC Pack C-18 using a gradient of acetonitrile in trifluoroacetic acid (0.1%) to give 17 mg (82% of the example as TFA salt. (M+H)$^+$=561; $^1$H NMR (400 MHz, CDCl$_3$) δppm 1.62 (s, 6H), 2.88 (m, 2H) 3.14 (t, J=5.2 Hz, 2H), 3.50 (t, J=5.2 Hz, 2H), 3.65 (m, 2H), 3.81-3.93 (m, 4H), 6.92 (m, 1H), 7.01 (m, 1H), 7.14-7.19 (m, 3H), 7.31-7.36 (m, 2H), 7.51 (m, 2H), 7.76 (m 1H), 8.36 (s, 1H), 8.66 (m, 1H), 9.31 (s, 1H).

Example 650 (TFA salt) was prepared using a similar procedure as described in Example 649 using diisobutylamine. (M+H)$^+$=603; $^1$H NMR (400 MHz, CDCl$_3$) δppm 0.99 (d, 12H), 1.67 (s, 6H), 2.09 (m, 2H), 2.95-3.04 (m, 2H), 3.24-3.33 (m, 2H), 3.32 (m, 2H), 3.62 (m, 2H), 6.94 (m, 1H), 7.10 (s, 1H), 7.15-7.26 (m, 4H), 7.33-7.40 (m, 2H), 7.54 (m, 2H), 7.77 (m, 1H), 8.47 (s(br), 1H), 8.69 (m, 1H).

Example 651

1-(2-{2-[1-(2-Isobutylsulfanyl-ethoxy)-1-methyl-ethyl]-phenoxy}-pyridin-3-yl)-3-(4-trifluoromethoxy-phenyl)-urea A solution of Example 648 (15 mg, 0.023 mmol) in tetrahydrofuran at rt was treated with 2-methyl-1-propanethiol (3 mg, 0.035 mmol) and sodium hydride (60%) (1 mg, 0.025 mmol). The mixture was stirred 10 min at rt and 15 min at 40° C., cooled to rt and diluted with dichloromethane and brine. The organic layer was separated, dried (Na$_2$SO$_4$), filtered and concentrated under vacuum. The residue was purified by preparative LC on YMC Pack C-18 using a gradient of acetonitrile in trifluoroacetic acid (0.1%) to give 10 mg (78%) of Example 651. (M–H)$^-$=562; $^1$H NMR (400 MHz, CDCl$_3$) δppm 0.87 (d, J = 7.1 Hz, 6H), 1.63 (s, 6H), 1.66 (m, 1H), 2.33 (d, J=7.2 Hz, 2H), 2.76 (t, J=5.7 Hz, 2H), 3.49 (t, J=5.7 Hz, 2H), 7.04 (m, 1H), 7.17-7.20 (m, 3H), 7.36-7.42 (m, 2H), 7.56 (m, 2H), 7.78 (s, 1H), 7.81 (m 1H), 7.93 (m, 1H), 8.62 (m, 1H), 8.72 (s, 1H).

Example 652

1-[2-(2-{1-Methyl-1-[2-(pyridin-2-ylsulfanyl)-ethoxy]-phenoxy)-pyridin-3-yl]-3-(4-trifluoromethoxy-phenyl)-urea Example 652 was prepared using a similar procedure as described in Example 651 using 2-mercaptopyridine. (M+H)$^+$=585; $^1$H NMR (400 MHz, CDCl$_3$) δppm 1.54 (s, 6H), 3.43-3.48 (m, 4H), 6.99-7.03 (m, 2H), 7.11-7.14 (m, 3H), 7.19 (m, 1H), 7.26-7.32 (m, 2H), 7.37-7.47 (m, 4H), 7.77 (m, 1H), 8.37 (m, 1H), 8.45 (m, 1H), 8.63 (m, 1H), 8.68 (s, 1H).

Example 653

1-[2-(2-{1-[2-(Furan-2-ylmethylsulfanyl)-ethoxy]-1-methyl-ethyl}-phenoxy)-pyridin-3-yl]-3-(4-trifluoromethoxy-phenyl)-urea Example 653 was prepared using a similar procedure as described in Example 651 using 2-furanmethanethiol. (M+H)$^+$=588; $^1$H NMR (400 MHz, CDCl$_3$) δppm 1.65 (s, 6H), 2.80 (t, J=5.8 Hz, 2H), 3.49 (t, J=5.8 Hz, 2H), 3.71 (s, 2H), 6.04 (m, 1H), 6.21 (m, 1H), 7.06 (m, 1H), 7.18-7.24 (m, 3H), 7.37-7.45 (m, 3H), 7.55 (m, 2H), 7.61 (s, 1H), 7.83 (m, 1H), 8.02 (m, 1H), 8.63 (m, 1H), 8.66 (s, 1H).

Example 654

1-[2-(2-{1-Methyl-1-[2-(2-methyl-propane-1-sulfinyl)-ethoxy)-ethyl}-phenoxy)-pyridin-3-yl]-3-(4-trifluoromethoxy-phenyl)-urea A solution of 1-(2-{2[1-(2-isobutylsulfanyl-ethoxy)-1-methyl-ethyl]-phenoxy}-pyridin-3-yl)-3-(4-trifluoromethoxy-phenyl)-urea (3.2 mg, 0.0056 mmol) in dichloromethane (1 mL) at –20° C. was treated dropwise with a solution of 3-chloroperbenzoic acid (80%, 2 mg, 0.0092 mmol) in dichloromethane (1 mL) and the mixture was stirred 45 min at –20° C. The mixture was treated with a solution of sodium bicarbonate (sat), diluted with dichloromethane and the organic layer was separated, dried (Na$_2$SO$_4$), filtered and concentrated under vacuum. The residue was purified by flash chromatography on silica gel using a gradient of ethyl acetate in toluene (15 and 16%) to give 2.0 mg of Example 654. (M+Na+CH$_3$CN)$^+$=642; $^1$H NMR (400 MHz, CDCl$_3$) δppm 1.05 (d, J=6.9 Hz, 6H), 1.60 (s, 6H), 2.25 (m, 1H), 3.23 (d, J=6.9 Hz, 2H), 3.25 (t, J=5.4 Hz, 2H), 3.66 (t, J=5.4 Hz, 2H), 6.92 (m, 1H), 7.07 (m, 1H), 7.17-7.22 (m, 3H), 7.34 (m, 1H), 7.44 (m, 1H), 7.58 (m, 2H), 7.81 (m, 1H), 8.06 (s, 1H), 8.52 (s, 1H), 8.75 (m, 1H).

Example 655

1-[2-(2-{1-Methyl-1-[2-(pyridine-2-sulfonyl)-ethoxy)-ethyl}-phenoxy)-pyridin-3-yl]-3-(4-trifluoromethoxy-phenyl)-urea Example 655 was prepared using a similar procedure as described in Example 654 using Example 652. (M+H)$^+$=617; $^1$H NMR (400 MHz, CDCl$_3$) δppm 1.34 (s, 6H), 3.62 (m 2H), 3.70 (m, 2H), 7.04 (m, 2H), 7.08-7.13 (m, 3H), 7.24-7.32 (m, 2H), 7.43 (m 1H), 7.60 (m, 2H), 7.77 (m, 1H), 7.81 (m 1H), 8.01 (m, 1H), 8.30 (s, 1H), 8.61 (m, 1H), 8.65 (s, 1H), 8.69 (m, 1H).

Examples 656 was prepared according to the procedure described for the preparation of Example 634 (using 634a as starting material). Examples 657 to 680 were prepared according to the procedure described for the preparation of Example 632 (using 238f as starting material).

Example 681

1-(2-(2-tert-butylphenoxy)pyridin-3-yl)-3-(4-vinylphenyl)urea

Example 681 was isolated from the reaction conditions of Example 213. C$_{24}$H$_{25}$N$_3$O$_2$ [M+H]$^+$ 388.19.

Tables 1-6 below summarize examples of the prepared compounds in the present invention.

TABLE 1

| Ex # | Y | R$^1$ | R$^2$ | R$^3$ | R$^4$ | R$^5$ | R$^6$ | MS (M + 1) |
|---|---|---|---|---|---|---|---|---|
| 1 | O | H | H | t-Bu | H | H | 2-i-Pr-Ph | 404.67 |
| 2 | O | H | H | OCF$_3$ | H | H | 2-t-Bu-Ph | 446.12 |
| 3 | O | H | H | cyclohexyl | H | H | 2-t-Bu-Ph | 444.19 |
| 4 | O | H | H | O-t-Bu | H | H | 2-t-Bu-Ph | 434.38 |
| 5 | O | F | H | F | H | H | 2-CF$_3$-Ph | 410.13 |
| 6 | O | F | H | F | H | H | 3-Et-Ph | 370.43 |
| 7 | O | F | H | F | H | H | 3-Ph-Ph | 418.37 |
| 8 | O | F | H | F | H | H | 2-i-Pr-Ph | 384.43 |
| 9 | O | H | CF$_3$ | H | H | H | 3-CF$_3$-Ph | 404.11 |
| 10 | O | H | Cl | Me | H | H | 3-CF$_3$-Ph | 422.08 |
| 11 | O | H | CF$_3$ | Cl | H | H | 3-CF$_3$-Ph | 476.06 |
| 12 | O | H | (fused phenyl R$^2$/R$^3$) | | H | H | 3-CF$_3$-Ph | 424.11 |
| 13 | O | H | Cl | F | H | H | 3-CF$_3$-Ph | 426.04 |
| 14 | O | H | H | Ph | H | H | 3-CF$_3$-Ph | 450.15 |
| 15 | O | H | H | t-Bu | H | H | 3-CF$_3$-Ph | 430.16 |
| 16 | O | H | F | F | H | H | 3-CF$_3$-Ph | 410.08 |
| 17 | O | H | H | Bn | H | H | 3-CF$_3$-Ph | 464.16 |
| 18 | O | H | H | Ph | H | H | 2-i-Pr-Ph | 424.60 |
| 19 | O | H | H | OCF$_3$ | H | H | 2-i-Pr-Ph | 432.57 |
| 20 | O | H | H | t-Bu | H | H | 2-i-Pr-Ph | 404.67 |
| 21 | O | H | H | Ph | H | H | 2-t-Bu-Ph | 438.26 |
| 22 | O | H | H | t-Bu | H | H | 2-t-Bu-Ph | 418.32 |
| 23 | O | H | H | Me | H | H | 2-t-Bu-Ph | 376.68 |
| 24 | O | H | H | t-Bu | H | H | 3-t-Bu-Ph | 418.68 |

TABLE 1-continued

| Ex # | Y | R¹ | R² | R³ | R⁴ | R⁵ | R⁶ | MS (M + 1) |
|---|---|---|---|---|---|---|---|---|
| 25 | O | F | H | Cl | H | H | 2-t-Bu-Ph | 414.34 |
| 26 | O | F | H | Me | H | H | 2-t-Bu-Ph | 394.41 |
| 27 | S | H | H | Me | H | H | 2-t-Bu-Ph | 392.40 |
| 28 | O | H | H | NMe₂ | H | H | 2-t-Bu-Ph | 405.22 |
| 29 | O | H | H | OCF₃ | H | H | 2-Pr-Ph | 432.10 |
| 30 | O | H | H | CF₃ | H | H | 2-t-Bu-Ph | 430.17 |
| 31 | O | H | H | OMe | H | H | 2-t-Bu-Ph | 392.20 |
| 32 | O | H | H | OPh | H | H | 2-t-Bu-Ph | 454.35 |
| 33 | O | H | H | O-i-Pr | H | H | 2-t-Bu-Ph | 420.20 |
| 34 | O | H | H | OCF₃ | H | H | 2-OCF₃-Ph | 474.21 |
| 35 | O | H | H | NMe₂ | H | H | 2-OCF₃-Ph | 432.21 |
| 36 | O | H | H | t-Bu | H | H | 2-OCF₃-Ph | 446.31 |
| 37 | O | H | H | O-t-Bu | H | H | 2-OCF₃-Ph | 462.31 |
| 38 | O | H | \[pyrimidinyl fused\] | | H | H | 2-t-Bu-Ph | 413.34 |
| 39 | O | H | H | NHPh | H | H | 2-t-Bu-Ph | 453.06 |
| 40 | O | H | \[N-ethyl-o-toluidinyl\] | | H | H | 2-t-Bu-Ph | 479.23 |
| 41 | O | H | H | NEt₂ | H | H | 2-t-Bu-Ph | 433.25 |
| 42 | O | H | H | morpholinyl | H | H | 2-t-Bu-Ph | 447.24 |
| 43 | O | F | H | F | H | H | 3-CF₃-Ph | 410.09 |
| 44 | O | H | H | —CH₂CO₂Me | H | H | 2-t-Bu-Ph | 434.29 |
| 45 | O | H | H | —C(Me)₂CO₂Me | H | H | 2-t-Bu-Ph | 464.25 |
| 53 | O | H | H | 5-Me-3-CO₂Et-pyrazol-1-yl | H | H | 2-t-Bu-Ph | 514.34 |
| 54 | O | F | H | 2-CH₂N(Me)₂-Ph | H | H | 2-t-Bu-Ph | 513.28 |
| 55 | O | F | H | morpholinyl | H | H | 2-t-Bu-Ph | 465.33 |

TABLE 1-continued

| Ex # | Y | R¹ | R² | R³ | R⁴ | R⁵ | R⁶ | MS (M + 1) |
|---|---|---|---|---|---|---|---|---|
| 83 | NH | H | H | t-Bu | H | H | 2-t-Bu-Ph | 417.36 |
| 98 | O | H | H | cyclopropyl-CO₂Me | H | H | 2-t-Bu-Ph | 460.11 |
| 99 | O | H | H | cyclobutyl-CO₂Me | H | H | 2-t-Bu-Ph | 474.14 |
| 100 | O | H | H | cyclopentyl-CO₂Me | H | H | 2-t-Bu-Ph | 488.39 |
| 101 | O | H | H | cyclohexyl-CO₂Me | H | H | 2-t-Bu-Ph | 502.40 |
| 102 | O | H | H | cyclopropyl-CH₂OMe | H | H | 2-t-Bu-Ph | 446.14 |
| 103 | O | H | H | OCF₃ | H | H | 2-SiMe₃-Ph | 462.05 |
| 104 | O | H | H | OCF₃ | H | H | 3-SiMe₃-Ph | 462.27 |
| 105 | O | H | H | t-Bu | H | H | 2-SiMe₃-Ph | 434.33 |
| 106 | O | H | H | OCF₃ | H | H | 2-cyclopentyl-Ph | 458.30 |
| 107 | O | H | H | piperidinyl | H | H | 2-t-Bu-Ph | 445.32 |
| 108 | O | H | H | 4-Bn-piperazinyl | H | H | 2-t-Bu-Ph | 536.19 |
| 113 | O | F | H | O-i-Pr | H | H | 2-t-Bu-Ph | 438.2 |
| 114 | O | H | Br | OCF₃ | H | H | 2-t-Bu-Ph | 524.1 |
| 115 | O | F | H | OEt | H | H | 2-t-Bu-Ph | 424.2 |

TABLE 1-continued
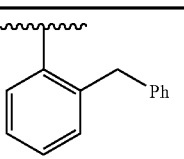
| Ex # | Y | R¹ | R² | R³ | R⁴ | R⁵ | R⁶ | MS (M + 1) |
|---|---|---|---|---|---|---|---|---|
| 116 | O | H | H | OCF₃ | H | H | 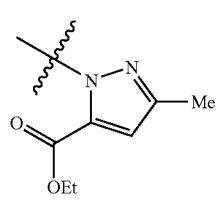 | 480.21 |
| 117 | O | F | H | OMe | H | H | 2-t-Bu-Ph | 410.2 |
| 118 | O | H | H | 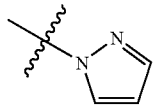 | H | H | 2-t-Bu-Ph | 514.3 |
| 119 | O | H | NO₂ | OCF₃ | H | H | 2-t-Bu-Ph | 491.2 |
| 120 | O | H | H | 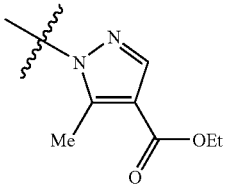 | H | H | 2-t-Bu-Ph | 428.15 |
| 121 | O | H | H | 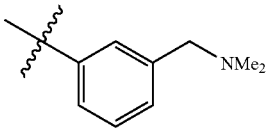 | H | H | 2-t-Bu-Ph | 514.19 |
| 122 | O | F | H | 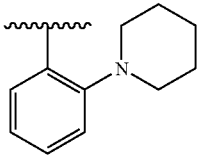 | H | H | 2-t-Bu-Ph | 513.44 |
| 123 | O | H | H | OCF₃ | H | H | 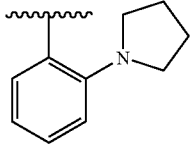 | 473.44 |
| 124 | O | H | H | OCF₃ | H | H |  | 459.5 |

TABLE 1-continued

| Ex # | Y | R¹ | R² | R³ | R⁴ | R⁵ | R⁶ | MS (M + 1) |
|---|---|---|---|---|---|---|---|---|
| 125 | O | F | H | 4-(CH₂NMe₂)-Ph | H | H | 2-t-Bu-Ph | 513.3 |
| 126 | O | H | H | OCF₃ | H | H | 2-S(i-Pr)-Ph | 464.26 |
| 127 | O | H | H | OCF₃ | H | H | 2-I-Ph | 516 |
| 128 | O | F | H | 2-(CH₂OH)-Ph | H | H | 2-t-Bu-Ph | 486 |
| 129 | O | H | H | OCF₃ | H | H | 2-SMe-Ph | 436 |
| 130 | O | H | H | OCF₃ | H | H | 3-COPh-Ph | 494 |
| 131 | O | H | H | OCF₃ | H | H | 2-t-Bu-6-CN-Ph | 471.2 |
| 132 | O | H | H | OCF₃ | H | H | 2-(C(Pr)(Pr)OH)-Ph | 504 |
| 133 | O | H | pyrrolidinyl | | H | H | 2-t-Bu-Ph | 403.09 |
| 134 | O | H | indanonyl | | H | H | 2-t-Bu-Ph | 464.07 |
| 135 | O | H | H | OCF₃ | H | H | 2-(1-Bn-piperidin-4-yl)-Ph | 563 |

TABLE 1-continued

| Ex # | Y | R¹ | R² | R³ | R⁴ | R⁵ | R⁶ | MS (M + 1) |
|---|---|---|---|---|---|---|---|---|
| 136 | O | H | | cyclopentanone | H | H | 2-t-Bu-Ph | 416.06 |
| 137 | O | H | H | OCF₃ | H | H | 2-(1-hydroxy-1-diallyl)-Ph | 500 |
| 138 | O | F | H | OP(O)(OEt)₂ | H | H | 2-t-Bu-Ph | 532.3 |
| 139 | O | H | H | OCF₃ | H | H | 2-(4-Bn-piperazin-1-yl)-Ph | 564 |
| 140 | O | H | H | 1-(hydroxymethyl)cyclopropyl | H | H | 2-t-Bu-Ph | 432 |
| 141 | O | H | H | OCF₃ | H | H | 2-Me-5-F-Ph | 421.2 |
| 142 | O | H | H | NH₂ | H | H | 2-t-Bu-Ph | 377.14 |
| 143 | O | H | H | OCF₃ | H | H | 2-[2-(5-(4-methoxyphenyl)-4,5-dihydro-1,2,4-oxadiazol-3-yl)propan-2-yl]-Ph | 608 |

TABLE 1-continued
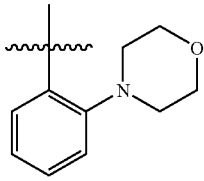
| Ex # | Y | R¹ | R² | R³ | R⁴ | R⁵ | R⁶ | MS (M + 1) |
|---|---|---|---|---|---|---|---|---|
| 144 | O | H | H | OCF₃ | H | H | 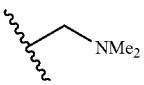 | 475 |
| 145 | O | F | H | 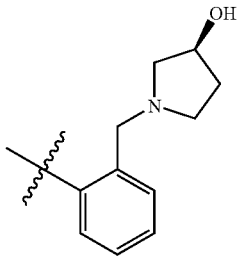 | H | H | 2-t-Bu-Ph | 437.2 |
| 146 | O | F | H | 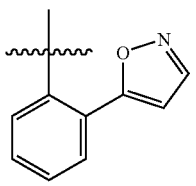 | H | H | 2-t-Bu-Ph | 555.36 |
| 147 | O | H | H | OCF₃ | H | H | 2,3-di-OMe-Ph | 450.05 |
| 148 | O | H | H | OCF₃ | H | H | 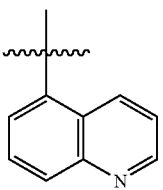 | 457 |
| 149 | O | H | H | OCF₃ | H | H | 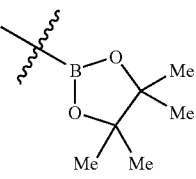 | 441 |
| 150 | O | H | H |  | H | H | 2-t-Bu-Ph | 488.07 |

TABLE 1-continued

| Ex # | Y | R¹ | R² | R³ | R⁴ | R⁵ | R⁶ | MS (M + 1) |
|---|---|---|---|---|---|---|---|---|
| 151 | O | H | 2-(Me₂NCH₂)-Ph | H | H | H | 2-t-Bu-Ph | 495.24 |
| 152 | O | H | H | CH(OH)Me | H | H | 2-t-Bu-Ph | 406.21 |
| 153 | O | H | H | OCF₃ | H | H | 2-(C(Me)₂OEt)-Ph | 430 (M − EtOH) |
| 154 | O | H | H | OCF₃ | H | H | 2-(C(Et)₂OEt)-Ph | 502 (M − H) |
| 155 | O | H | H | OCF₃ | H | H | 2-(C(Me)₂OMe)-Ph | 460 (M − H) |
| 156 | O | H | H | OCF₃ | H | H | 2-(C(Et)₂OMe)-Ph | 488 (M − H) |
| 157 | O | H | H | OCF₃ | H | H | 2-(C(Me)₂OPr)-Ph | 488 (M − H) |

TABLE 1-continued

| Ex # | Y | R¹ | R² | R³ | R⁴ | R⁵ | R⁶ | MS (M + 1) |
|------|---|----|----|----|----|----|----|-----------|
| 158 | O | H | H | OCF₃ | H | H | 3-(C(Me)₂OEt)-Ph | 476 |
| 159 | O | H | H | OCF₃ | H | H | 2-(C(Me)₂O(CH₂)₂OMe)-Ph | 506 |
| 160 | O | H | H | OCF₃ | H | H | 2-(CH(Me)O(CH₂)₂OMe)-Ph | 492 |
| 161 | O | H | H | OCF₃ | H | H | 2-(C(Me)₂CN)-Ph | 457 |
| 162 | O | H | H | OCF₃ | H | H | 2-vinyl-Ph | 416 |
| 163 | O | H | H | OCF₃ | H | H | 2-(isopropenyl)-Ph | 430 |
| 164 | O | H | H | OCF₃ | H | H | 2-cyclopropyl-Ph | 430 (M − EtOH) |
| 165 | O | H | H | OCF₃ | H | H | 2-(CH=CH-CO₂(t-Bu))-Ph | 516 |
| 280 | O | F | H | Me | H | H | 3-CF₃-Ph | 406.55 |

TABLE 1-continued

| Ex # | Y | R¹ | R² | R³ | R⁴ | R⁵ | R⁶ | MS (M + 1) |
|---|---|---|---|---|---|---|---|---|
| 281 | O | F | H | Cl | H | H | 3-CF₃-Ph | 426.45 |
| 282 | O | H | H | Me | H | H | 2-t-Bu-Ph | 375.24 |
| 283 | O | H | Me | H | H | H | 2-t-Bu-Ph | 375.25 |
| 284 | O | H | Cl | Me | H | H | 2-t-Bu-Ph | 410.6 |
| 285 | O | H | H | Br | H | H | 2-t-Bu-Ph | 440.48 |
| 286 | O | H | Cl | Me | H | H | 2-t-Bu-Ph | 410.59 |
| 287 | O | H | H | Br | H | H | 2-i-Pr-Ph | 426.5 |
| 288 | O | H | Me | Me | H | H | 2-t-Bu-Ph | 390.67 |
| 289 | O | H | H | OCF₃ | H | H | 3-i-Pr-Ph | 432.56 |
| 290 | O | H | H | Me | H | H | 2-i-Pr-Ph | 362.69 |
| 291 | O | H | Cl | Cl | H | H | 2-t-Bu-Ph | 428.34 (M − H) |
| 292 | O | H | H | Me | H | H | 2-Pr-Ph | 362.14 |
| 293 | O | H | Me | Me | H | H | 2-i-Pr-Ph | 376.69 |
| 294 | O | F | H | F | H | H | 2-t-Bu-Ph | 398.43 |
| 295 | O | H | Cl | Me | H | H | 2-i-Pr-Ph | 396.6 |
| 296 | O | H | H | Me | H | H | 2-i-Bu-Ph | 376.15 |
| 297 | O | H | H | OCF₃ | H | H | 2-Et-Ph | 415.69 (M − H) |
| 298 | O | H | H | Ph | H | H | 3-i-Pr-Ph | 424.61 |
| 299 | O | H | H | Me | H | H | 3-t-Bu-Ph | 376.67 |
| 300 | O | H | Cl | Cl | H | H | 3-t-Bu-Ph | 430.49 |
| 301 | O | H | H | Br | H | H | 3-t-Bu-Ph | 440.48 |
| 302 | O | H | Me | Me | H | H | 2-Et-Ph | 362.68 |
| 303 | O | F | H | F | H | H | 3-t-Bu-Ph | 398.43 |
| 304 | O | H | H | t-Bu | H | H | 3-Et-Ph | 390.68 |
| 305 | O | H | H | Ph | H | H | 3-Et-Ph | 410.61 |
| 306 | O | H | Cl | Cl | H | H | 3-i-Pr-Ph | 415.61 (M − H) |
| 307 | O | H | H | Me | H | H | 3-Ph-Ph | 396.61 |
| 308 | O | H | Me | Me | H | H | 3-t-Bu-Ph | 390.68 |
| 309 | O | H | H | OCF₃ | H | H | 2-i-Bu-Ph | 446.04 |
| 310 | O | H | H | Me | H | H | 3-Et-Ph | 348.68 |
| 311 | O | F | H | F | H | H | 3-i-Pr-Ph | 384.42 |
| 312 | O | H | H | Ph | H | H | 2-Et-Ph | 410.63 |
| 313 | O | H | H | OCF₃ | H | H | 3-Et-Ph | 415.62 (M − H) |
| 314 | O | H | Me | Me | H | H | 2-i-Pr-Ph | 376.68 |
| 315 | O | H | H | t-Bu | H | H | 2-Et-Ph | 390.69 |
| 316 | O | H | Cl | Me | H | H | 2-Et-Ph | 382.6 |
| 317 | O | F | H | F | H | H | 2-OCF₃-Ph | 426.29 |
| 318 | O | H | H | Ph | H | H | 3-Ph-Ph | 458.54 |
| 319 | O | H | H | Ph | H | H | 2-OCF₃-Ph | 466.48 |
| 320 | O | H | Cl | Me | H | H | 3-Et-Ph | 382.6 |
| 321 | O | H | H | OCF₃ | H | H | 2-t-Bu-5-Me-Ph | 460.2 |
| 322 | O | H | Me | Me | H | H | 2-OCF₃-Ph | 418.57 |
| 323 | O | H | H | Me | H | H | 2-Et-Ph | 348.68 |
| 324 | O | H | H | Me | H | H | 2-i-Pr-5-Me-Ph | 375.95 |
| 325 | O | H | H | Br | H | H | 3-Et-Ph | 412.49 |
| 326 | O | H | H | OCF₃ | H | H | 2-i-Pr-5-Me-Ph | 446.14 |
| 327 | O | H | H | OCF₃ | H | H | 3-Ph-Ph | 466.46 |
| 328 | O | F | H | F | H | H | 2-Et-Ph | 370.43 |
| 329 | O | H | H | Br | H | H | 3-Ph-Ph | 460.42 |
| 330 | O | H | H | Ph | H | H | 3-t-Bu-Ph | 438.62 |
| 331 | O | H | Cl | Cl | H | H | 3-Et-Ph | 402.52 |
| 332 | O | H | H | Br | H | H | 2-Et-Ph | 410.17 (M − H) |
| 333 | O | H | Me | Me | H | H | 3-Et-Ph | 362.69 |
| 334 | O | H | Cl | Cl | H | H | 2-i-Pr-Ph | 416.51 |
| 335 | O | H | H | t-Bu | H | H | 3-Ph-Ph | 438.62 |
| 336 | O | F | H | F | H | H | 2-Ph-Ph | 418.35 |
| 337 | O | F | H | F | H | H | 3-OCF₃-Ph | 426.31 |

TABLE 1-continued

| Ex # | Y | R¹ | R² | R³ | R⁴ | R⁵ | R⁶ | MS (M + 1) |
|---|---|---|---|---|---|---|---|---|
| 338 | O | F | H | F | H | H | 3-CF₃-Ph | 409.01 |
| 339 | O | F | H | F | H | H | 2-F-3-CF₃-Ph | 428.3 |
| 340 | O | F | H | F | H | H | 1-naphthyl | 392.39 |
| 341 | O | F | H | F | H | H | 3-Br-Ph | 418.42 (M − H) |
| 342 | O | F | H | F | H | H | 2-Cl-5-CF₃-Ph | 444.23 |
| 343 | O | H | Me | Me | H | H | 3-Ph-Ph | 410.62 |
| 344 | O | F | H | F | H | H | 2,3-di-Cl-Ph | 410.26 |
| 345 | O | F | H | F | H | H | 3-Me-Ph | 356.48 |
| 346 | O | H | Cl | Cl | H | H | 3-Ph-Ph | 450.43 |
| 347 | O | H | H | OCF₃ | H | H | 2-i-Bu-4-Me-Ph | 460.15 |
| 348 | O | F | H | F | H | H | 2-Me-Ph | 356.49 |
| 349 | O | F | H | F | H | H | 2,6-di-Me-Ph | 370.12 |
| 350 | O | H | Cl | Cl | H | H | 2-Et-Ph | 402.51 |
| 351 | O | H | H | Me | H | H | 2-t-Bu-cyclohexyl | 380.42 (M − H) |
| 352 | O | F | H | F | H | H | 2-F-5-CF₃-Ph | 426.32 (M − H) |
| 353 | NH | H | H | OCF₃ | H | H | 2-t-Bu-Ph | 446.12 |
| 354 | O | F | H | Br | H | H | 2-CF₃-Ph | 470.14 |
| 355 | O | F | H | Br | H | H | 2-t-Bu-Ph | 458.23 |
| 356 | O | H | H | —C(Me)₂CO₂Me | H | H | 2-t-Bu-Ph | 478.29 |
| 357 | O | H | H | —C(CF₃)₂OH | H | H | 2-t-Bu-Ph | 528.27 |
| 358 | O | H | H | —C(Me)₂CH₂OH | H | H | 2-t-Bu-Ph | 434.40 |
| 359 | O | H | H | O-t-Bu | H | H | 2-CF₃-Ph | 446.32 |
| 360 | O | H | H | t-Bu | H | H | 2-(OCH₂CO₂(t-Bu))-Ph | 492.33 |
| 361 | O | H | H | OCF₃ | H | H | 2-(OCH₂CO₂(t-Bu))-Ph | 520.26 |
| 362 | O | H | H | Me | H | H | 2-CF₃-Ph | 388.22 |
| 363 | O | H | H | OCF₃ | H | H | 2-CF₃-Ph | 458.23 |
| 364 | O | H | H | —C(Me)₂OH | H | H | 2-t-Bu-Ph | 420.2 |
| 365 | O | H | H | OCF₃ | H | H | 3-(cyclopent-1-enyl)pyridin-2-yl | 457.1 |
| 366 | O | H | H | OCF₃ | H | H | 3-cyclopentylpyridin-2-yl | 459.1 |
| 367 | O | F | H | H | H | H | 3-CF₃-Ph | 392.11 |
| 368 | O | H | H | OMe | H | H | 3-CF₃-Ph | 404.04 |

TABLE 1-continued

| Ex # | Y | R¹ | R² | R³ | R⁴ | R⁵ | R⁶ | MS (M + 1) |
|---|---|---|---|---|---|---|---|---|
| 369 | O | H | H | OPh | H | H | 3-CF₃-Ph | 466.10 |
| 370 | O | H | H | Me | H | H | 3-CF₃-Ph | 388.13 |
| 371 | O | H | Cl | H | H | H | 3-CF₃-Ph | 408.09 |
| 372 | O | H | Cl | Cl | H | H | 3-CF₃-Ph | 441.96 (M − H) |
| 373 | O | H | Me | H | H | H | 3-CF₃-Ph | 388.13 |
| 374 | O | H | H | Br | H | H | 3-CF₃-Ph | 452.02 |
| 375 | O | H | H | F | H | H | 3-CF₃-Ph | 392.09 |
| 376 | O | H | H | Cl | H | H | 3-CF₃-Ph | 408.08 |
| 377 | O | H | H | CF₃ | H | H | 3-CF₃-Ph | 442.10 |
| 378 | O | F | H | H | F | H | 3-CF₃-Ph | 410.08 |
| 379 | O | H | Cl | H | Cl | H | 3-CF₃-Ph | 442.02 |
| 380 | O | H | Me | Me | H | H | 3-CF₃-Ph | 402.13 |
| 381 | O | H | Me | H | Me | H | 3-CF₃-Ph | 402.12 |
| 382 | O | H | H | OCF₃ | H | H | 3-CF₃-Ph | 458.1 |
| 383 | O | H | F | Me | H | H | 3-CF₃-Ph | 406 |
| 384 | O | H | H | OCH₂Ph | H | H | 3-CF₃-Ph | 480.15 |
| 385 | O | F | H | H | Me | H | 3-CF₃-Ph | 406.10 |
| 386 | O | H | H | OCHF₂ | H | H | 3-CF₃-Ph | 440.09 |
| 387 | O | H | OPh | H | H | H | 3-CF₃-Ph | 466.12 |
| 388 | O | H | —(CH₂)₄— (R²–R³ fused ring) | | H | H | 3-CF₃-Ph | 414.13 |
| 389 | O | H | Cl | OMe | H | H | 3-CF₃-Ph | 438.07 |
| 390 | O | H | F | H | F | H | 2-t-Bu-Ph | 410.09 |
| 391 | O | F | H | H | H | H | 2-t-Bu-Ph | 380.19 |
| 392 | O | Cl | H | H | H | H | 2-t-Bu-Ph | 396.15 |
| 393 | O | OH | H | H | H | H | 2-t-Bu-Ph | 378.19 |
| 394 | O | H | CN | H | H | H | 2-t-Bu-Ph | 387.20 |
| 395 | O | H | Cl | H | H | H | 2-t-Bu-Ph | 396.17 |
| 396 | O | H | Cl | OMe | H | H | 2-t-Bu-Ph | 426.17 |
| 397 | O | H | Cl | H | H | OMe | 2-t-Bu-Ph | 426.17 |
| 398 | O | H | OMe | H | H | H | 2-t-Bu-Ph | 392.20 |
| 399 | O | H | Me | H | H | H | 2-t-Bu-Ph | 376.21 |
| 400 | O | H | H | CN | H | H | 2-t-Bu-Ph | 387.19 |
| 401 | O | H | H | Cl | H | H | 2-t-Bu-Ph | 396.15 |
| 402 | O | H | H | COMe | H | H | 2-t-Bu-Ph | 404.20 |
| 403 | O | H | OPh | H | H | H | 3-CF₃-Ph | 454.21 |
| 404 | O | H | OCF₃ | H | H | H | 2-t-Bu-Ph | 458.10 |
| 405 | O | H | Cl | H | OMe | H | 2-t-Bu-Ph | 426.16 |
| 406 | O | H | Ph | H | H | H | 2-t-Bu-Ph | 438.24 |
| 407 | O | H | Ph | H | H | H | 3-CF₃-Ph | 450.15 |
| 408 | O | H | H | cyclohexyl | H | H | 2-t-Bu-Ph | 454.53 (M − H) |
| 409 | O | H | H | H | H | H | 2-t-Bu-Ph | 360.19 |
| 410 | O | H | F | H | H | H | 2-t-Bu-Ph | 378.18 |
| 411 | O | H | CF₃ | H | H | H | 2-t-Bu-Ph | 430.16 |
| 412 | O | H | CF₃ | Cl | H | H | 2-t-Bu-Ph | 462.14 (M − H) |
| 413 | O | H | CF₃ | Cl | H | H | 2-(2-phenyl-4,4-dimethylchroman-2-yl) | 564 |

TABLE 1-continued
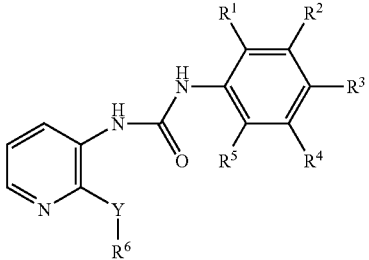
| Ex # | Y | R¹ | R² | R³ | R⁴ | R⁵ | R⁶ | MS (M + 1) |
|---|---|---|---|---|---|---|---|---|
| 414 | O | H | H | OCF₃ | H | H | 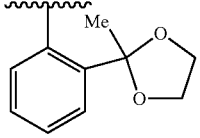 | 476 |
| 415 | O | H | H | OCF₃ | H | H | 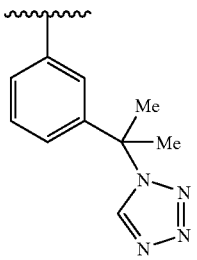 | 498 (M − H) |
| 416 | O | H | H | OCF₃ | H | H | 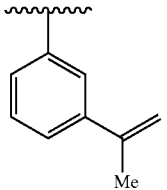 | 430 |
| 417 | O | H | H | OCF₃ | H | H | 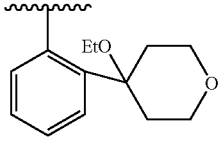 | 516 (M − H) |
| 418 | O | H | H | OCF₃ | H | H | 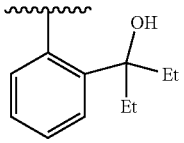 | 474 (M − H) |
| 625 | O | H | H | OCF₃ | H | H | 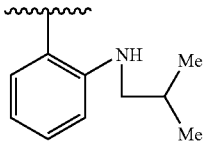 | 461 |

TABLE 2
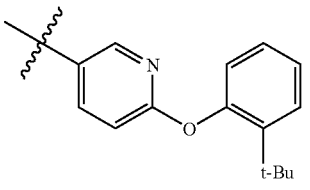
| Ex # | A | MS (M + 1) |
|---|---|---|
| 46 | 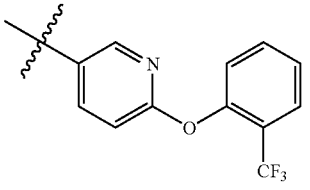 | 511.43 |
| 47 | 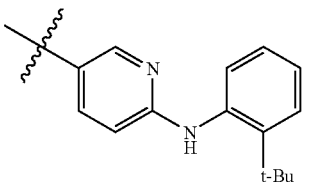 | 522.29 |
| 48 | 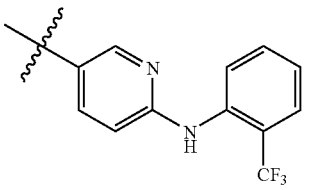 | 510.39 |
| 49 | 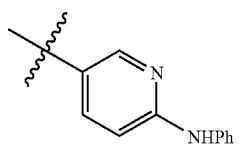 | 522.31 |
| 50 | 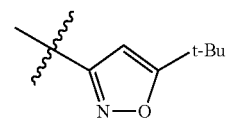 | 454.17 |
| 51 | 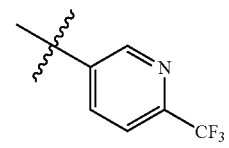 | 409.18 |
| 52 | | 431.14 |

TABLE 2-continued

| Ex # | A | MS (M + 1) |
|---|---|---|
| 86 | 4-(OBu)phenyl | 434.17 |
| 87 | 4-(cyclopentyloxy)phenyl | 446.40 |
| 88 | 4-(3,3-dimethylbutoxy)phenyl | 462.44 |
| 89 | 4-(2-cyclohexylethoxy)phenyl | 488.45 |
| 90 | 4-(1-methyl-2-t-butoxyethoxy)phenyl | 492.44 |
| 91 | 4-((3-methoxybenzyl)oxy)phenyl | 498.40 |
| 92 | 4-((4-trifluoromethoxybenzyl)oxy)phenyl | 552.38 |

TABLE 2-continued
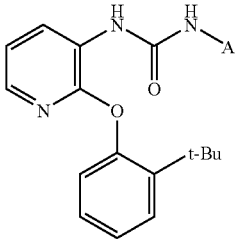
| Ex # | A | MS (M + 1) |
|---|---|---|
| 93 | 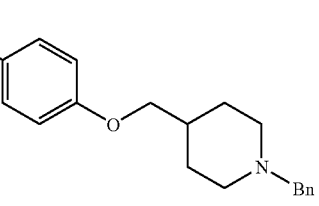 | 565.27 |
| 94 | 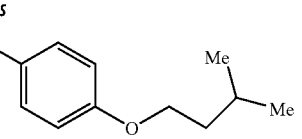 | 420.43 |
| 95 | 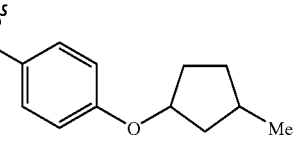 | 448.10 |
| 96 | 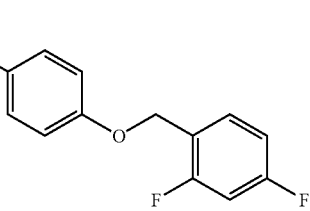 | 460.08 |
| 97 | 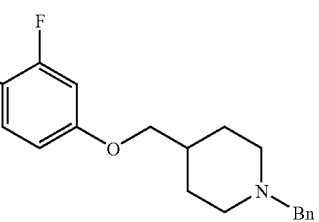 | 504.01 |
| 109 | | 583.46 |

TABLE 2-continued
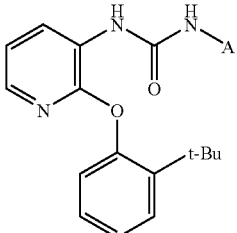
| Ex # | A | MS (M + 1) |
|---|---|---|
| 110 | 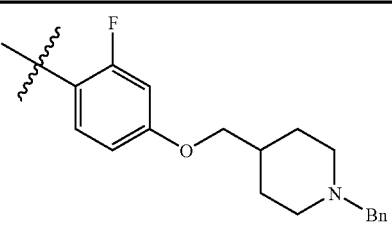 | 509.26 |
| 111 | 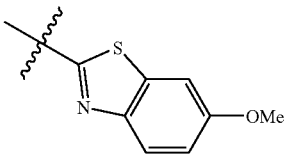 | 491.28 |
| 112 | 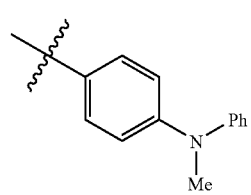 | 449.4 |
| 166 | 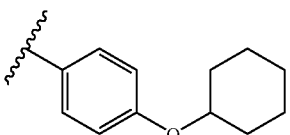 | 467.2 |
| 167 | 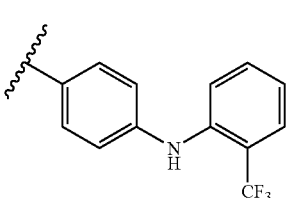 | 460.25 |
| 168 | 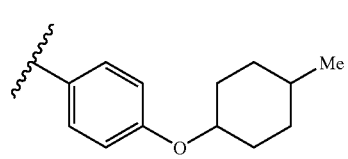 | 521.37 |
| 169 | | 474.14 |

TABLE 2-continued
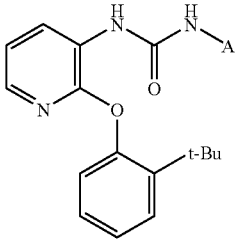
| Ex # | A | MS (M + 1) |
|---|---|---|
| 170 | 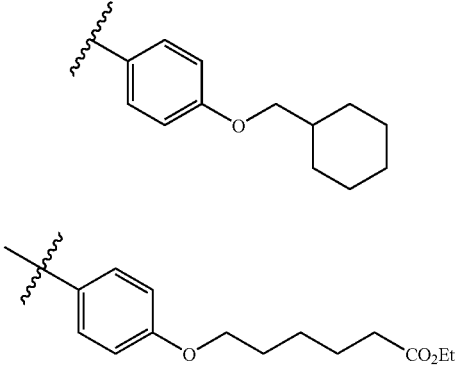 | 474.26 |
| 171 | 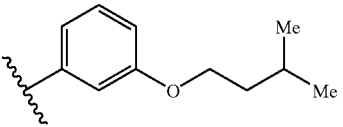 | 520.20 |
| 172 | 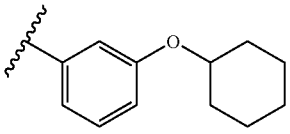 | 448.26 |
| 173 | 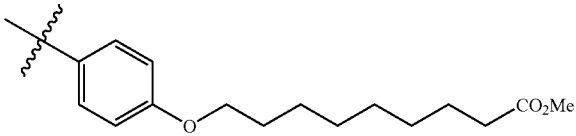 | 460.25 |
| 174 | 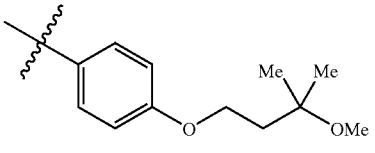 | 548 |
| 175 | 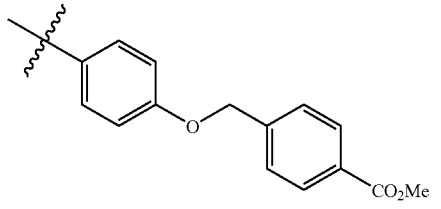 | 478 |
| 176 | | 526.13 |

TABLE 2-continued
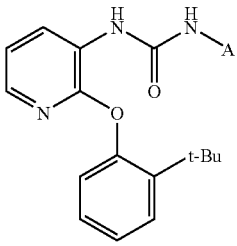
| Ex # | A | MS (M + 1) |
|---|---|---|
| 177 | 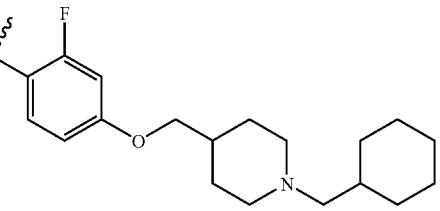 | 589.26 |
| 178 | 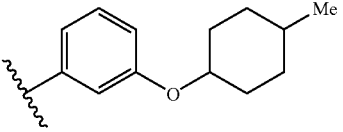 | 532.17 |
| 179 | 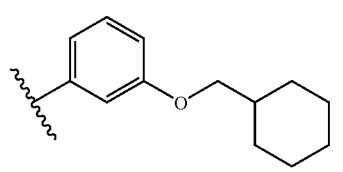 | 474.15 |
| 180 | 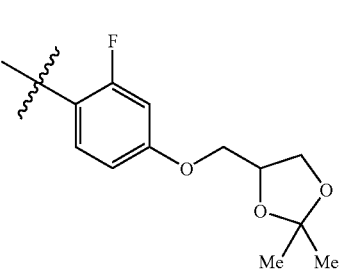 | 474.26 |
| 181 | 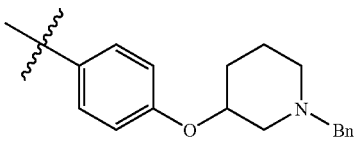 | 510.1 |
| 182 | 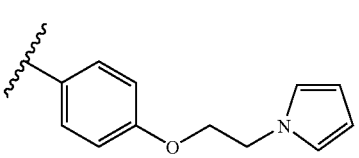 | 551.23 |
| 183 | | 471.09 |

TABLE 2-continued

| Ex # | A | MS (M + 1) |
|---|---|---|
| 184 | | 551.26 |
| 185 | | 593.6 |
| 186 | | 609.43 |
| 187 | | 571.49 |
| 188 | | 483.39 |
| 189 | | 537.19 |

TABLE 2-continued

| Ex # | A | MS (M + 1) |
|---|---|---|
| 190 | 3-(4-(methoxycarbonyl)benzyloxy)phenyl | 526.15 |
| 191 | 4-((3S)-1-benzylpyrrolidin-3-yloxy)phenyl | 537.19 |
| 192 | 3-((4-benzylmorpholin-2-yl)methoxy)phenyl | 567.26 |
| 193 | 3-((8-methoxy-8-oxooctyl)oxy)phenyl | 548.25 |
| 194 | 3-(3-methoxy-3-methylbutoxy)phenyl | 478.15 |
| 195 | 4-(1-benzylpiperidin-4-yloxy)phenyl | 551.21 |
| 196 | 3-((1-phenyl-1H-1,2,3-triazol-4-yl)methoxy)phenyl | 535.17 |

TABLE 2-continued

[Structure: pyridine with NH-C(=O)-NH-A group at position 3, and O-(2-t-Bu-phenyl) at position 2]

| Ex # | A | MS (M + 1) |
|---|---|---|
| 197 | 4-(1-benzylpyrrolidin-3-ylmethoxy)phenyl | 551.26 |
| 198 | 3-((3R)-1-benzylpiperidin-3-yloxy)phenyl | 551.24 |
| 199 | 3-(2-(1H-pyrrol-1-yl)ethoxy)phenyl | 471.12 |
| 200 | 4-((1-phenethylpiperidin-4-yl)methoxy)phenyl | 579.46 |
| 201 | 3-(1-benzylpiperidin-3-yloxy)phenyl | 551.22 |
| 202 | 4-((1-phenyl-1H-1,2,3-triazol-4-yl)methoxy)phenyl | 535.14 |

TABLE 2-continued

| Ex # | A | MS (M + 1) |
|---|---|---|
| 203 | | 551.23 |
| 204 | | 567.25 |
| 205 | | 537.19 |
| 206 | | 537.19 |
| 207 | | 566.44 |
| 208 | | 563.51 |
| 209 | | 464.06 |

TABLE 2-continued
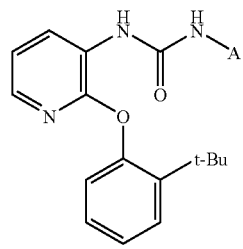
| Ex # | A | MS (M + 1) |
|---|---|---|
| 210 | | 566.44 |
| 211 | | 551.25 |
| 212 | | 514.17 |
| 213 | | 577.28 |
| 214 | | 515.31 |
| 214A | | 515.31 |
| 214B | | 515.31 |

TABLE 2-continued

| Ex # | A | MS (M + 1) |
|---|---|---|
| 215 | | 499.27 |
| 216 | | 579.33 |
| 217 | | 593.47 |
| 218 | | 448.26 |
| 219 | | 462.27 |
| 220 | | 564.25 |

TABLE 2-continued

[Structure: pyridine with NH-C(=O)-NH-A substituent at 3-position and O-(2-t-Bu-phenyl) at 2-position]

| Ex # | A | MS (M + 1) |
|---|---|---|
| 221 | 4-[1-(4-trifluoromethylbenzyloxy)ethyl]phenyl | 564.25 |
| 222 | 3-fluoro-4-[(1-isobutylpiperidin-4-yl)methoxy]phenyl | 549.54 |
| 223 | 4-[(1-isobutylpiperidin-4-yl)methoxy]phenyl | 531.48 |
| 224 | 4,6-difluorobenzothiazol-2-yl | 454.98 |
| 225 | 6-isopropylbenzothiazol-2-yl | 461.36 |
| 226 | 6-methylbenzothiazol-2-yl | 433.11 |
| 227 | 6-ethoxycarbonylbenzothiazol-2-yl | 491.17 |
| 228 | 4-chlorobenzothiazol-2-yl | 453.02 |

TABLE 2-continued

[Structure: pyridine with NH-C(O)-NH-A urea at 3-position, and 2-(2-t-butylphenoxy) substituent]

| Ex # | A | MS (M + 1) |
|------|---|------------|
| 229 | 4-methyl-6-methoxy-benzothiazol-2-yl | 463.11 |
| 230 | 4-fluoro-6-(2-(dimethylaminomethyl)phenyl)-benzothiazol-2-yl | 570.45 |
| 231 | 2-methyl-5-phenyl-furan-3-yl | 442 |
| 419 | 5,6-dihydro-4H-cyclopenta[d]thiazol-2-yl | 409.32 |
| 420 | 4-methyl-5-(methoxycarbonyl)-thiazol-2-yl | 455.3 |
| 421 | 4,5-dimethyl-thiazol-2-yl | 397.29 |
| 422 | 2,3-dihydro-1,4-benzodioxin-6-yl | 420.31 |

TABLE 2-continued
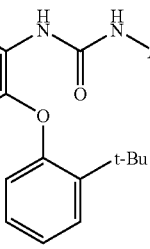
| Ex # | A | MS (M + 1) |
|---|---|---|
| 423 | 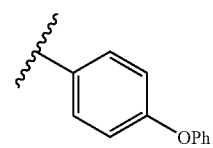 | 453.25 |
| 424 | 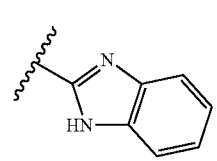 | 367.14 |
| 425 | 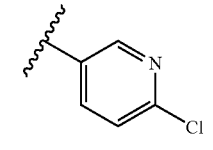 | 402.23 |
| 426 | 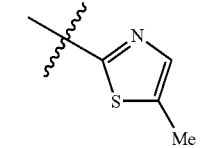 | 397.09 |
| 427 | 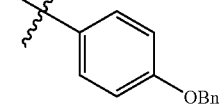 | 383.07 |
| 428 | 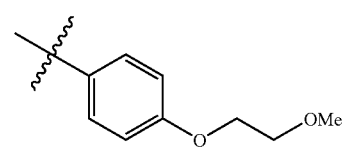 | 468.37 |
| 429 | 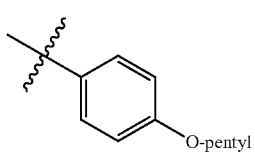 | 436.37 |
| 430 | | 448.42 |

TABLE 2-continued
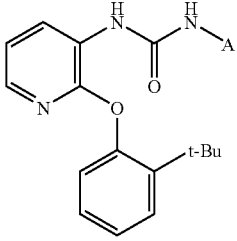
| Ex # | A | MS (M + 1) |
|---|---|---|
| 431 | 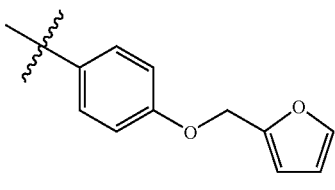 | 458.36 |
| 432 | 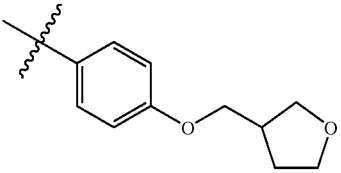 | 458.35 |
| 433 | 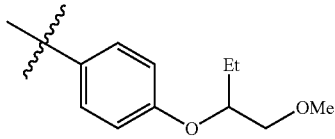 | 462.38 |
| 434 | 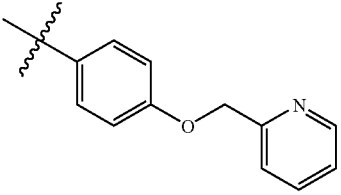 | 464.41 |
| 435 | 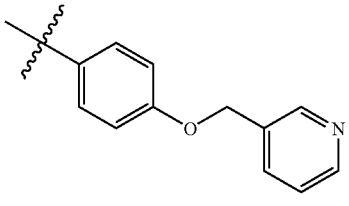 | 469.36 |
| 436 |  | 469.36 |

TABLE 2-continued
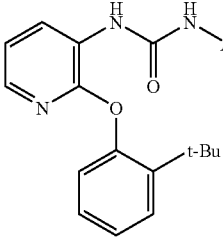
| Ex # | A | MS (M + 1) |
|---|---|---|
| 437 | 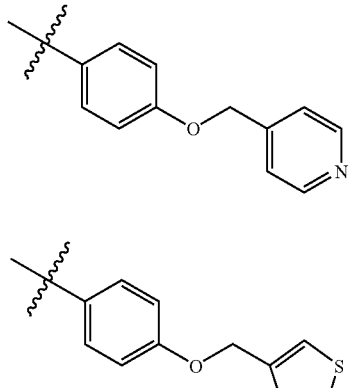 | 469.36 |
| 438 | 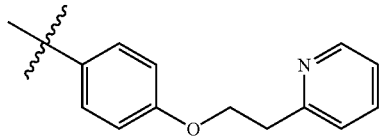 | 474.33 |
| 439 | 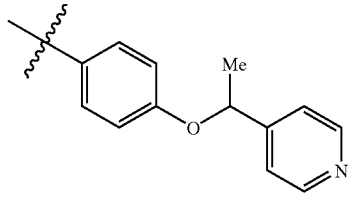 | 483.39 |
| 440 | 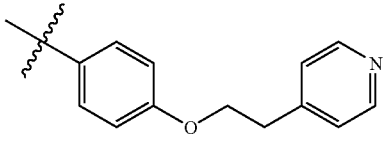 | 483.4 |
| 441 | 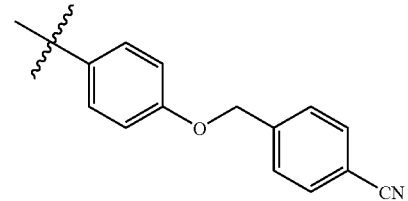 | 483.39 |
| 442 |  | 493.37 |

TABLE 2-continued

| Ex # | A | MS (M + 1) |
|---|---|---|
| 443 | 4-(3-cyanobenzyloxy)phenyl | 493.37 |
| 444 | 4-(2-methoxybenzyloxy)phenyl | 498.4 |
| 445 | 4-(4-methoxybenzyloxy)phenyl | 498.4 |
| 446 | 4-(4-chlorobenzyloxy)phenyl | 502.36 |
| 447 | 4-(3-dimethylaminobenzyloxy)phenyl | 511.43 |
| 448 | 4-(naphthalen-2-ylmethoxy)phenyl | 518.4 |

TABLE 2-continued
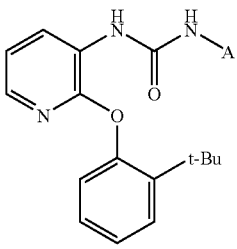
| Ex # | A | MS (M + 1) |
|---|---|---|
| 449 | 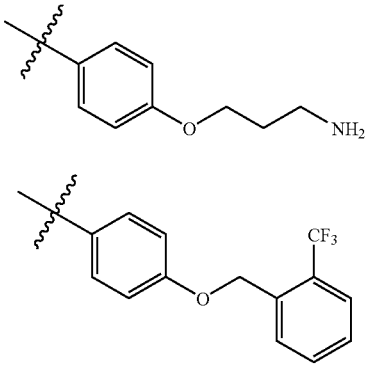 | 435.37 |
| 450 | 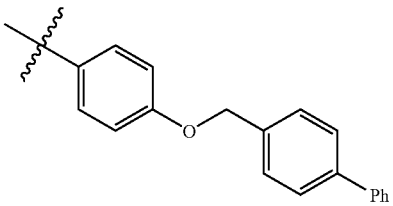 | 536.39 |
| 451 | 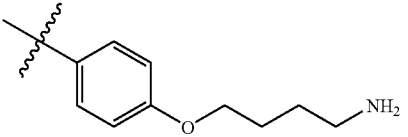 | 544.44 |
| 452 | 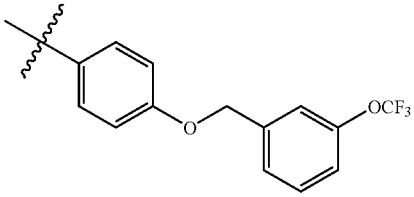 | 449.38 |
| 453 | 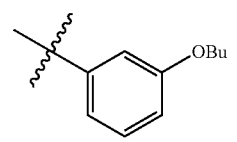 | 552.38 |
| 454 | 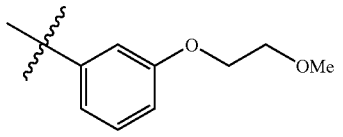 | 434.38 |
| 455 | | 436.36 |

TABLE 2-continued
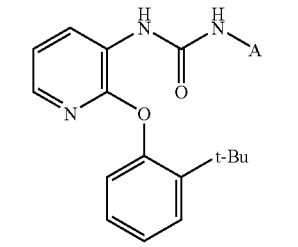
| Ex # | A | MS (M + 1) |
|---|---|---|
| 456 | 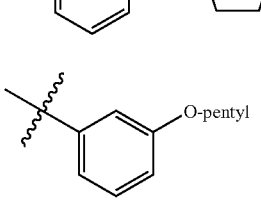 | 446.39 |
| 457 | 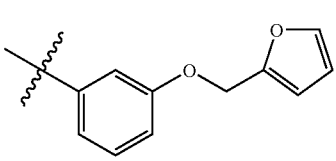 | 448.4 |
| 458 | 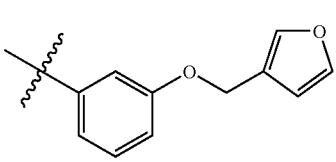 | 458.34 |
| 459 | 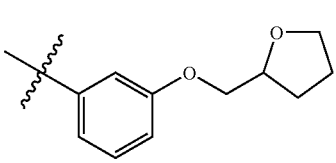 | 458.35 |
| 460 | 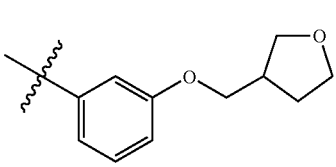 | 462.39 |
| 461 | 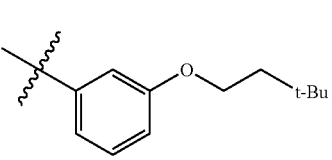 | 462.39 |
| 462 | 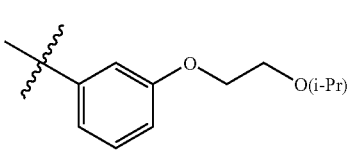 | 462.38 |
| 463 |  | 464.4 |

TABLE 2-continued

| Ex # | A | MS (M + 1) |
|---|---|---|
| 464 | | 464.4 |
| 465 | | 468.38 |
| 466 | | 469.38 |
| 467 | | 469.36 |
| 468 | | 474.33 |
| 469 | | 483.4 |
| 470 | | 483.39 |
| 471 | | 483.39 |

TABLE 2-continued

[Structure: pyridine ring with NH-C(=O)-NH-A substituent at 3-position, and O-phenyl(2-t-Bu) substituent at 2-position]

| Ex # | A | MS (M + 1) |
|---|---|---|
| 472 | 3-(2-cyclohexylethoxy)phenyl | 488.48 |
| 473 | 3-(3-(dimethylamino)-2,2-dimethylpropoxy)phenyl | 491.46 |
| 474 | 3-(1-methyl-2-(t-butoxy)ethoxy)phenyl | 492.44 |
| 475 | 3-((4-cyanobenzyl)oxy)phenyl | 493.38 |
| 476 | 3-((3-cyanobenzyl)oxy)phenyl | 493.38 |
| 477 | 3-((2-methoxybenzyl)oxy)phenyl | 498.4 |
| 478 | 3-((4-methoxybenzyl)oxy)phenyl | 498.39 |

TABLE 2-continued
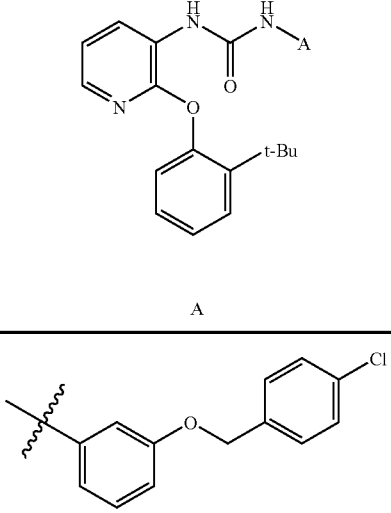
| Ex # | A | MS (M + 1) |
|---|---|---|
| 479 | 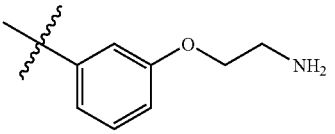 | 502.34 |
| 480 | 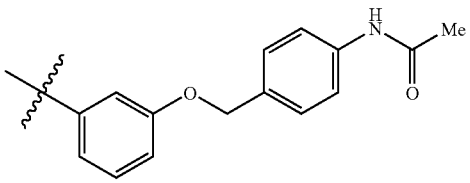 | 421.36 |
| 481 | 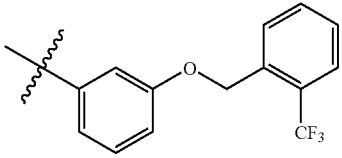 | 525.43 |
| 482 | 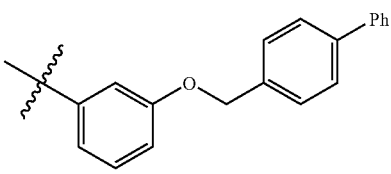 | 536.39 |
| 483 | 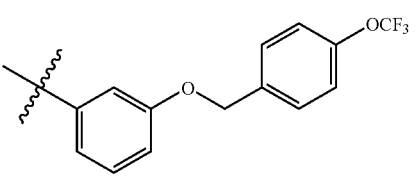 | 544.43 |
| 484 | 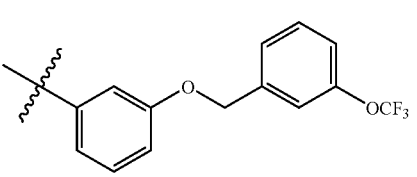 | 552.38 |
| 485 | | 552.38 |

TABLE 2-continued
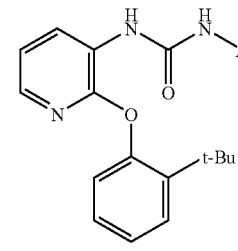
| Ex # | A | MS (M + 1) |
|---|---|---|
| 486 | 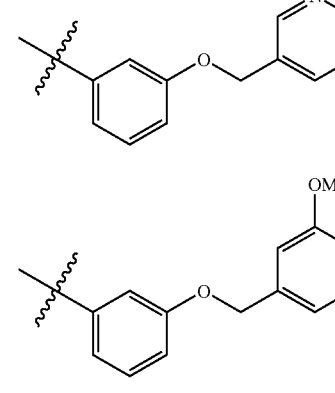 | 469.36 |
| 487 | 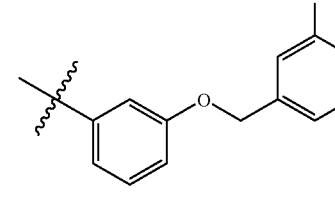 | 498.39 |
| 488 | 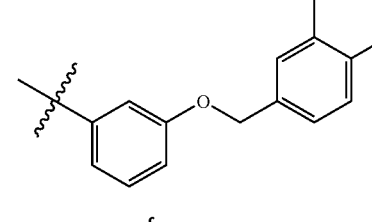 | 511.41 |
| 489 | 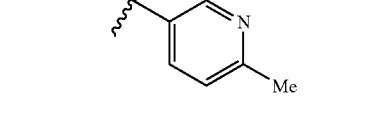 | 518.38 |
| 490 | 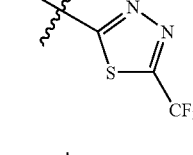 | 377.22 |
| 491 | 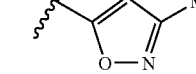 | 438.17 |
| 492 | | 367.21 |

TABLE 2-continued
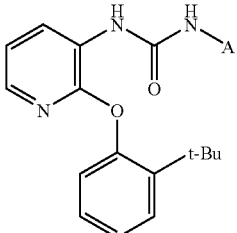
| Ex # | A | MS (M + 1) |
|---|---|---|
| 493 | 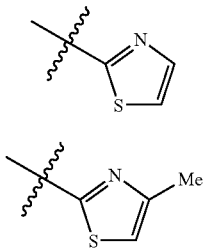 | 369.18 |
| 494 | 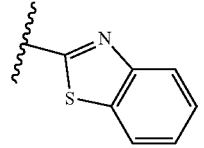 | 383.19 |
| 495 | 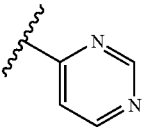 | 419.20 |
| 496 | 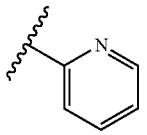 | 364.21 |
| 497 | 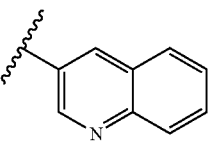 | 363.20 |
| 498 | 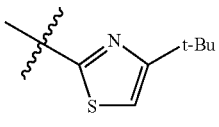 | 413.23 |
| 499 | 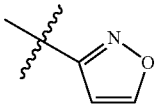 | 425.20 |
| 500 | 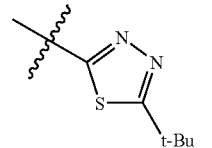 | 353.46 |
| 501 |  | 426.47 |

TABLE 2-continued
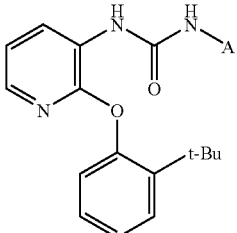
| Ex # | A | MS (M + 1) |
|---|---|---|
| 502 | 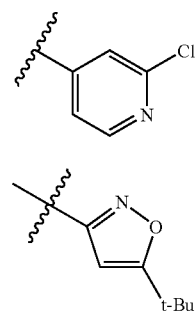 | 397.43 |
| 503 | | 421.43 |
| 628 | | 509.32 |
| 681 | | 388.19 |
TABLE 3
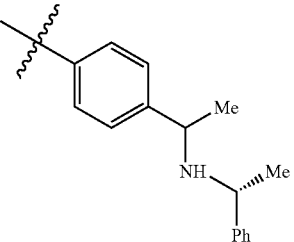
| Ex # | R$^1$ | R$^2$ | R$^3$ | R$^6$ | R$^7$ | R$^8$ | R$^9$ | MS (M + 1) |
|---|---|---|---|---|---|---|---|---|
| 56 | H | H | O-t-Bu | 2-t-Bu-Ph | Cl | H | H | 468.33 |
| 57 | H | H | O-t-Bu | 2-t-Bu-Ph | CN | H | H | 459.38 |
| 58 | H | H | OCF$_3$ | 2-t-Bu-Ph | OMe | H | H | 476.20 |
| 59 | H | H | t-Bu | 2-t-Bu-Ph | SMe | H | H | 464.37 |
| 60 | H | H | OCF$_3$ | 2-t-Bu-Ph | NHMe | H | H | 475.32 |
| 61 | H | H | OCF$_3$ | 2-t-Bu-Ph | H | Me | H | 460.28 |

TABLE 3-continued
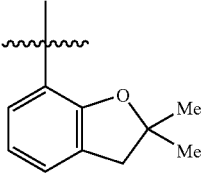
| Ex # | R¹ | R² | R³ | R⁶ | R⁷ | R⁸ | R⁹ | MS (M + 1) |
|---|---|---|---|---|---|---|---|---|
| 62 | H | H | OCF₃ | 2-t-Bu-Ph | H | Cl | H | 480.2 |
| 63 | H | H | t-Bu | 2-t-Bu-Ph | H | CN | H | 443.3 |
| 64 | F | H | F | 2-t-Bu-Ph | OMe | H | H | 428.20 |
| 65 | H | H | t-Bu | 2-t-Bu-Ph | Cl | H | H | 452.23 |
| 66 | H | H | OCF₃ | 2-t-Bu-Ph | Br | H | H | 524.12 |
| 67 | H | H | Me | 2-t-Bu-Ph | NHMe | H | H | 405.35 |
| 68 | H | H | NMe₂ | 2-t-Bu-Ph | CN | H | H | 430.39 |
| 69 | H | H | t-Bu | 2-t-Bu-Ph | CN | H | H | 443.39 |
| 70 | H | H | OCF₃ | 2-t-Bu-Ph | CN | H | H | 471.26 |
| 71 | H | H | NMe₂ | 2-t-Bu-Ph | SMe | H | H | 451.37 |
| 72 | H | H | t-Bu | 2-t-Bu-Ph | H | Me | H | 432.42 |
| 73 | H | H | O-t-Bu | 2-t-Bu-Ph | H | Me | H | 448.40 |
| 74 | H | H | O-t-Bu | 2-t-Bu-Ph | OMe | H | H | 464.35 |
| 75 | H | H | Me | 2-t-Bu-Ph | H | Cl | H | 410.24 |
| 76 | H | H | OCF₃ | 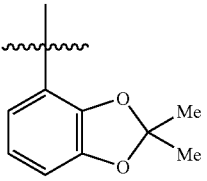 | H | H | H | 460.24 |
| 77 | H | H | OCF₃ | 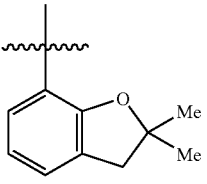 | H | H | H | 462.26 |
| 78 | H | H | t-Bu | 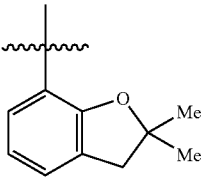 | H | H | H | 432.35 |
| 79 | H | H | NMe₂ | 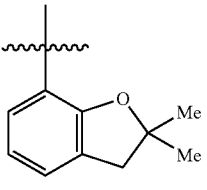 | H | H | H | 472.17 |
| 80 | H | H | O-t-Bu |  | H | H | H | 448.38 |

TABLE 3-continued

| Ex # | R¹ | R² | R³ | R⁶ | R⁷ | R⁸ | R⁹ | MS (M + 1) |
|---|---|---|---|---|---|---|---|---|
| 81 | H | H | O-t-Bu | 2,2-dimethyl-benzo[1,3]dioxol-4-yl | H | H | H | 450.35 |
| 82 | H | H | t-Bu | 2,2-dimethyl-benzo[1,3]dioxol-4-yl | H | H | H | 434.27 |
| 232 | H | H | OCF₃ | 2,2-dimethyl-benzo[1,3]dioxol-4-yl | H | CN | H | 485.24 |
| 233 | H | H | OCF₃ | 5,6,7,8-tetrahydronaphthalen-1-yl | H | H | H | 444 |
| 234 | H | H | OCF₃ | 1,2,3,4-tetrahydroquinolin-8-yl | H | H | H | 445 |
| 235 | H | H | OCF₃ | 1-methyl-1,2,3,4-tetrahydroquinolin-8-yl | H | H | H | 459 |

TABLE 3-continued

[Structure: pyridine bearing R⁷, R⁸, R⁹, and OR⁶ substituents, linked via NH-C(O)-NH urea to a phenyl ring bearing R¹, R², R³]

| Ex # | R¹ | R² | R³ | R⁶ | R⁷ | R⁸ | R⁹ | MS (M + 1) |
|---|---|---|---|---|---|---|---|---|
| 236 | H | H | OCF₃ | 3,3-dimethyl-2,3-dihydro-1H-indol-4-yl (attached at 4-position) | H | H | H | 459 |
| 237 | H | H | OCF₃ | 3-t-Bu-1-methyl-2-oxoindolin-4-yl | H | H | H | 515 |
| 238 | H | H | OCF₃ | 2-benzyl-1,2,3,4-tetrahydroisoquinolin-5-yl | H | H | H | 535 |
| 239 | H | H | OCF₃ | 1,2,3,4-tetrahydroquinolin-5-yl | H | H | H | 445 |
| 240 | H | H | OCF₃ | 3,4-dihydro-2H-benzo[b][1,4]oxazin-8-yl | H | H | H | 447 |
| 504 | H | H | OCF₃ | 2-t-Bu-5-Me-Ph | OMe | H | H | 487.78 (M − H) |
| 505 | H | H | OCF₃ | 2-Pr-Ph | OMe | H | H | 462.04 |
| 506 | H | H | OCF₃ | 2-i-Pr-5-Me-Ph | OMe | H | H | 476.09 |
| 507 | H | H | OCF₃ | 1-(2-phenyl)propyl with Me and Et (sec-butyl-type attachment to phenyl) | OMe | H | H | 476.07 |

TABLE 3-continued

| Ex # | R¹ | R² | R³ | R⁶ | R⁷ | R⁸ | R⁹ | MS (M + 1) |
|---|---|---|---|---|---|---|---|---|
| 508 | H | H | Me | 2-t-Bu-5-Me-Ph | OMe | H | H | 420.2 |
| 509 | H | H | Me | 2-i-Pr-5-Me-Ph | OMe | H | H | 406.17 |
| 510 | H | H | Me | 2-Pr-Ph | OMe | H | H | 392.12 |
| 511 | H | H | Me | (1-phenylpropyl, 2-Me-substituted phenyl; see structure) | OMe | H | H | 406.17 |
| 512 | F | H | F | (4,7-disubstituted indanyl, 7-Me; see structure) | H | H | H | 396.16 |
| 513 | H | H | t-Bu | 2-t-Bu-Ph | OMe | H | H | 448.30 |
| 514 | H | H | Me | 2-t-Bu-Ph | OMe | H | H | 406.27 |
| 515 | H | H | Me | 2-t-Bu-Ph | H | H | Me | 390.24 |
| 516 | F | H | F | 2-t-Bu-Ph | H | H | Me | 412.23 |
| 517 | H | H | Ph | 2-t-Bu-Ph | OMe | H | H | 468.20 |
| 518 | H | H | Ph | 2-t-Bu-Ph | H | H | Me | 452.26 |
| 519 | H | H | t-Bu | 2-t-Bu-Ph | OH | H | H | 434.29 |
| 520 | H | H | OCF₃ | 2-t-Bu-Ph | OH | H | H | 462.17 |
| 521 | H | H | Me | 2-t-Bu-Ph | Br | H | H | 454.14 |
| 522 | H | H | t-Bu | 2-t-Bu-Ph | Br | H | H | 496.20 |
| 523 | H | H | Me | 2-t-Bu-Ph | Cl | H | H | 410.22 |
| 524 | H | H | OCF₃ | 2-t-Bu-Ph | Cl | H | H | 480.13 |
| 525 | H | H | CF₃ | 2-t-Bu-Ph | Cl | H | H | 464.15 |
| 526 | H | H | CF₃ | 2-t-Bu-Ph | Br | H | H | 508.14 |
| 527 | H | H | Me | 2-t-Bu-Ph | NMe₂ | H | H | 419.39 |
| 528 | H | H | OCF₃ | 2-t-Bu-Ph | NMe₂ | H | H | 489.32 |
| 529 | F | H | Br | 2-t-Bu-Ph | Cl | H | H | 493.21 |
| 530 | F | H | Br | 2-t-Bu-Ph | OMe | H | H | 488.26 |
| 531 | H | H | Cl | 2-t-Bu-Ph | CN | H | H | 421.31 |
| 532 | H | H | OCF₃ | 2-t-Bu-Ph | imidazol-1-yl | H | H | 512.36 |
| 533 | H | H | t-Bu | 2-t-Bu-Ph | imidazol-1-yl | H | H | 484.41 |
| 534 | H | H | Cl | 2-t-Bu-Ph | imidazol-1-yl | H | H | 462.30 |
| 535 | H | H | t-Bu | 2-t-Bu-Ph | CO₂Me | H | H | 476.39 |
| 536 | H | H | OCF₃ | 2-t-Bu-Ph | CO₂Me | H | H | 504.34 |
| 537 | H | H | Cl | 2-t-Bu-Ph | CO₂Me | H | H | 454.29 |
| 538 | H | H | OCF₃ | (2,2-dimethyl-2,3-dihydrobenzofuran-7-yl; see structure) | H | Me | H | 474.29 |

TABLE 3-continued
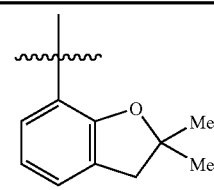
| Ex # | R¹ | R² | R³ | R⁶ | R⁷ | R⁸ | R⁹ | MS (M + 1) |
|---|---|---|---|---|---|---|---|---|
| 539 | H | H | O-t-Bu | 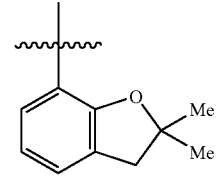 | H | Me | H | 462.37 |
| 540 | H | H | t-Bu | 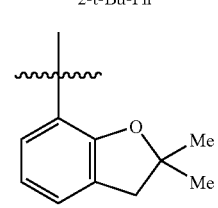 | H | Me | H | 446.40 |
| 541 | H | H | O-t-Bu | 2-t-Bu-Ph | H | CF₃ | H | 502.37 |
| 542 | H | H | O-t-Bu | 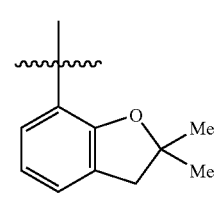 | Br | H | H | 526.24 |
| 543 | H | H | Me | 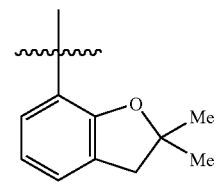 | Br | H | H | 468.21 |
| 544 | H | H | t-Bu | 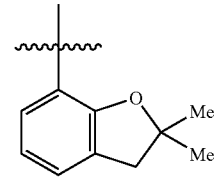 | Br | H | H | 510.25 |
| 545 | H | H | OCF₃ |  | Br | H | H | 538.17 |
| 546 | H | H | O-t-Bu | 2-OCF₃-Ph | Br | H | H | 540.18 |
| 547 | H | H | Me | 2-OCF₃-Ph | Br | H | H | 482.13 |
| 548 | H | H | OCF₃ | 2-OCF₃-Ph | Br | H | H | 552.11 |

TABLE 3-continued

| Ex # | R¹ | R² | R³ | R⁶ | R⁷ | R⁸ | R⁹ | MS (M + 1) |
|---|---|---|---|---|---|---|---|---|
| 549 | H | H | O-t-Bu | 7-(2,2-dimethyl-2,3-dihydrobenzofuran) | H | Cl | H | 482.28 |
| 550 | H | H | t-Bu | 7-(2,2-dimethyl-2,3-dihydrobenzofuran) | H | Cl | H | 466.28 |
| 551 | H | H | OCF₃ | 7-(2,2-dimethyl-2,3-dihydrobenzofuran) | H | Cl | H | 494.20 |
| 552 | H | H | O-t-Bu | 2-t-Bu-Ph | H | Cl | H | 468.29 |
| 553 | H | H | t-Bu | 2-t-Bu-Ph | H | Cl | H | 452.30 |
| 554 | H | H | OCF₃ | 7-(2,2-dimethyl-2,3-dihydrobenzofuran) | H | Br | H | 538.15 |
| 555 | H | H | Me | 2-t-Bu-Ph | H | Br | H | 454.19 |
| 556 | H | H | t-Bu | 2-t-Bu-Ph | H | Br | H | 496.24 |
| 557 | H | H | OCF₃ | 2-t-Bu-Ph | H | Br | H | 524.17 |
| 558 | H | H | O-t-Bu | 2-t-Bu-Ph | H | CN | H | 459.32 |
| 559 | H | H | Me | 2-t-Bu-Ph | H | CN | H | 401.28 |
| 560 | H | H | t-Bu | 2-OCF₃-Ph | Br | H | H | 524.16 |
| 561 | H | H | O-t-Bu | 7-(2,2-dimethyl-2,3-dihydrobenzofuran) | CN | H | H | 473.28 |

TABLE 3-continued

| Ex # | R¹ | R² | R³ | R⁶ | R⁷ | R⁸ | R⁹ | MS (M + 1) |
|---|---|---|---|---|---|---|---|---|
| 562 | H | H | Me | 2,2-dimethyl-2,3-dihydrobenzofuran-7-yl | CN | H | H | 415.23 |
| 563 | H | H | t-Bu | 2,2-dimethyl-2,3-dihydrobenzofuran-7-yl | CN | H | H | 457.29 |
| 564 | H | H | OCF₃ | 2,2-dimethyl-2,3-dihydrobenzofuran-7-yl | CN | H | H | 485.21 |
| 565 | H | H | Me | 2-OCF₃-Ph | CN | H | H | 429.16 |
| 566 | H | H | OCF₃ | 2-OCF₃-Ph | CN | H | H | 499.15 |
| 567 | H | H | Me | 2,2-dimethyl-2,3-dihydrobenzofuran-7-yl | H | Cl | H | 424.19 |
| 568 | H | H | O-t-Bu | 2,2-dimethyl-2,3-dihydrobenzofuran-7-yl | H | Br | H | 526.21 |
| 569 | H | H | Me | 2,2-dimethyl-2,3-dihydrobenzofuran-7-yl | H | Br | H | 468.16 |

TABLE 3-continued

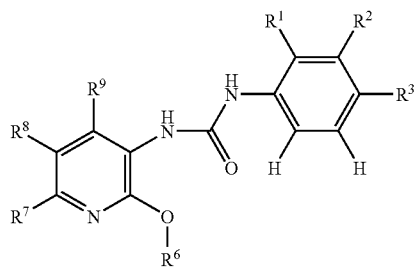

| Ex # | R¹ | R² | R³ | R⁶ | R⁷ | R⁸ | R⁹ | MS (M + 1) |
|---|---|---|---|---|---|---|---|---|
| 570 | H | H | t-Bu | 2,2-dimethyl-2,3-dihydrobenzofuran-7-yl | H | Br | H | 510.21 |
| 571 | H | H | O-t-Bu | 2-t-Bu-Ph | H | Br | H | 512.22 |
| 572 | H | H | Me | 2,2-dimethyl-2,3-dihydrobenzofuran-7-yl | H | CN | H | 415.24 |
| 573 | H | H | t-Bu | 2,2-dimethyl-2,3-dihydrobenzofuran-7-yl | H | CN | H | 457.28 |
| 574 | H | H | OCF₃ | 2-t-Bu-Ph | H | CN | H | 471.24 |
| 575 | H | H | t-Bu | 2-t-Bu-Ph | —CH₂NH(C=O)H | H | H | 475.37 |
| 576 | H | H | Me | 2-t-Bu-Ph | H | CF₃ | H | 444.24 |
| 577 | H | H | t-Bu | 2-t-Bu-Ph | H | CF₃ | H | 486.29 |
| 578 | H | H | OCF₃ | 2-t-Bu-Ph | H | CF₃ | H | 514.23 |
| 579 | H | H | t-Bu | 2-OCF₃-Ph | CN | H | H | 471.23 |
| 580 | H | H | OCF₃ | 2,2-dimethyl-2,3-dihydrobenzofuran-7-yl | H | CN | H | 485.24 |
| 581 | H | H | OCF₃ | 2-(2-ethoxypropan-2-yl)phenyl | CN | H | H | 499 (M − H) |

TABLE 3-continued
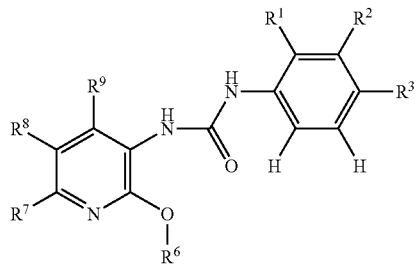
| Ex # | R¹ | R² | R³ | R⁶ | R⁷ | R⁸ | R⁹ | MS (M + 1) |
|---|---|---|---|---|---|---|---|---|
| 582 | H | H | OCF₃ | 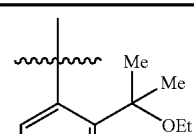 | Br | H | H | 508, 510 (M − OEt) |
TABLE 3a
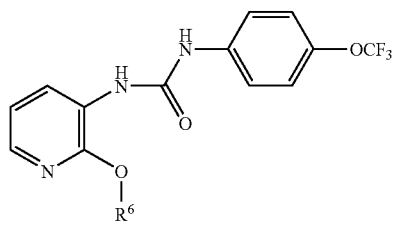
| Ex # | R⁶ | MS (M + 1) |
|---|---|---|
| 626 | 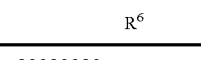 | 487 |
| 627 | | 442 |
| 629 | | 460 |
| 630 | | 466 |
TABLE 3a-continued
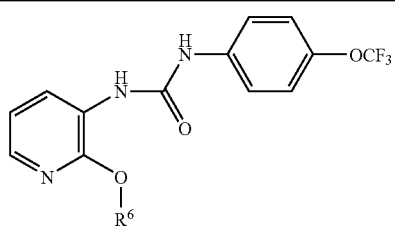
| Ex # | R⁶ | MS (M + 1) |
|---|---|---|
| 631 | | 450 |
| 632 | | 541 |
| 633 | | 577 |

TABLE 3a-continued

| Ex # | R⁶ | MS (M + 1) |
|---|---|---|
| 634 | (piperidine-phenyl with N-CH2-t-Bu) | 543 |
| 635 | (isoindoline-phenyl, N-(4-OMe-Bn)) | 551 |
| 636 | (isoindoline-phenyl, N-CH2-t-Bu) | 501 |
| 637 | (tetrahydroisoquinoline, N-CH2-t-Bu) | 515 |
| 638 | (isoindoline, t-Bu, N-OMe) | 517 |
| 639 | (isoindoline, t-Bu, NH) | 487 |
| 640 | (phenyl, C(OH)(CH2-CH=CH2)2) | 500 |

TABLE 3a-continued

| Ex # | R⁶ | MS (M + 1) |
|---|---|---|
| 641 | (phenyl-CO2Et) | 462 |
| 642 | (phenyl, C(OMe)(CH2-CH=CH2)2) | 514 |
| 643 | (phenyl-cyclopentyl) | 458 |
| 644 | (phenyl, C(Me)(OMe)(CH2OMe)) | 492 |
| 645 | (dimethylphthalide) | 474 |
| 646 | (phenyl, CMe2-CH2-O-Si(Me)2-t-Bu) | 576 |
| 647 | (phenyl, CMe2-O-CH2CH2-O-Si(Me)2-t-Bu) | 605 |

TABLE 3a-continued

[Structure: pyridine-NH-C(=O)-NH-phenyl-OCF₃ with O-R⁶ on pyridine]

| Ex # | R⁶ | MS (M + 1) |
|---|---|---|
| 649 | phenyl-C(Me)(Me)-O-Bu | 502 |
| 650 | phenyl-C(Me)(Me)-O-CH₂CH₂-N(i-Bu)₂ | 603 |
| 651 | phenyl-C(Me)(Me)-O-CH₂CH₂-S-i-Bu | 562 |
| 652 | phenyl-C(Me)(Me)-O-CH₂CH₂-S-(2-pyridyl) | 585 |
| 653 | phenyl-C(Me)(Me)-O-CH₂CH₂-S-CH₂-(2-furyl) | 588 |
| 654 | phenyl-C(Me)(Me)-O-CH₂CH₂-S(=O)-i-Bu | (M + Na + CH₃CN)⁺ 642 |
| 655 | phenyl-C(Me)(Me)-O-CH₂CH₂-S(=O)₂-(2-pyridyl) | 617 |
| 656 | phenyl-(4-piperidyl)-N-i-Bu | 529 |
| 657 | tetrahydroisoquinoline-N-CH₂-(2-furyl) | 525 |
| 658 | tetrahydroisoquinoline-N-CH₂-(2-morpholinophenyl) | 596 |
| 659 | tetrahydroisoquinoline-N-CH(Me)-Et | 516 |
| 660 | tetrahydroisoquinoline-N-CH₂CH₂-t-Bu | 530 |
| 661 | tetrahydroisoquinoline-N-CH₂-(norbornene) | 552 |
| 662 | tetrahydroisoquinoline-N-Bu | 502 |

TABLE 3a-continued
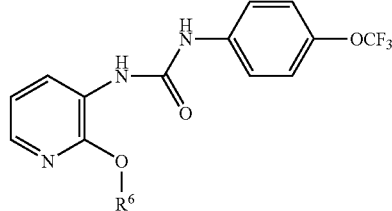
| Ex # | R⁶ | MS (M + 1) |
|---|---|---|
| 663 | 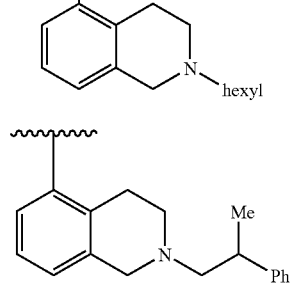 | 530 |
| 664 | 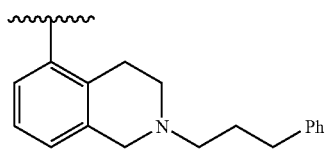 | 564 |
| 665 | 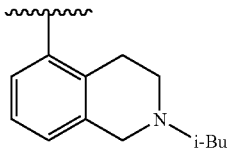 | 564 |
| 666 | 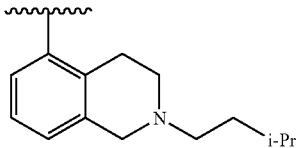 | 502 |
| 667 | 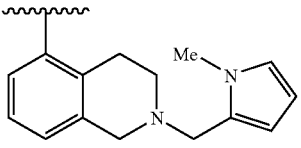 | 516 |
| 668 | 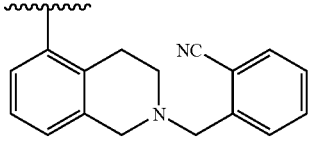 | 539 |
| 669 | 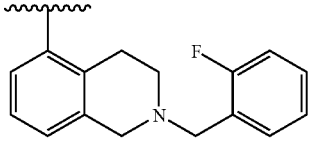 | 561 |
| 670 | 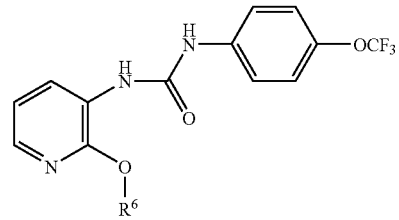 | 554 |
TABLE 3a-continued
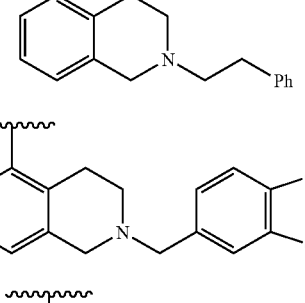
| Ex # | R⁶ | MS (M + 1) |
|---|---|---|
| 671 | 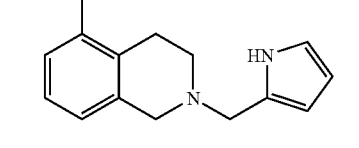 | 550 |
| 672 | 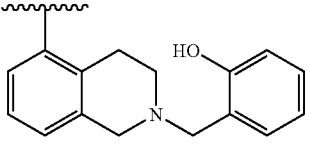 | 580 |
| 673 | 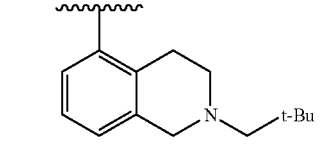 | 525 |
| 674 | 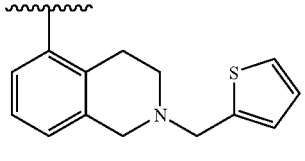 | 552 |
| 675 | 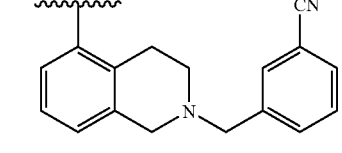 | 516 |
| 676 | 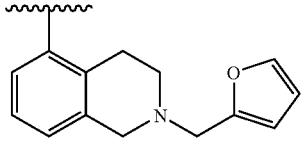 | 542 |
| 677 |  | 561 |
| 678 | | 526 |

TABLE 3a-continued

| Ex # | R⁶ | MS (M + 1) |
|---|---|---|
| 679 | (5-substituted-1,2,3,4-tetrahydroisoquinolin-2-yl)methyl-4-cyanophenyl | 561 |
| 680 | (5-substituted-1,2,3,4-tetrahydroisoquinolin-2-yl)methyl-4-methoxycarbonylphenyl | 594 |

TABLE 4

| Ex # | R¹ | R² | R³ | B | R⁶ | MS (M + 1) |
|---|---|---|---|---|---|---|
| 84 | H | H | t-Bu | pyridin-3,4-diyl | 2-t-Bu-Ph | 446.27 |
| 85 | H | H | OCF₃ | pyridin-3,4-diyl | 2-t-Bu-Ph | 418.41 |
| 241 | H | H | OCF₃ | pyridazin-3,4-diyl | 2-t-Bu-Ph | 419.3 |

TABLE 4-continued

| Ex # | R¹ | R² | R³ | B | R⁶ | MS (M + 1) |
|---|---|---|---|---|---|---|
| 583 | H | H | O-t-Bu | pyridin-3,4-diyl | 2-t-Bu-Ph | 434.41 |
| 584 | F | H | Br | pyridin-3,4-diyl | 2-t-Bu-Ph | 458.23 |
| 585 | H | H | NMe₂ | pyridin-3,4-diyl | 2-t-Bu-Ph | 405.38 |
| 586 | H | H | Cl | pyridin-3,4-diyl | 2-t-Bu-Ph | 396.27 |
| 587 | H | H | t-Bu | pyridin-3,4-diyl | 2-t-Bu-Ph | 418.40 |
| 588 | H | H | O-t-Bu | pyridin-3,4-diyl | 2-t-Bu-Ph | 434.41 |
| 589 | H | H | Me | thiophen-2,3-diyl | 2-t-Bu-Ph | 381.25 |

TABLE 4-continued

| Ex # | R¹ | R² | R³ | B | R⁶ | MS (M + 1) |
|---|---|---|---|---|---|---|
| 590 | H | H | Me | pyridine | 2-t-Bu-Ph | 376.28 |
| 591 | H | H | OCF₃ | thiophene | 2-t-Bu-Ph | 451.24 |
| 592 | H | H | OCF₃ | pyridine | 2-t-Bu-Ph | 446.29 |
| 593 | H | H | t-Bu | pyridine N-oxide | 2-t-Bu-Ph | 434.31 |
| 594 | F | H | Br | pyridinone | 2-t-Bu-Ph | 474.22 |

TABLE 5

| Ex # | W | X | A | R⁶ | MS (M + 1) |
|---|---|---|---|---|---|
| 242 | S | bond | 2,4-dichlorophenyl | 2-t-Bu-Ph | 447 |
| 243 | S | bond | 4-OCF₃-2-Me-phenyl | 2-t-Bu-Ph | 476 |

TABLE 5-continued
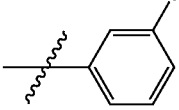
| Ex # | W | X | A | R⁶ | MS (M + 1) |
|---|---|---|---|---|---|
| 244 | S | bond | 3-t-Bu-Ph | 2-t-Bu-Ph | 433 |
| 245 | S | bond | 4-Me-Ph | 2-t-Bu-Ph | 392 |
| 246 | S | bond | 4-OMe-Ph | 2-t-Bu-Ph | 408.06 |
| 247 | S | bond | 3,4-diMe-Ph | 2-t-Bu-Ph | 406 |
| 248 | O | —CH₂CH₂— | 4-OPh-Ph | 2-t-Bu-Ph | 482.32 |
| 249 | O | —CH₂CH₂— | 4-Cl-Ph | 2-t-Bu-Ph | 424.18 |
| 250 | O | —CH₂CH₂— | 4-Br-Ph | 2-t-Bu-Ph | 468.13 |
| 251 | O | —CH₂CH₂— | 1-Me-indol-3-yl | 2-t-Bu-Ph | 443 |
| 252 | O | —CH₂CH₂— | 3,4-di-OBn-Ph | 2-t-Bu-Ph | 602.3 |
| 253 | O | —CH₂CH₂— | 3-F-Ph | 2-t-Bu-Ph | 408.26 |

TABLE 5-continued
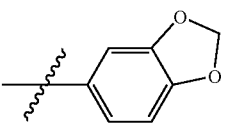
| Ex # | W | X | A | R⁶ | MS (M + 1) |
|---|---|---|---|---|---|
| 254 | O | —CH₂CH₂— |  | 2-t-Bu-Ph | 434.26 |
| 255 | O | —CH₂CH₂— | 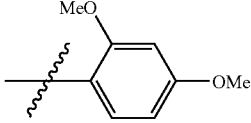 | 2-t-Bu-Ph | 420.28 |
| 256 | O | —CH₂CH₂— | 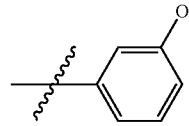 | 2-t-Bu-Ph | 450.24 |
| 257 | O | —CH₂CH₂— | 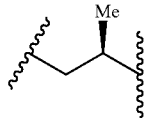 | 2-t-Bu-Ph | 420.28 |
| 258 | O | 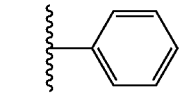 | 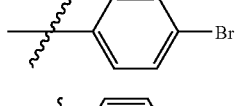 | 2-t-Bu-Ph | 404.32 |
| 259 | O | —CH₂C(=O)— | 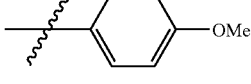 | 2-t-Bu-Ph | 482.17 |
| 260 | O | —CH₂C(=O)— | 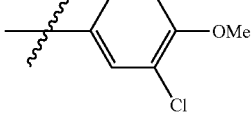 | 2-t-Bu-Ph | 434.25 |
| 261 | O | —CH₂— | 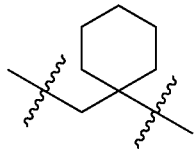 | 2-t-Bu-Ph | 440.10 |
| 262 | O | 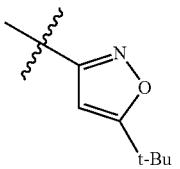 | Ph | 2-t-Bu-Ph | 468 |
| 503 | O | bond |  | 3-CF₃-Ph | 421.43 |

TABLE 5-continued

| Ex # | W | X | A | R⁶ | MS (M + 1) |
|---|---|---|---|---|---|
| 595 | O | cyclopropyl (1,2-disubstituted) | Ph | 2-t-Bu-Ph | 400.3 (M − H) |
| 596 | O | —CH(Me)CH₂— | 4-Cl-Ph | 2-t-Bu-Ph | 438.18 |
| 597 | O | —CH(Me)CH₂— | Ph | 2-t-Bu-Ph | 404.38 |
| 598 | O | —CH₂— | 2-Ph-Ph | 2-t-Bu-Ph | 452.30 |
| 599 | O | —CH₂— | 4-Br-Ph | 2-t-Bu-Ph | 452.10 (M − H) |
| 600 | O | —CH₂— | 4-Ph-Ph | 2-t-Bu-Ph | 452.20 |
| 601 | O | —CH₂— | 4-Cl-3-CF₃-Ph | 2-t-Bu-Ph | 478.20 |
| 602 | O | —CH₂— | 2,4-diCl-Ph | 2-t-Bu-Ph | 404.69 |
| 603 | O | —CH₂— | 4-F-Ph | 2-t-Bu-Ph | 404.69 |
| 604 | O | —CH₂— | 4-Me-Ph | 2-t-Bu-Ph | 404.69 |

TABLE 5-continued
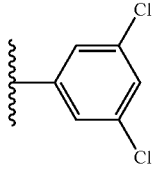
| Ex # | W | X | A | R⁶ | MS (M + 1) |
|---|---|---|---|---|---|
| 605 | O | —CH₂— | 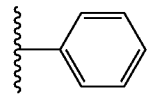 3,5-diCl-Ph | 2-t-Bu-Ph | 404.69 |
| 606 | O | —CH₂CH₂CH₂— | 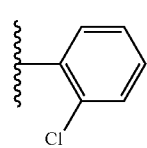 Ph | 2-t-Bu-Ph | 404.69 |
| 607 | O | —CH₂CH₂-t-Bu | — | 2-t-Bu-Ph | 370.22 |
| 608 | O | —CH₂— | 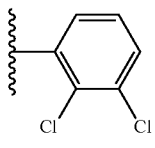 2-Cl-Ph | 2-t-Bu-Ph | 409.96 |
| 609 | O | —CH₂— | 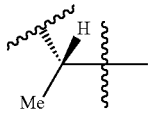 2,3-diCl-Ph | 2-t-Bu-Ph | 444.13 |
| 610 | O | 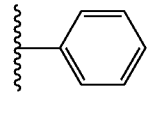 | 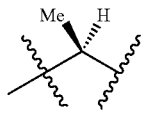 Ph | 2-t-Bu-Ph | 390.33 |
| 611 | O | 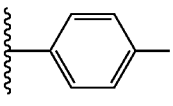 | 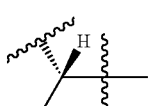 4-Br-Ph | 2-t-Bu-Ph | 468.24 |
| 612 | O | 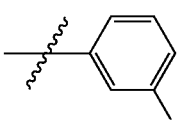 | 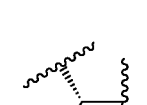 3-OMe-Ph | 2-t-Bu-Ph | 420.39 |
| 614 | O | 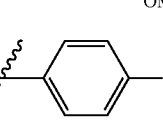 | 4-OMe-Ph | 2-t-Bu-Ph | 420.03 |
| 615 | O | —CH₂— | 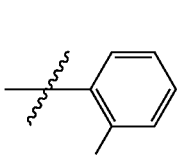 2-CF₃-Ph | 2-t-Bu-Ph | 444.41 |

TABLE 5-continued
| Ex # | W | X | A | R⁶ | MS (M + 1) |
|---|---|---|---|---|---|
| 616 | O | Bond | (thiazol-2-yl) | 3-CF₃-Ph | 381.11 |
TABLE 6
| Ex # | Y | B | R³ | R⁶ | MS (M + 1) |
|---|---|---|---|---|---|
| 263 | -O-CH₂- | pyridine | t-Bu | 2-CF₃-Ph | 444.4 |
| 264 | O | 3-Me-phenyl | t-Bu | 2-t-Bu-Ph | 431.4 |
| 265 | O | phenyl | OCF₃ | 3-I-Ph | 515.1 |
| 266 | O | phenyl | OCF₃ | 5-F-2-Me-Ph | 421.2 |

TABLE 6-continued

| Ex # | Y | B | R³ | R⁶ | MS (M + 1) |
|---|---|---|---|---|---|
| 267 | O | 3-NH₂-phenylene | t-Bu | 2-t-Bu-Ph | 432.4 |
| 268 | OCH(Me) | phenylene | OCF₃ | Ph | 417.1 |
| 269 | OCH₂ | pyridinyl | t-Bu | Ph | 376.5 |
| 270 | OCH₂ | phenylene | OCF₃ | Ph | 403.3 |
| 271 | OCH₂ | phenylene | OCF₃ | 3-CH₂OMe-Ph | 433.2 |
| 272 | OC(Me)(CO₂Me) | phenylene | OCF₃ | Ph | 475.1 |

TABLE 6-continued

| Ex # | Y | B | R³ | R⁶ | MS (M + 1) |
|---|---|---|---|---|---|
| 273 | -O-CH2- | benzene | OCF₃ | 4-t-Bu-phenyl | 459.02 |
| 274 | -O-CH2- | benzene | OCF₃ | 4-Br-phenyl | 480.89 |
| 275 | -O-CH2- | benzene | OCF₃ | 4-OCF₃-phenyl | 486.96 |
| 276 | -CH=CH- | benzene | OCF₃ | 4-F-phenyl | 417 |
| 277 | -CH=CH- | benzene | OCF₃ | phenyl | 399 |

TABLE 6-continued
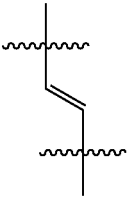
| Ex # | Y | B | R³ | R⁶ | MS (M + 1) |
|---|---|---|---|---|---|
| 278 | 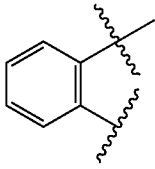 | 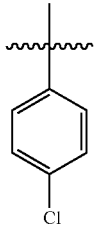 | OCF₃ | 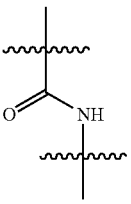 | 433 |
| 279 | 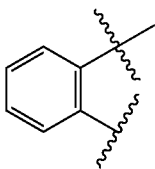 | 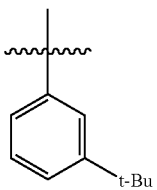 | OCF₃ | 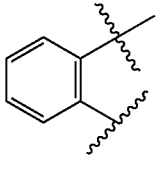 | 472.32 |
| 617 | O | 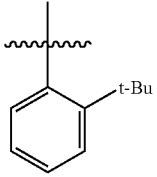 | O-t-Bu | 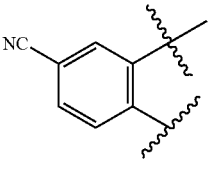 | 433.39 |
| 618 | O | 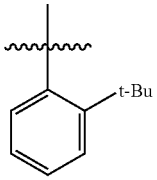 | Me | 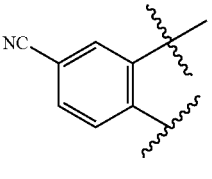 | 400.28 |
| 619 | O | 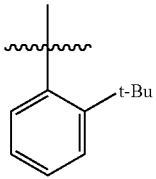 | OCF₃ | 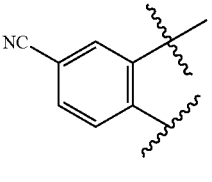 | 470.25 |
| 620 | O | 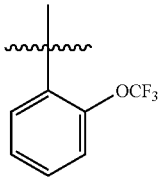 | O-t-Bu |  | 487.23 |

TABLE 6-continued

| Ex # | Y | B | R³ | R⁶ | MS (M + 1) |
|---|---|---|---|---|---|
| 621 | O | NC-phenyl | O-t-Bu | o-t-Bu-phenyl | 458.30 |
| 622 | O | NC-phenyl | t-Bu | o-t-Bu-phenyl | 442.30 |
| 623 | O | MeO₂C-phenyl | Me | o-t-Bu-phenyl | 433.26 |
| 624 | O | MeO₂C-phenyl | OCF₃ | o-t-Bu-phenyl | 503.24 |

UTILITY

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated or cured by the administration of an anti-platelet agent. Thus, the compounds of the present invention are useful in the treatment or prevention of various platelet associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastases and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic never transmission would be of therapeutic benefit such as nociception or neuronal tissue regeneration. These and many other potential utilities for P2Y$_1$ antagonists have been recently reviewed (Burnstock, G. and Williams, M. *J. Pharm. Exp Ther.* 2000, 295, 862-9) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

P2Y$_1$ Assays

A. Binding Assay

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al. *Current Protocols in Molecular Biology* 1995 John Wiley and Sons, NY, N.Y.). The essential coding sequences were subcloned into pCDNA 3.1 (Invitrogen) to produce a P2Y$_1$ expression construct. This construct was then transfected into the human embryonic kidney cell line HEK-293 and stable transfectants selected in Genetcin® (G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCl$_2$, 5 mM EDTA, 5 mM KCl) and stored at −70° C. until used.

Binding reactions were performed in WGA FlashPlates (PerkinElmer Life Sciences, Cat # SMP105A) in a volume of 200 µL containing ~45 fmol of P2Y$_1$ receptor (5 µg of total protein), 0.5 nM [$^{33}$P] 2MeS-ADP (PerkinElmer; 2,000 Ci/mmol), and various concentrations of the test compound (usually between 50 µM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

In general, preferred compounds of the present invention, such as the particular compounds disclosed in the above examples, have been identified to exhibit K$_i$'s of equal to or less than 10 µM in the P2Y$_1$ binding assay, thereby demonstrating these preferred compounds of the present invention as especially effective modulators of P2Y$_1$ activity. More preferred compounds have K$_i$'s of equal to or less than 5 µM, preferably equal to or less than 1 µM, more preferably equal to or less than 0.5 µM.

The compounds of the present invention may be used in combination with each other, or with other anti-platelet agents. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phosphodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as I$_{Ach}$ inhibitors, and I$_{Kur}$ inhibitors (e.g., compounds such as those disclosed in U.S. Application Publication US 20030022890).

Examples of suitable anti-hypertensive agents for use in combination with the compounds of the present invention include: alpha adrenergic blockers; beta adrenergic blockers; calcium channel blockers (e.g. diltiazem, verapamil, nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates); and β-blockers (e.g., propanolol, nadolo, or carvedilol).

The term anti-platelet agents (or platelet inhibitory agents), as used herein, denotes agents that inhibit platelet function, for example, by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include GPIIb/IIIa blockers (e.g., abciximab, eptifibatide, tirofiban, integrelin), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

Other examples of suitable anti-platelet agents for use in combination with the compounds of the present invention, with or without aspirin, include: ADP (adenosine diphosphate) receptor antagonists including $P2Y_{12}$ antagonists and other $P2Y_1$ antagonist. Preferred $P2Y_{12}$ receptor antagonists, but are not limited to, clopidogrel, ticlopidine, Prasugrel, and CS-747, including pharmaceutically acceptable salts or prodrugs thereof. Clopidogrel is an even more preferred agent.

Examples of suitable anti-coagulants (or coagulation inhibitory agents) for use in combination with the compounds of the present invention include warfarin and heparin (either unfractionated heparin such as enoxaparin and dalteparin or any commercially available low molecular weight heparin, for example LOVENOX™), synthetic pentasaccharide, direct acting thrombin inhibitors including hirudin and argatroban, factor VIIa, IXa, Xa, or XIa inhibitors, known in the art.

Examples of suitable anti-thrombotic and/or anti-thrombolytic agents for use in combination with the compounds of the present invention include: tissue plasminogen activator (natural or recombinant), tenecteplase (TNK), and lanoteplase (nPA); factor VIIa inhibitors; factor Xa inhibitors; factor XIa inhibitors; thrombin inhibitors (such as hirudin and argatroban); PAI-1 inhibitors (i.e., inactivators of tissue plasminogen activator inhibitors); alpha2-antiplasmin inhibitors; streptokinase, urokinase and prourokinase; and anisoylated plasminogen streptokinase activator complex.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diuretics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Pat. No. 6,548,529, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat and aP2 inhibitors (such as those disclosed in U.S. Pat. No. 6,548,529.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention are also useful as standard or reference compounds, for example as a quality standard or control, in tests or assays involving the inhibition of platelet ADP receptor. Such compounds may be provided in a commercial kit, for example, for use in pharmaceutical research involving platelet ADP receptor. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving platelet ADP receptor. For example, the presence of $P2Y_1$ in an unknown sample could be determined by addition of the relevant radiolabled compound to the sample and measuring the extend of binding to the $P2Y_1$ receptor.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylacetic acid, polyglycolic acid, copolymers of polylacetic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or admin-

What is claimed is:

1. A compound of Formula (IIb):

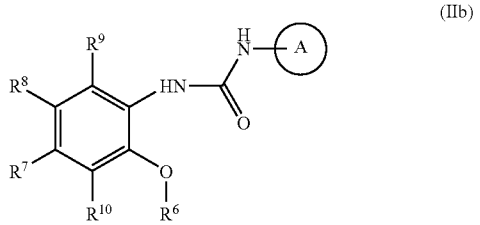

(IIb)

or a stereoisomer or a pharmaceutically acceptable salt thereof, wherein:

ring A is

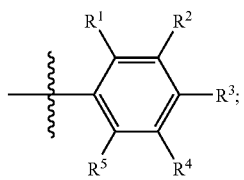

$R^1$ is H, F, Cl, or OH;

$R^2$ is H, F, Cl, Br, Me, t-Bu, OMe, OBu, pentoxy, isopentoxy, neohexoxy, —O(CH$_2$)$_2$OMe, —O(CH$_2$)$_2$O(i-Pr), —O(CH$_2$)$_8$CO$_2$Me, —O(CH$_2$)$_2$C(Me)$_2$OMe, —O(CH$_2$)$_2$NMe$_2$, —OCH$_2$C(Me)$_2$CH$_2$NMe$_2$, —O(CH$_2$)$_2$OCOMe, —OCH(Et)CH$_2$OMe, —OCH(Me)CH$_2$O(t-Bu), NO$_2$, CF$_3$, OCF$_3$, 2-CH$_2$N(Me)$_2$-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe$_2$-benzoxy, 2-CF$_3$-benzoxy, 3-OCF$_3$-benzoxy, 4-OCF$_3$-benzoxy, 4-CO$_2$Me-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl)ethoxy, or —OCH(Et)(pyridine-4-yl);

$R^3$ is H, F, Cl, Br, —OCH(Me)CH$_2$O-t-Bu, CF$_3$, OCHF$_2$, OCF$_3$, —O(CH$_2$)$_2$OMe, —O(CH$_2$)$_3$NMe$_2$, —O(CH$_2$)$_4$NMe$_2$, —OCH(Et)CH$_2$OMe, CN, NH$_2$, NMe$_2$, —CH$_2$NMe$_2$, NEt$_2$, —NHPh, —N(Me)Ph, —NH(4-OMe-Ph), —NH(2-CF$_3$-Ph), —CH(Me)NHCH(Me)Ph, —CH(Me)N(Me)(3-CF$_3$-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF$_3$-Bn), —CH(Me)O(4-CF$_3$-Bn), —CH(Me)O(1-Bn-pyrrolidin-3-ylmethyl), —C(CF$_3$)$_2$OH, —COMe, CO$_2$Et, —CH$_2$CO$_2$Me, —C(Me)$_2$CO$_2$Me, —O(CH$_2$)$_5$CO$_2$Et, —O(CH$_2$)$_8$CO$_2$Me, —O(CH$_2$)$_2$C(Me)$_2$OMe, —O(CH$_2$)$_2$OCOMe, —OCH$_2$C(Me)$_2$CH$_2$NMe$_2$, Ph, 2-CH$_2$OH-Ph, 2-CH$_2$N(Me)-2-Ph, 3-CH$_2$N(Me)-2-Ph, 4-CH$_2$N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 4-OMe-benzoxy, 3-CN-benzoxy, 4-CN-benzoxy, 3-NMe$_2$-benzoxy, 4-CO$_2$Me-benzoxy, 3-CF$_3$-benzoxy, 3-OCF$_3$-benzoxy, 4-OCF$_3$-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO$_2$Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO$_2$Et-5-Me-1H-pyrazol-1-yl, 4-CO$_2$Et-5-Me-1H-pyrazol-1-yl, 5-CO$_2$Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO$_2$(t-Bu)-piperidin-4-yl)methoxy, (1-CO$_2$Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 4,4,5,5-tetramethyl-1,3,2-dioxaborolanyl, —OP(O)(OEt)$_2$, $C_{1-6}$ alkyl, $C_{1-6}$ alkoxy, or $C_{3-6}$ cycloalkyl optionally substituted with the group selected from: —CO$_2$Me, —CH$_2$OH, and —CH$_2$OMe; and $R^4$, and $R^5$, are, independently at each occurrence, H, F, Cl, Me, or OMe;

$R^6$ is 2-Me-Ph, 3-Me-Ph, 2-Et-Ph, 3-Et-Ph, 2-Pr-Ph, 2-i-Pr-Ph, 3-i-Pr-Ph, 2-i-Bu-Ph, 2-t-Bu-Ph, 3-t-Bu-Ph, 2-vinyl-Ph, 2-isopropenyl-Ph, 3-isopropenyl-Ph, 3-Br-Ph, 2-I-Ph, 2-SMe-Ph, 2-S(i-Pr)-Ph, 2-C(Me)$_2$CN-Ph, 2-CF$_3$-Ph, 3-CF$_3$-Ph, 2-OCF$_3$-Ph, 3-OCF$_3$-Ph, 3-Ph-Ph, 2-Bn-Ph, 2-SiMe$_3$-Ph, 3-SiMe$_3$-Ph, 2-C(Me)$_2$OMe-Ph, 2-C(Me)$_2$OEt-Ph, 2-C(Me)$_2$OPr-Ph, 2-CH(Me)O(CH$_2$)$_2$OMe-Ph, 2-C(Me)$_2$O(CH$_2$)$_2$OMe-Ph, 2-C(Et)$_2$OH-Ph, 2-C(Et)$_2$OMe-Ph, 2-C(Et)$_2$OEt-Ph, 2-C(Et)$_2$OPr-Ph, 3-COPh-Ph, 2-CO$_2$Et-Ph, 3-CO$_2$Et-Ph, 2-NH(i-Bu)-Ph, 2-cyclopropyl-Ph, 2-cyclopentyl-Ph, 2,3-dimethoxy-Ph, 2,3-diCl-Ph, 2,6-diMe-Ph, 2-Me-5-F-Ph, 2-i-Pr-5-Me-Ph, 2-t-Bu-4-Me-Ph, 2-t-Bu-5-Me-Ph, 2-t-Bu-6-CN-Ph, 2-F-3-CF$_3$-Ph, 2-F-5-CF$_3$-Ph, 2-Cl-5-CF$_3$-Ph, 2-COMe-3-F-Ph, 2-CO$_2$Me-3-F-Ph, 2-CF$_3$-Bn,

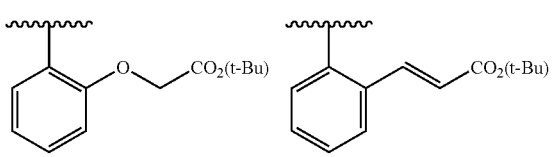

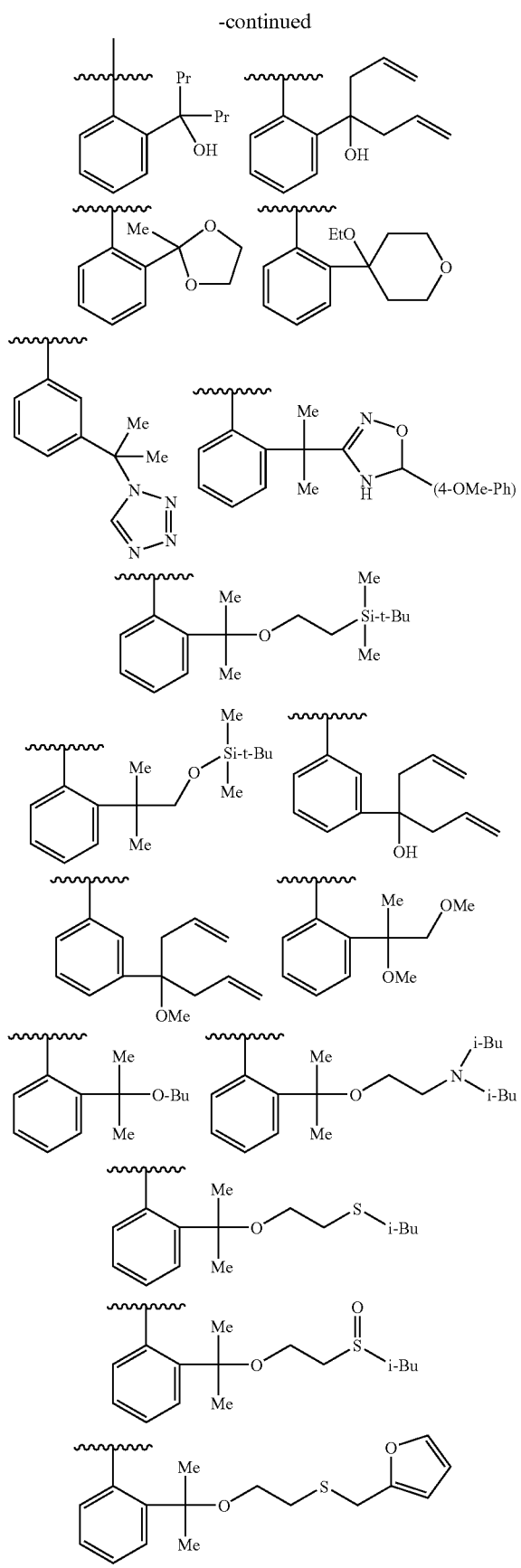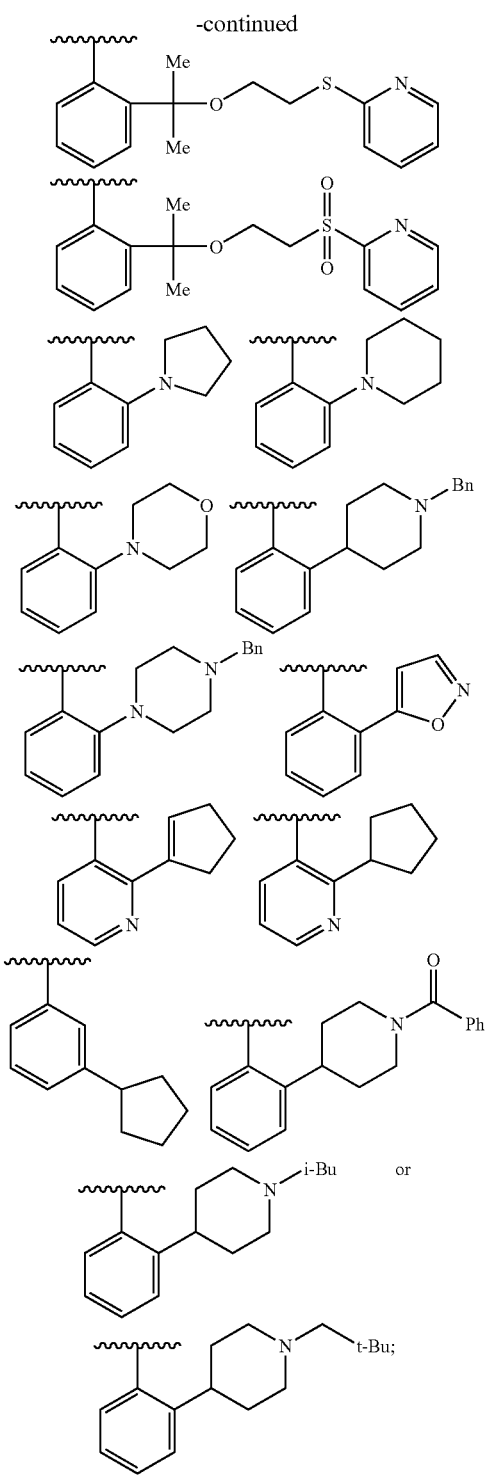
$R^7$ is H, Me, Cl, Br, CN, OH, OMe, SMe, NHMe, $NMe_2$, $CO_2Me$, imidazol-1-yl, or —$CH_2NH(CO)H$;
$R^8$ is H, Me, Cl, Br, or CN;
$R^9$ is H or Me;
$R^{10}$ is H or Me; and
$R^{11}$ is, independently at each occurrence, H, $C_{1-6}$ alkyl, OMe, —C(O)($C_{1-6}$ alkyl), —C(O)phenyl, —C(O)benzyl, —C(O)O($C_{1-16}$ alkyl), —C(O)Obenzyl, —$S(O)_2$ ($C_{1-6}$ alkyl), —$S(O)_2$phenyl, —$S(O)_2$benzyl, cyclohexylmethyl, phenyl, benzyl, phenethyl, phenylpropyl, —CH₂CH(Me)Ph, 1H-pyrrol-2-ylmethyl, 1-Me-pyrrol-2-ylmethyl, thieny-2-ylmethyl, furan-2-ylmethyl, furan-3-ylmethyl, 2-F-Bn, 2-OH-Bn, 2-CN-Bn, 3-CN-Bn, 4-CN-Bn, 4-OMe-Bn, 4-CO₂Me-Bn,

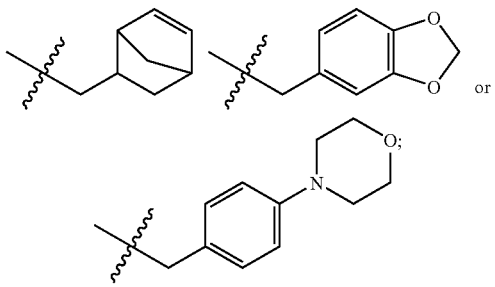

provided that:
(a) when R² is CF₃, then R³ is other than CF₃; or
(b) ring A is other than dichloro substituted phenyl.
2. A compound according to claim 1, wherein:
ring A is

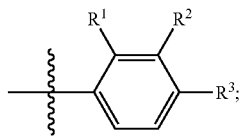

R¹ is H or F;
R² is H, F, Cl, Br, Me, t-Bu, OMe, OBu, pentoxy, isopentoxy, neohexoxy, —O(CH₂)₂OMe, —O(CH₂)₂O(i-Pr), —O(CH₂)₈CO₂Me, —O(CH₂)₂C(Me)₂OMe, —O(CH₂)₂NMe₂, —OCH₂C(Me)₂CH₂NMe₂, —O(CH₂)₂OCOMe, —OCH(Et)CH₂OMe, —OCH(Me)CH₂O(t-Bu), NO₂, CF₃, OCF₃, 2-CH₂N(Me)₂-Ph, cyclopenoxy, cyclohexoxy, 4-Me-cyclohexoxy, cyclohexylmethoxy, cyclohexylethoxy, phenyl, phenoxy, benzoxy, 2-OMe-benzoxy, 3-OMe-benzoxy, 4-OMe-benzoxy, 4-Cl-benzoxy, 3-CN-benzoxy, 4-CN-benzoxy, 3-NMe₂-benzoxy, 2-CF₃-benzoxy, 3-OCF₃-benzoxy, 4-OCF₃-benzoxy, 4-CO₂Me-benzoxy, 4-NHCOMe-benzoxy, 4-Ph-benzoxy, (2-naphthyl)methoxy, (1-Bn-pyrrolidin-3-yl)oxy, (1-Bn-pyrrolidin-3-yl)methoxy, (furan-2-yl)methoxy, (furan-3-yl)methoxy, (tetrahydrofuran-2-yl)methoxy, (tetrahydrofuran-3-yl)methoxy, (thien-3-yl)methoxy, (1H-pyrrol-1-yl)ethoxy, (2-Bu-1H-imidazol-4-yl)methoxy, (1-Ph-1H-1,2,3-triazol-4-yl)methoxy, 1-Bn-piperidin-3-oxy, 1-Bn-piperidin-4-oxy, (4-Bn-morpholin-2-yl)methoxy, (pyridin-2-yl)methoxy, (pyridin-3-yl)methoxy, (pyridin-4-yl)methoxy, (pyridin-2-yl)ethoxy, (pyridin-4-yl)ethoxy, or —OCH(Et)(pyridine-4-yl);
R³ is H, F, Cl, Br, Me, Et, Pr, Bu, t-Bu, OMe, OEt, OPr, O-i-Pr, OBu, O-t-Bu, pentoxy, isopentoxy, neohexoxy, —OCH(Me)CH₂O-t-Bu, CF₃, OCHF₂, OCF₃, —O(CH₂)₂OMe, —O(CH₂)₃NMe₂, —O(CH₂)₄NMe₂, —OCH(Et)CH₂OMe, CN, NH₂, NMe₂, —CH₂NMe₂, NEt₂, —NHPh, —N(Me)Ph, —NH(4-OMe-Ph), —NH(2-CF₃-Ph), —CH(Me)NHCH(Me)Ph, —CH(Me)N(Me)(3-CF₃-Bn), —CH(Me)N(Me)(furan-2-ylmethyl), —CH(Me)N(Me)(thien-2-ylmethyl), —CH(Me)OH, —CH(Me)O(i-Pr), —CH(Me)O(i-Bu), —CH(Me)O(3-CF₃-Bn), —CH(Me)O(4-CF₃-Bn), —CH(Me)O(1-Bn-pyrrolidin-3-ylmethyl), —C(Me)₂OH, —C(Me)₂CH₂OH, —C(CF₃)₂OH, —COMe, CO₂Et, —CH₂CO₂Me, —C(Me)₂CO₂Me, —O(CH₂)₅CO₂Et, —O(CH₂)₈CO₂Me, —O(CH₂)₂C(Me)₂OMe, —O(CH₂)₂OCOMe, —OCH₂C(Me)₂CH₂NMe₂, Ph, 2-CH₂OH-Ph, 2-CH₂N(Me)-2-Ph, 3-CH₂N(Me)-2-Ph, 4-CH₂N(Me)-2-Ph, 2-((3-OH-pyrrolidin-1-yl)methyl)-Ph, phenoxy, Bn, benzoxy, 4-Cl-benzoxy, 2-OMe-benzoxy, 3-OMe-benzoxy, 4-OMe-benzoxy, 3-CN-benzoxy, 4-CN-benzoxy, 3-NMe₂-benzoxy, 4-CO₂Me-benzoxy, 3-CF₃-benzoxy, 3-OCF₃-benzoxy, 4-OCF₃-benzoxy, 4-Ph-benzoxy, 2,4-diF-benzoxy, (2-naphthyl)methoxy, cyclohexylmethoxy, cyclohexylethoxy, cyclopentoxy, 3-Me-cyclopentoxy, cyclohexoxy, 4-Me-cyclohexoxy, 4-CO₂Et-cyclohexoxy, 1-Bn-pyrrolidin-3-oxy, (1-Bn-pyrrolidin-3-yl)methoxy, (furan-2-yl)methoxy, (furan-3-yl)methoxy, (tetrahydrofuran-3-yl)methoxy, (thien-3-yl)methoxy, thiazol-2-yl, 1H-pyrazol-1-yl, 3-CO₂Et-5-Me-1H-pyrazol-1-yl, 4-CO₂Et-5-Me-1H-pyrazol-1-yl, 5-CO₂Et-3-Me-1H-pyrazol-1-yl, (2-Bu-1H-imidazol-4-yl)methoxy, 1H-1,2,4-triazol-1-yl, (1-Ph-1H-1,2,3-triazol-4-yl)methoxy, 2-(1H-pyrrol-1-yl)-ethoxy, 1-piperidinyl, 1-Bn-piperazin-4-yl, (2,2-dimethyl-1,3-dioxolan-4-yl)-methoxy, 1-Bn-piperidin-3-oxy, 1-Bn-piperidin-4-oxy, (1-(i-Bu)-piperidin-4-yl)methoxy, (1-isopentyl-piperidin-4-yl)methoxy, (1-CO₂(t-Bu)-piperidin-4-yl)methoxy, (1-CO₂Bn-piperidin-4-yl)methoxy, (1-Bn-piperidin-4-yl)methoxy, (1-phenethyl-piperidin-4-yl)methoxy, (1-(4-phenylbutyl)-piperidin-4-yl)methoxy, (1-cyclohexylmethyl-piperidin-4-yl)methoxy, (1-((pyridin-2-yl)methyl)-piperidin-4-yl)methoxy, (1-((pyridin-4-yl)methyl)-piperidin-4-yl)methoxy, (1-((1,3-dioxolan-2-yl)methyl)piperidin-4-yl)methoxy, N-morpholinyl, (pyridin-2-yl)methoxy, (pyridin-3-yl)methoxy, (pyridin-4-yl)methoxy, (pyridin-4-yl)ethoxy, (4-Bn-morpholin-2-yl)methoxy, 1-CH₂OH-cyclopropyl, 1-CO₂Me-cyclopropyl, 1-CH₂OMe-cyclopropyl, 1-CO₂Me-cyclobutyl, 1-CO₂Me-cyclopentyl, cyclohexyl, 1-CO₂Me-cyclohexyl, 4,4,5,5-tetramethyl-1,3,2-dioxaborolanyl, or —OP(O)(OEt)₂;
R⁷ is H, Me, Cl, Br, CN, OH, OMe, SMe, NHMe, NMe₂, CO₂Me, imidazol-1-yl, or —CH₂NH(CO)H; and
R⁸ is H, Me, Cl, Br, or CN;
provided that:
(a) when R is CF₃, then is other than CF₃; or
(b) ring A is other than dichloro substituted phenyl.
3. A compound of Formula (IIc):

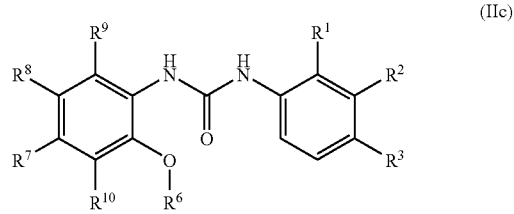

or a stereoisomer or a pharmaceutically acceptable salt thereof, wherein:
R¹ is H or F;
R² is H or F;
R³ is H, Me, t-Bu, F, OCF₃, or O-t-Bu;

$R^6$ is 2-t-Bu-Ph, 3-CF$_3$-Ph, 3-I-Ph, 3-CH$_2$OMe-Ph, 2-Me-5-F-Ph, Bn, 4-t-Bu-Bn, 4-Br-Bn, 4-OCF$_3$-Bn, —CH(Me)Ph, or —CH(CO$_2$Me)Ph;
$R^7$ is H or CN;
$R^8$ is H, CN, CO$_2$Me;
$R^9$ is H; and
$R^{10}$ is H, Me, NH$_2$, or —CH$_2$OMe.

4. A compound according to claim 3, wherein $R^1$ is H; $R^2$ is H; $R^9$ is H; and $R^3$, $R^6$, $R^8$, and $R^{10}$ are selected in concert from the group consisting of:

| $R^3$ | $R^6$ | $R^8$ | $R^{10}$ |
|---|---|---|---|
| t-Bu | 2-t-Bu-Ph | H | Me |
| OCF$_3$ | 3-I-Ph | H | H |
| OCF$_3$ | 5-F-2-Me-Ph | H | H |
| t-Bu | 2-t-Bu-Ph | H | NH$_2$ |
| OCF$_3$ | Bn | H | H |
| OCF$_3$ | 3-CH$_2$OMe-Bn | H | H |
| OCF$_3$ | 4-t-Bu-Bn | H | H |
| OCF$_3$ | 4-Br-Bn | H | H |
| OCF$_3$ | 4-OCF$_3$-Bn | H | H |
| O-t-Bu | 2-t-Bu-Ph | H | H |
| Me | 2-t-Bu-Ph | CN | H |

-continued

| $R^3$ | $R^6$ | $R^8$ | $R^{10}$ |
|---|---|---|---|
| OCF$_3$ | 2-t-Bu-Ph | CN | H |
| O-t-Bu | 2-OCF$_3$-Ph | CN | H |
| O-t-Bu | 2-t-Bu-Ph | CN | H |
| t-Bu | 2-t-Bu-Ph | CN | H |
| Me | 2-t-Bu-Ph | CO$_2$Me | H |
| OCF$_3$ | 2-t-Bu-Ph | CO$_2$Me | H. |

5. A pharmaceutical composition, comprising: a pharmaceutically acceptable carrier and a therapeutically effective amount of a compound of claim 1.

6. A pharmaceutical composition, comprising: a pharmaceutically acceptable carrier and a therapeutically effective amount of a compound of claim 2.

7. A pharmaceutical composition, comprising: a pharmaceutically acceptable carrier and a therapeutically effective amount of a compound of claim 3.

8. A pharmaceutical composition, comprising: a pharmaceutically acceptable carrier and a therapeutically effective amount of a compound of claim 4.

* * * * *